(12) United States Patent
La et al.

(10) Patent No.: US 11,665,961 B2
(45) Date of Patent: May 30, 2023

(54) HETEROCYCLIC COMPOUND AND ORGANIC LIGHT EMITTING DEVICE USING SAME

(71) Applicant: LT MATERIALS CO., LTD., Yongin (KR)

(72) Inventors: Hyun-Ju La, Hwaseong-si (KR); Yu-Jin Heo, Osan-si (KR); Won-Jang Jeong, Hwaseong-si (KR); Jin-Seok Choi, Suwon-si (KR); Dae-Hyuk Choi, Yongin-si (KR); Joo-Dong Lee, Seongnam-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 413 days.

(21) Appl. No.: 16/757,086

(22) PCT Filed: Oct. 18, 2018

(86) PCT No.: PCT/KR2018/012327
§ 371 (c)(1),
(2) Date: Apr. 17, 2020

(87) PCT Pub. No.: WO2019/078636
PCT Pub. Date: Apr. 25, 2019

(65) Prior Publication Data
US 2020/0243775 A1    Jul. 30, 2020

(30) Foreign Application Priority Data

Oct. 19, 2017 (KR) .................. 10-2017-0135673

(51) Int. Cl.
*H01L 51/00* (2006.01)
*C07D 471/04* (2006.01)
(Continued)

(52) U.S. Cl.
CPC ........ *H01L 51/0072* (2013.01); *C07D 401/14* (2013.01); *C07D 403/14* (2013.01);
(Continued)

(58) Field of Classification Search
CPC ............ H01L 51/0085; H01L 51/0072; H01L 51/00; H01L 51/0067; H01L 51/5088;
(Continued)

(56) References Cited

U.S. PATENT DOCUMENTS 4,356,429 A    10/1982    Tang
8,344,365 B2    1/2013    Kim et al.
(Continued)

FOREIGN PATENT DOCUMENTS

CN    104810802 A    7/2015
EP    3174124 A1 *    5/2017    ........... C07D 471/04
(Continued)

OTHER PUBLICATIONS

International Search Report (PCT/ISA/210) issued in PCT/KR2018/012327, dated Jan. 21, 2019.
(Continued)

*Primary Examiner* — Younes Boulghassoul
*Assistant Examiner* — Quinton A Brasfield
(74) *Attorney, Agent, or Firm* — Birch Stewart, Kolasch & Birch, LLP

(57) ABSTRACT

The present specification relates to a hetero-cyclic compound represented by Chemical Formula 1, and an organic light emitting device comprising the same.

13 Claims, 3 Drawing Sheets

(51) Int. Cl.
*C07D 403/14* (2006.01)
*C07D 409/14* (2006.01)
*C07D 405/14* (2006.01)
*C07D 411/14* (2006.01)
*C07D 413/14* (2006.01)
*C07D 401/14* (2006.01)
*H01L 51/50* (2006.01)

(52) U.S. Cl.
CPC ......... *C07D 405/14* (2013.01); *C07D 409/14* (2013.01); *C07D 411/14* (2013.01); *C07D 413/14* (2013.01); *C07D 471/04* (2013.01); *H01L 51/0067* (2013.01); *H01L 51/0071* (2013.01); *H01L 51/5044* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC ................ C07D 401/10; C07D 403/10; C07D 405/10; C07D 409/10; C07D 471/04; C07D 401/14; C07D 403/14; C07D 405/14; C07D 409/14; C07D 411/14; C07D 413/14
See application file for complete search history.

(56) References Cited

U.S. PATENT DOCUMENTS

| | | | |
|---|---|---|---|
| 8,889,267 B2 | 11/2014 | Kim et al. | |
| 9,595,822 B2 | 3/2017 | Park | |
| 9,673,259 B2 * | 6/2017 | Park | H01L 51/0094 |
| 9,728,731 B2 | 8/2017 | La et al. | |
| 10,193,078 B2 | 1/2019 | Ito et al. | |
| 10,446,765 B2 | 10/2019 | Lee et al. | |
| 2015/0303380 A1 * | 10/2015 | Kambe | H01L 51/0068 257/40 |
| 2016/0005980 A1 * | 1/2016 | Ito | C09B 57/10 257/40 |
| 2017/0040554 A1 | 2/2017 | Brooks et al. | |
| 2018/0090686 A1 * | 3/2018 | Yoon | C07D 409/14 |
| 2019/0288218 A1 | 9/2019 | La et al. | |

FOREIGN PATENT DOCUMENTS

| | | |
|---|---|---|
| KR | 10-08331356 B1 | 5/2008 |
| KR | 10-1117724 B1 | 3/2012 |
| KR | 10-1182438 B1 | 9/2012 |
| KR | 10-2014-0029182 A | 3/2014 |
| KR | 10-2015-0077383 A | 7/2015 |
| KR | 10-2016-0002408 A | 1/2016 |
| KR | 10-2016-0005196 A | 1/2016 |
| WO | WO 2018/101764 A1 | 6/2018 |

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4, 4', 4"-Tris(3-methylphenylphenyl-amino)triphenylamine (m-MTDATA), as Hole-Transport Materials", Advanced Materials, 1994, vol. 6, No. 9, pp. 677-679.

* cited by examiner

[FIG. 1]
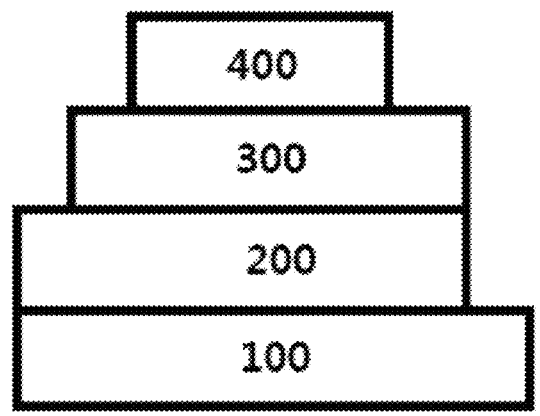
[FIG. 2]
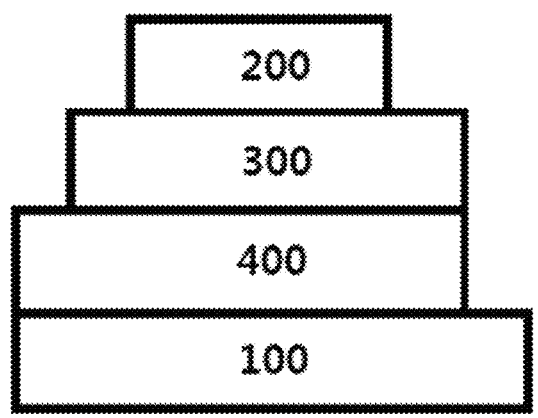

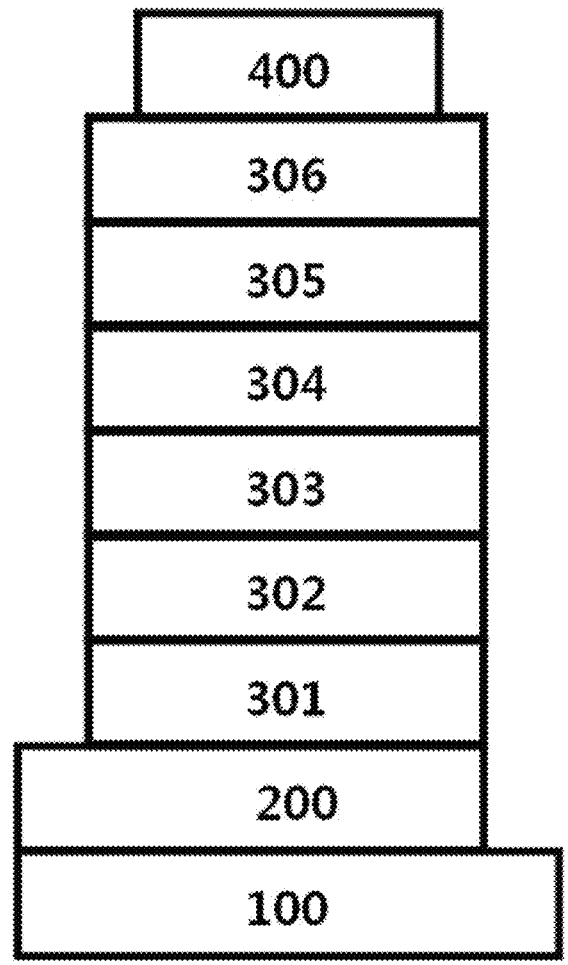
[FIG. 3]

[FIG. 4]

| CATHODE |
| --- |
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT EMITTING DEVICE USING SAME

TECHNICAL FIELD

This application claims priority to and the benefits of Korean Patent Application No. 10-2017-0135673, filed with the Korean Intellectual Property Office on Oct. 19, 2017, the entire contents of which are incorporated herein by reference.

The present application relates to a hetero-cyclic compound and an organic light emitting device using the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present application is directed to providing a novel hetero-cyclic compound and an organic light emitting device using the same.

Technical Solution

One embodiment of the present application provides a hetero-cyclic compound represented by the following Chemical Formula 1.

[Chemical Formula 1]

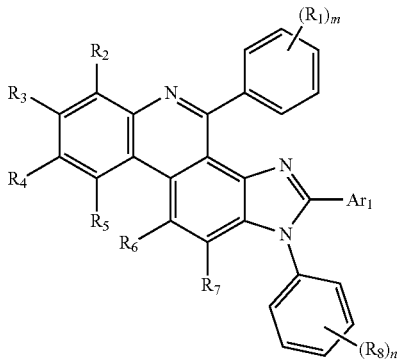

In Chemical Formula 1, $R_1$ is hydrogen; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R"; —P(=O)RR'; or —CN, $R_2$ to $R_8$ are the same as or different from each other, and each independently selected from the group consisting of hydrogen; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, $Ar_1$ is a substituted or unsubstituted $C_1$ to $C_{60}$ alkyl group, m and n are each independently an integer of 0 to 5, R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

Another embodiment of the present application provides an organic light emitting device comprising a first electrode, a second electrode, and one or more organic material layers provided between the first electrode and the second electrode, wherein one or more layers of the organic material layers comprise the hetero-cyclic compound.

Advantageous Effects

The hetero-cyclic compound according to one embodiment of the present application can be used as an organic material layer material of an organic light emitting device. The hetero-cyclic compound can be used as a material of a hole injection layer, a hole transfer layer, a light emitting layer, an electron transfer layer, an electron injection layer, a charge generation layer or the like in an organic light emitting device. Particularly, the hetero-cyclic compound represented by Chemical Formula 1 can be used as a material of an electron transfer layer or a charge generation layer in an organic light emitting device. In addition, using the hetero-cyclic compound represented by Chemical Formula 1 in an organic light emitting device lowers a driving voltage of the device, enhances light efficiency, and can enhance lifetime properties of the device with thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

A hetero-cyclic compound according to one embodiment of the present application is represented by Chemical Formula 1. More specifically, due to structural properties of a core structure and substituents as above, a hetero-cyclic compound represented by Chemical Formula 1 may be used as an organic material layer material of an organic light emitting device.

In one embodiment of the present application, when m of Chemical Formula 1 is 2 or greater, two or more $R_1$s may be the same as or different from each other. In addition, when n of Chemical Formula 1 is 2 or greater, two or more $R_8$s may be the same as or different from each other.

In one embodiment of the present application, $R_1$ of Chemical Formula 1 may be hydrogen; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R"; —P(=O)RR'; or —CN.

In another embodiment, $R_1$ of Chemical Formula 1 may be hydrogen; a substituted or unsubstituted $C_1$ to $C_{40}$ alkyl group; a substituted or unsubstituted $C_6$ to $C_{40}$ aryl group; a substituted or unsubstituted $C_2$ to $C_{40}$ heteroaryl group; —SiRR'R"; —P(=O)RR'; or —CN.

In one embodiment of the present application, $R_2$ to $R_8$ of Chemical Formula 1 are the same as or different from each other, and may be each independently selected form the group consisting of hydrogen; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group.

In another embodiment, $R_2$ to $R_8$ of Chemical Formula 1 are the same as or different from each other, and may be each independently hydrogen; a substituted or unsubstituted $C_6$ to $C_{40}$ aryl group; a substituted or unsubstituted $C_2$ to $C_{40}$ heteroaryl group.

In another embodiment, $R_2$ to $R_8$ of Chemical Formula 1 may be hydrogen.

In one embodiment of the present application, $Ar_1$ of Chemical Formula 1 may be a substituted or unsubstituted $C_1$ to $C_{60}$ alkyl group.

In another embodiment, $Ar_1$ of Chemical Formula 1 may be a substituted or unsubstituted $C_1$ to $C_{40}$ alkyl group.

In another embodiment, $Ar_1$ of Chemical Formula 1 may be a $C_1$ to $C_{40}$ alkyl group.

In another embodiment, $Ar_1$ of Chemical Formula 1 may be selected from the group consisting of a methyl group; an ethyl group; a propyl group; or a butyl group.

In another embodiment, $Ar_1$ of Chemical Formula 1 may be an ethyl group.

In one embodiment of the present application, $R_1$ of Chemical Formula 1 may be represented by $-(L)_p-(Z)_q$, L is a direct bond; a substituted or unsubstituted $C_6$ to $C_{60}$ arylene group; or a substituted or unsubstituted $C_2$ to $C_{60}$ heteroarylene group, Z is hydrogen; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —CN; —SiRR'R"; or —P(=O)RR', R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, and p and q are an integer of 1 to 4.

In one embodiment of the present application, L may be a direct bond; a substituted or unsubstituted $C_6$ to $C_{40}$ arylene group; or a substituted or unsubstituted $C_2$ to $C_{40}$ heteroarylene group.

In another embodiment, L may be a direct bond; a $C_6$ to $C_{40}$ arylene group; or a $C_2$ to $C_{40}$ heteroarylene group.

In another embodiment, L may be a direct bond; a $C_6$ to $C_{40}$ monocyclic or polycyclic arylene group; or a $C_2$ to $C_{40}$ monocyclic or polycyclic heteroarylene group.

In another embodiment, L may be a direct bond; a $C_6$ to $C_{40}$ monocyclic or polycyclic arylene group; or a $C_2$ to $C_{40}$ monocyclic or polycyclic N-containing heteroarylene group.

In another embodiment, L may be a direct bond; a phenylene group; a naphthalene group; an anthracenylene group; a divalent pyridine group; a divalent pyrimidine group; a divalent triazine group; or a divalent quinazoline group.

In one embodiment of the present application, Z may be hydrogen; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —CN; —SiRR'R"; or —P(=O)RR'.

In another embodiment, Z may be hydrogen; a substituted or unsubstituted $C_6$ to $C_{40}$ aryl group; a substituted or unsubstituted $C_2$ to $C_{60}$ heteroaryl group; —CN; or —P(=O)RR'.

In another embodiment, Z may be hydrogen; a substituted or unsubstituted $C_6$ to $C_{40}$ monocyclic or polycyclic aryl group; a substituted or unsubstituted $C_2$ to $C_{60}$ monocyclic or polycyclic heteroaryl group; —CN; or —P(=O)RR'.

In another embodiment, Z may be hydrogen; a $C_6$ to $C_{40}$ monocyclic or polycyclic aryl group unsubstituted or substituted with one or more substituents selected from the group consisting of a $C_6$ to $C_{40}$ aryl group, a $C_2$ to $C_{40}$ heteroaryl group and —CN; a $C_2$ to $C_{60}$ monocyclic or polycyclic heteroaryl group unsubstituted or substituted with one or more substituents selected from the group consisting of a $C_1$ to $C_{40}$ alkyl group, a $C_6$ to $C_{40}$ aryl group and a $C_2$ to $C_{40}$ heteroaryl group; —CN; or —P(=O)RR'.

In another embodiment, Z may be hydrogen; P(=O)RR'; or —CN.

In another embodiment, Z may be a phenyl group unsubstituted or substituted with one or more substituents selected from the group consisting of a phenyl group, a carbazole group and —CN; a biphenyl group; a naphthyl group; a phenanthrene group; or a triphenylene group.

In another embodiment, Z may be a pyridine group unsubstituted or substituted with one or more substituents selected from the group consisting of a phenyl group and a pyridine group; a pyrimidine group unsubstituted or substituted with one or more substituents selected from the group consisting of a phenyl group, a biphenyl group, a naphthyl group and a pyridine group; a triazine group unsubstituted or substituted with one or more substituents selected from the group consisting of a phenyl group, a biphenyl group, a naphthyl group and a pyridine group; a quinazoline group unsubstituted or substituted with one or more substituents selected from the group consisting of a phenyl group, a biphenyl group and a naphthyl group; a carbazole group; a phenanthroline group unsubstituted or substituted with a phenyl group; a quinoline group; a 1,5-naphthyridyl group; a benzimidazole group unsubstituted or substituted with a methyl group, an ethyl group or a phenyl group; a benzothiazole group unsubstituted or substituted with a phenyl group; a 1,3,4-oxadiazole group unsubstituted or substituted with a phenyl group; an imidazo[1,2-a]pyridine group unsubstituted or substituted with a phenyl group; a pyrido[1,2-b]indazole group; or a pyrazolo[1,5-c]quinazolinyl group unsubstituted or substituted with a phenyl group.

In one embodiment of the present application, R, R' and R" are the same as or different from each other, and may be each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

In another embodiment, R, R' and R" are the same as or different from each other, and may be each independently hydrogen; a substituted or unsubstituted $C_6$ to $C_{40}$ aryl group; or a substituted or unsubstituted $C_2$ to $C_{40}$ heteroaryl group.

In another embodiment, R, R' and R" are the same as or different from each other, and may be each independently hydrogen; a $C_6$ to $C_{60}$ aryl group; or a $C_2$ to $C_{60}$ heteroaryl group.

In another embodiment, R, R' and R" are the same as or different from each other, and may be each independently a $C_6$ to $C_{60}$ aryl group.

In another embodiment, R, R' and R" are the same as or different from each other, and may be each independently a phenyl group.

In one embodiment of the present application, m may be 1.

In one embodiment of the present application, m may be 2.

In one embodiment of the present application, n may be 1.

In one embodiment of the present application, n may be 2.

In the hetero-cyclic compound provided in one embodiment of the present application, Chemical Formula 1 is represented by the following Chemical Formula 2 or 3.

[Chemical Formula 2]

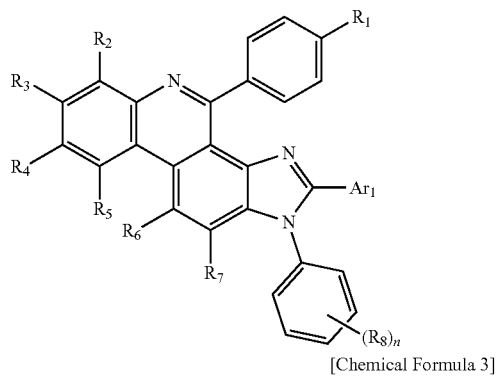

[Chemical Formula 3]

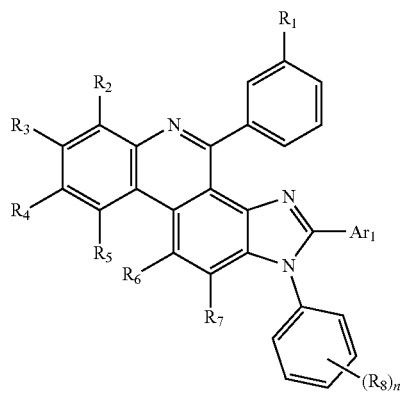

In Chemical Formulae 2 and 3, $Ar_1$, $R_1$ to $R_8$ and n have the same definitions as in Chemical Formula 1.

In the present specification, "substituted or unsubstituted" means being substituted with one or more substituents selected from the group consisting of deuterium; a halogen group; —CN; a $C_1$ to $C_{60}$ alkyl group; a $C_2$ to $C_{60}$ alkenyl group; a $C_2$ to $C_{60}$ alkynyl group; a $C_3$ to $C_{60}$ cycloalkyl group; a $C_2$ to $C_{60}$ heterocycloalkyl group; a $C_6$ to $C_{60}$ aryl group; a $C_2$ to $C_{60}$ heteroaryl group; —SiRR'R"; —P(=O)RR'; a $C_1$ to $C_{20}$ alkylamine group; a $C_6$ to $C_{60}$ arylamine group; and a $C_2$ to $C_{60}$ heteroarylamine group, or being unsubstituted, or being substituted with a substituent bonding two or more of the substituents illustrated above, or being unsubstituted, or being substituted with a substituent linking two or more substituents selected from among the substituents illustrated above, or being unsubstituted. For example, the "substituent linking two or more substituents" may be a biphenyl group. In other words, a biphenyl group may be an aryl group, or interpreted as a substituent linking two phenyl groups. The additional substituents may be further substituted. R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

According to one embodiment of the present application, the "substituted or unsubstituted" means being substituted with one or more substituents selected from the group consisting of deuterium, a halogen group, —CN, SiRR'R", P(=O)RR', a $C_1$ to $C_{20}$ linear or branched alkyl group, a $C_6$ to $C_{60}$ aryl group and a $C_2$ to $C_{60}$ heteroaryl group, or being unsubstituted, and R, R' and R" are the same as or different from each other, and each independently hydrogen; deuterium; —CN; a $C_1$ to $C_{60}$ alkyl group unsubstituted or substituted with deuterium, a halogen group, —CN, a $C_1$ to $C_{20}$ alkyl group, a $C_6$ to $C_{60}$ aryl group and a $C_2$ to $C_{60}$ heteroaryl group; a $C_3$ to $C_{60}$ cycloalkyl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group; a $C_6$ to $C_{60}$ aryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group; or a $C_2$ to $C_{60}$ heteroaryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group.

Particularly, compounds having $R_1$ substituting at a meta position or a para position of the phenyl group as in Chemical Formula 2 or Chemical Formula 3 have smooth electron migration between molecules due to smooth interactions between the molecules when used as an electron transfer layer material of an organic light emitting device afterword.

When $R_1$ of Chemical Formula 1 substitutes at an ortho position of the phenyl group, the molecular size increases compared to the compound having $R_1$ substituting at a meta position or a para position of the phenyl group as in Chemical Formula 2 or Chemical Formula 3, and the degree of electron migration decreases due to reduced molecular interactions.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenyl-vinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a Spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the spiro group is a group comprising a spiro structure, and may have 15 to 60 carbon atoms. For example, the spiro group may comprise a structure in which a 2,3-dihydro-1H-indene group or a cyclohexane group spiro bonds to a fluorenyl group. Specifically, the spiro group may comprise any one of groups of the following structural formulae.

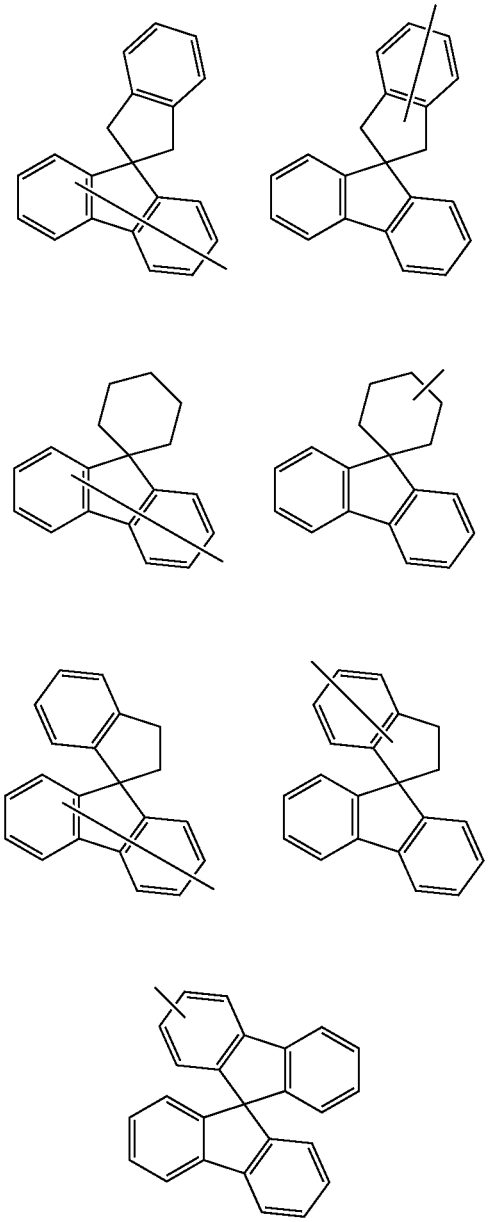

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, a thienyl group, a pyrido[1,2-b]indazole group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

According to one embodiment of the present application, Chemical Formula 1 may be represented by any one of the following compounds, but is not limited thereto.

1
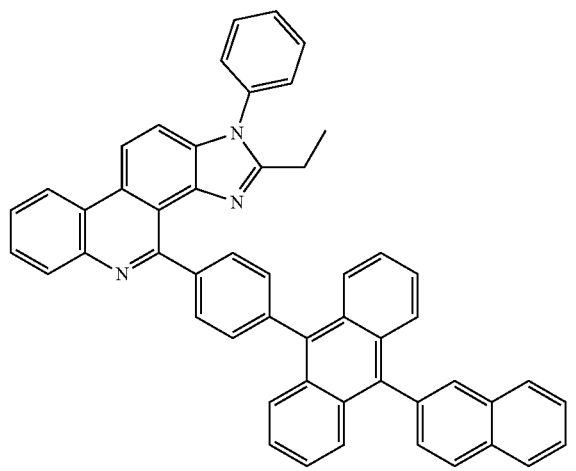
2
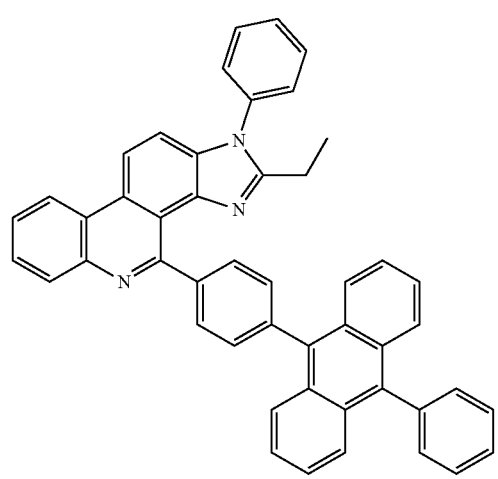
3
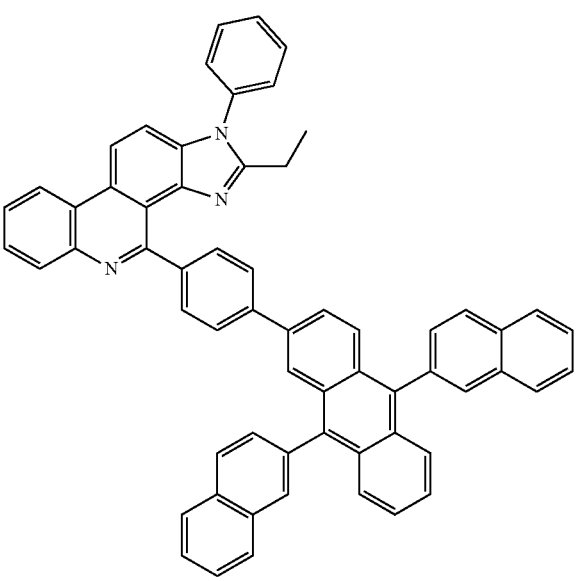
4
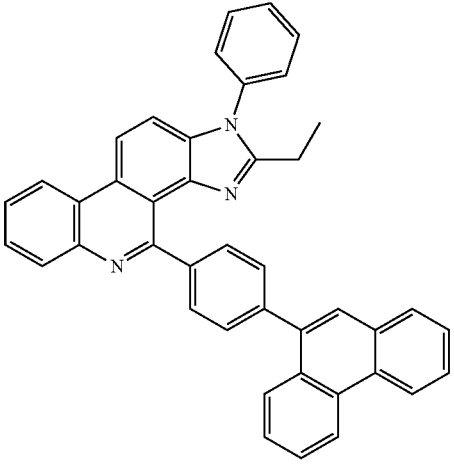
5
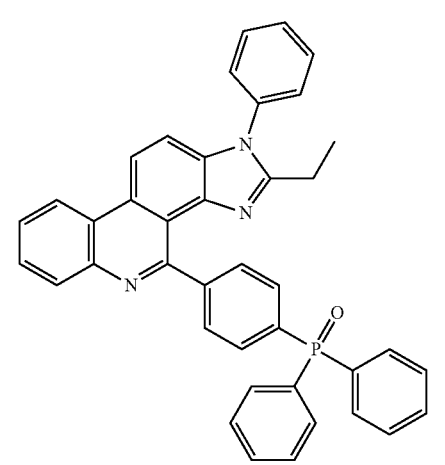
6
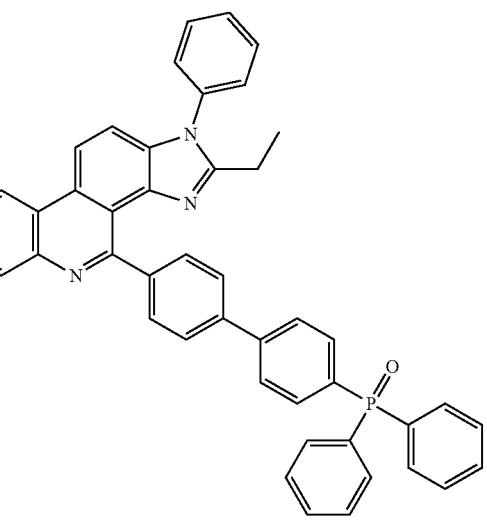

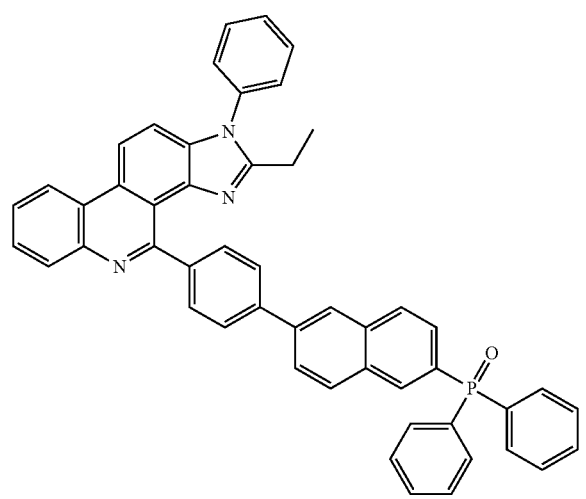
7
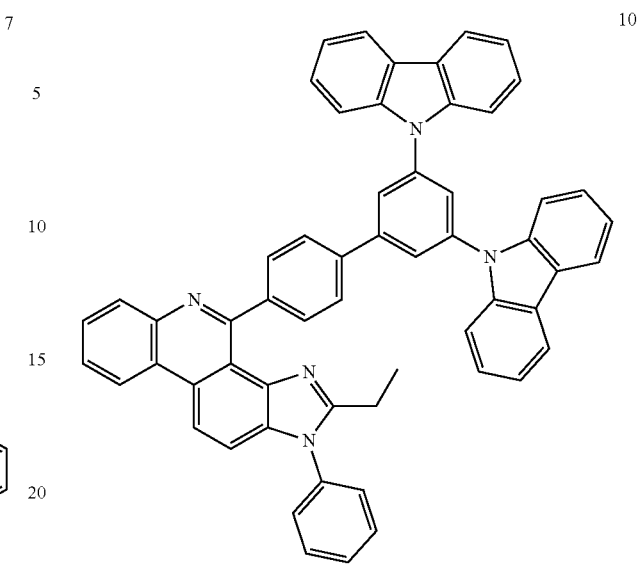
10
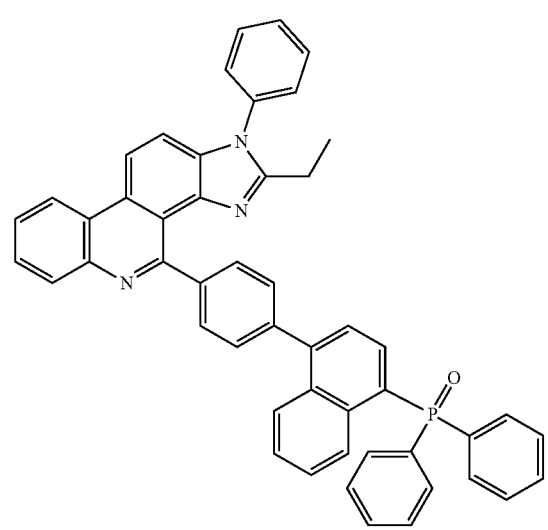
8
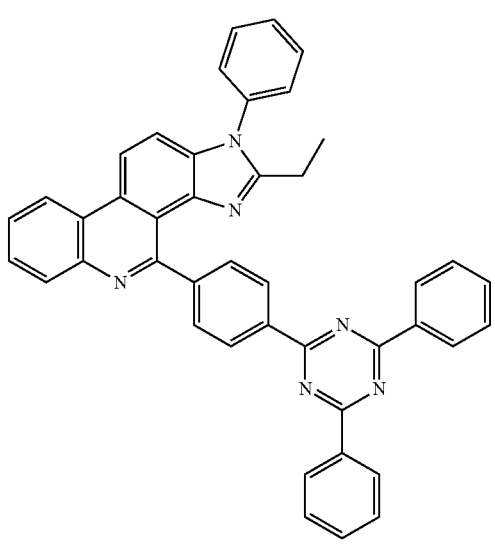
11
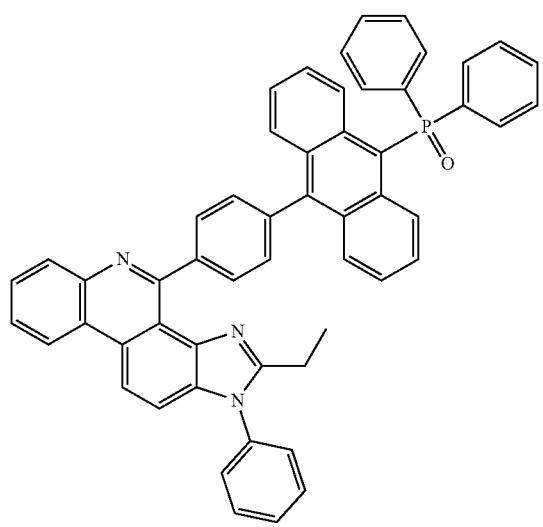
9
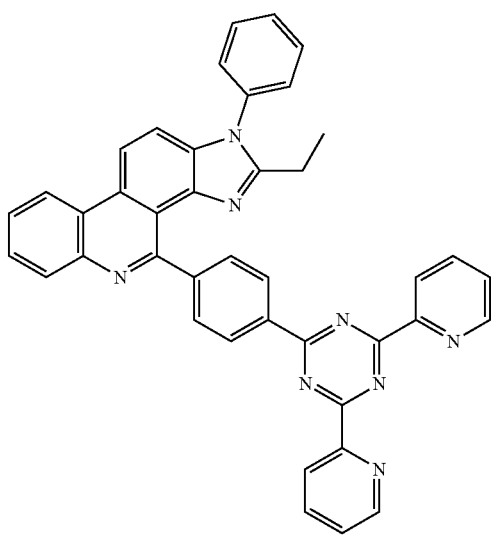
12

13
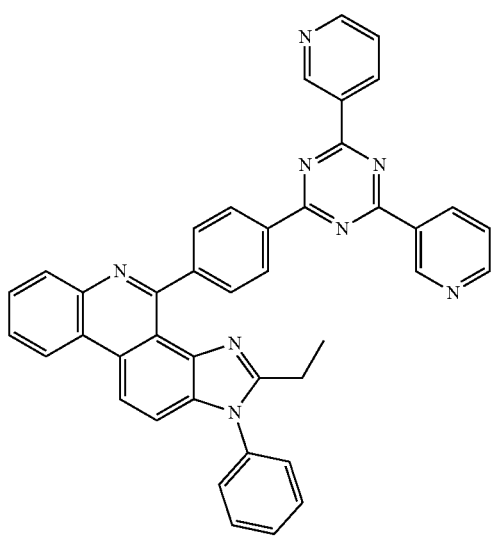
14
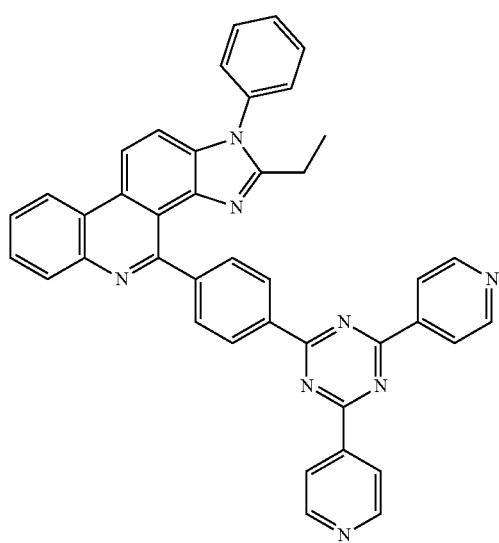
15
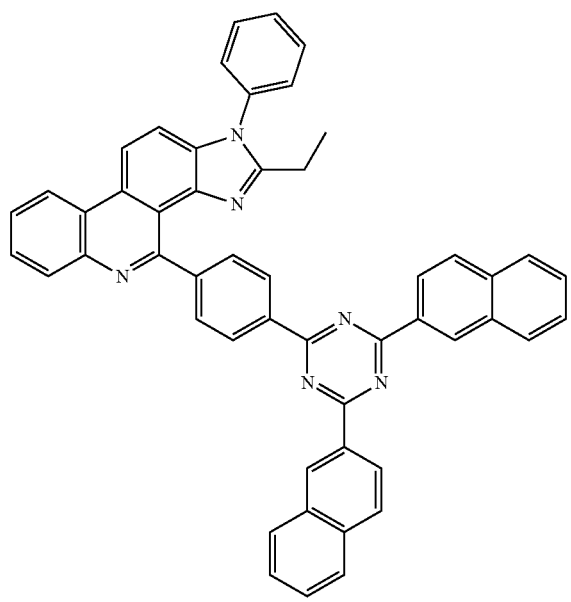
16
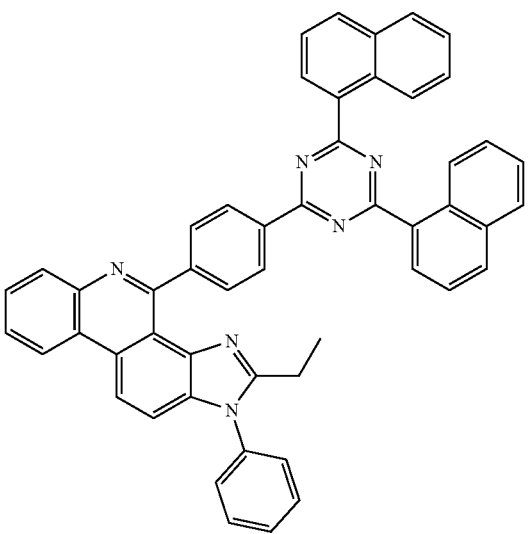

17
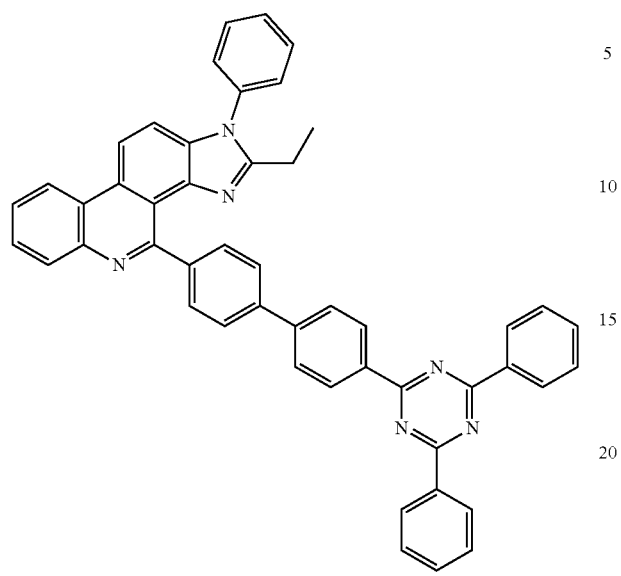
18
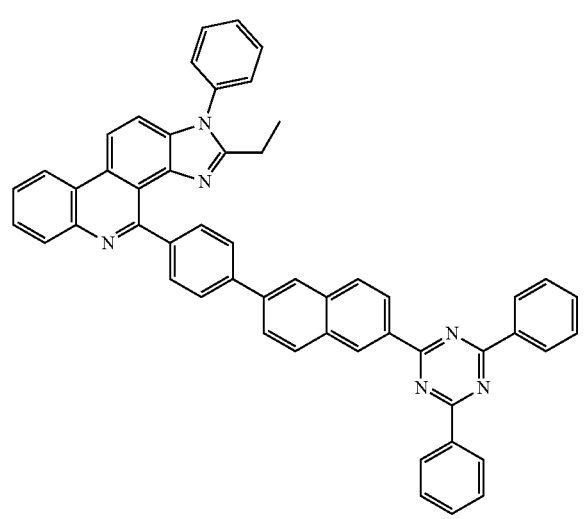
19
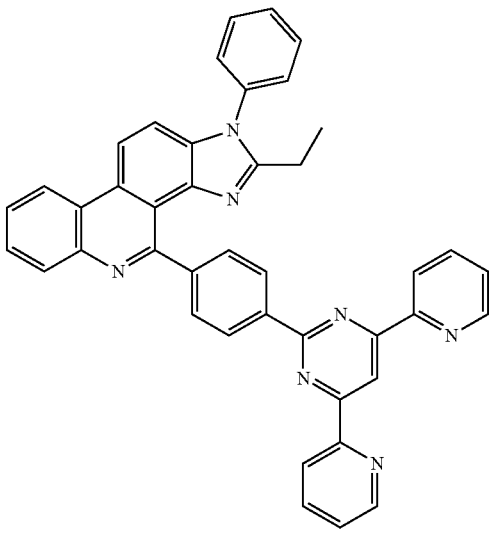
20
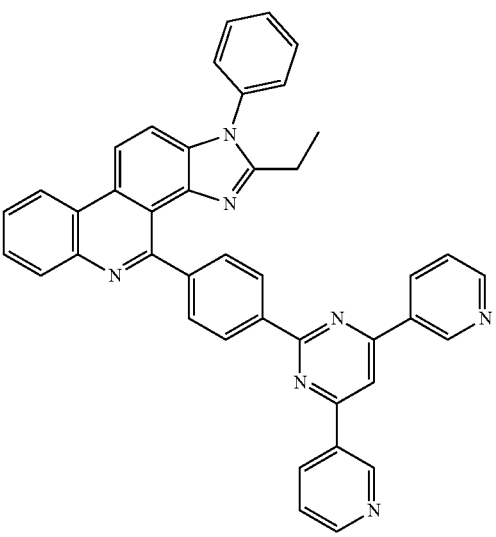
21
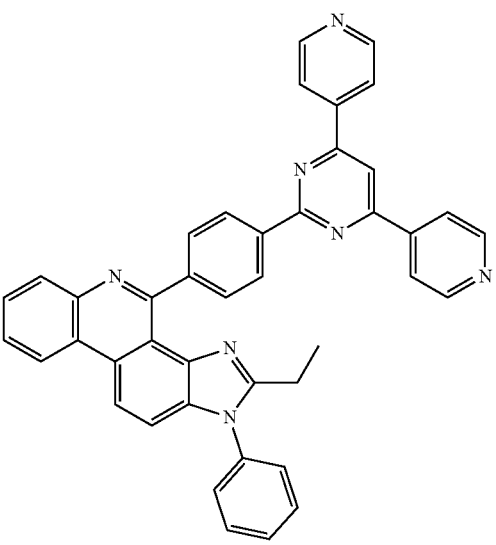
22

23

24

25

26

27
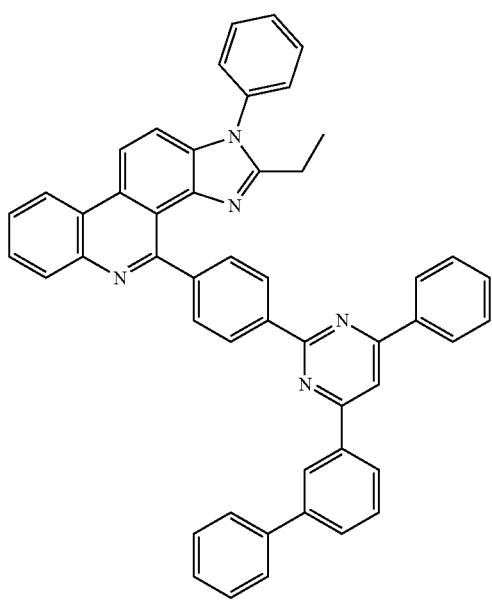
28
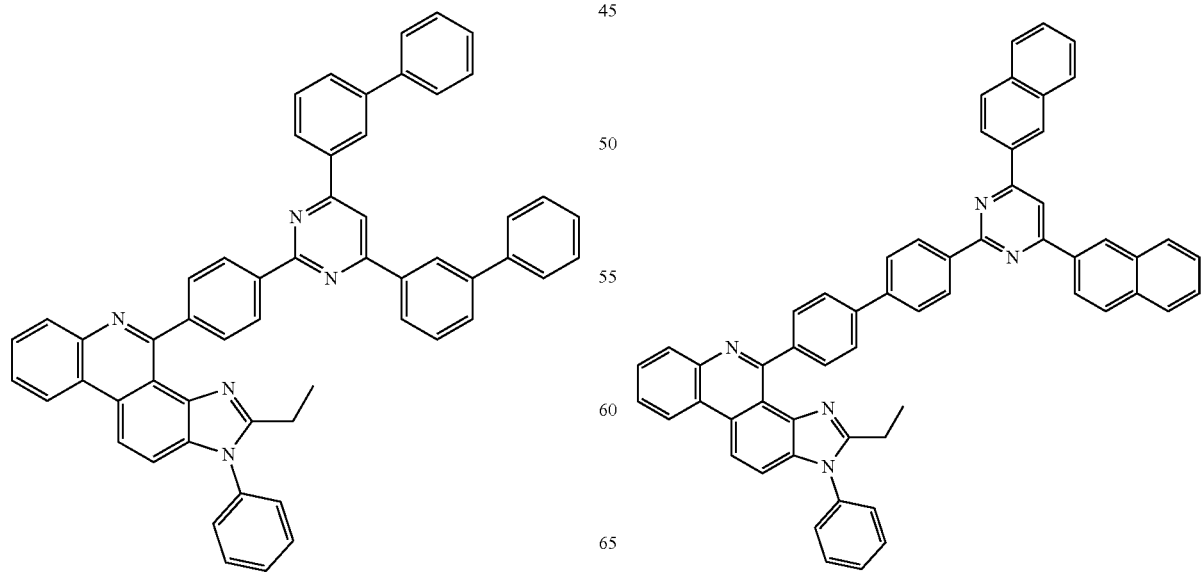
29
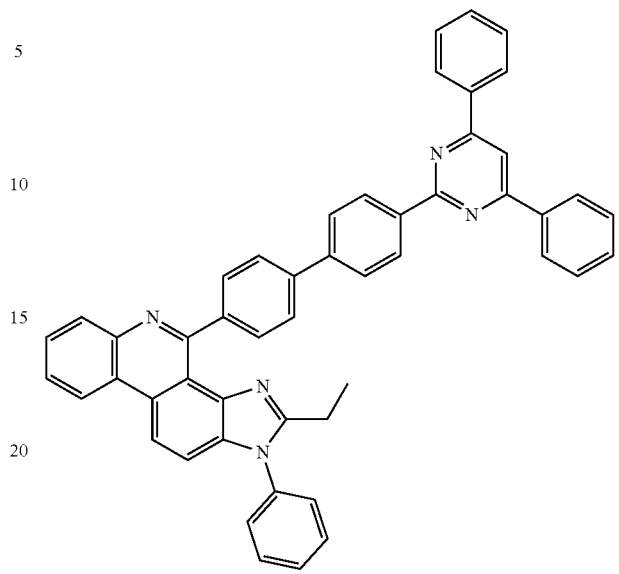
30

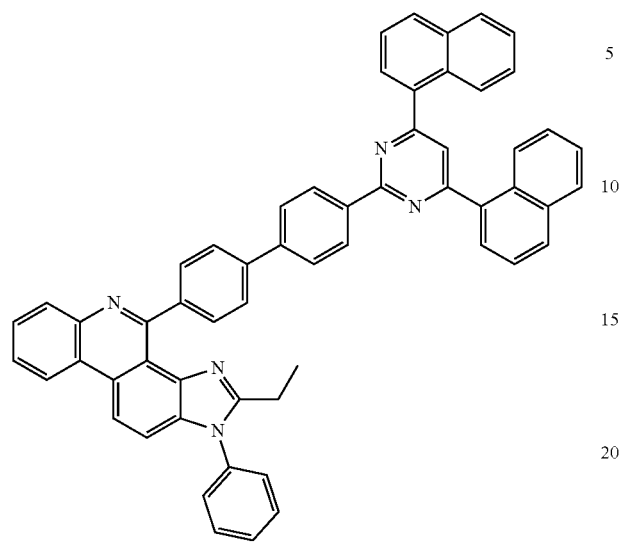
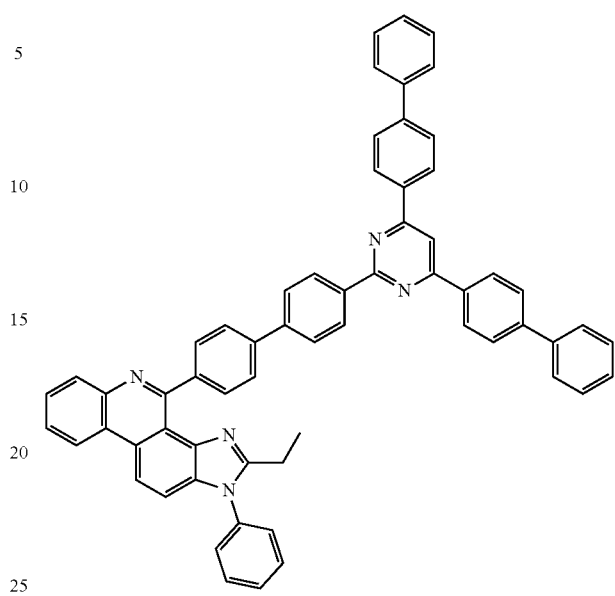
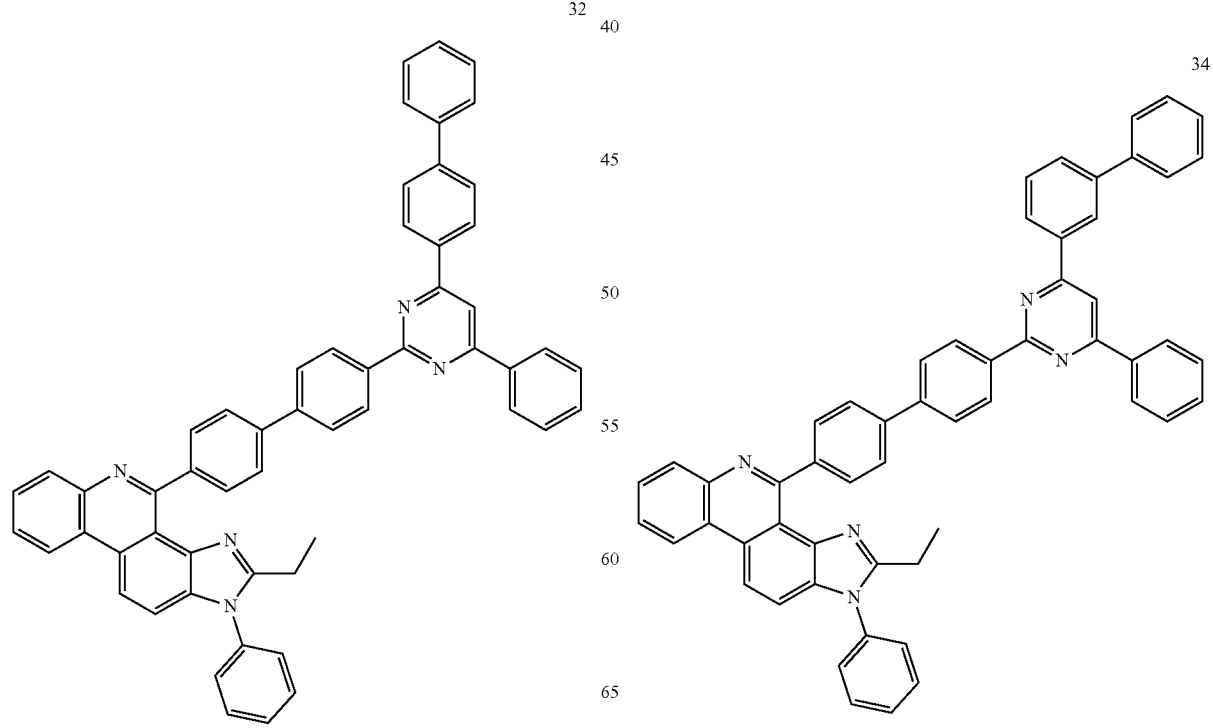

35
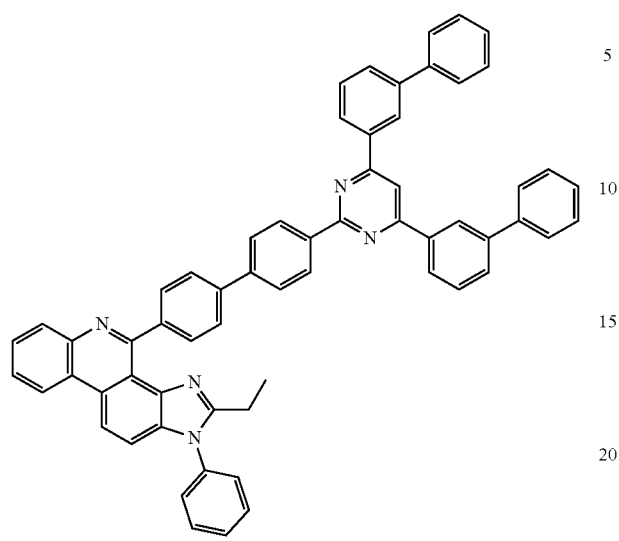
36
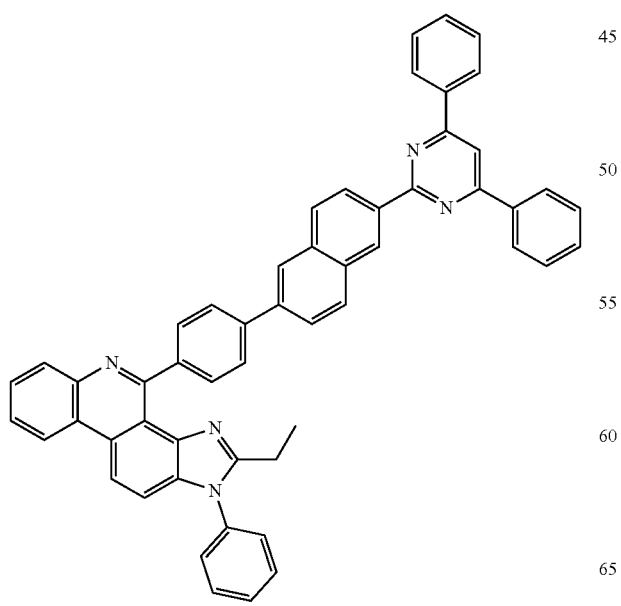
37
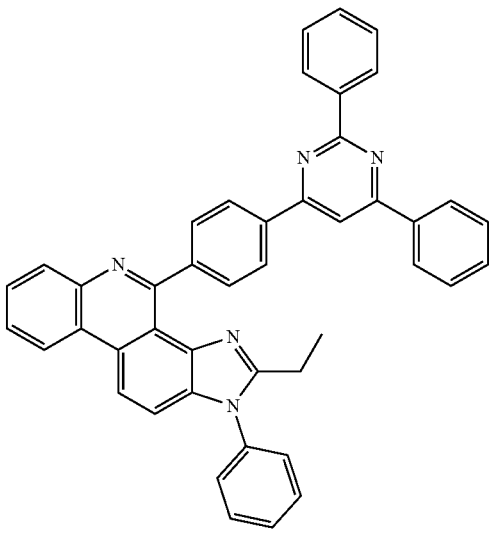
38
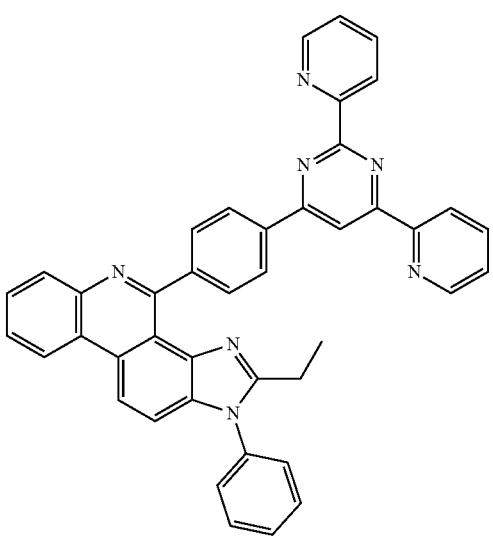
39
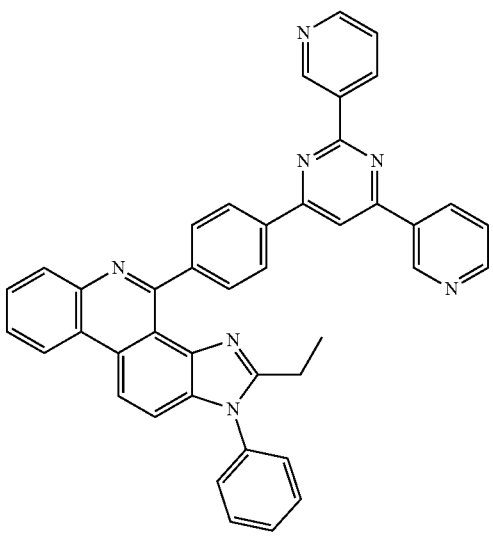

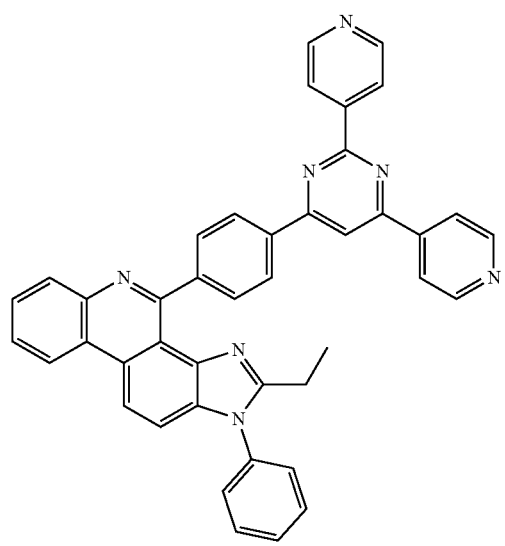
40
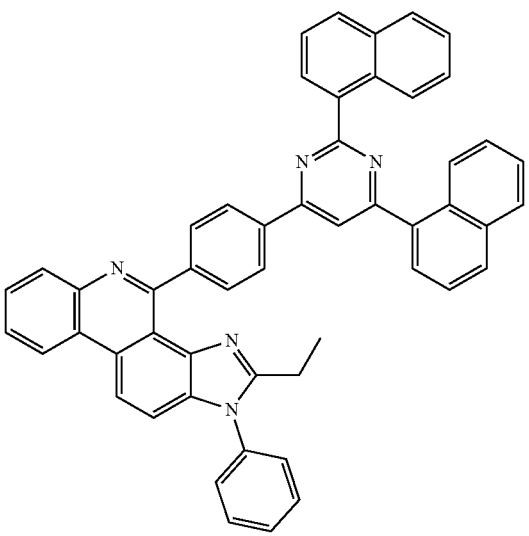
42
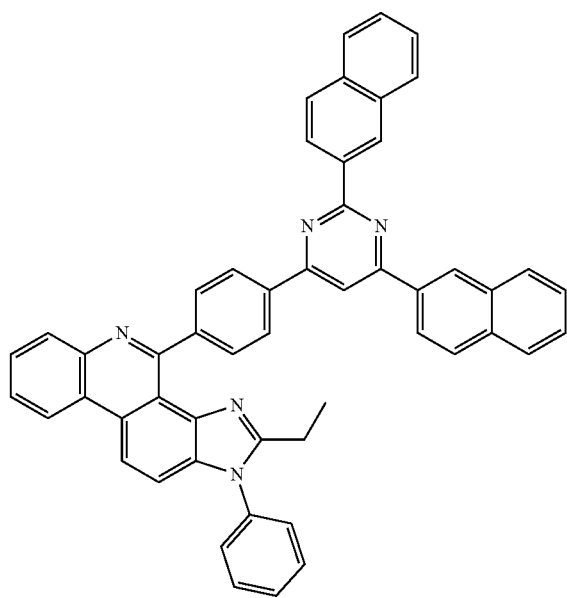
41

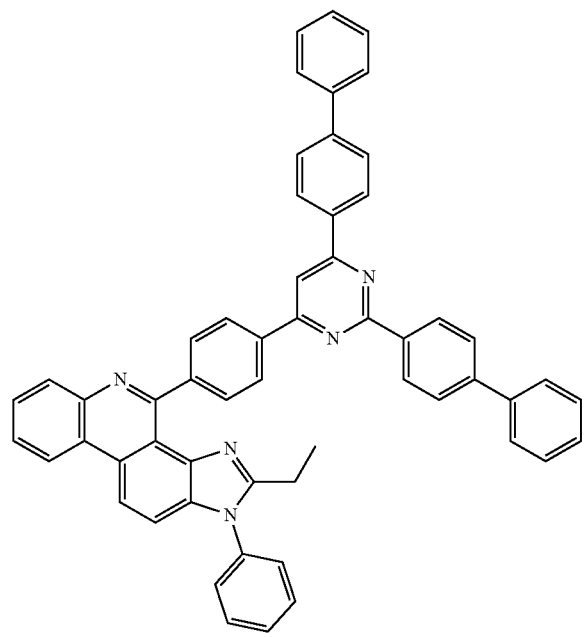
44
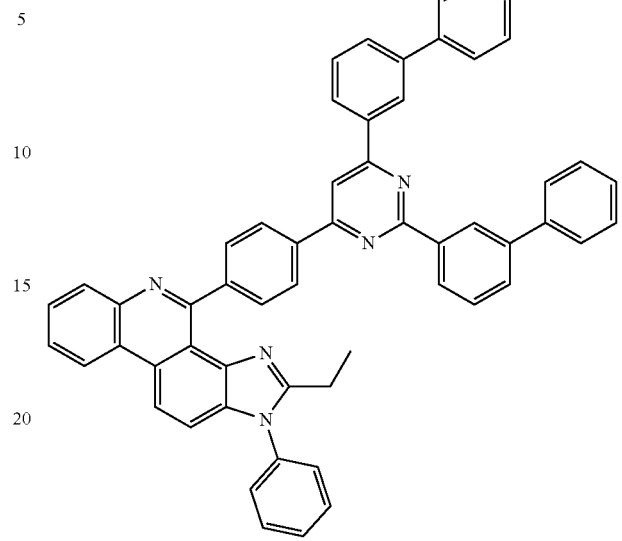
46
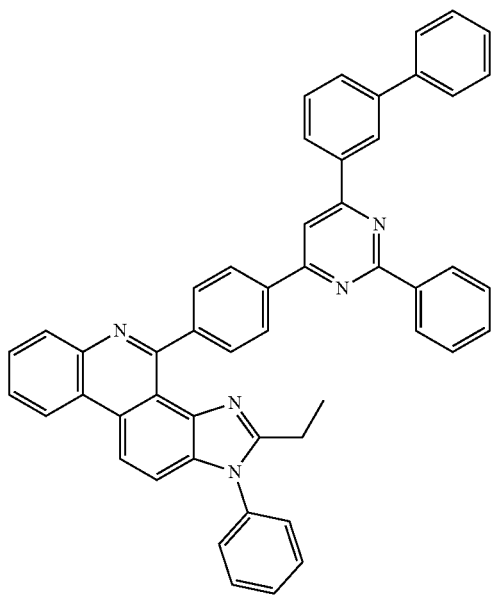
45
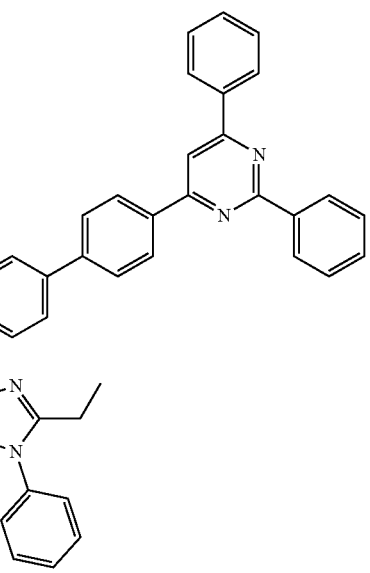
47

48
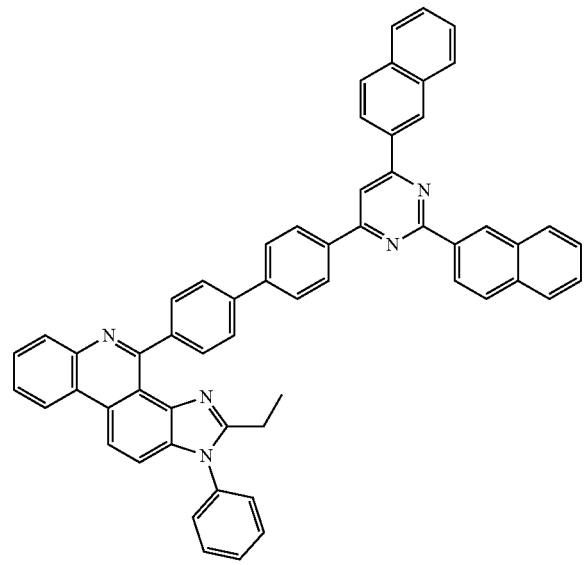
49
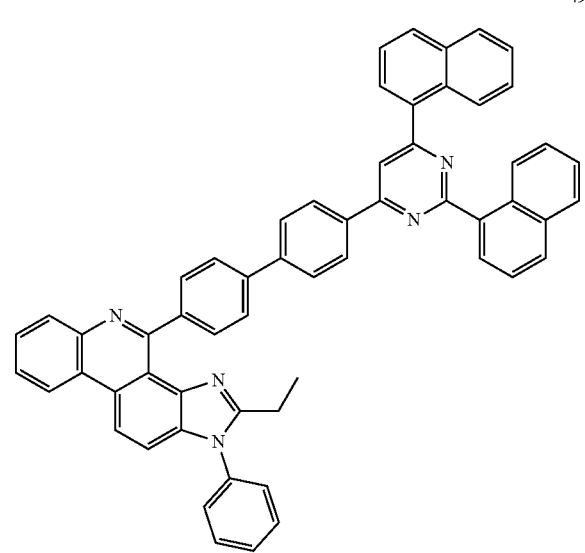
50
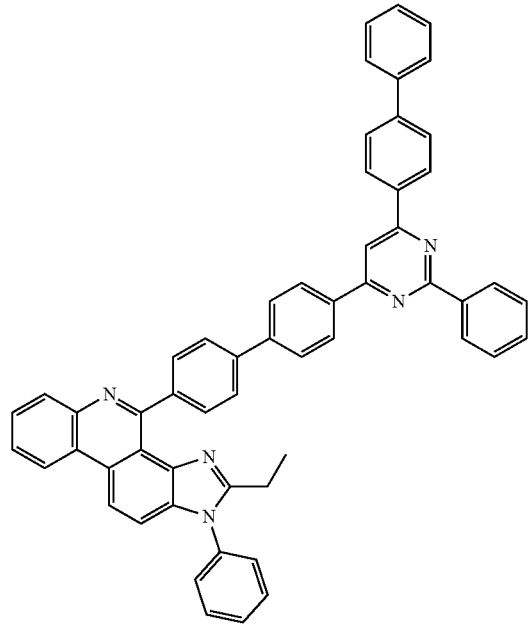
51
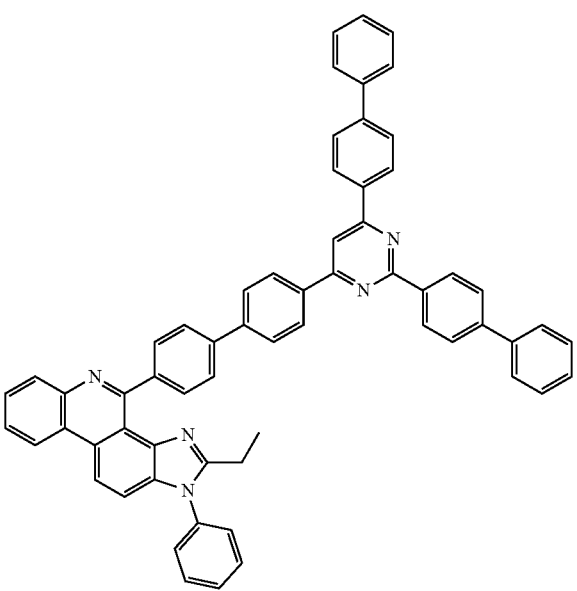

33
-continued
52
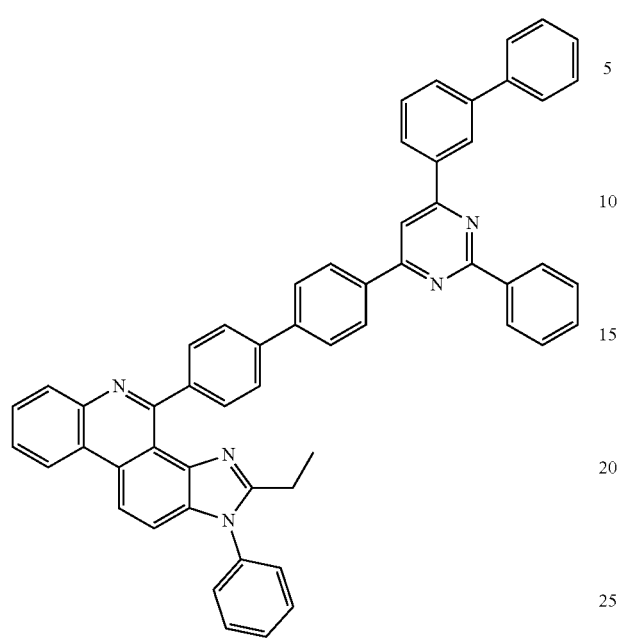
53
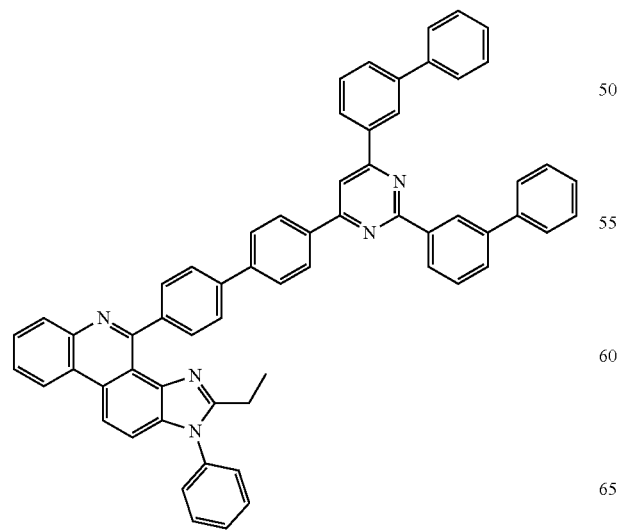
34
-continued
54
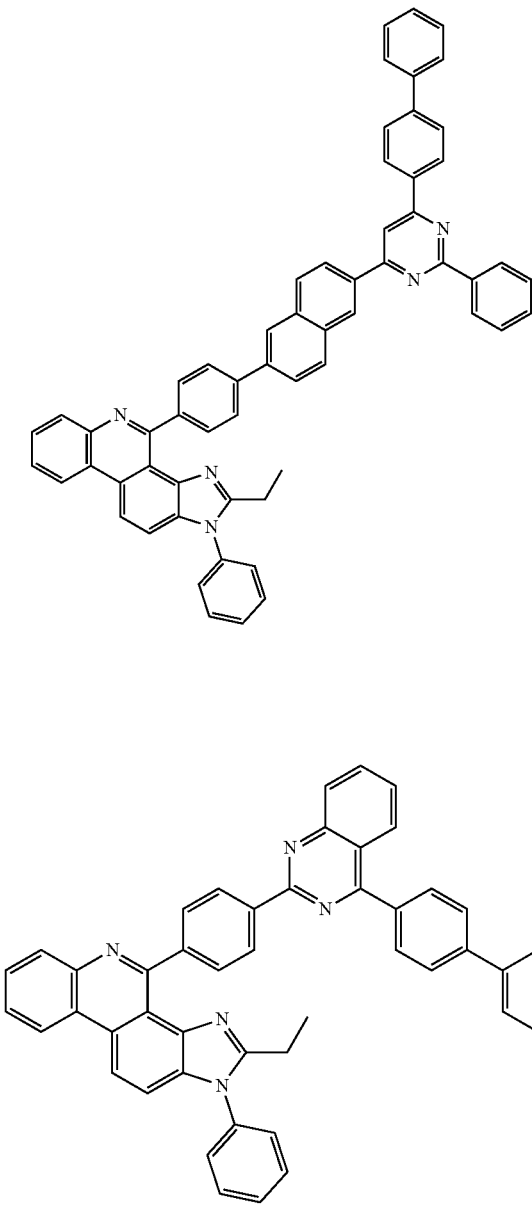
55
56
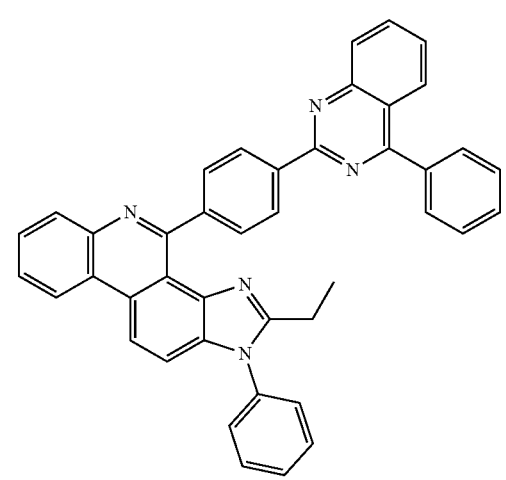

57
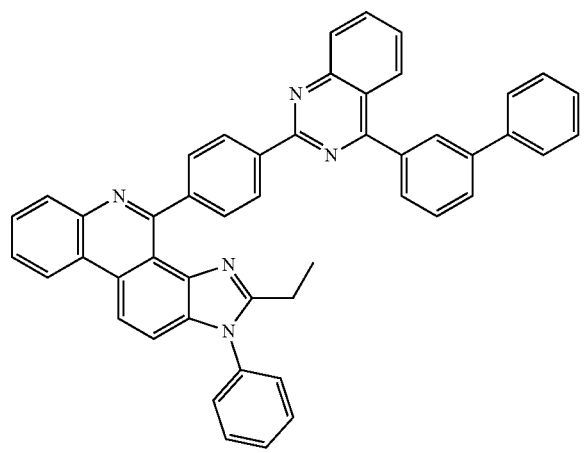
58
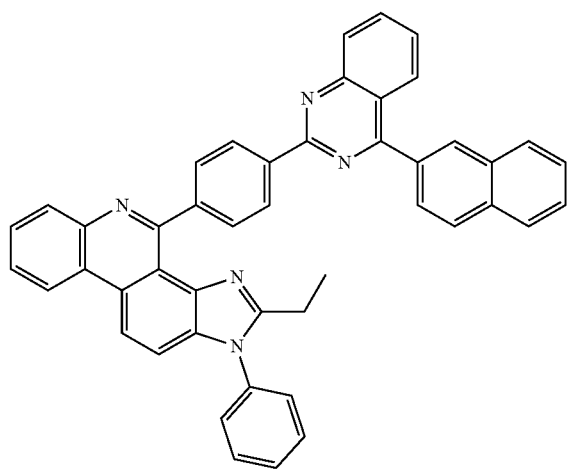
59
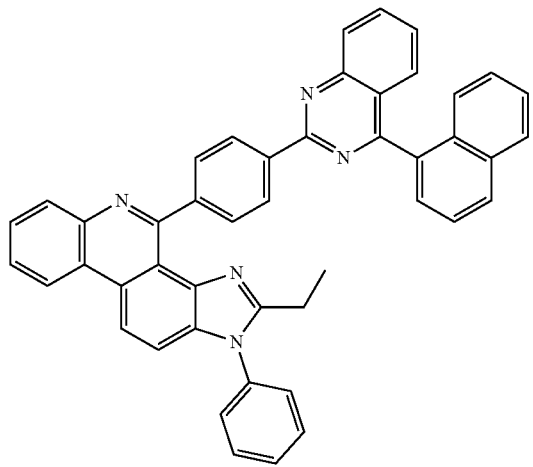
60
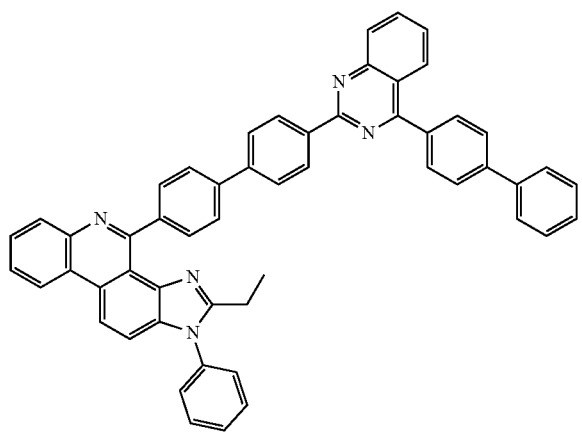
61
62

-continued
63
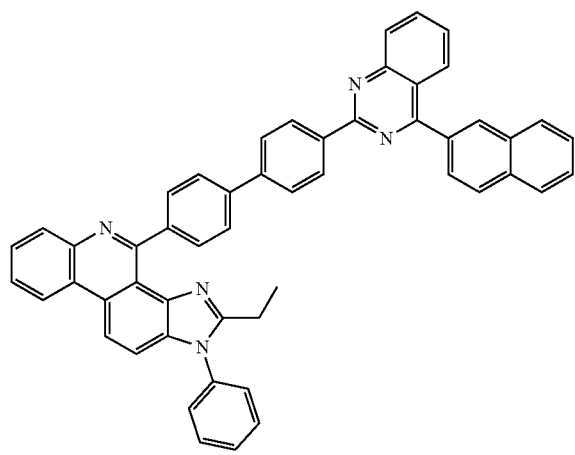
64
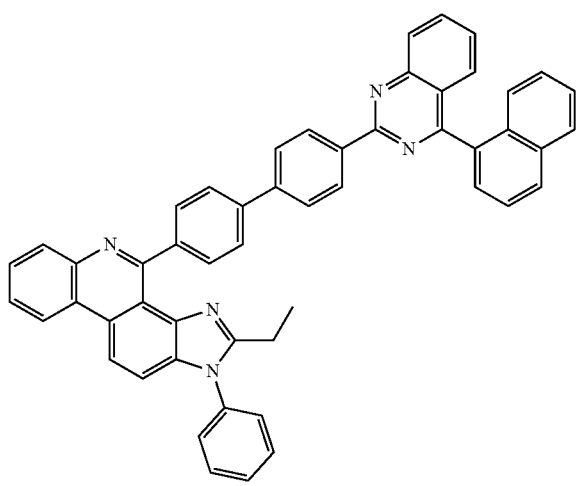
65
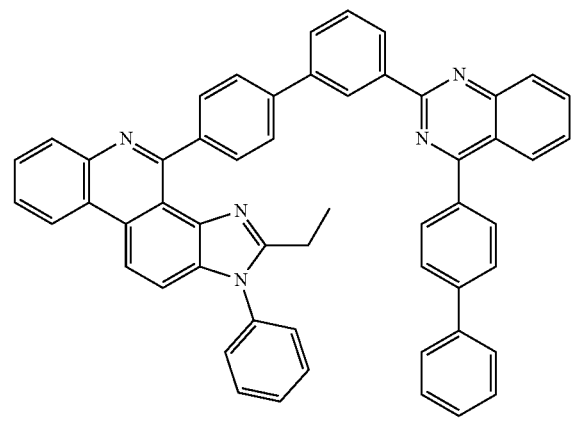
-continued
66
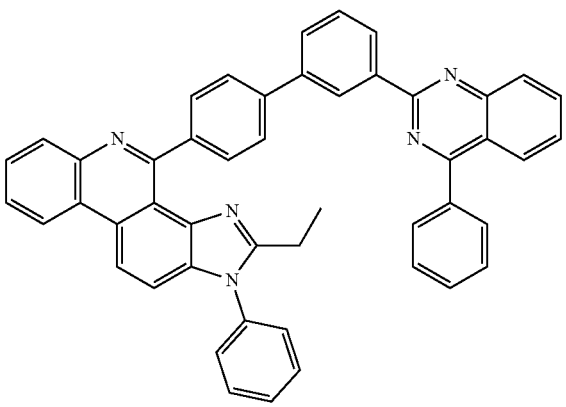
67
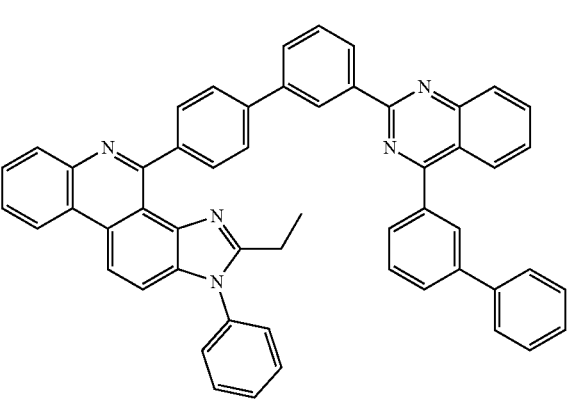
68
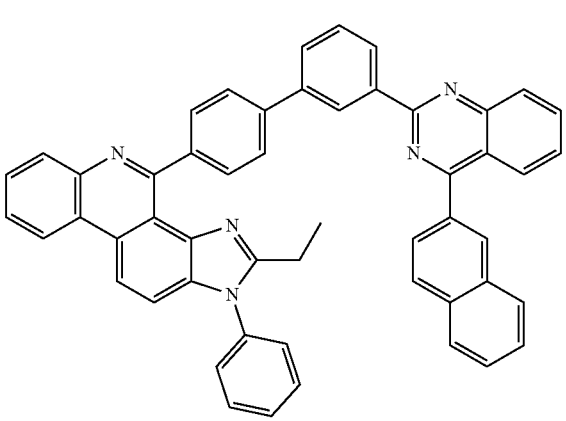

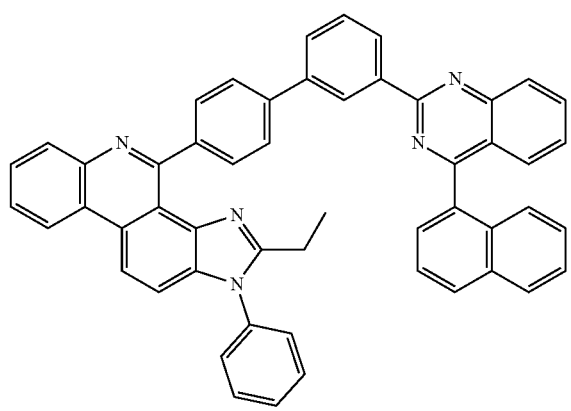
69
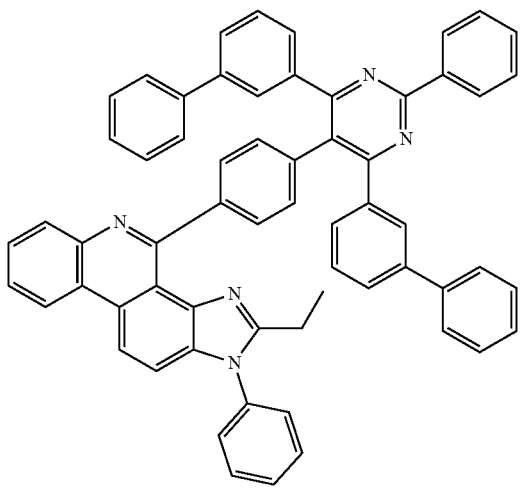
72
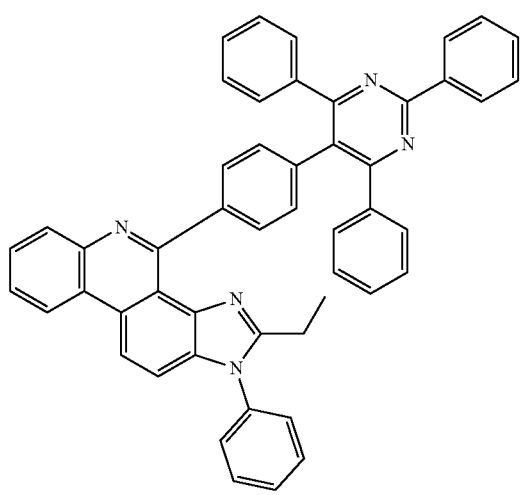
70
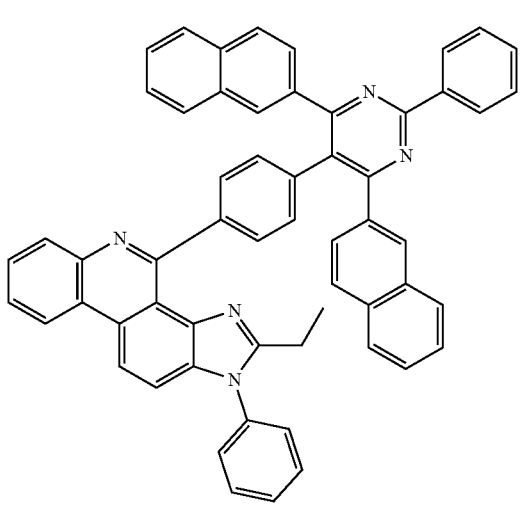
73
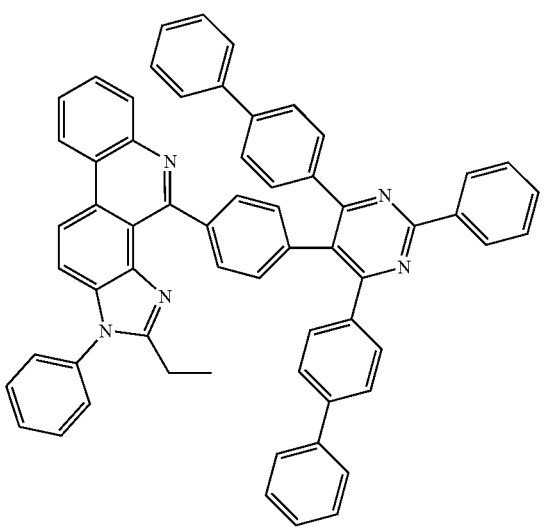
71
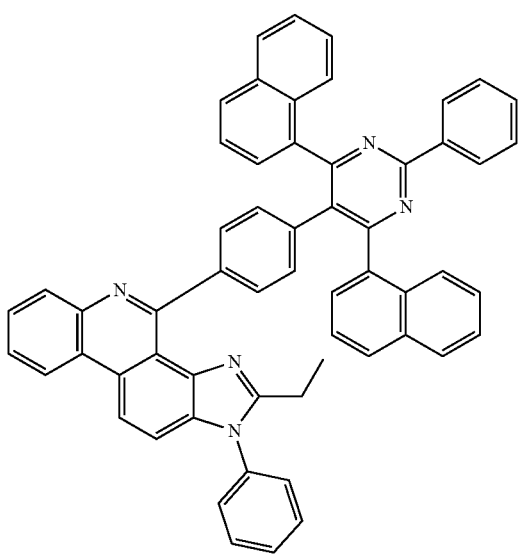
74

-continued
75
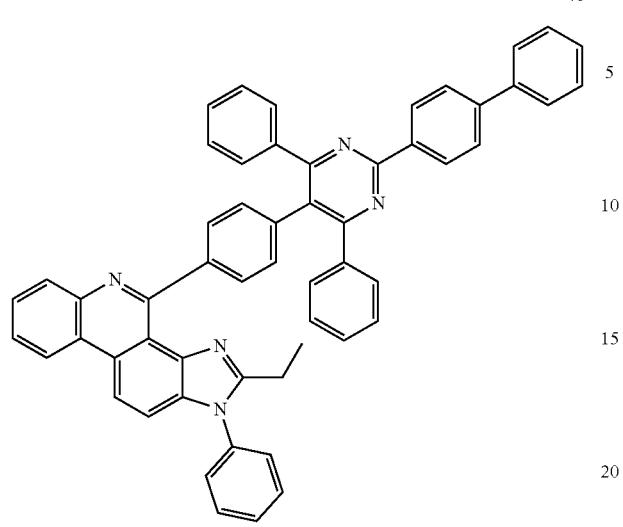
76
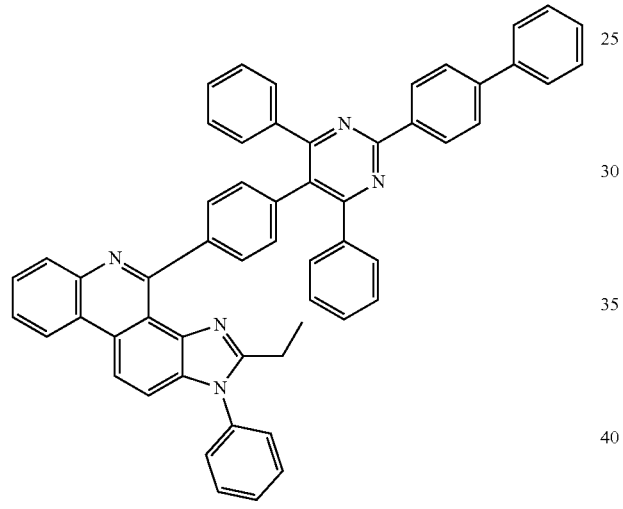
77
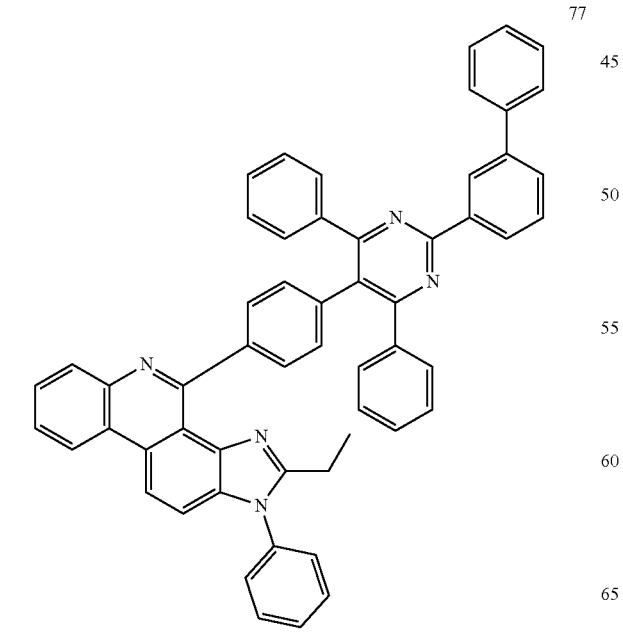
-continued
78
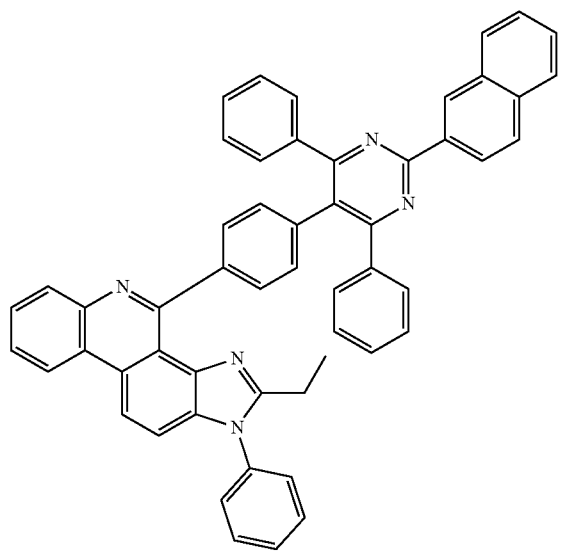
79
80
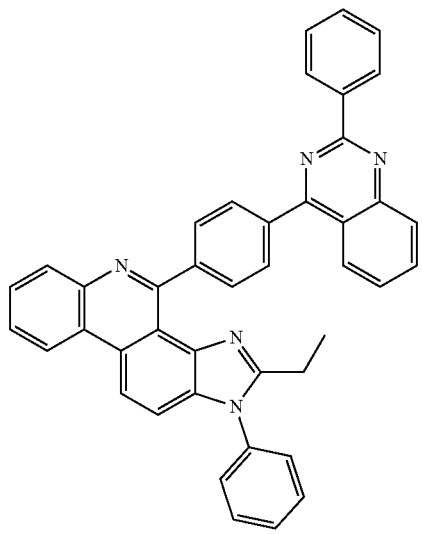

81
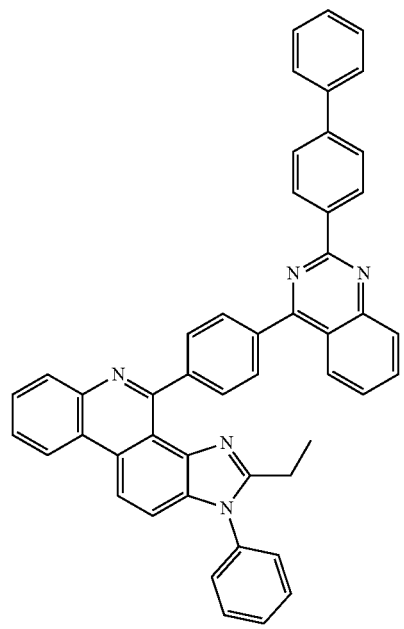
82
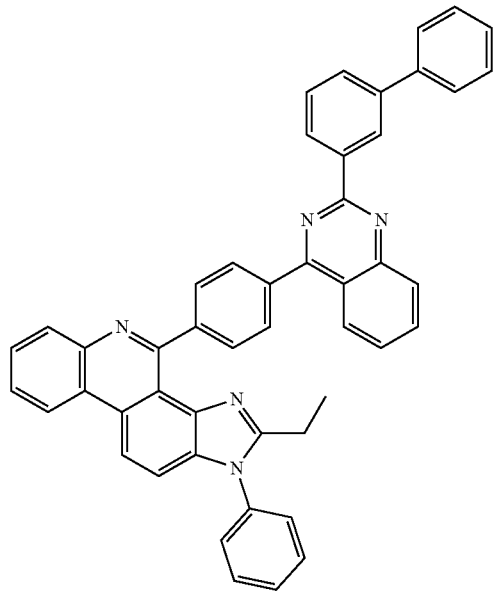
83
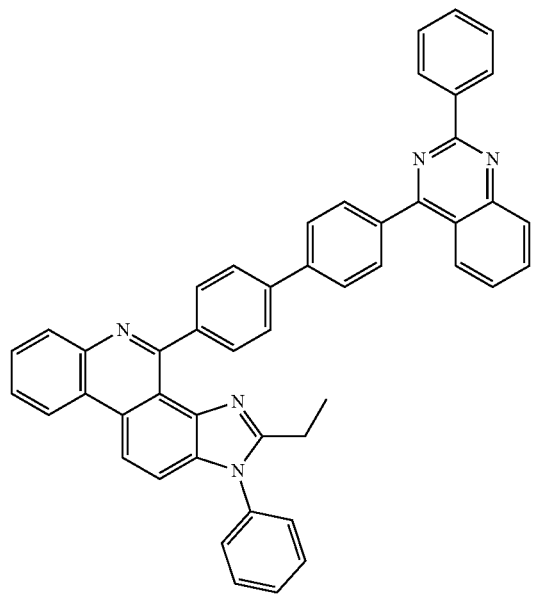
84
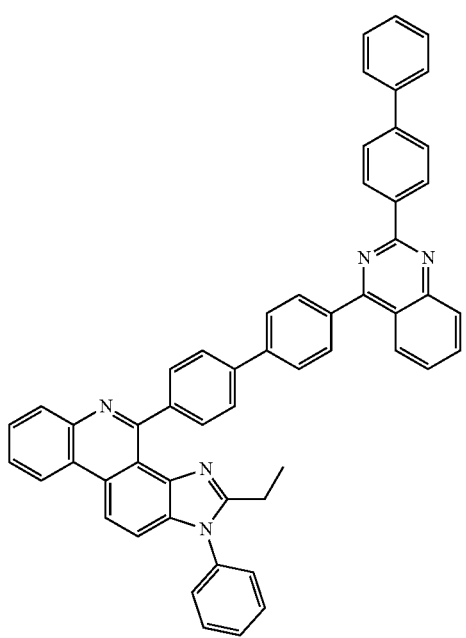

85
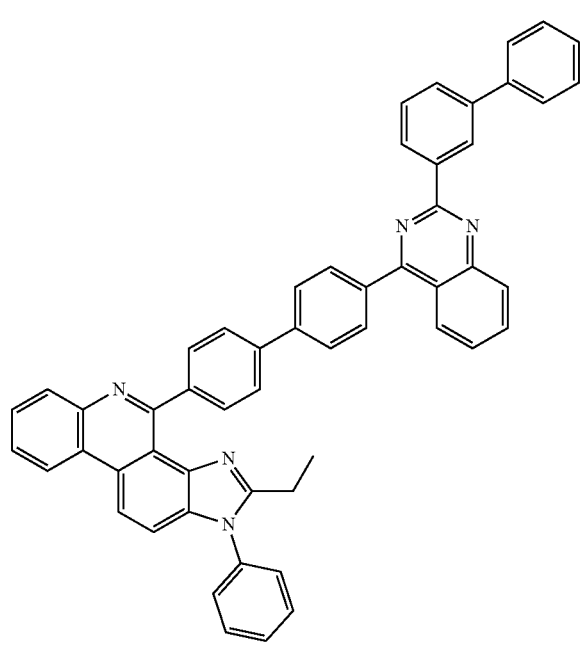
86
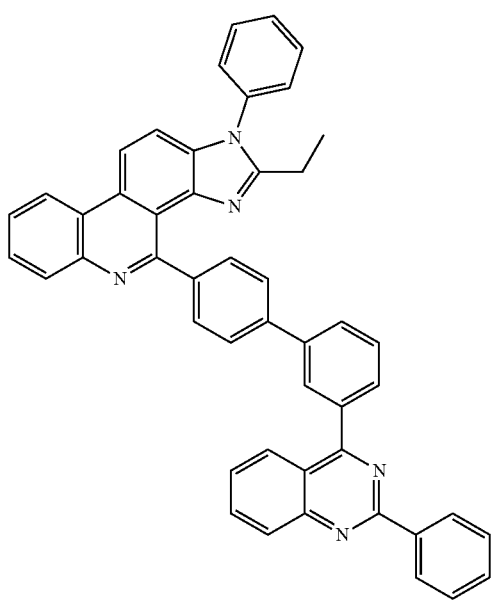
87
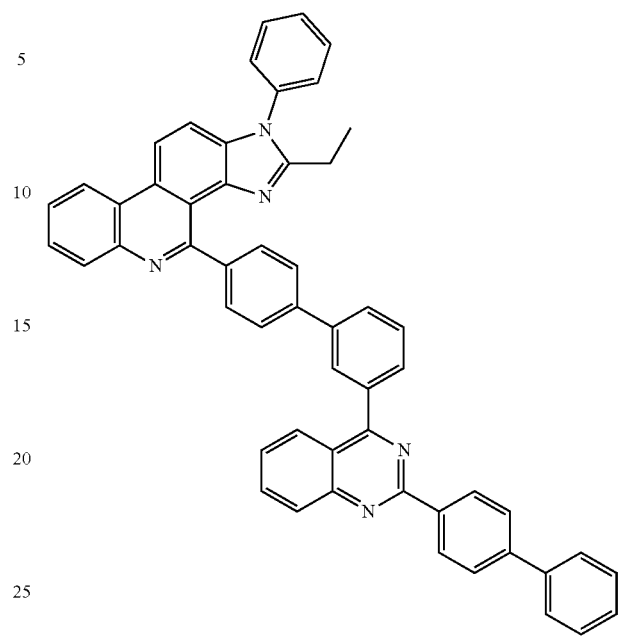
88
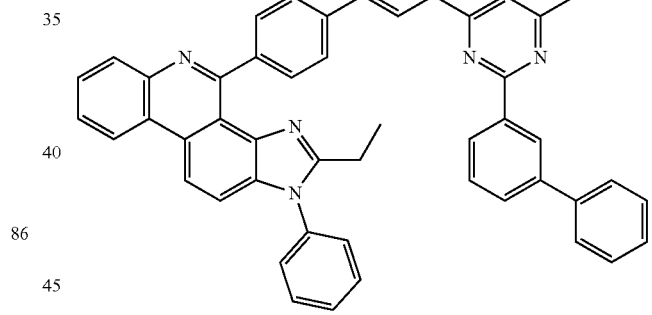
89

-continued
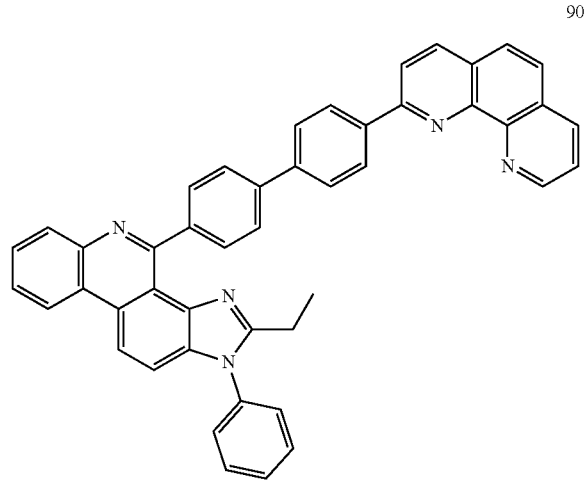
90
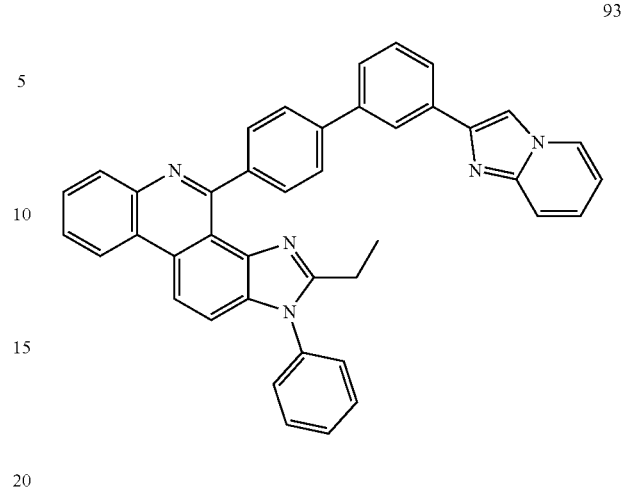
93
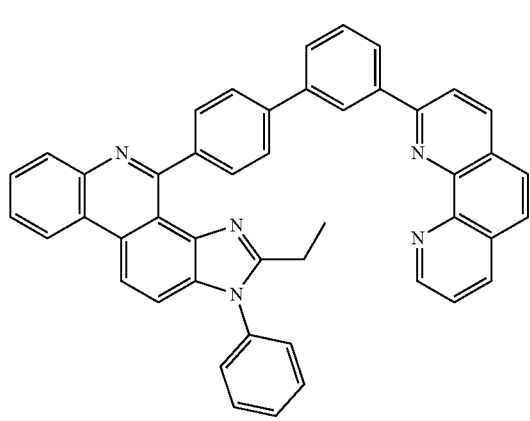
91
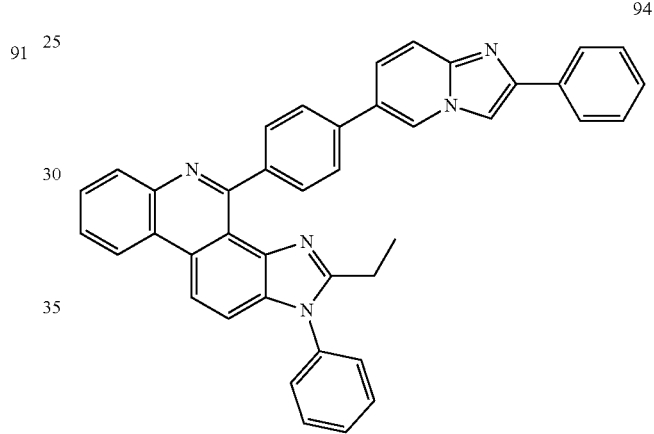
94
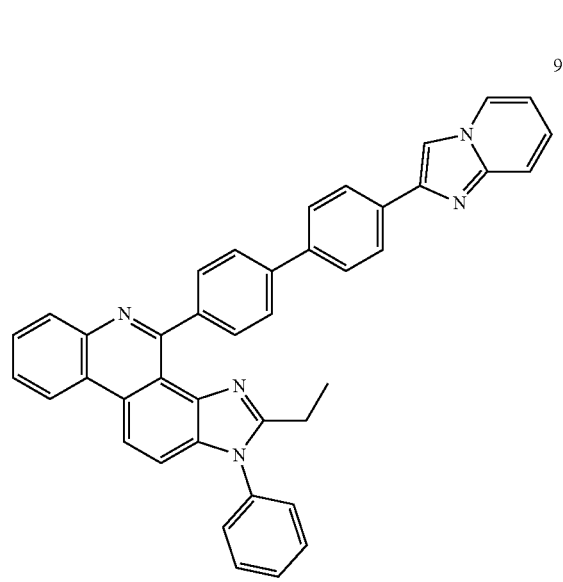
92
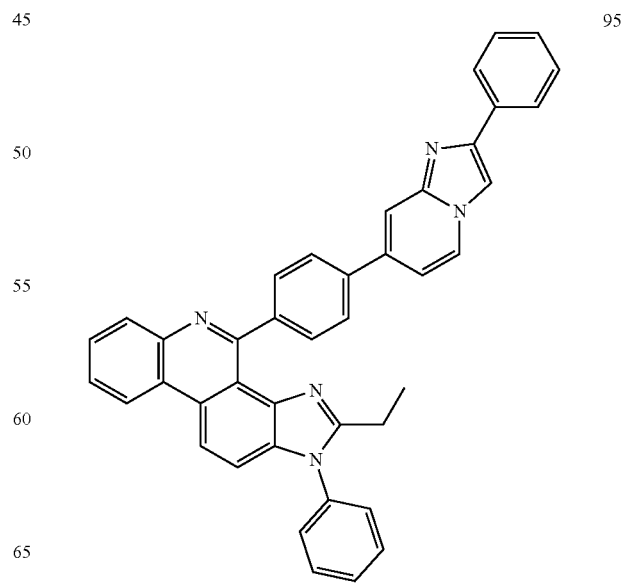
95

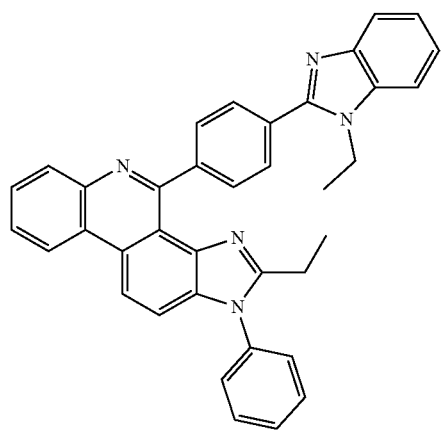
96
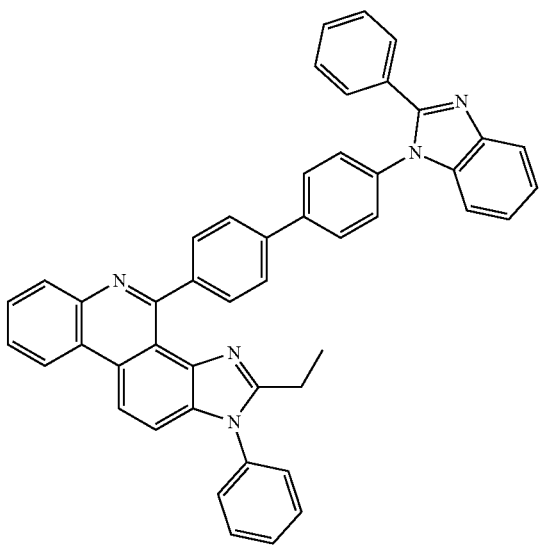
99
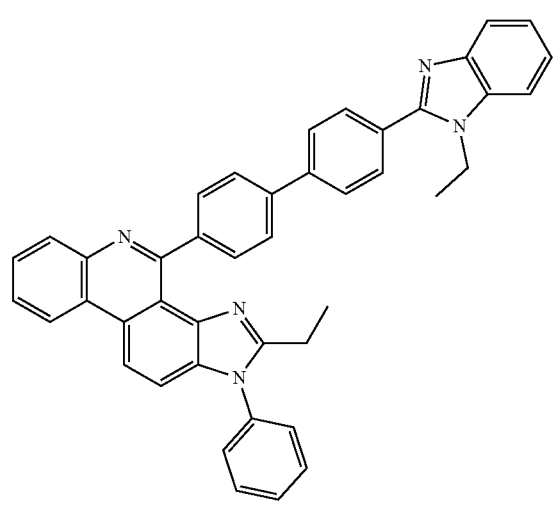
97
100
98
101
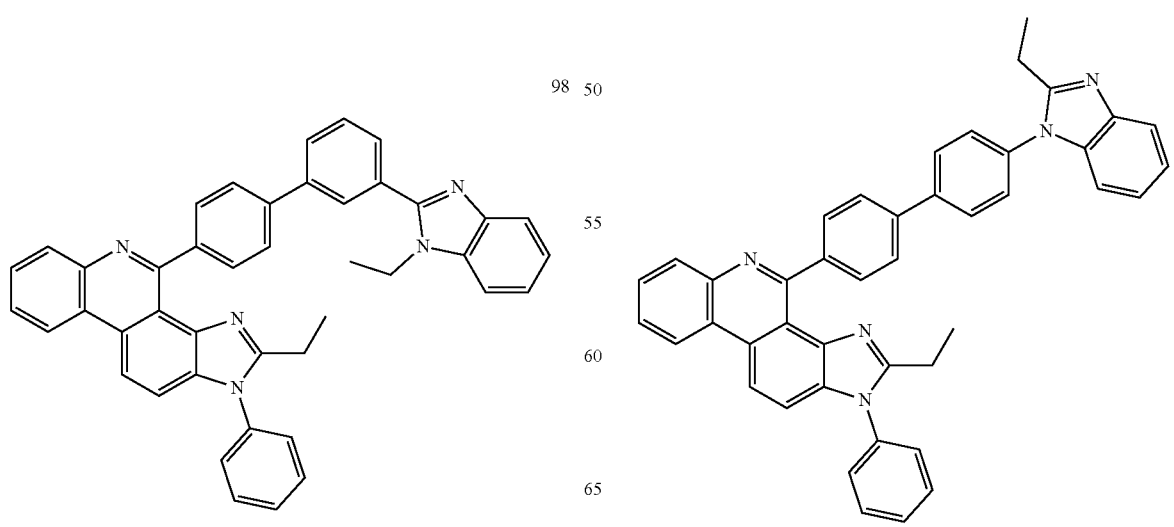

102
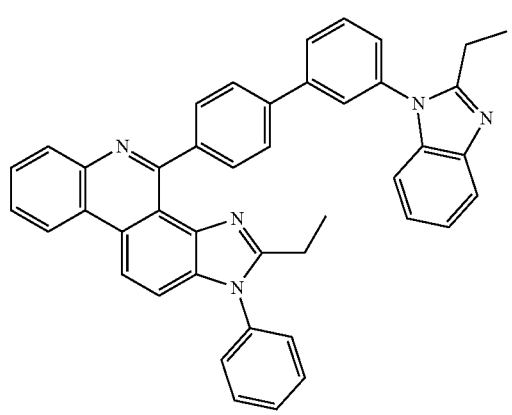
103
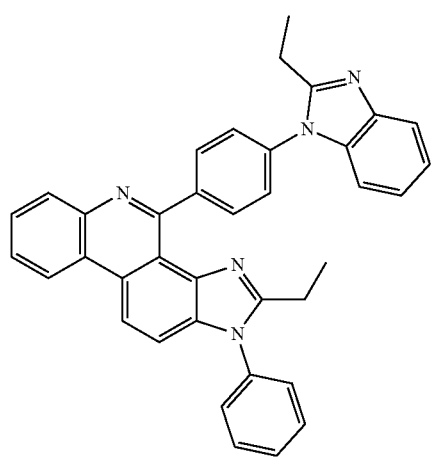
105
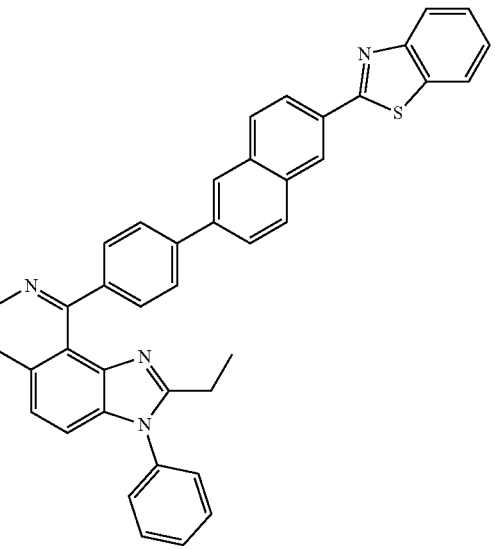
106
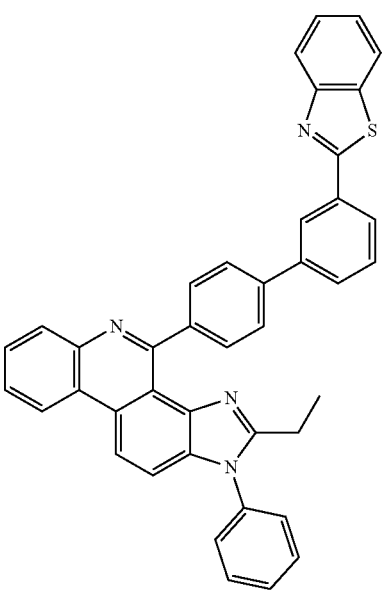
104
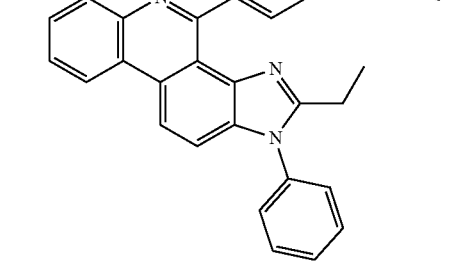

107
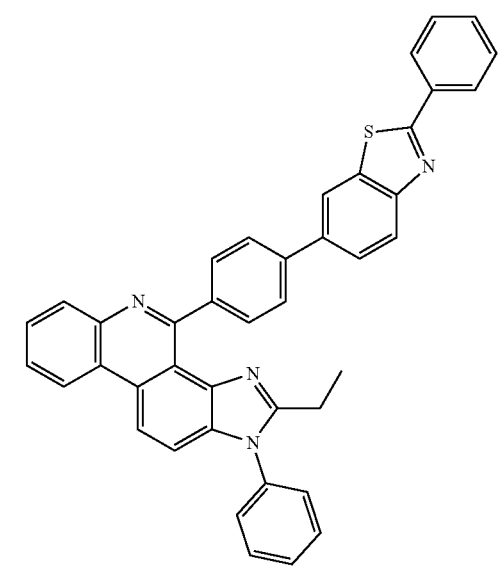
108
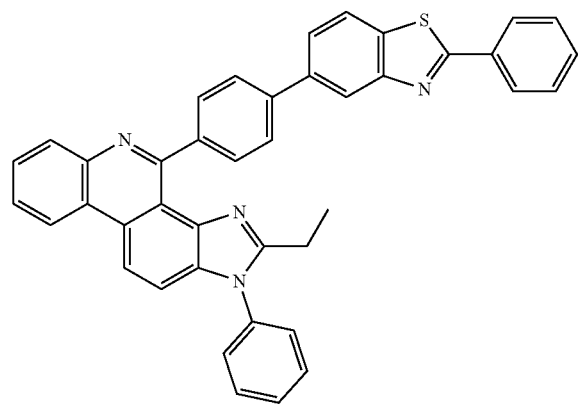
109
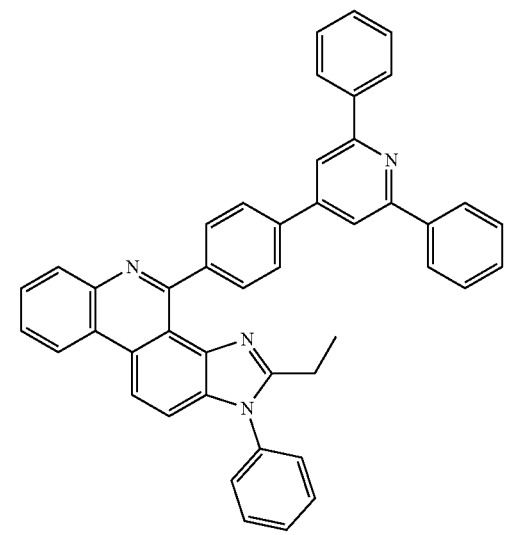
110
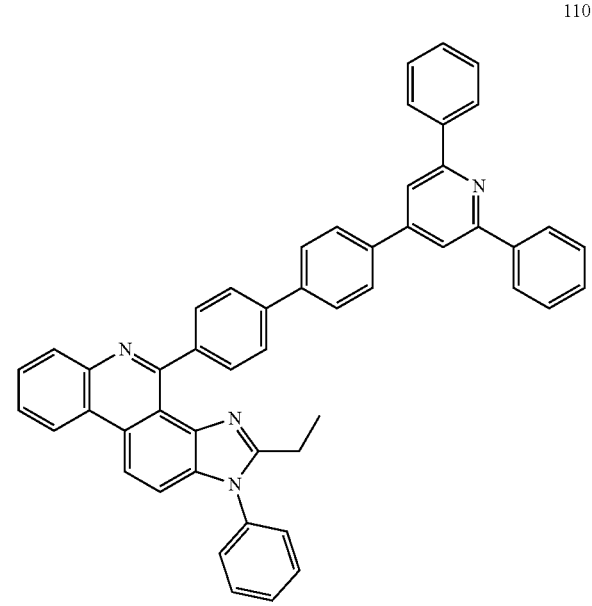
111
112

113
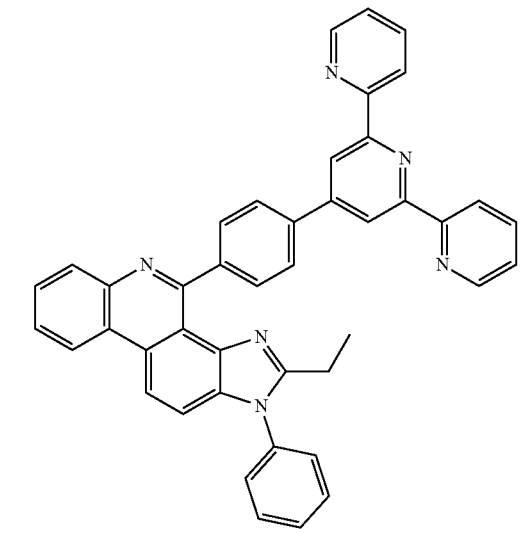
114
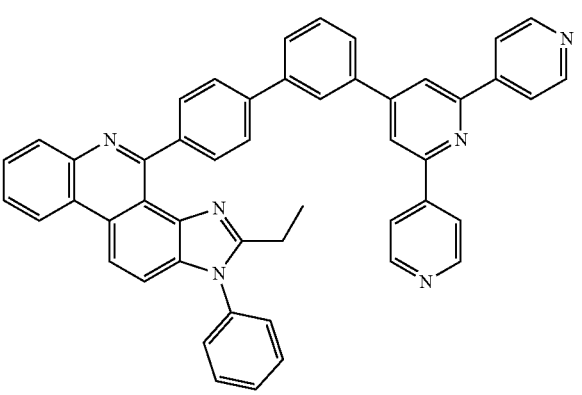
115
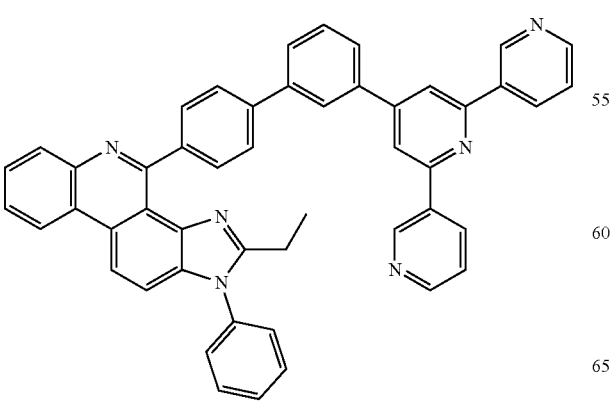
116
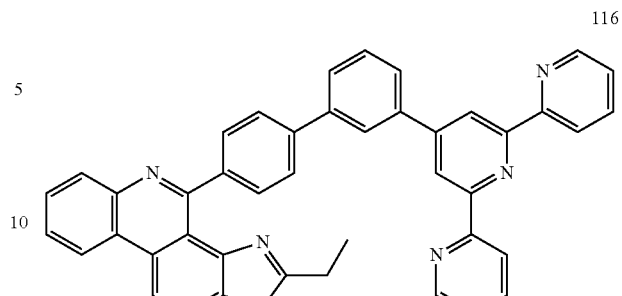
117
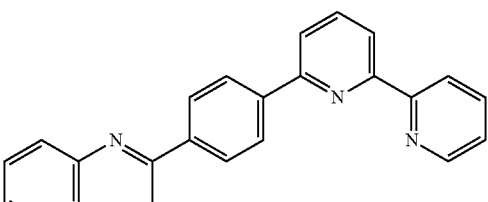
118
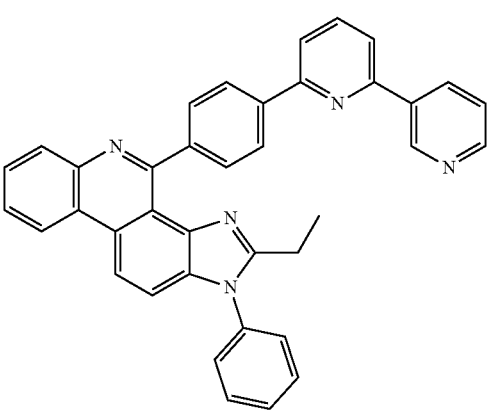
119
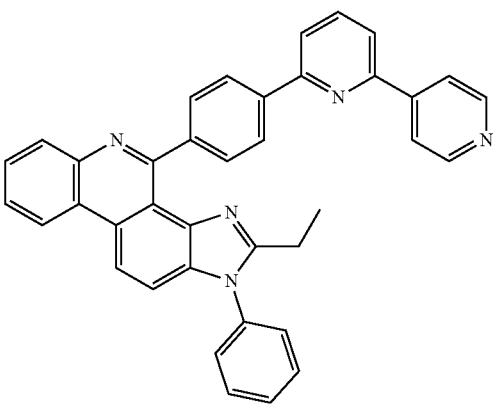

120
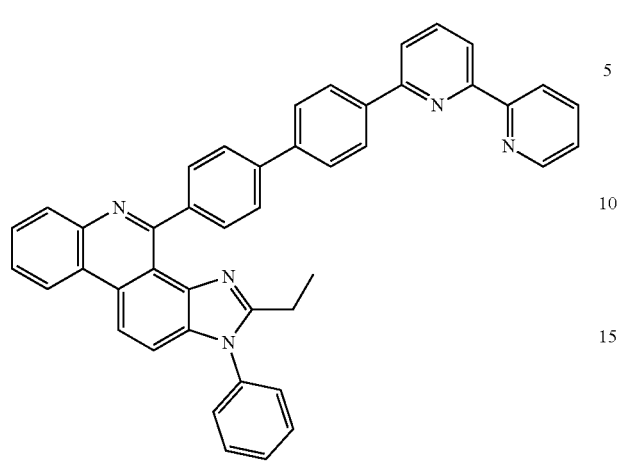
121
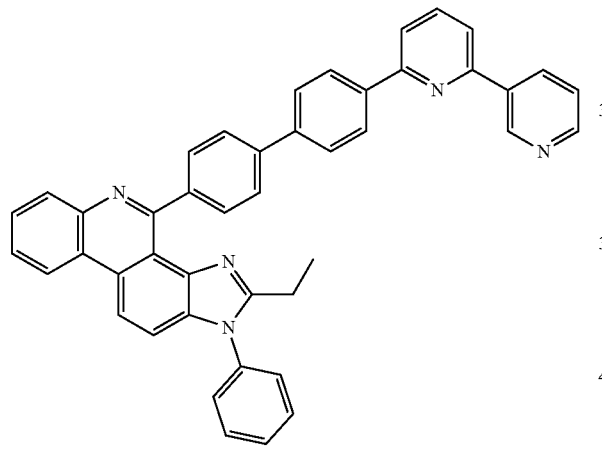
122
123
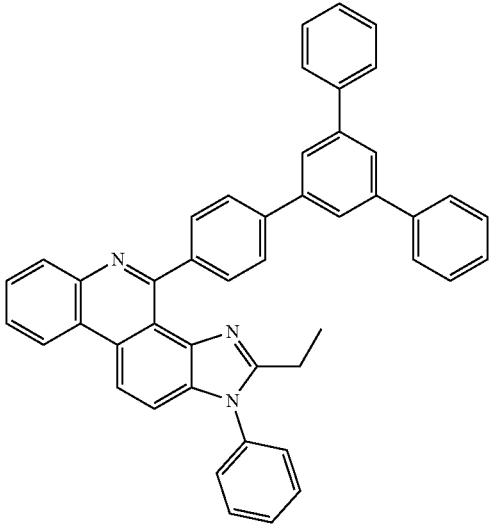
124
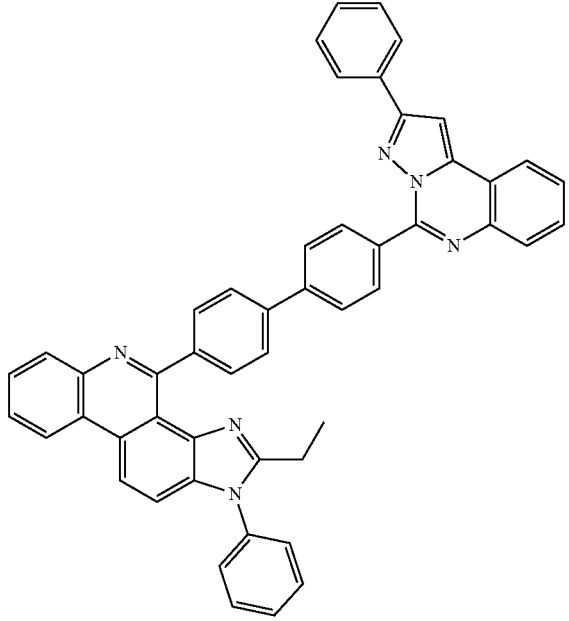
125
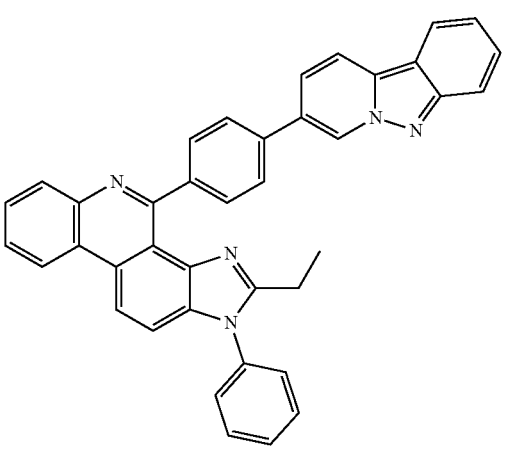

126 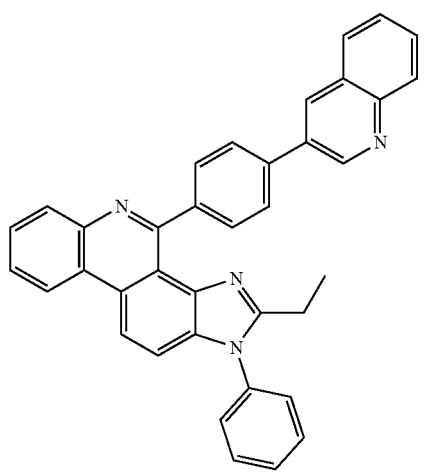
129 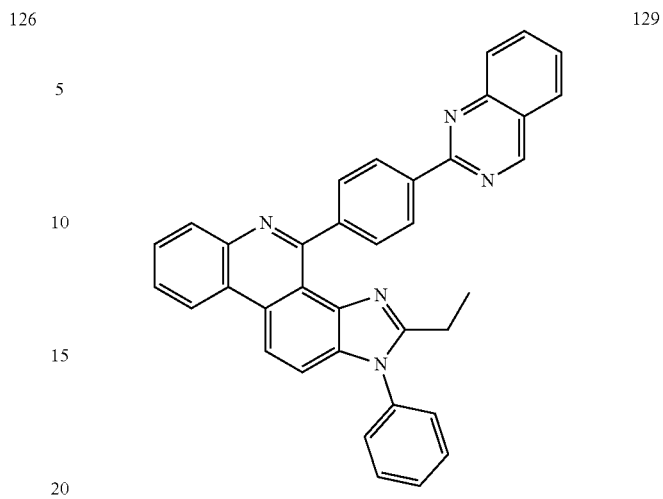
127 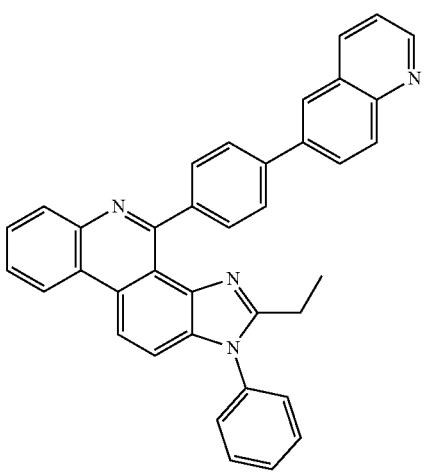
130 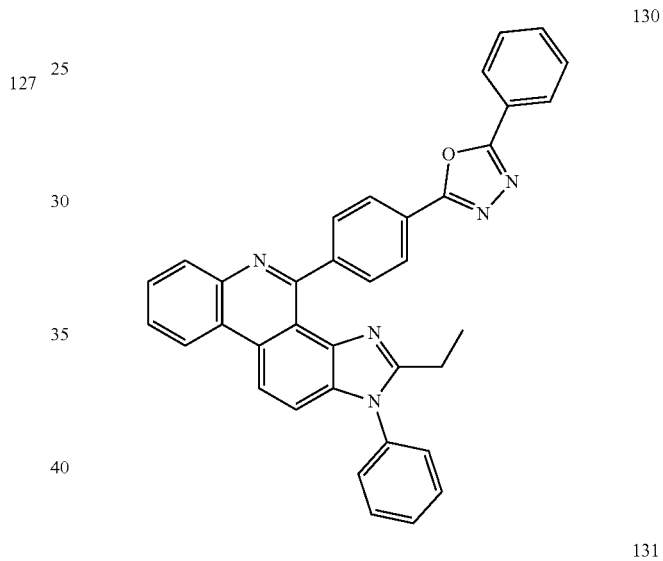
128 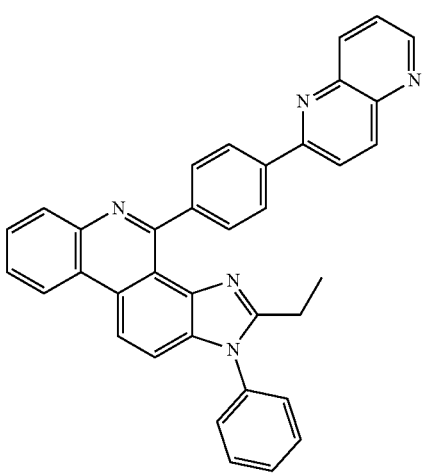
131 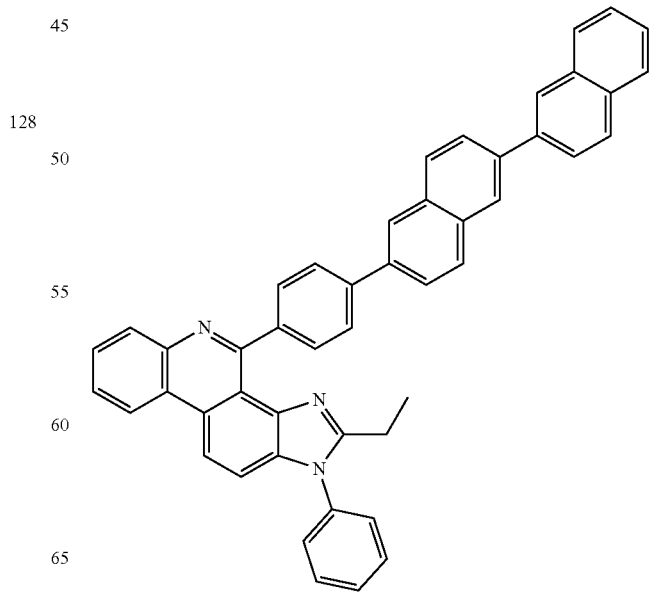

132 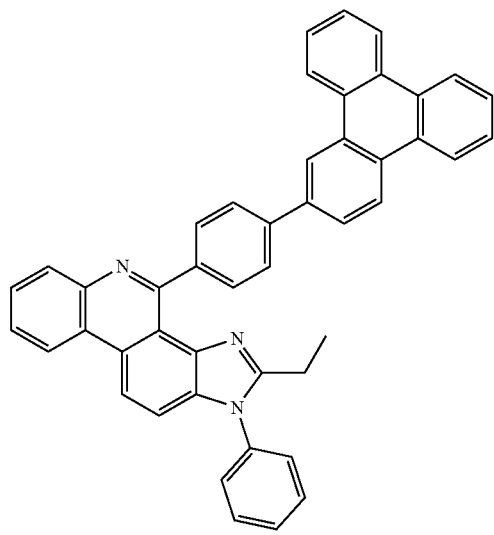
133 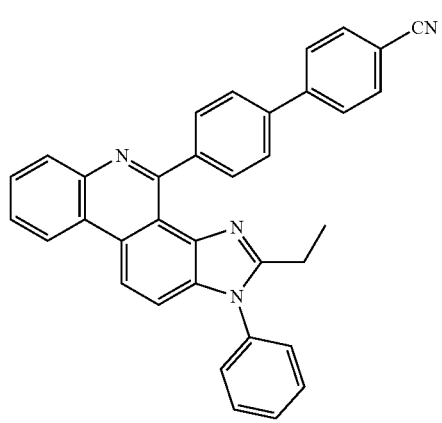
134 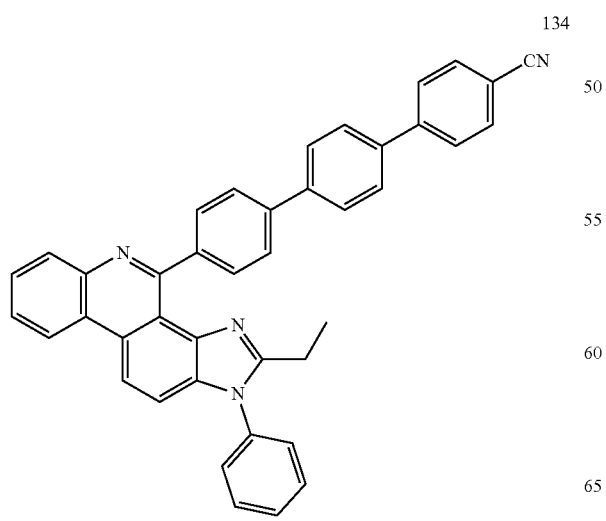
135 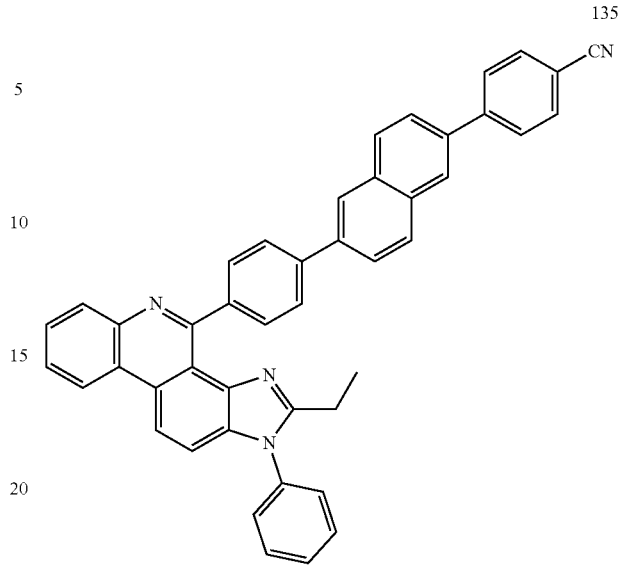
136 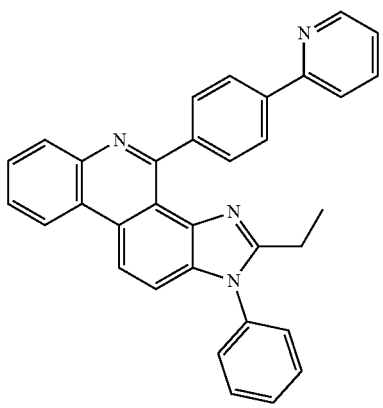
137 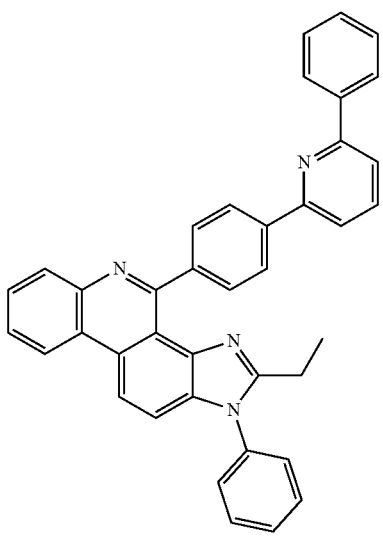

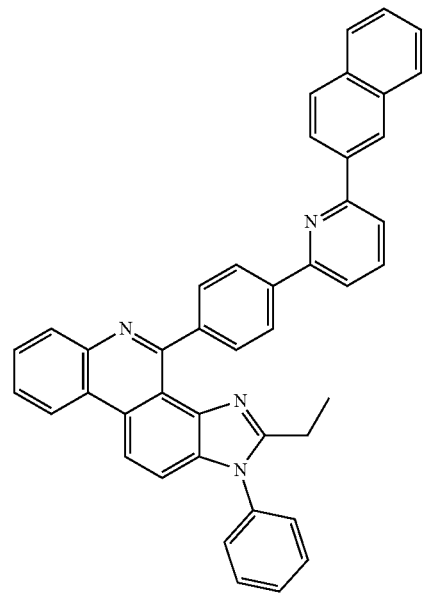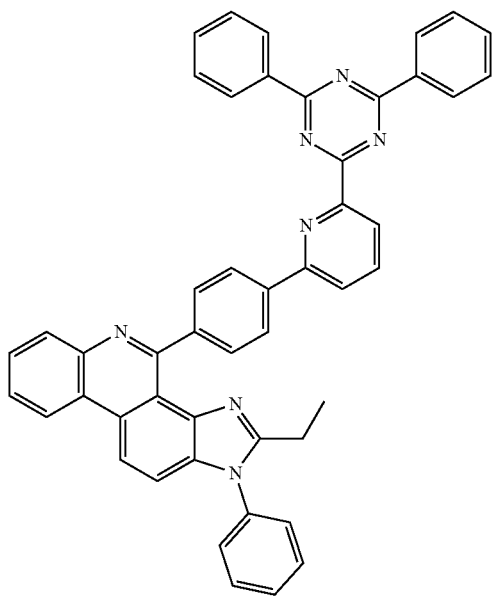

142
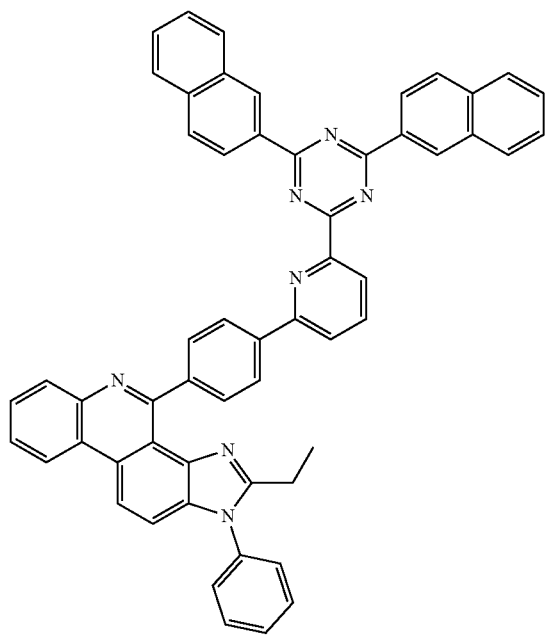
143
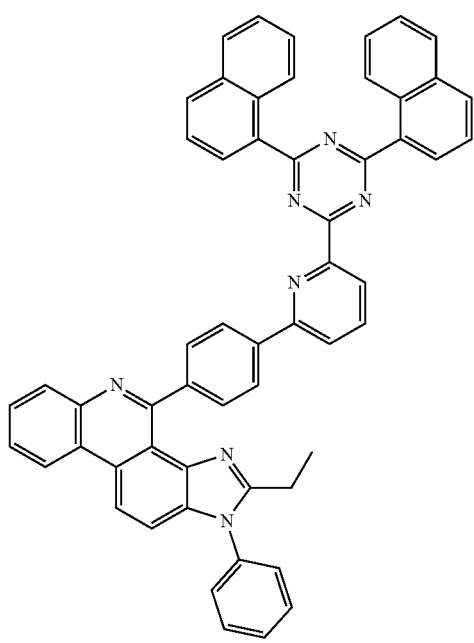
144
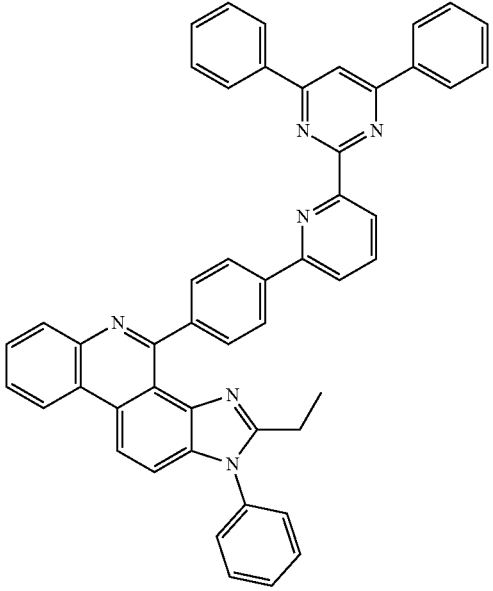
145
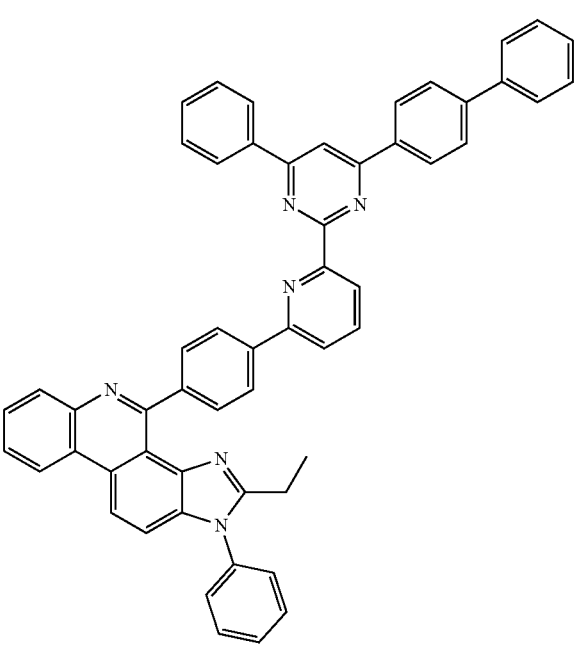

146
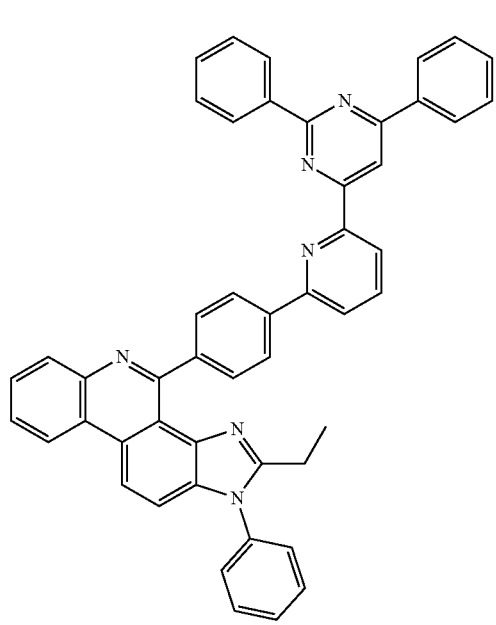
147
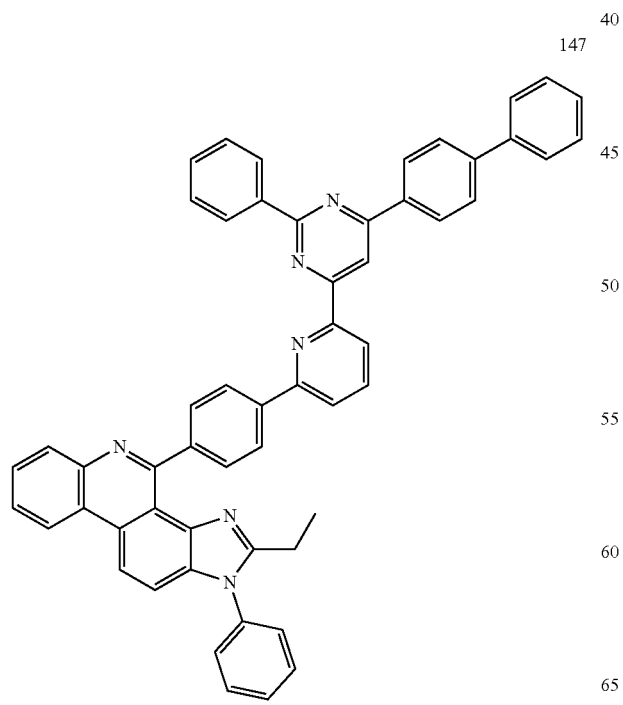
148
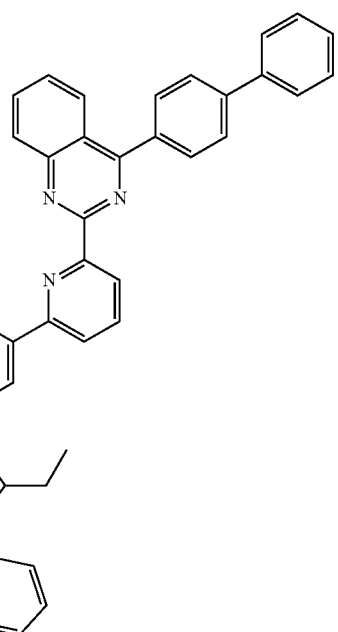
149
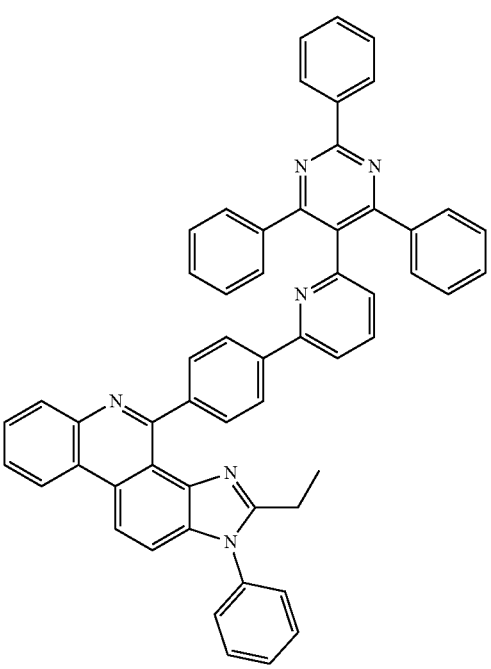

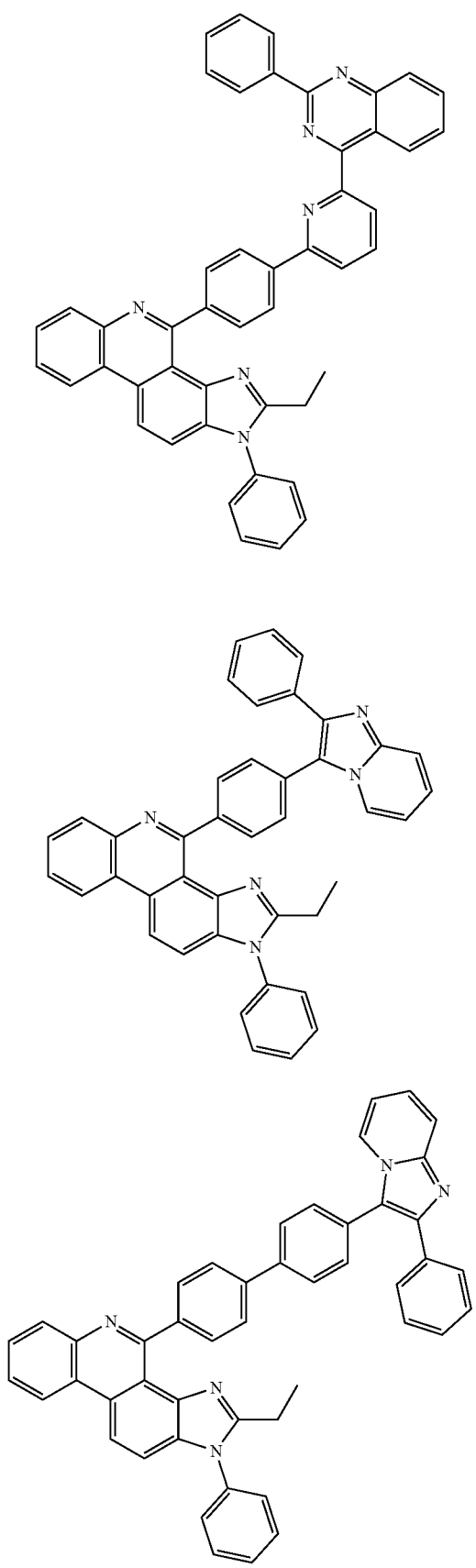
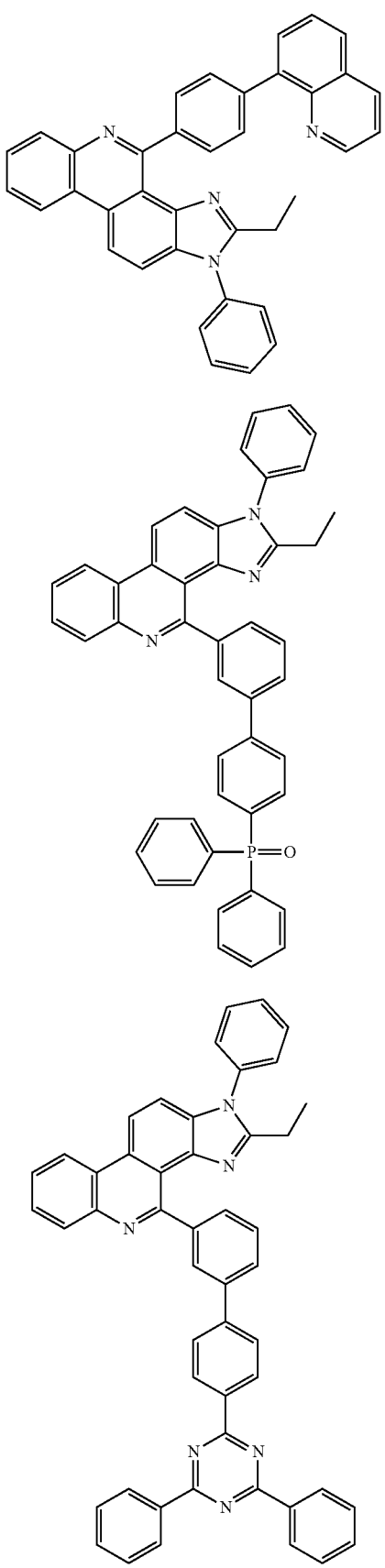

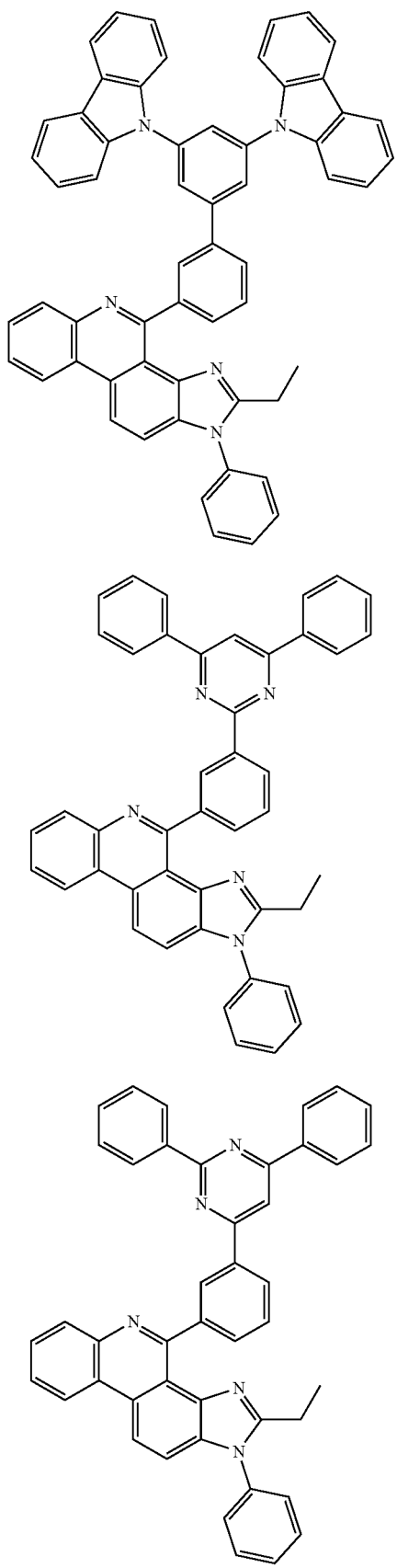

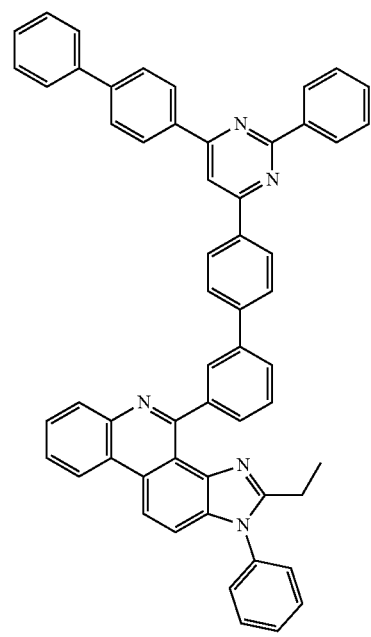
161
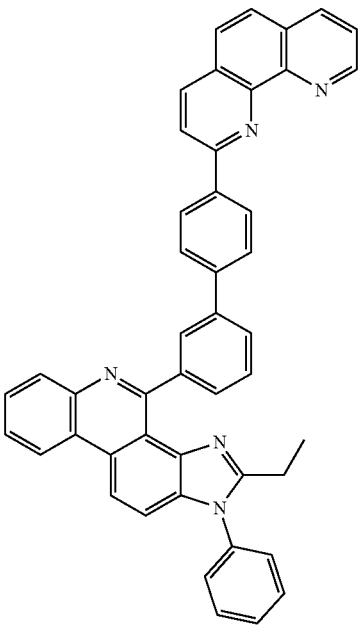
163
162
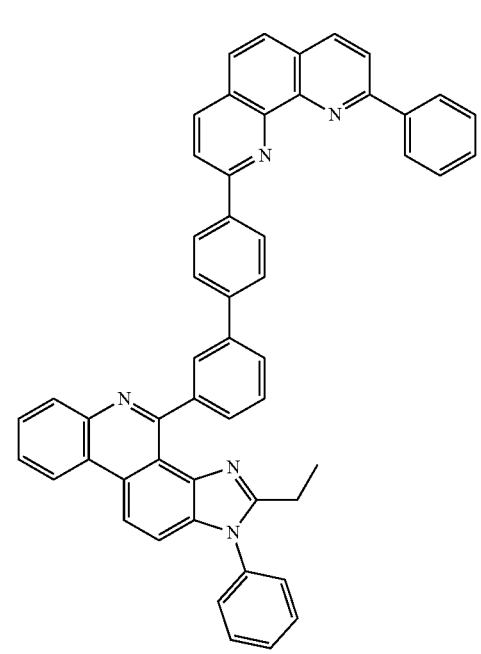
164

75
-continued
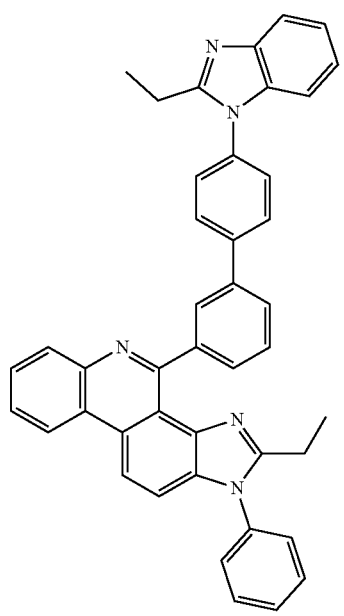
165
166
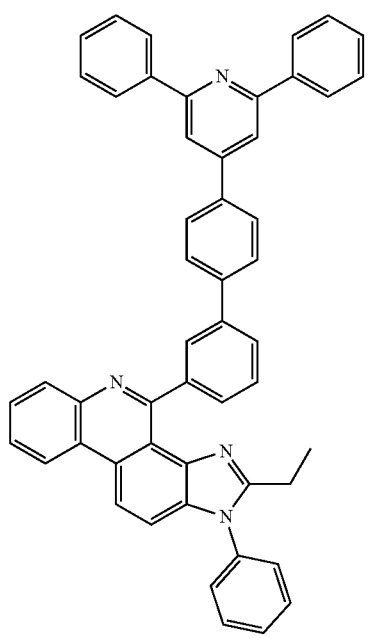
76
-continued
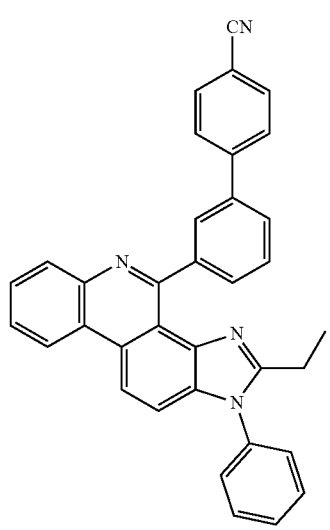
167
The compounds of Chemical Formulae 1 to 3 according to one embodiment of the present application may be prepared according to a preparation method of the following general formula.
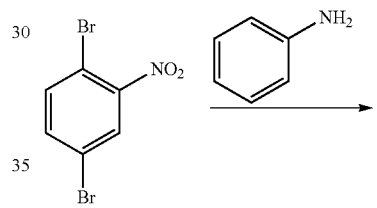
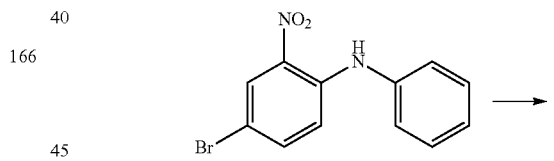
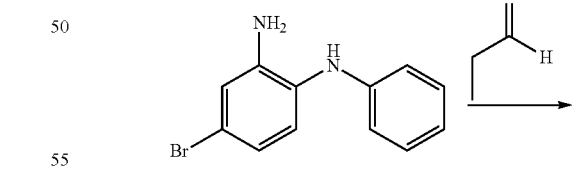
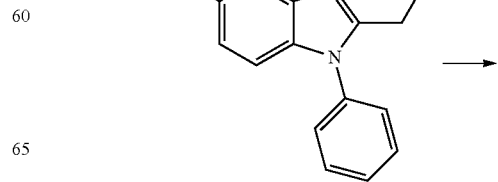

-continued

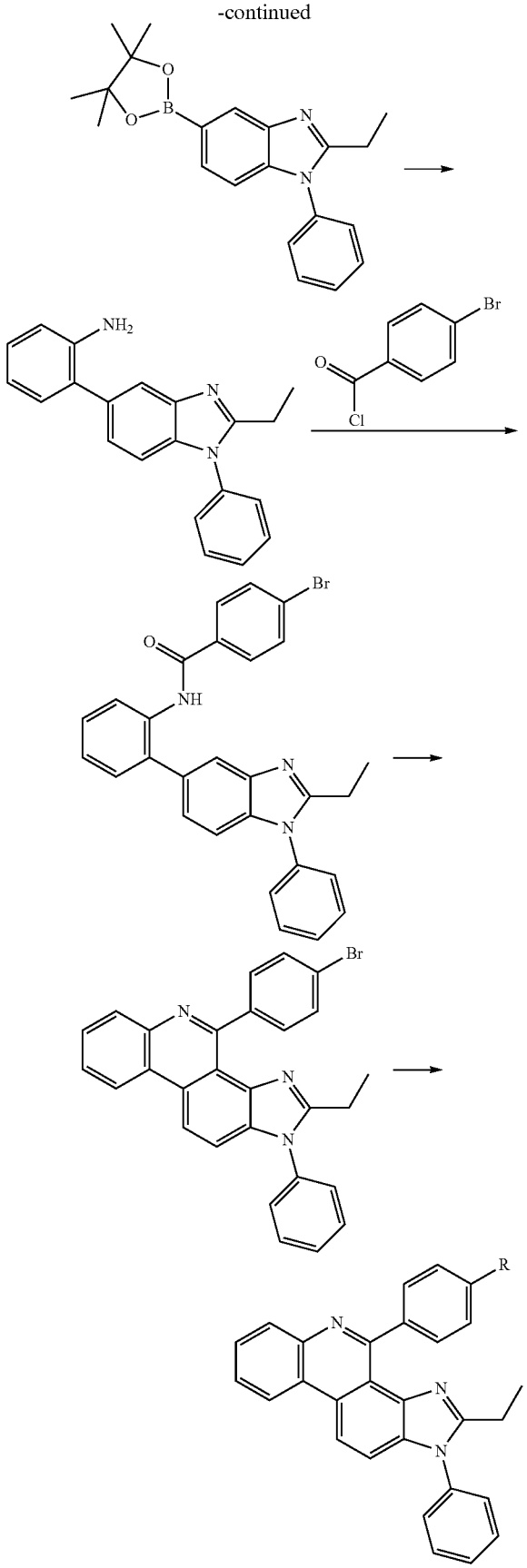

In the general formula, R has the same definition as $R_1$ of Chemical Formula 1.

In addition, by introducing various substituents to the structures of Chemical Formulae 1 to 3, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structures of Chemical Formulae 1 to 3, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

The hetero-cyclic compound according to one embodiment of the present application may be prepared through a multistep chemical reaction. Some intermediate compounds are prepared first, and the compound of Chemical Formula 1 may be prepared from the intermediate compounds. More specifically, the hetero-cyclic compound according to one embodiment of the present application may be prepared based on preparation examples to describe later.

Another embodiment of the present application provides an organic light emitting device comprising the hetero-cyclic compound represented by Chemical Formula 1.

In addition, in one embodiment of the present application, there is provided an organic light emitting device comprising a first electrode; a second electrode provided opposite to the first electrode; and one or more organic material layers provided between the first electrode and the second electrode, wherein one or more layers of the organic material layers comprise the hetero-cyclic compound according to Chemical Formula 1.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the hetero-cyclic compound according to Chemical Formula 1 may be used as a material of the blue organic light emitting device.

In one embodiment of the present application, the organic light emitting device may be a green organic light emitting device, and the hetero-cyclic compound according to Chemical Formula 1 may be used as a material of the green organic light emitting device.

In one embodiment of the present application, the organic light emitting device may be a red organic light emitting device, and the hetero-cyclic compound according to Chemical Formula 1 may be used as a material of the red organic light emitting device.

Specific descriptions on the hetero-cyclic compound represented by Chemical Formula 1 are the same as the descriptions provided above.

The organic light emitting device of the present disclosure may be manufactured using common organic light emitting device manufacturing methods and materials except that one or more organic material layers are formed using the hetero-cyclic compound described above.

The hetero-cyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

In the organic light emitting device of the present disclosure, the organic material layer comprises a hole transfer layer, and the hole transfer layer may comprise the hetero-cyclic compound.

In the organic light emitting device of the present disclosure, the organic material layer comprises an electron injection layer or an electron transfer layer, and the electron transfer layer or the electron injection layer may comprise the hetero-cyclic compound.

In another organic light emitting device, the organic material layer comprises an electron blocking layer or a hole blocking layer, and the electron blocking layer or the hole blocking layer may comprise the hetero-cyclic compound.

In another organic light emitting device, the organic material layer comprises an electron transfer layer, and the electron transfer layer may comprise the hetero-cyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the hetero-cyclic compound represented by Chemical Formula 1.

In addition, the organic light emitting device according to one embodiment of the present application may comprise an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the hetero-cyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the hetero-cyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first hole blocking layer and the second hole blocking layer and the like described in FIG. 4 may not be included in some cases.

The organic material layer comprising Chemical Formulae 1 to 3 may further comprise other materials as necessary.

In the organic light emitting device according to one embodiment of the present application, materials other than the compounds of Chemical Formulae 1 to 3 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The hetero-cyclic compound according to one embodiment of the present application may also be used in an organic electronic device comprising an organic solar cell, an organic photo conductor, an organic transistor and the like under a similar principle used in the organic light emitting device.

BEST MODE FOR DISCLOSURE

Hereinafter, the present specification will be described in more detail with reference to examples, however, these are for illustrative purposes only, and the scope of the present application is not limited thereto.

PREPARATION EXAMPLE

<Preparation Example 1> Synthesis of Compound 2

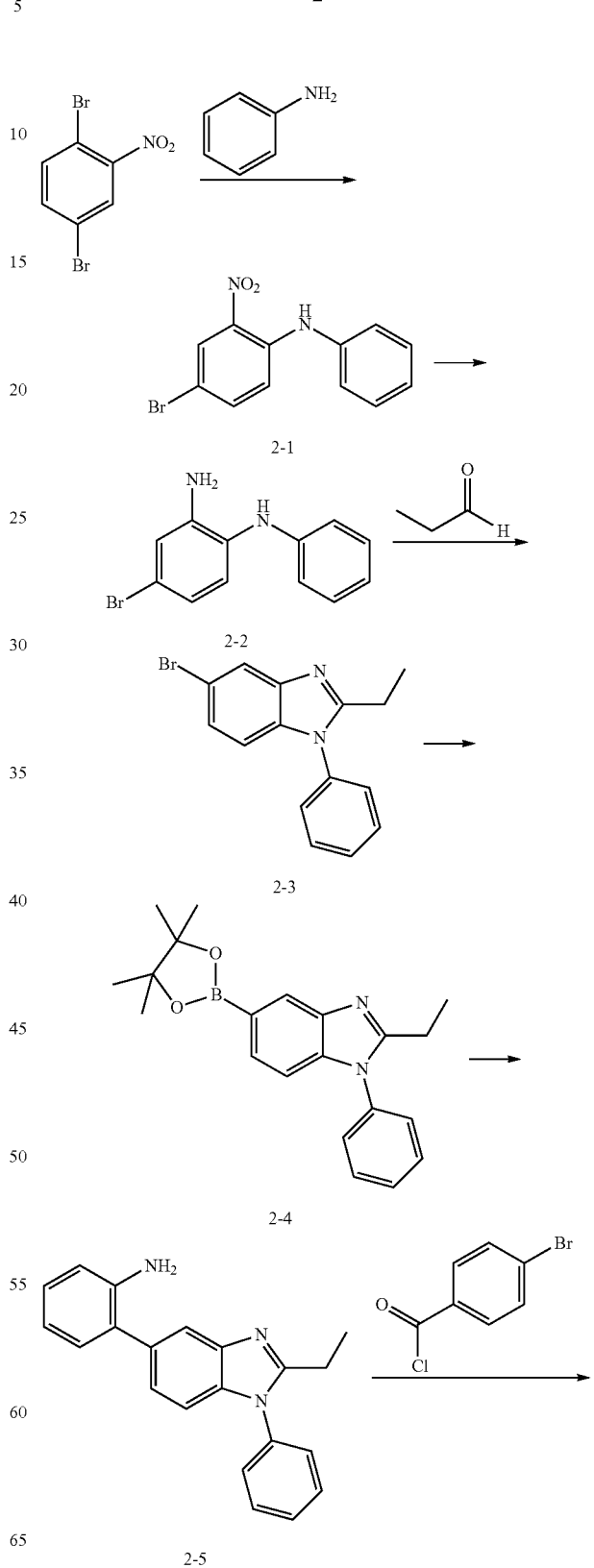

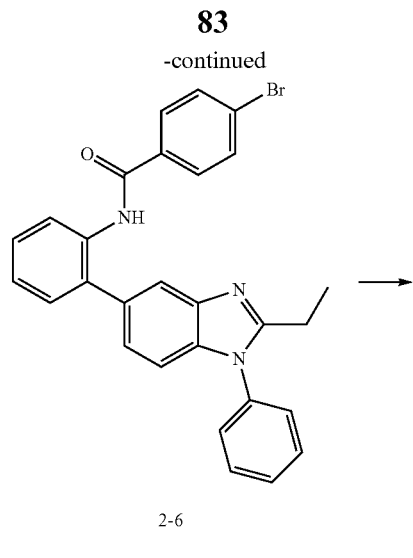

2-6

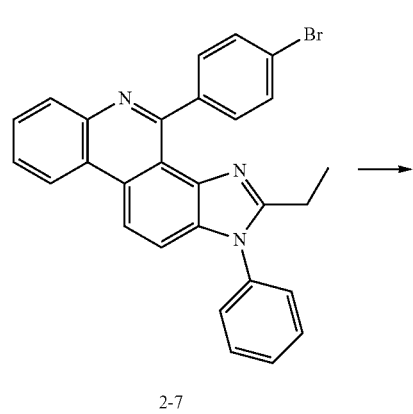

2-7

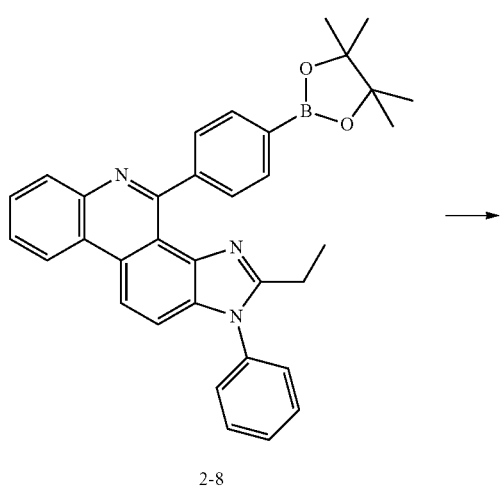

2-8

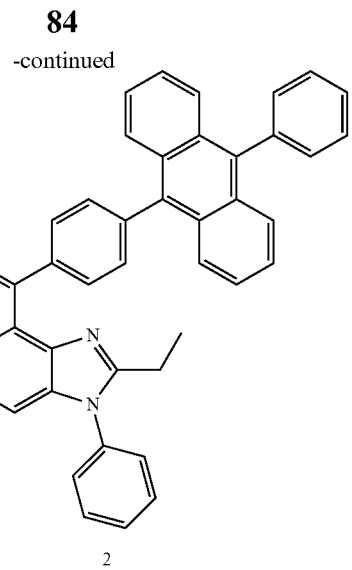

2

1) Synthesis of Compound 2-1

After adding aniline (132 ml, 213 mmol) and sodium acetate trihydrate (176 g, 318 mol) to 1,4-dibromo-2-nitrobenzene (200 g, 106 mmol), the result was stirred for 30 minutes at 80° C., and then refluxed for 72 hours at 160° C.

After the reaction was completed, the result was cooled to room temperature, and then extracted with distilled water and ethyl acetate (EA). The organic layer was dried with anhydrous $MgSO_4$, then the solvent was removed using a rotary evaporator, and the result was purified through column chromatography using dichloromethane and hexane as a developing solvent to obtain target Compound 2-1 (208 g, 67%).

2) Synthesis of Compound 2-2

After dissolving Compound 2-1 (31 g, 105 mmol) in tetrahydrofuran (THF) (210 ml), sodium dithionite (93 g, 525 mmol) dissolved in distilled water (370 ml) was added thereto, and the result was stirred for 12 hours at room temperature. After the reaction was completed, the result was extracted with distilled water and EA. After drying the organic layer with anhydrous $MgSO_4$, the solvent was removed using a rotary evaporator, and target Compound 2-2 (28 g, 100%) was obtained without further purification.

3) Synthesis of Compound 2-3

After dissolving Compound 2-2 (100 g, 380 mmol) in propionic acid, the result was stirred under reflux for 6 hours at 130° C. After the reaction was terminated, the result was cooled to room temperature, neutralized with sat. $NaHCO_3$, and then extracted with distilled water and EA. The organic layer was dried with anhydrous $MgSO_4$, then the solvent was removed using a rotary evaporator, and the result was purified through column chromatography using dichloromethane and hexane as a developing solvent to obtain target Compound 2-3 (44 g, 56%).

4) Synthesis of Compound 2-4

After dissolving Compound 2-3 (44 g, 146 mmol) in 1,4-dioxane, bis(pinacolato)diborone (74 g, 292 mmol), $Pd(dppf)Cl_2$ (5.3 g, 7.3 mmol) and potassium acetate (43 g, 438 mmol) were added thereto, and the result was stirred for 2 hours at 110° C. After the reaction was completed, the result was extracted with distilled water and EA. After drying the organic layer with anhydrous MgSO$_4$, the solvent was removed using a rotary evaporator, and target Compound 2-4 (57.8 g, 99%) was obtained without further purification.

5) Synthesis of Compound 2-5

After dissolving Compound 2-4 (57.8 g, 146 mmol) in toluene, EtOH and H$_2$O, 2-bromoaniline (30.1 g, 175 mmol), Pd(PPh$_3$)$_4$ (8.4 g, 7.3 mmol) and K$_2$CO$_3$ (60.5 g, 438 mmol) were added thereto, and the result was stirred for 12 hours at 110° C. After the reaction was completed, the result was cooled to room temperature, and then extracted with distilled water and EA. The organic layer was dried with anhydrous MgSO$_4$, then the solvent was removed using a rotary evaporator, and the result was purified through column chromatography using ethyl acetate and hexane as a developing solvent to obtain target Compound 2-5 (41 g, 89%).

6) Synthesis of Compound 2-6

After dissolving Compound 2-5 (41 g, 130.8 mmol) in THF, 4-bromobenzoyl chloride (26 ml, 196 mmol) and triethylamine (TEA) (55 ml, 392 mmol) were added thereto at 0° C., and the result was stirred for 2 hours at room temperature. After the reaction was completed, EA and distilled water were added to the reactor for solidification, and produced solids were collected to obtain target Compound 2-6 (43 g, 67%).

7) Synthesis of Compound 2-7

After dissolving Compound 2-6 (43 g, 87.2 mmol) in nitrobenzene, POCl$_3$ (8.2 ml, 87.2 mmol) was added thereto, and the result was stirred for 18 hours at 140° C. After the reaction was completed, the result was vacuum distilled to remove nitrobenzene, then cooled to room temperature, and extracted with distilled water and EA. The organic layer was dried with anhydrous MgSO$_4$, then the solvent was removed using a rotary evaporator, and the result was purified through column chromatography using dichloromethane and hexane as a developing solvent to obtain target Compound 2-7 (26 g, 62%).

8) Synthesis of Compound 2-8

After dissolving Compound 2-7 (16.0 g, 33.4 mmol) in 1,4-dioxane, bis(pinacolato)diborone, Pd(dppf)Cl$_2$ and potassium acetate were added thereto, and the result was stirred for 18 hours at 120° C. After the reaction was completed, the result was extracted with distilled water and EA. After drying the organic layer with anhydrous MgSO$_4$, the solvent was removed using a rotary evaporator, and target Compound 2-8 (17.0 g, 97%) was obtained without further purification.

9) Synthesis of Compound 2

After adding 9-bromo-10-phenylanthracene (5.6 g, 16.9 mmol), Pd(PPh$_3$)$_4$ (0.8 g, 0.71 mmol), K$_2$CO$_3$ (5.8 g, 42.3 mmol) and toluene/EtOH/H$_2$O to Compound 2-8 (8.0 g, 14.1 mmol), the result was stirred for 2 hours at 110° C. After the reaction was completed, the result was cooled to room temperature, and then extracted with distilled water and EA. The organic layer was dried with anhydrous MgSO$_4$, then the solvent was removed using a rotary evaporator, and the result was purified through column chromatography using dichloromethane and hexane as a developing solvent to obtain target Compound 2 (8.4 g, 86%).

<Preparation Example 2> Preparation of Compound 5

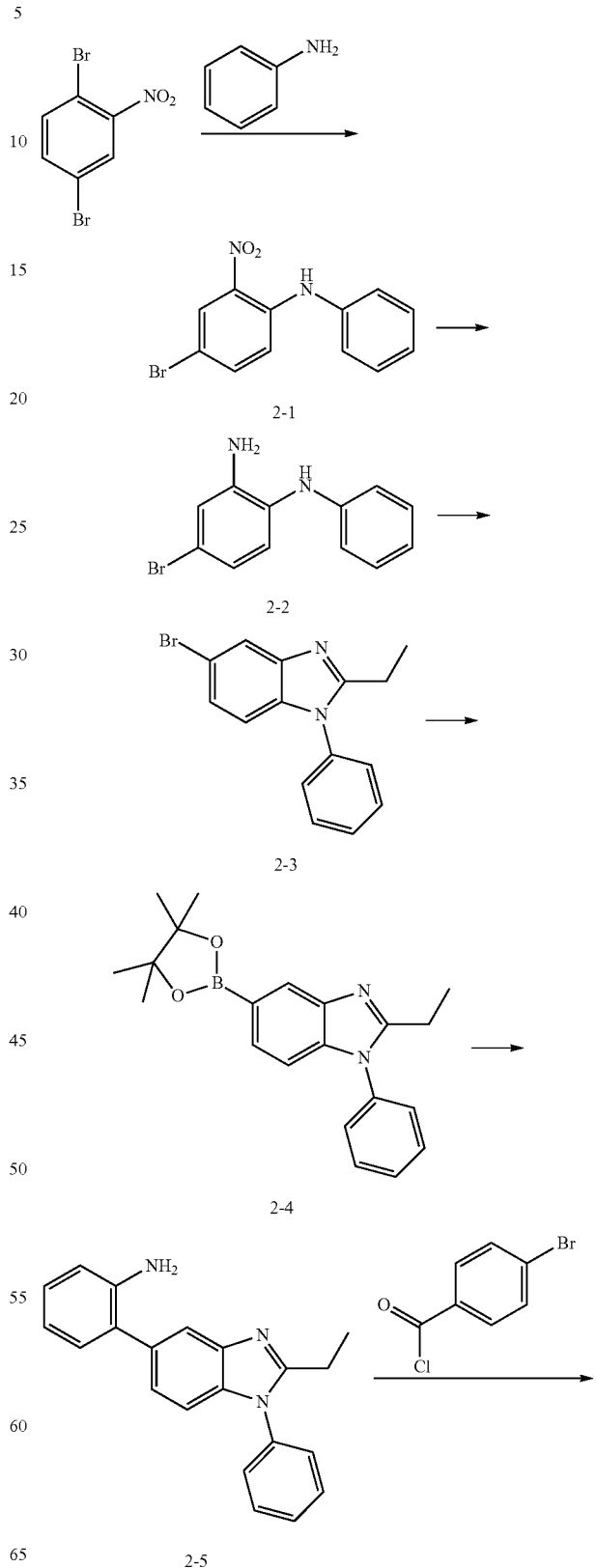

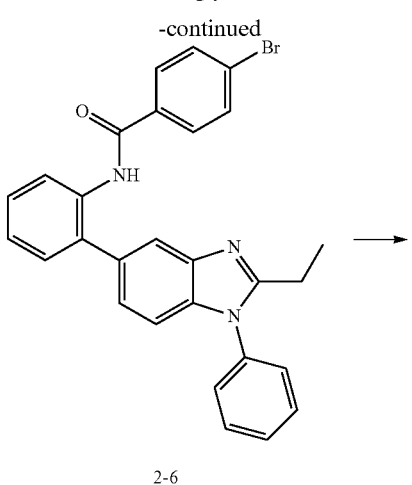

2-6

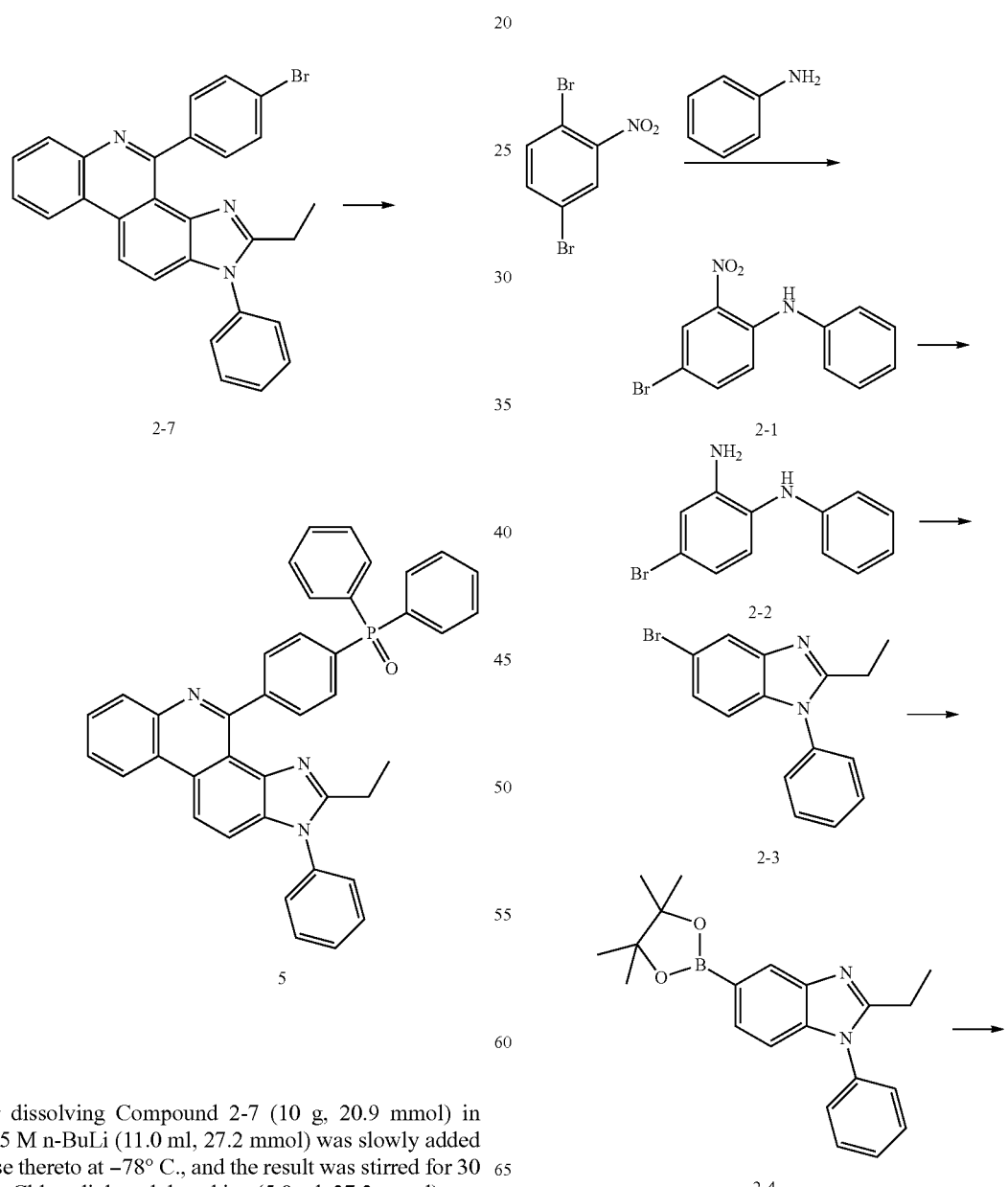

After the reaction was completed, methanol was added thereto, the result was stirred for 1 hour, and then extracted with distilled water and EA. The organic layer was dried with anhydrous MgSO₄, and the solvent was removed using a rotary evaporator. After dissolving the concentrate in dichloromethane (150 ml), hydrogen peroxide (7.0 ml) was added thereto, and the result was stirred for 3 hours at room temperature. After the reaction was terminated, the result was extracted with distilled water and EA. The organic layer was dried with anhydrous MgSO₄, then the solvent was removed using a rotary evaporator, toluene was added thereto, and then the result was heated for dissolution, and then recrystallized to obtain target Compound 5 (2.0 g, 16%).

<Preparation Example 3> Synthesis of Compound 10

After dissolving Compound 2-7 (10 g, 20.9 mmol) in THF, 2.5 M n-BuLi (11.0 ml, 27.2 mmol) was slowly added dropwise thereto at −78° C., and the result was stirred for 30 minutes. Chlorodiphenylphosphine (5.0 ml, 27.2 mmol) was added thereto, and then the result was stirred for 1 hour.

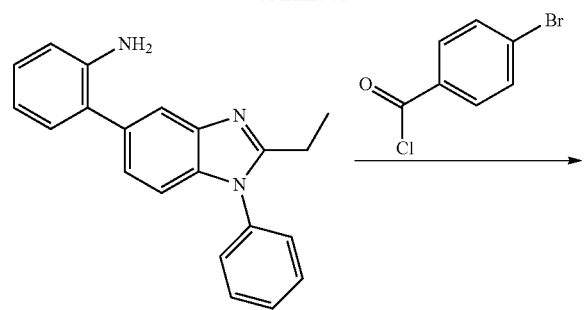
2-5
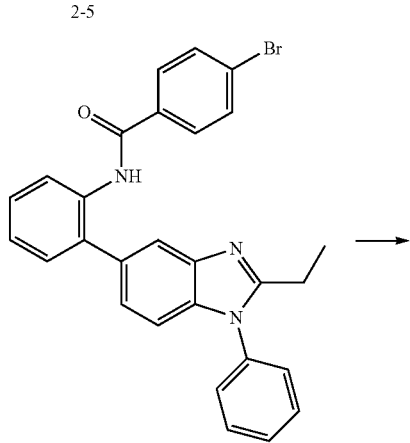
2-6
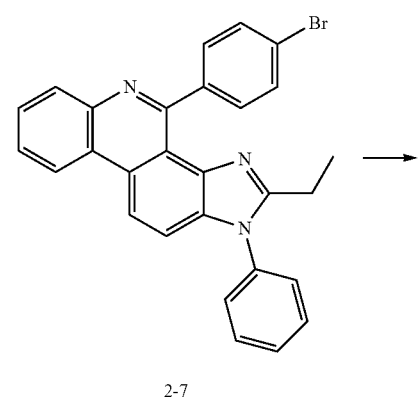
2-7
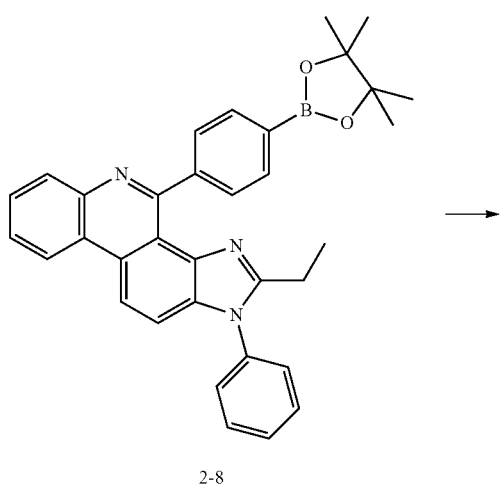
2-8
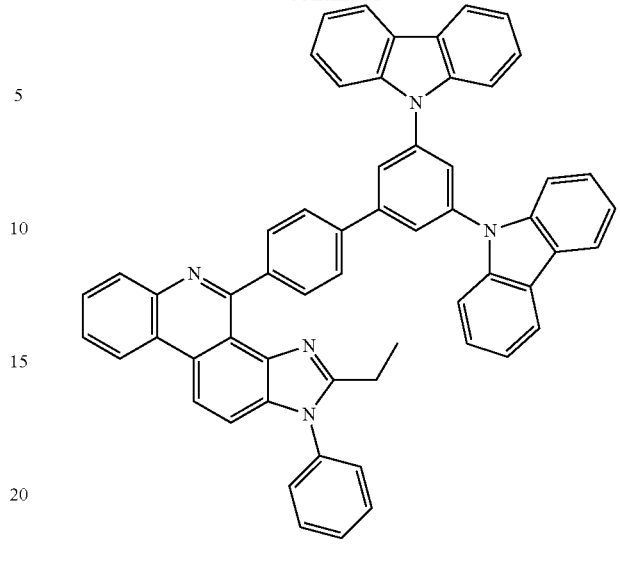
10
Target Compound 10 was prepared in the same manner as the preparation of Compound 2 in Preparation Example 1 except that 9,9'-(5-bromo-1,3-phenylene)bis(9H-carbazole) was used instead of 9-bromo-10-phenylanthracene.
<Preparation Example 4> Synthesis of Compound 11
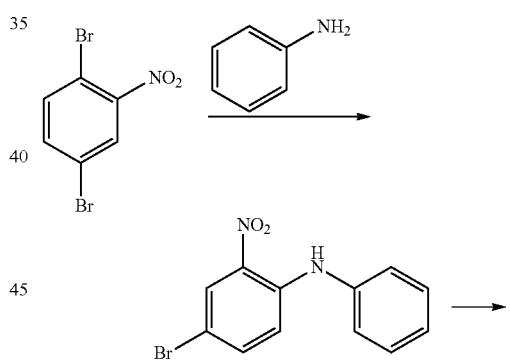
2-1
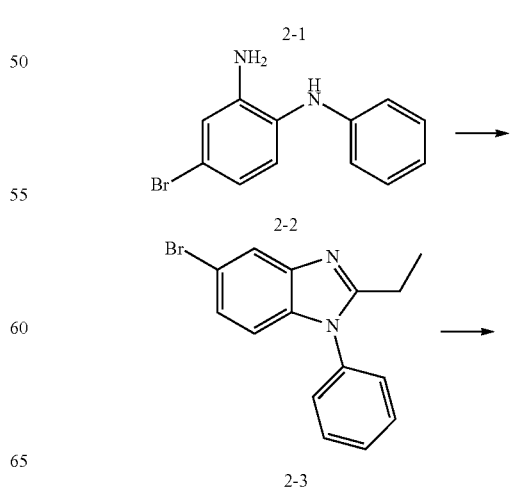
2-2
2-3

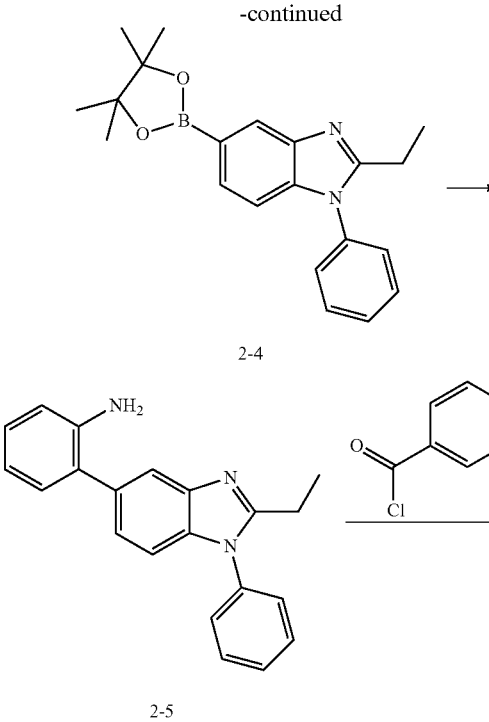
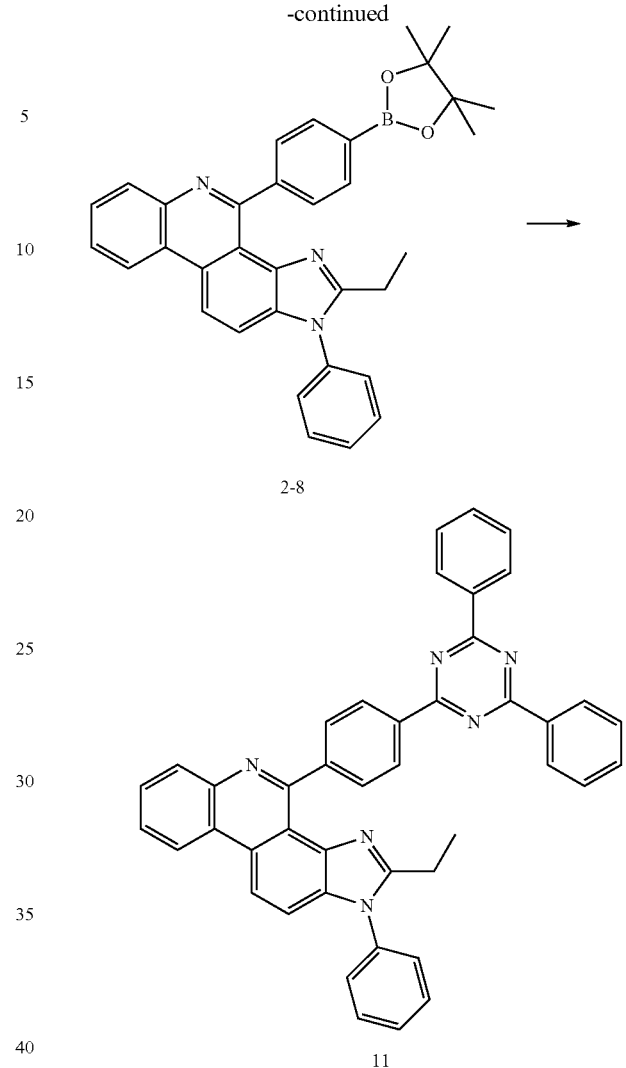
Target Compound 11 was prepared in the same manner as the preparation of Compound 2 in Preparation Example 1 except that 2-bromo-4,6-diphenyl-1,3,5-triazine was used instead of 9-bromo-10-phenylanthracene.
<Preparation Example 5> Synthesis of Compound 15
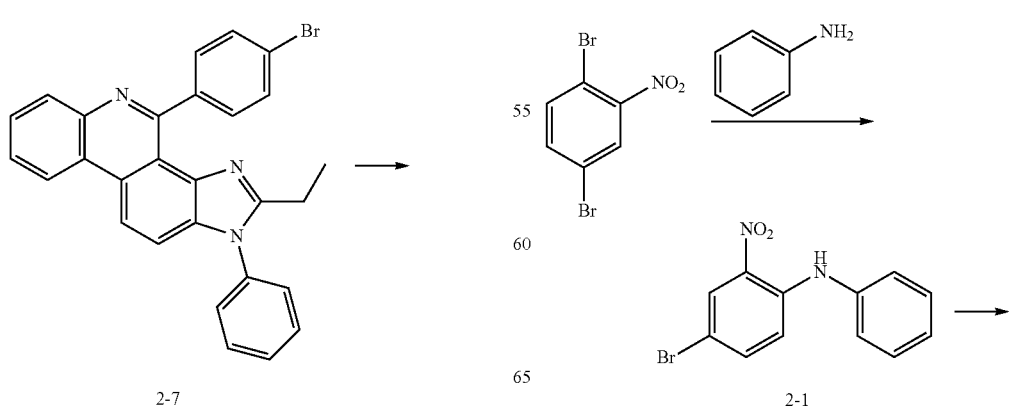

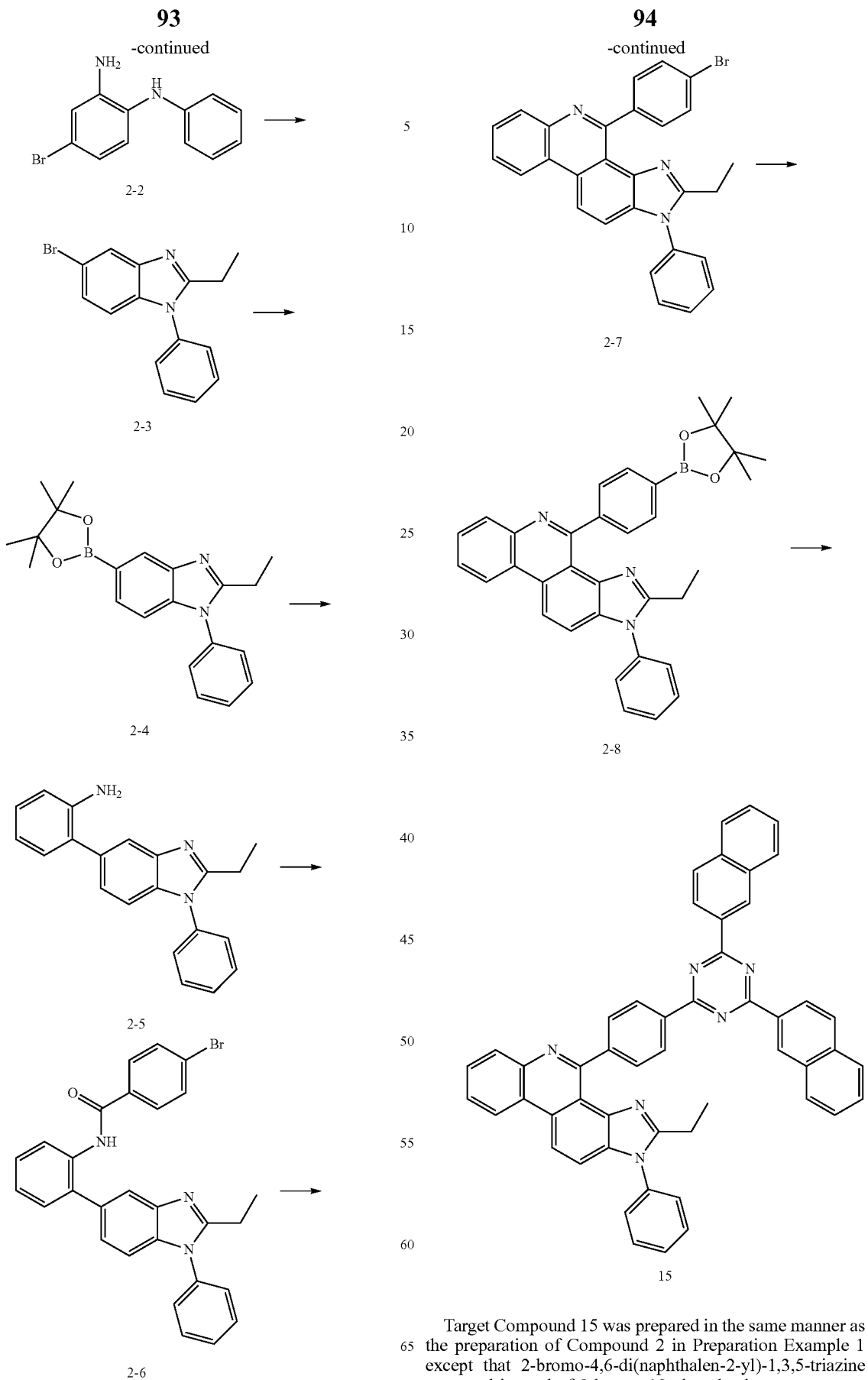
Target Compound 15 was prepared in the same manner as the preparation of Compound 2 in Preparation Example 1 except that 2-bromo-4,6-di(naphthalen-2-yl)-1,3,5-triazine was used instead of 9-bromo-10-phenylanthracene.

<Preparation Example 6> Synthesis of Compound 25
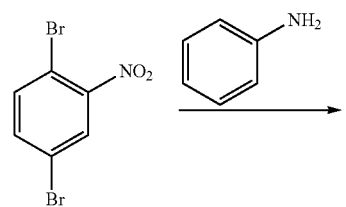
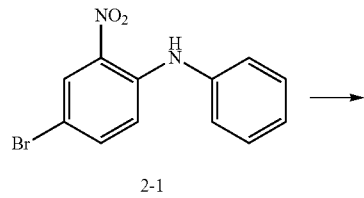
2-1
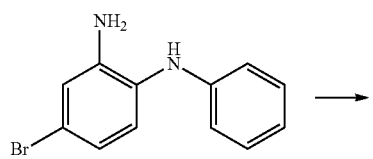
2-2
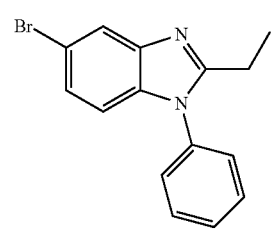
2-3
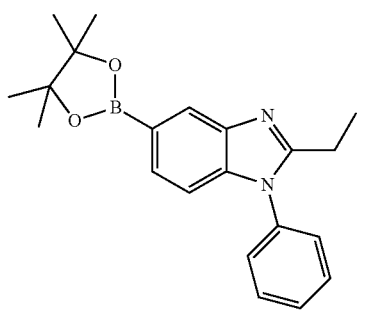
2-4
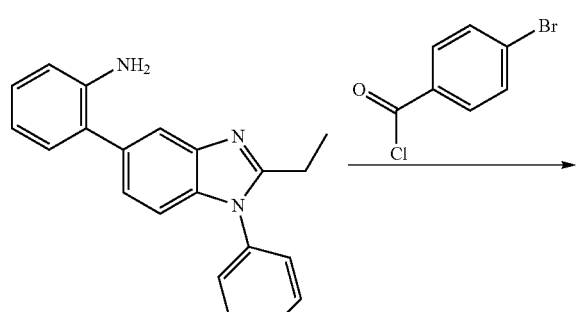
2-5
-continued
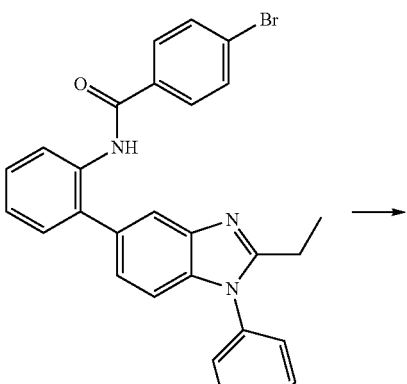
2-6
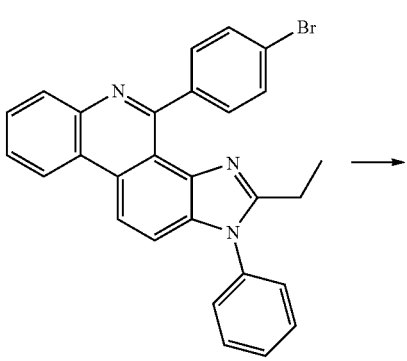
2-7
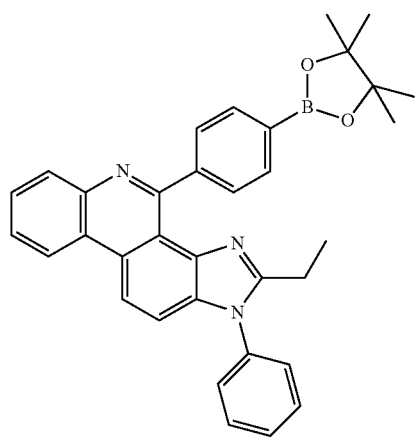
2-8

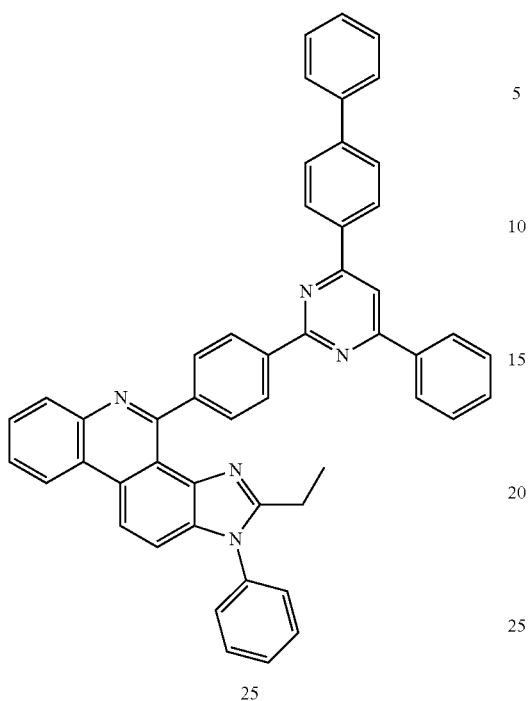
25
Target Compound 25 was prepared in the same manner as the preparation of Compound 2 in Preparation Example 1 except that 4-([1,1'-biphenyl]-4-yl)-2-bromo-6-phenylpyrimidine was used instead of 9-bromo-10-phenylanthracene.
<Preparation Example 7> Synthesis of Compound 55
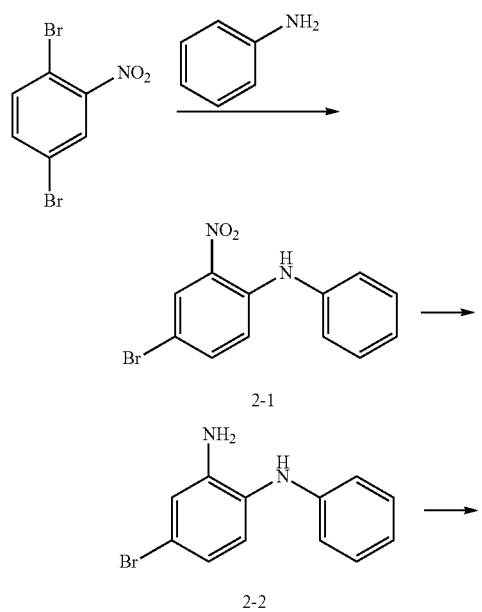
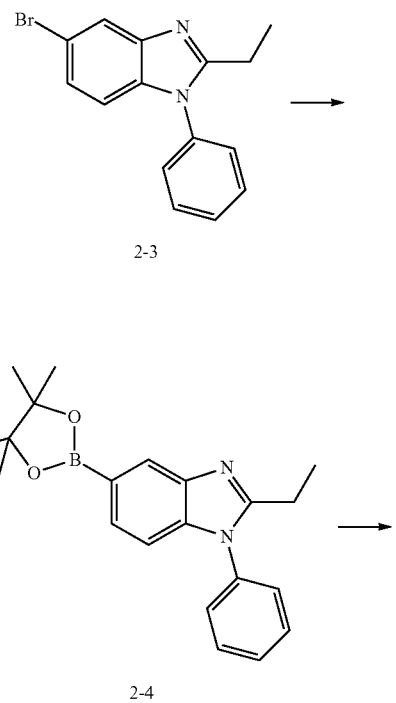
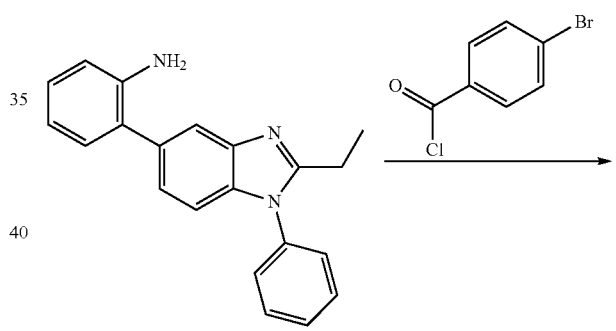
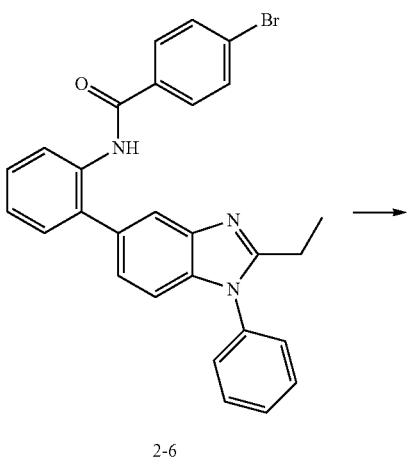

99
-continued
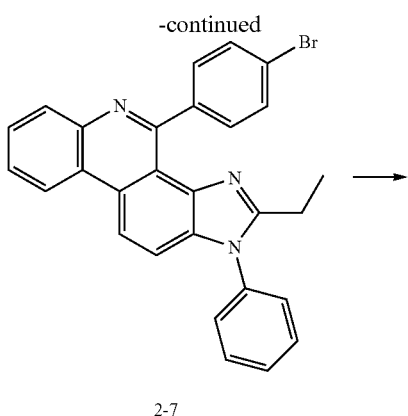
2-7
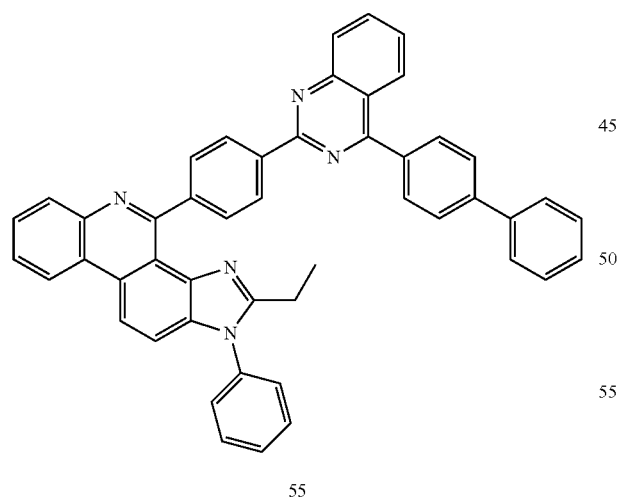
2-8
55
Target Compound 55 was prepared in the same manner as the preparation of Compound 2 in Preparation Example 1 except that 4-([1,1'-biphenyl]-4-yl)-2-bromoquinazoline was used instead of 9-bromo-10-phenylanthracene.
100
<Preparation Example 8> Synthesis of Compound 70
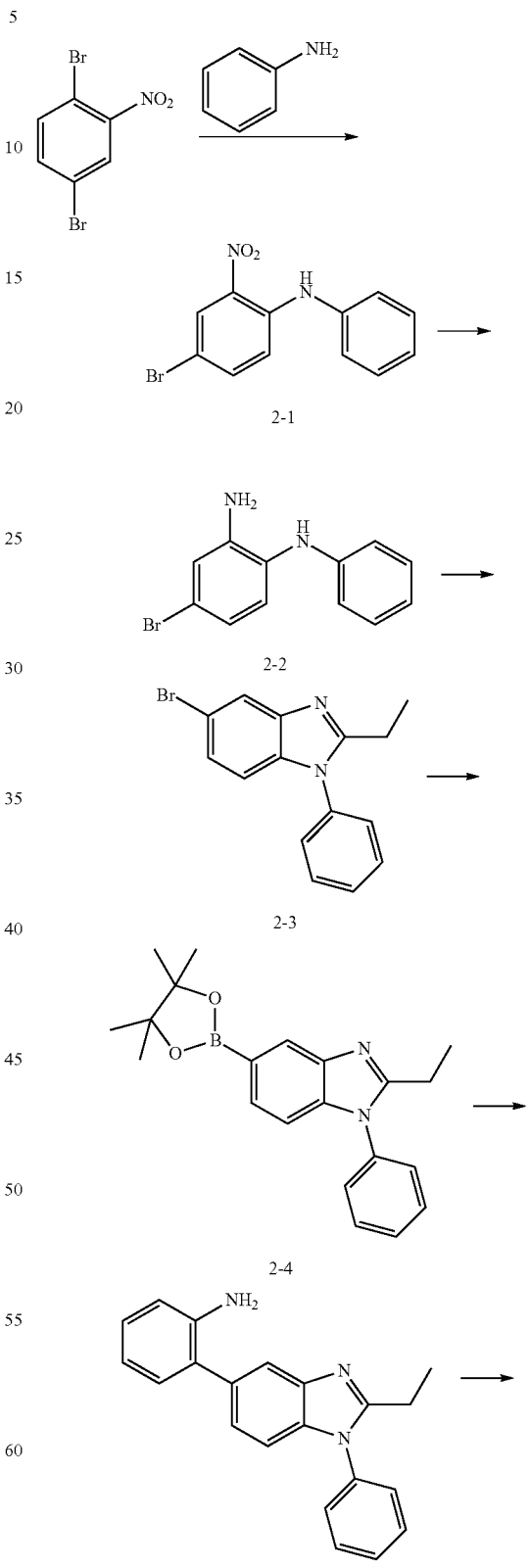

101
-continued
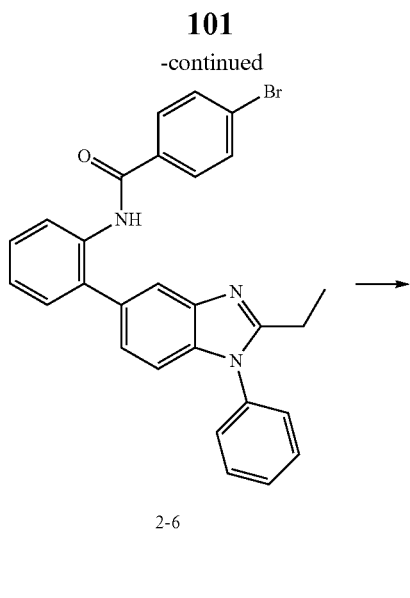
2-6
2-7
2-8
102
-continued
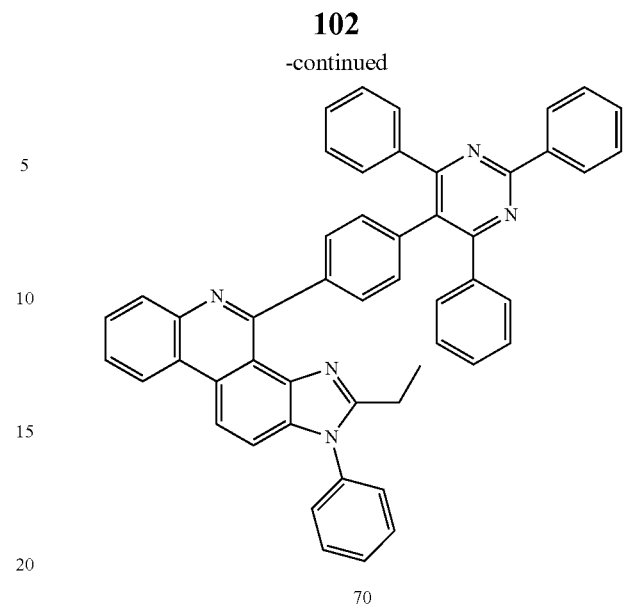
70
Target Compound 70 was prepared in the same manner as the preparation of Compound 2 in Preparation Example 1 except that 5-bromo-2,4,6-triphenylpyrimidine was used instead of 9-bromo-10-phenylanthracene.
<Preparation Example 9> Synthesis of Compound 89
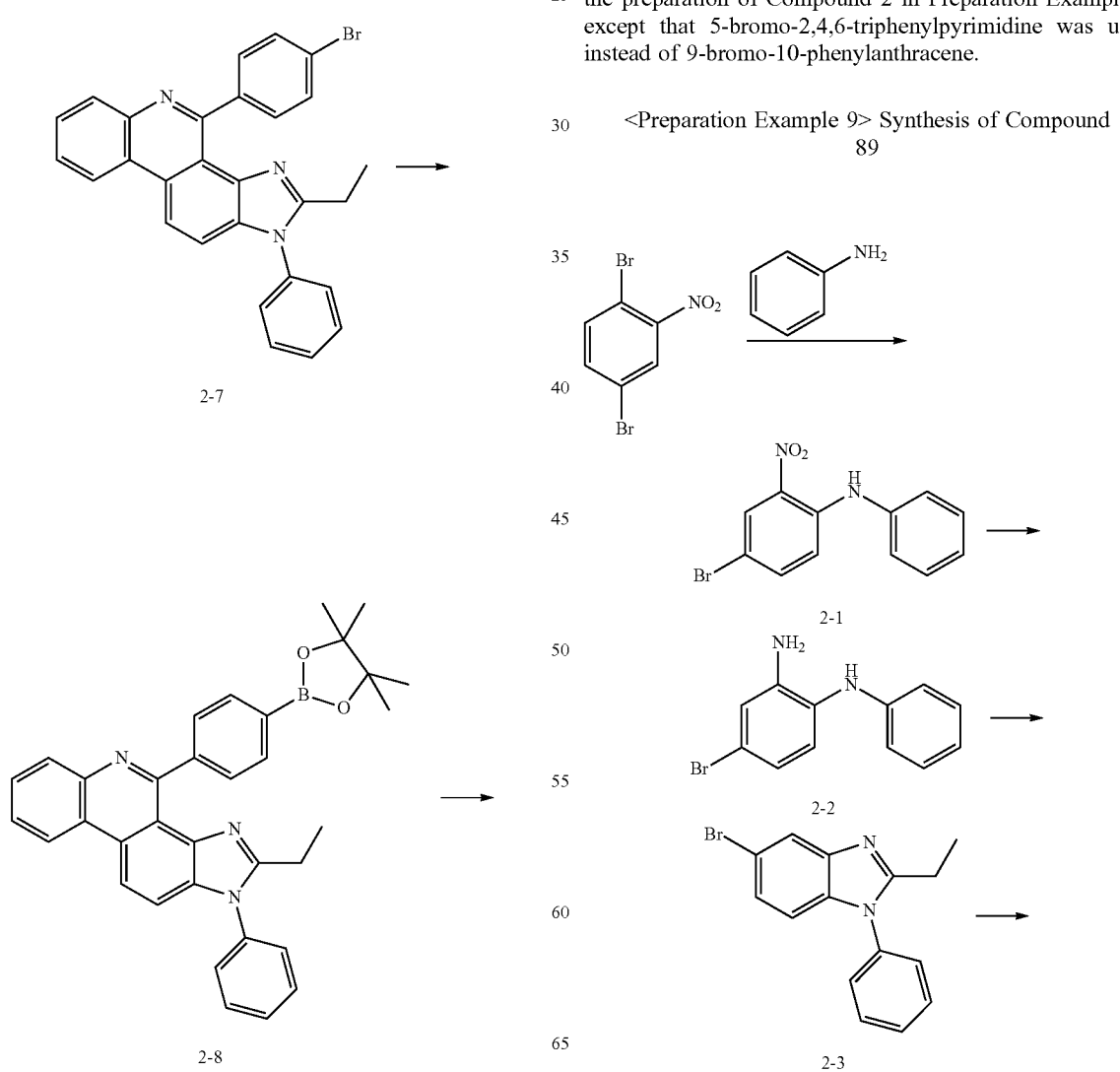
2-1
2-2
2-3

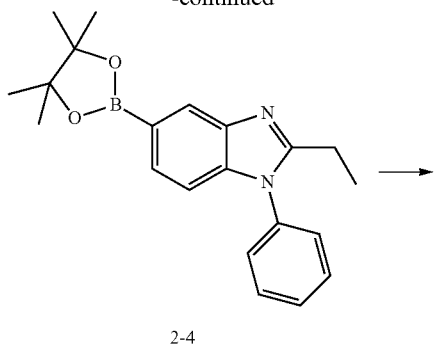
2-4
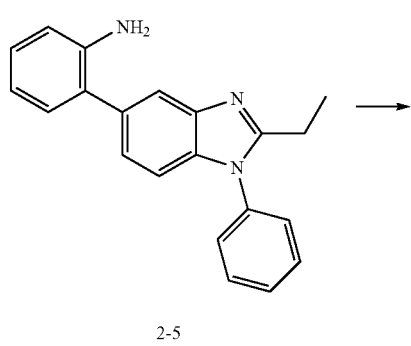
2-5
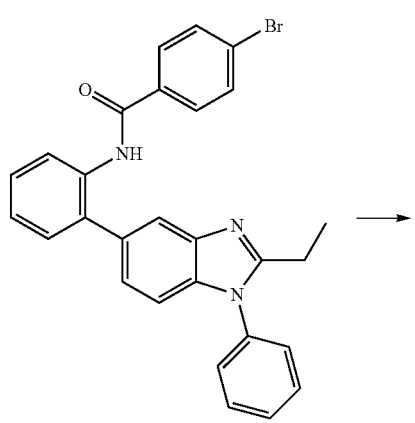
2-6
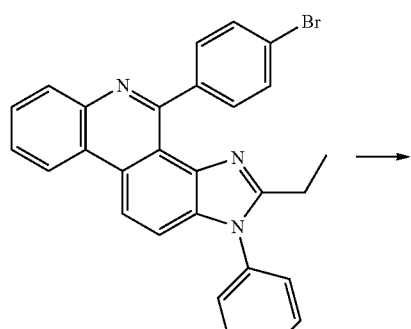
2-7
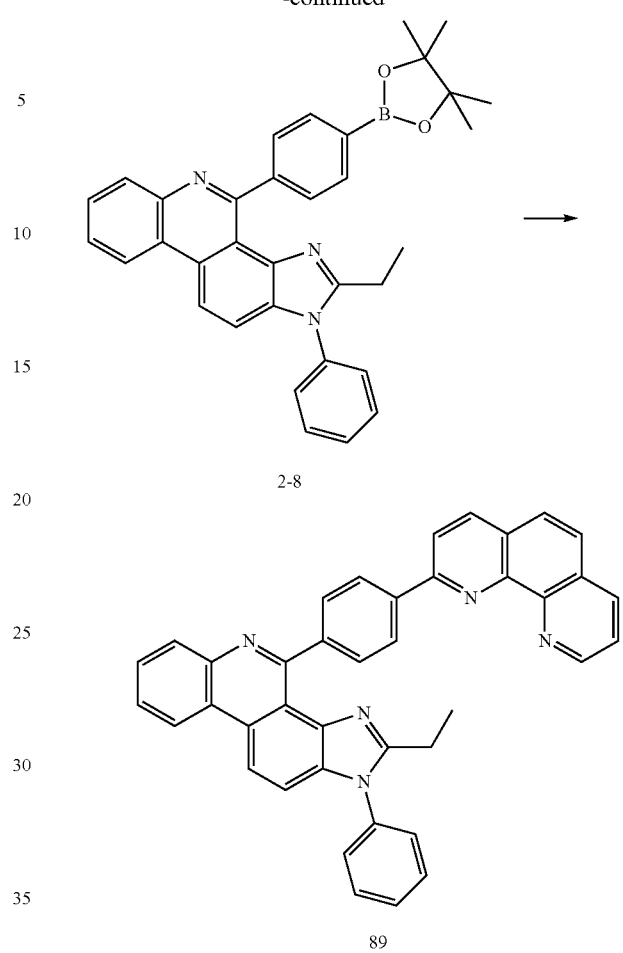
2-8
89
Target Compound 89 was prepared in the same manner as the preparation of Compound 2 in Preparation Example 1 except that 2-bromo-1,10-phenanthroline was used instead of 9-bromo-10-phenylanthracene.
<Preparation Example 10> Synthesis of Compound 94
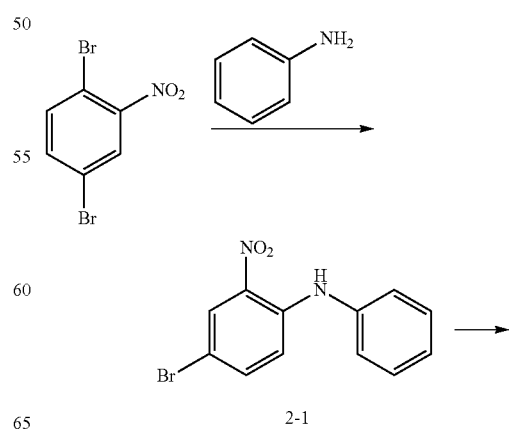
2-1

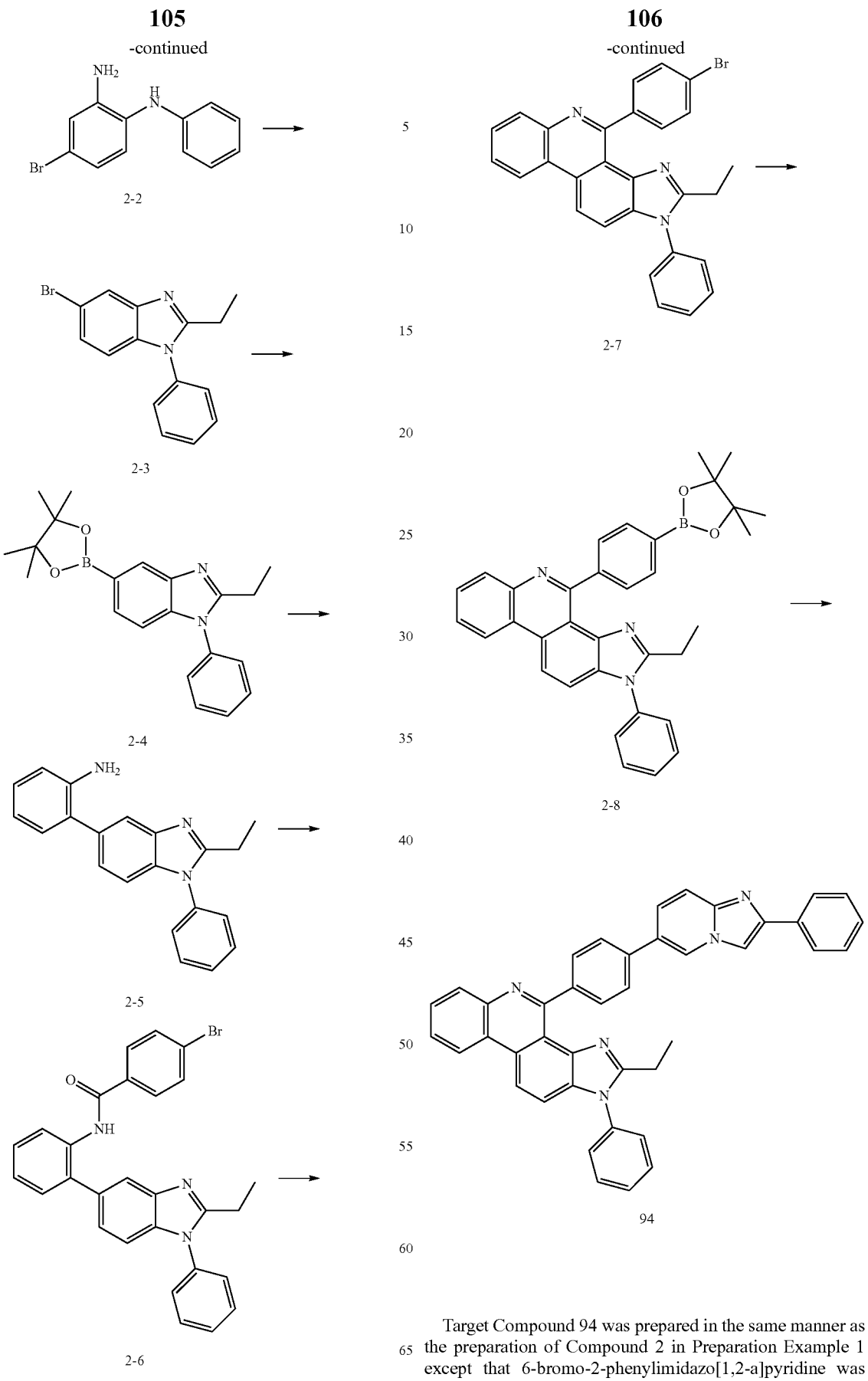
Target Compound 94 was prepared in the same manner as the preparation of Compound 2 in Preparation Example 1 except that 6-bromo-2-phenylimidazo[1,2-a]pyridine was used instead of 9-bromo-10-phenylanthracene.

<Preparation Example 11> Synthesis of Compound 101
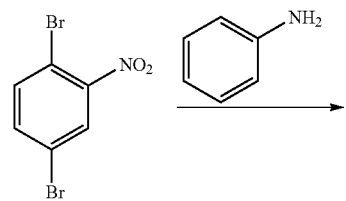
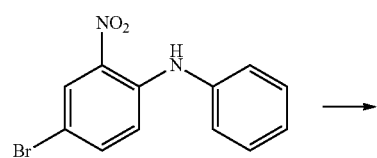
2-1
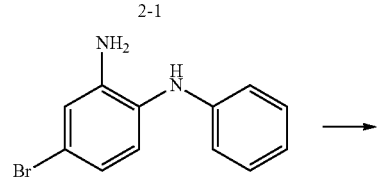
2-2
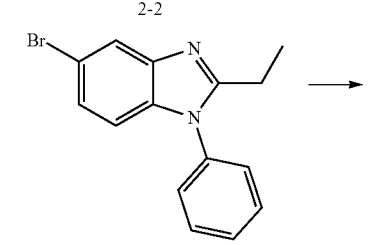
2-3
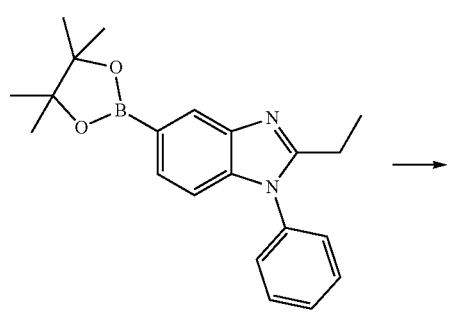
2-4
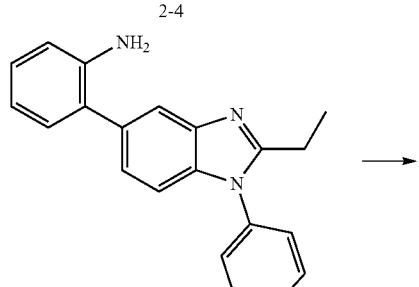
2-5
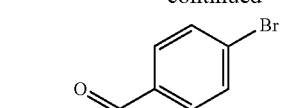
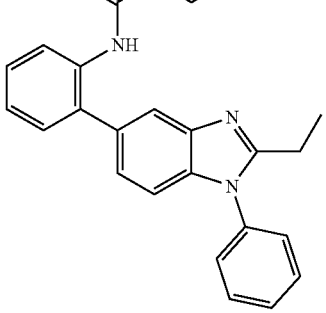
2-6
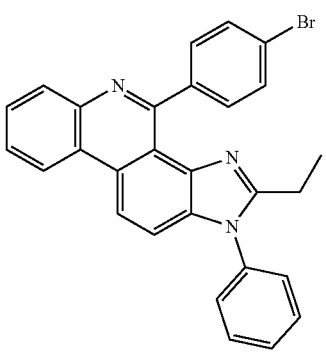
2-7
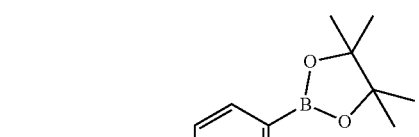
2-8

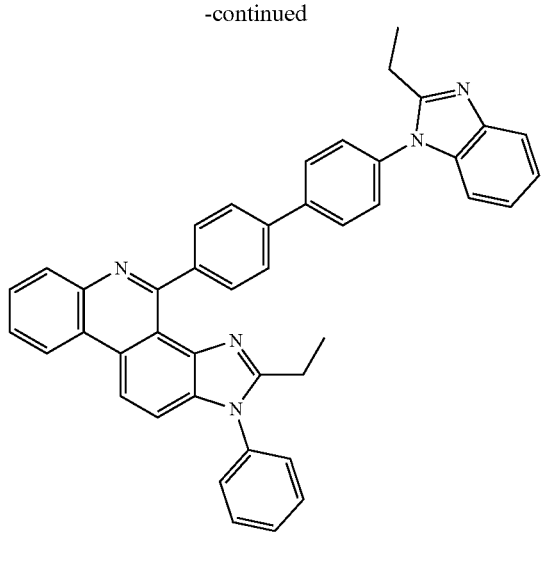
101
Target Compound 101 was prepared in the same manner as the preparation of Compound 2 in Preparation Example 1 except that 1-(4-bromophenyl)-2-ethyl-1H-benzo[d]imidazole was used instead of 9-bromo-10-phenylanthracene.
<Preparation Example 12> Synthesis of Compound 104
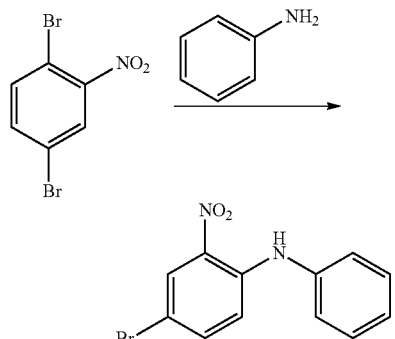
2-1
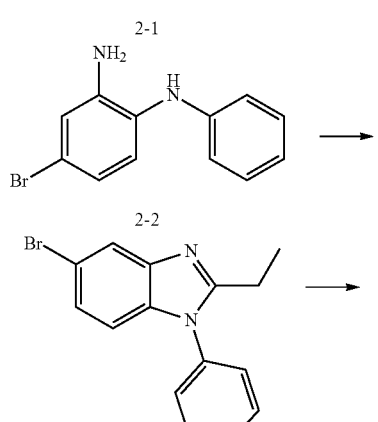
2-2
2-3
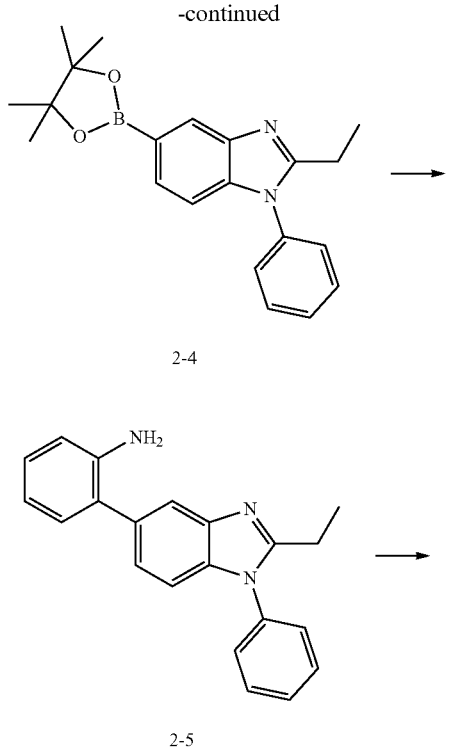
2-4
2-5
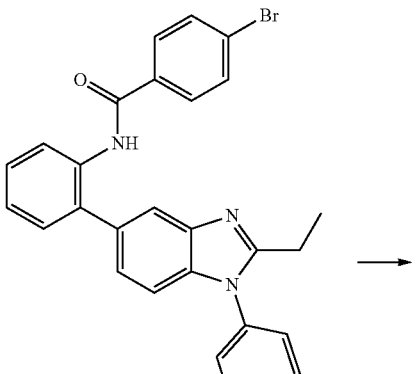
2-6
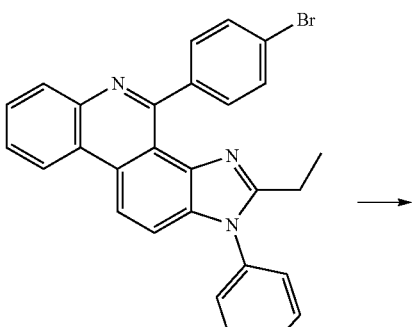
2-7

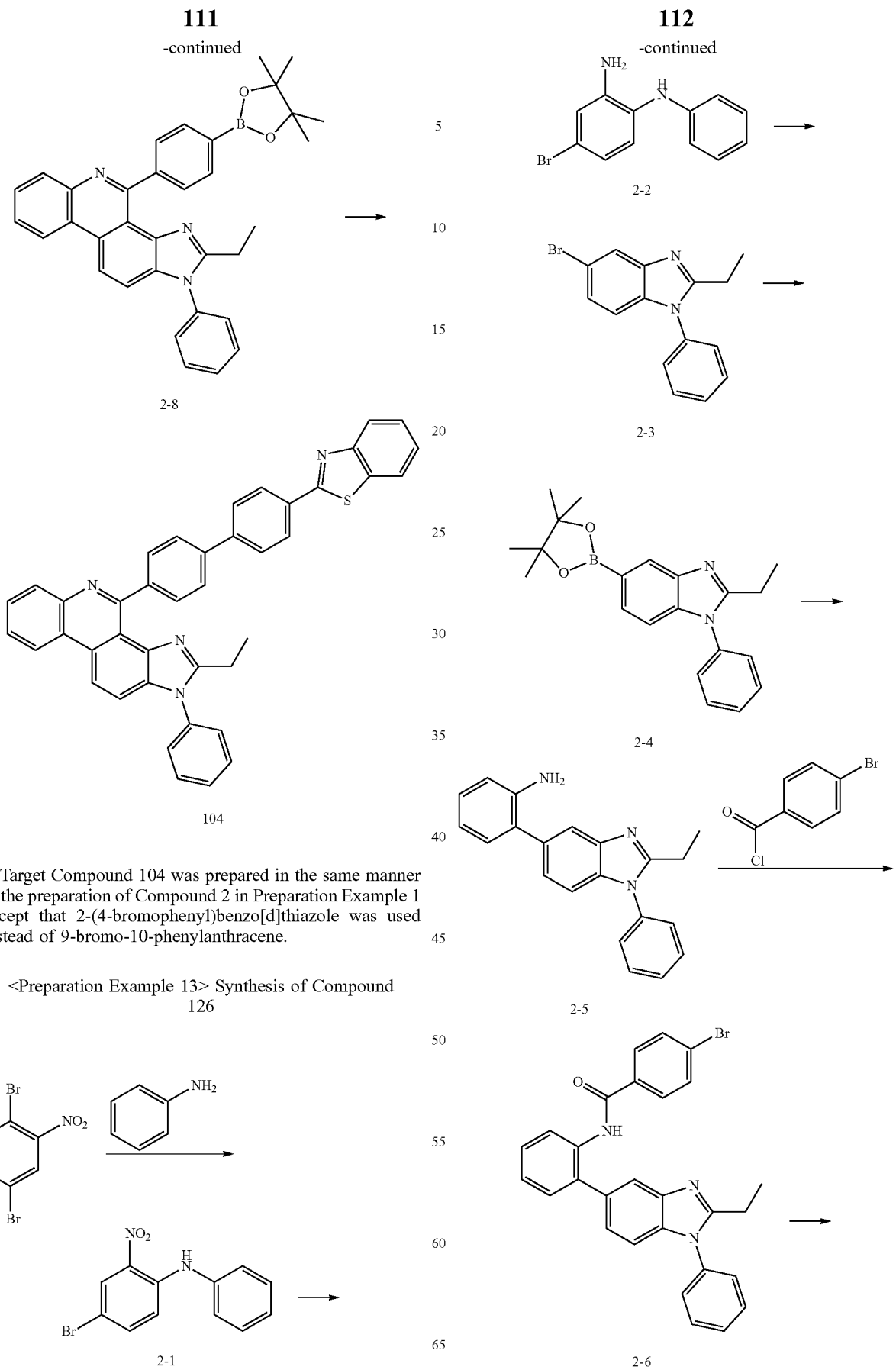
Target Compound 104 was prepared in the same manner as the preparation of Compound 2 in Preparation Example 1 except that 2-(4-bromophenyl)benzo[d]thiazole was used instead of 9-bromo-10-phenylanthracene.
<Preparation Example 13> Synthesis of Compound 126

-continued
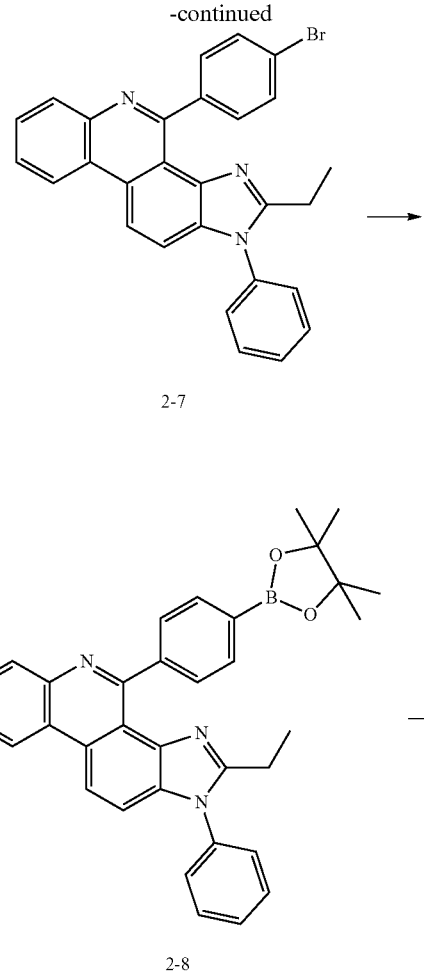
2-7
2-8
126
Target Compound 126 was prepared in the same manner as the preparation of Compound 2 in Preparation Example 1 except that 3-bromoquinoline was used instead of 9-bromo-10-phenylanthracene.
<Preparation Example 14> Synthesis of Compound 131
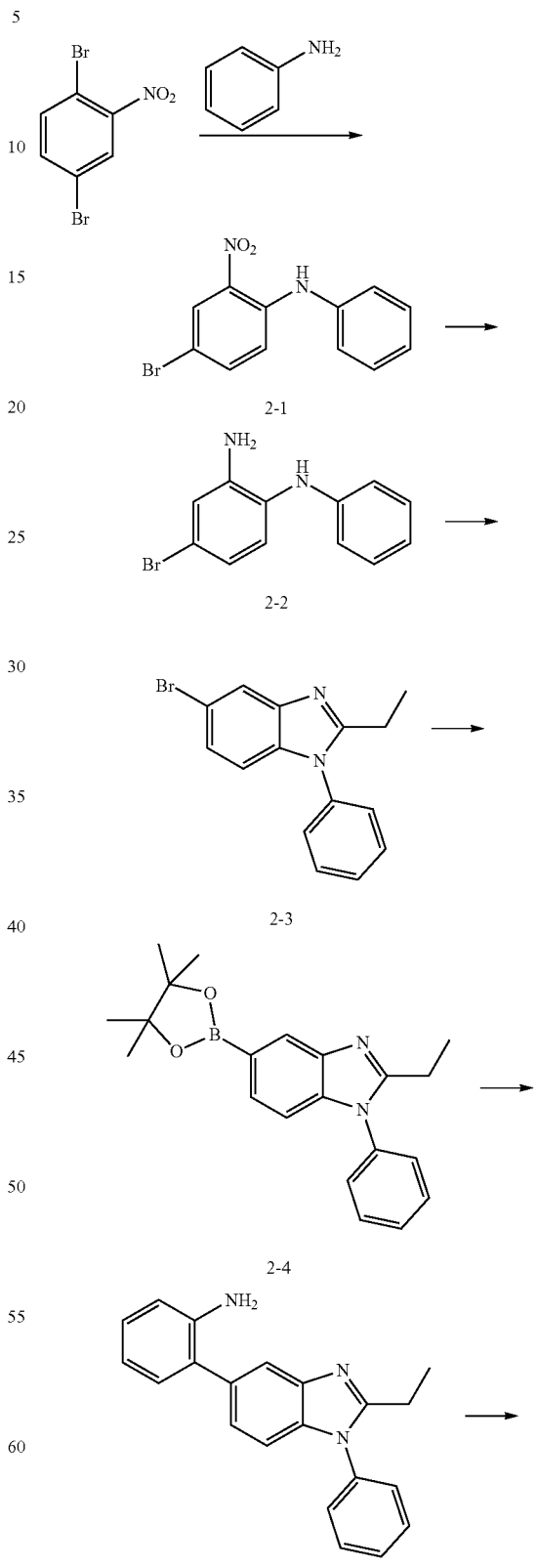
2-1
2-2
2-3
2-4
2-5

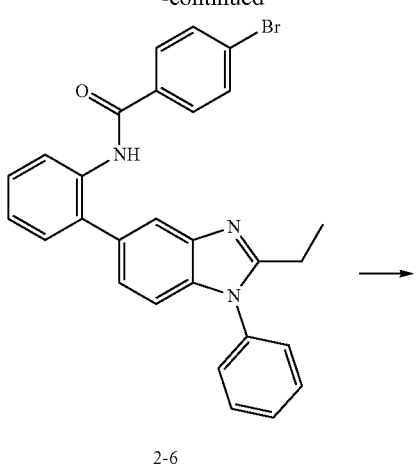
2-6
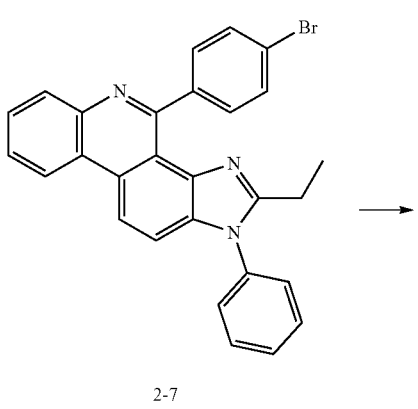
2-7
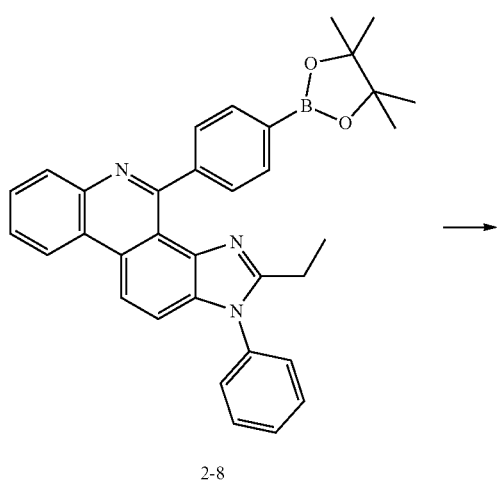
2-8
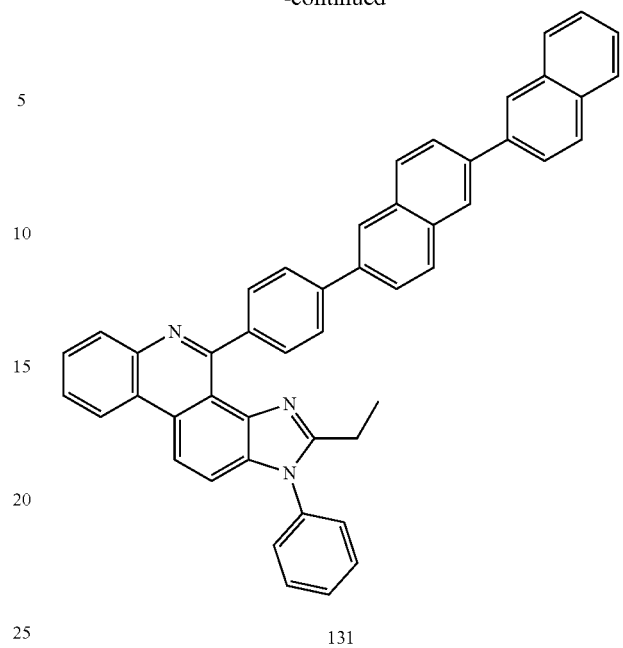
131
Target Compound 131 was prepared in the same manner as the preparation of Compound 2 in Preparation Example 1 except that 6-bromo-2,2'-binaphthalene was used instead of 9-bromo-10-phenylanthracene.
<Preparation Example 15> Synthesis of Compound 133
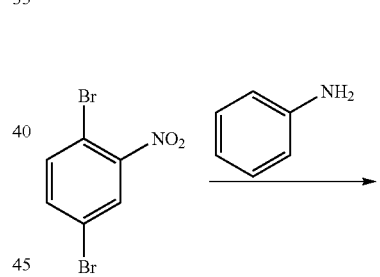
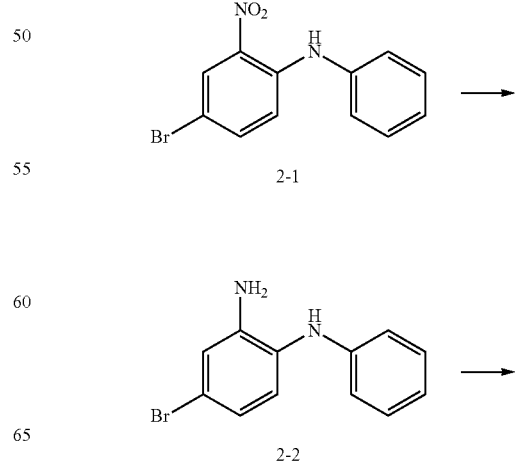
2-1
2-2

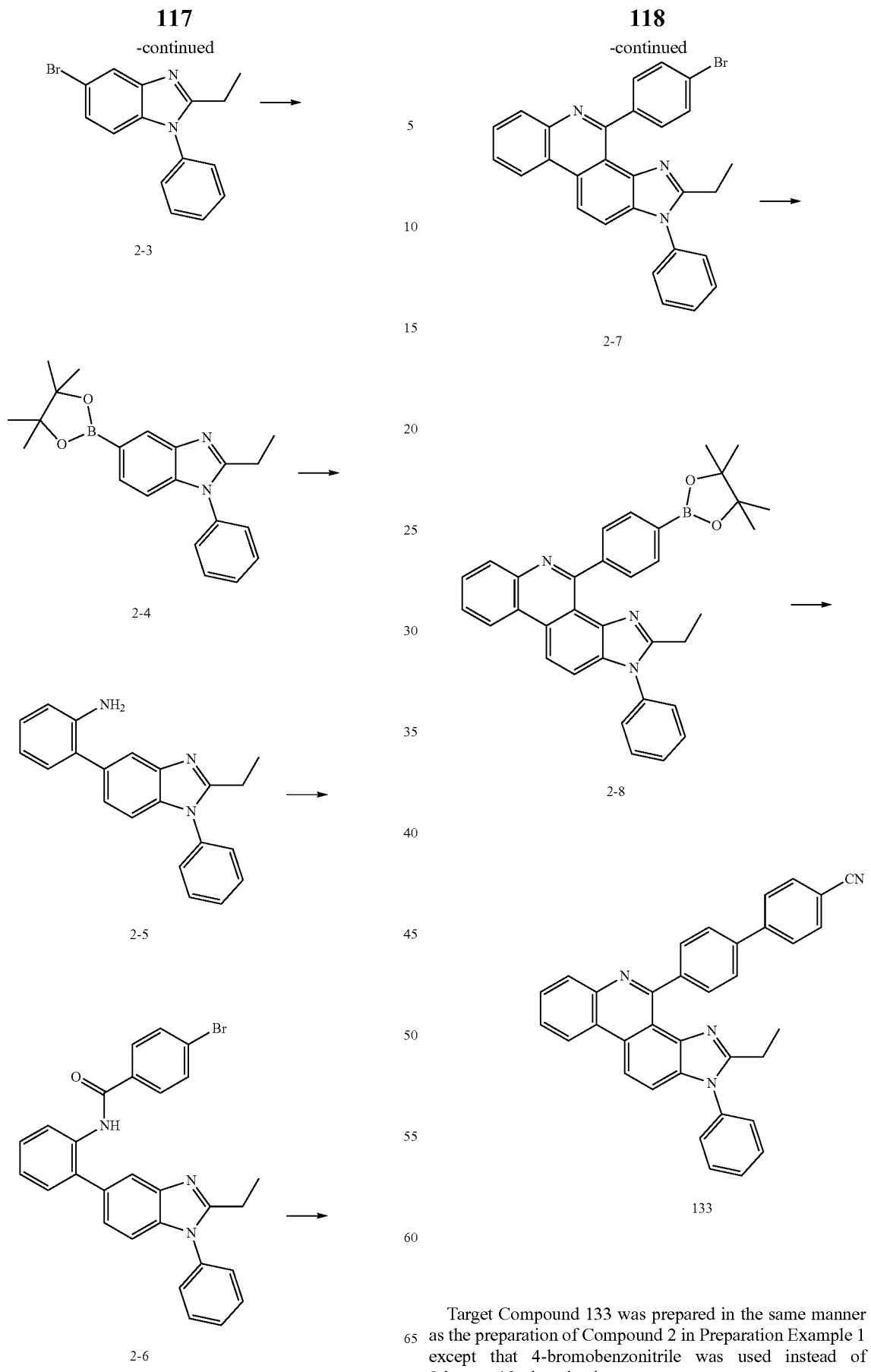
Target Compound 133 was prepared in the same manner as the preparation of Compound 2 in Preparation Example 1 except that 4-bromobenzonitrile was used instead of 9-bromo-10-phenylanthracene.

<Preparation Example 16> Synthesis of Compound 136
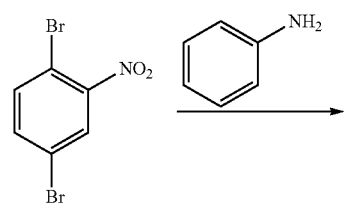
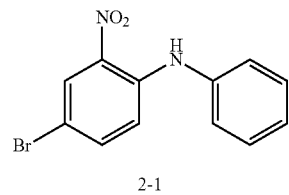
2-1
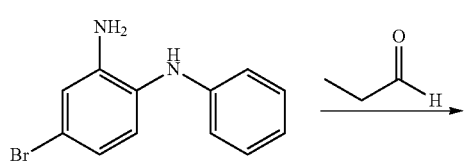
2-2
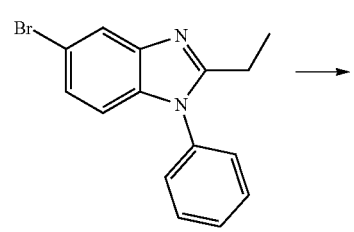
2-3
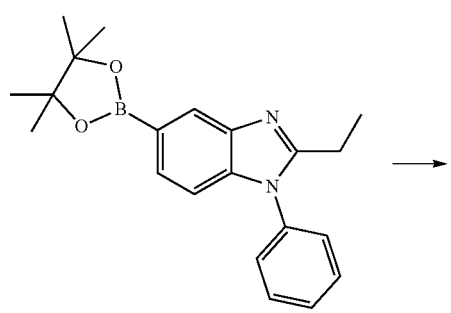
2-4
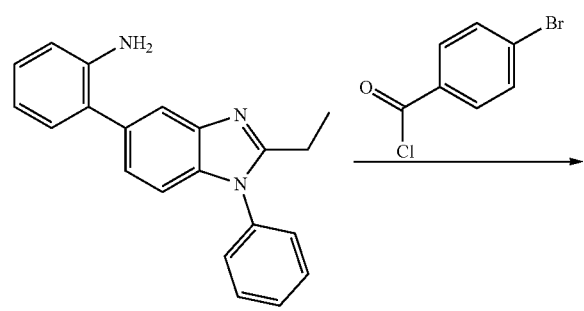
2-5
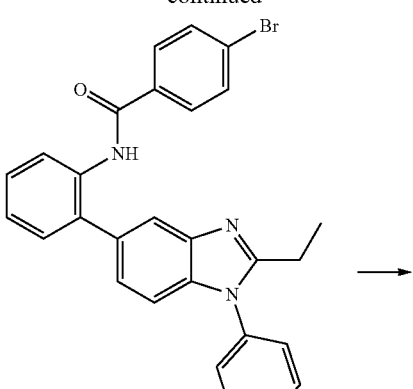
2-6
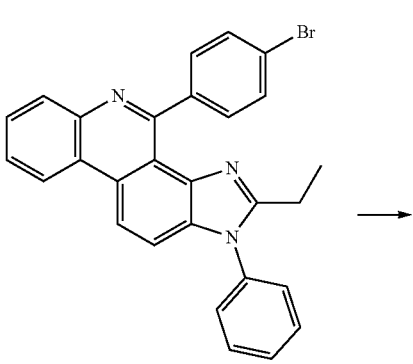
2-7
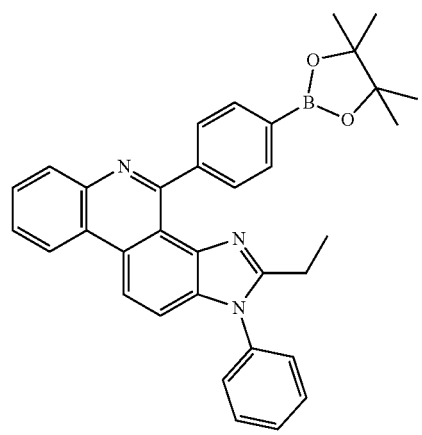
2-8

121
-continued
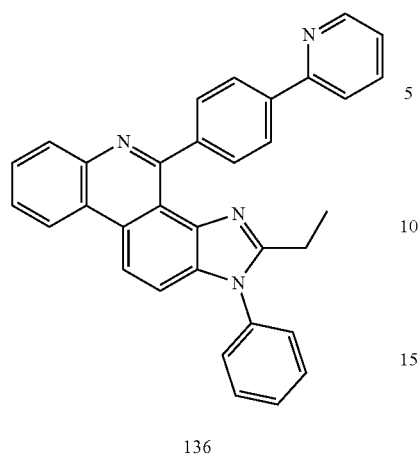
136
Target Compound 136 was prepared in the same manner as the preparation of Compound 2 in Preparation Example 1 except that 2-bromopyridine was used instead of 9-bromo-10-phenylanthracene.
<Preparation Example 17> Synthesis of Compound 152
122
-continued
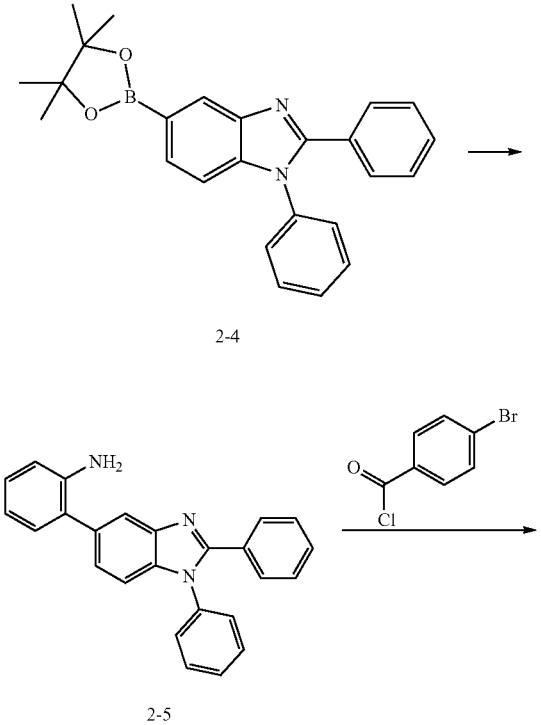
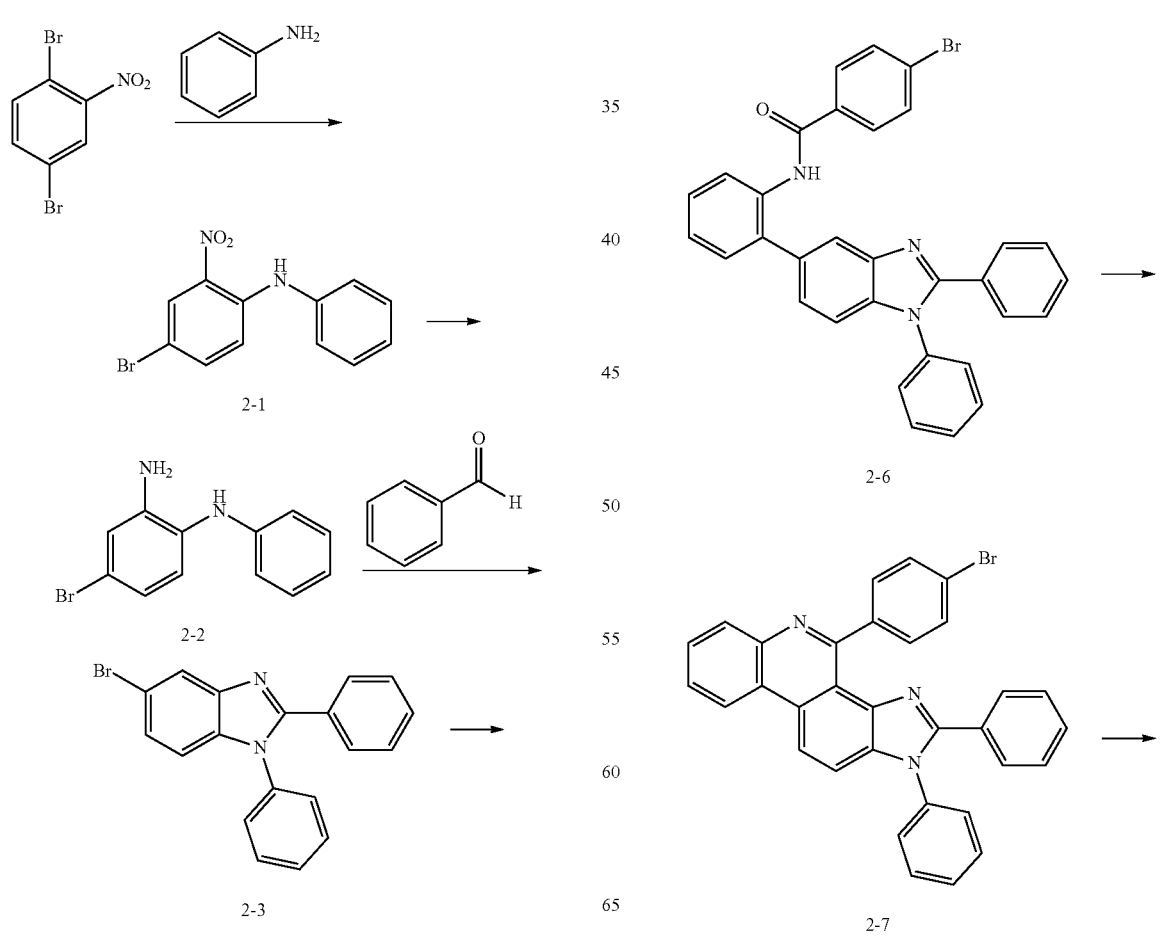

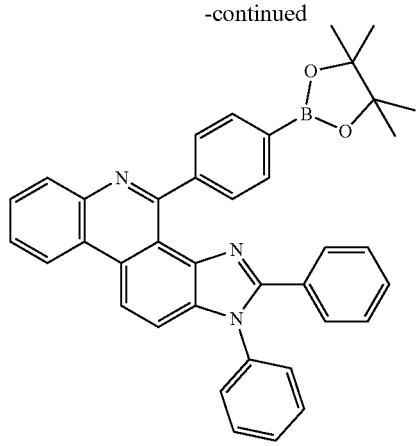
2-8
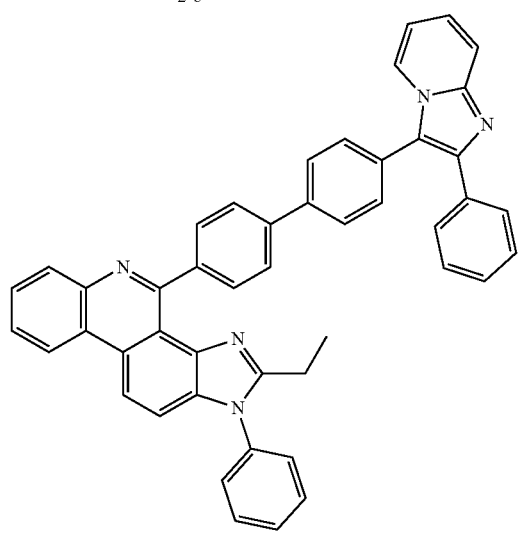
152
Target Compound 152 was prepared in the same manner as the preparation of Compound 2 in Preparation Example 1 except that 3-(4-bromophenyl)-2-phenylimidazo[1,2-a]pyridine was used instead of 9-bromo-10-phenylanthracene.
<Preparation Example 18> Synthesis of Compound 153
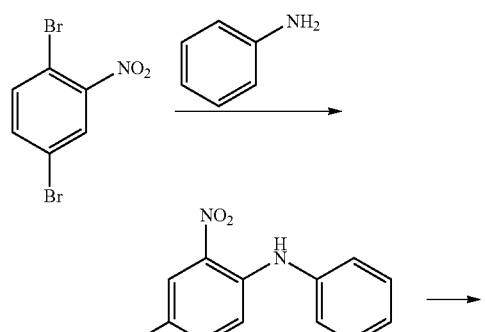
2-1
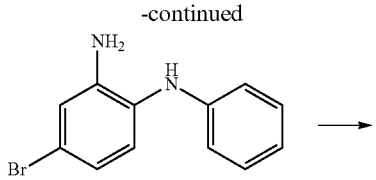
2-2
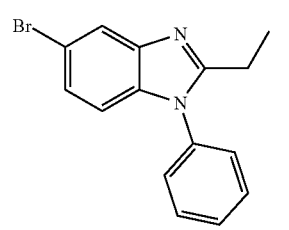
2-3
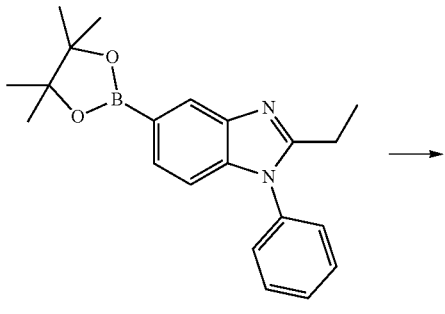
2-4
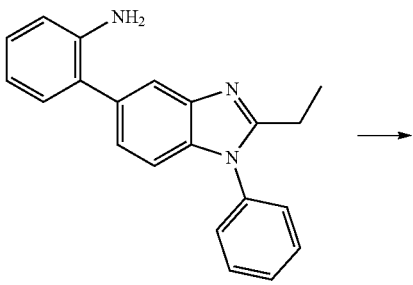
2-5
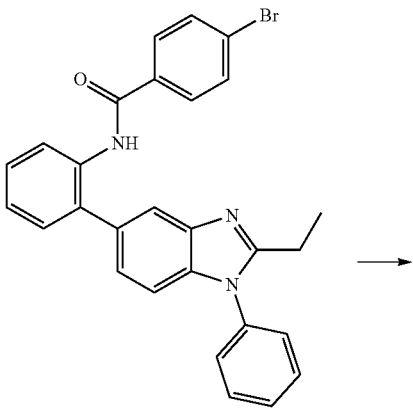
2-6

125
-continued
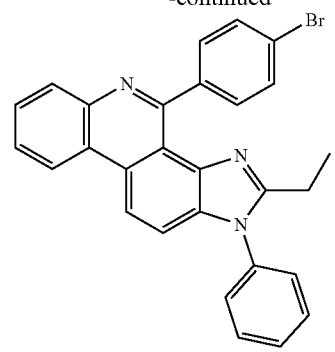
2-7
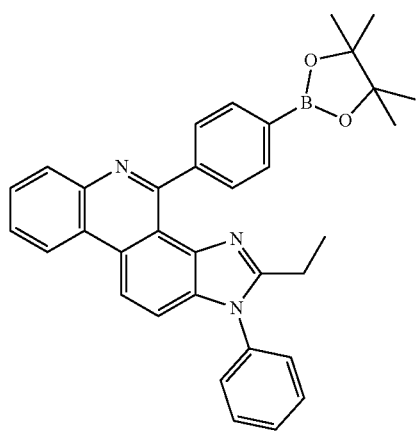
2-8
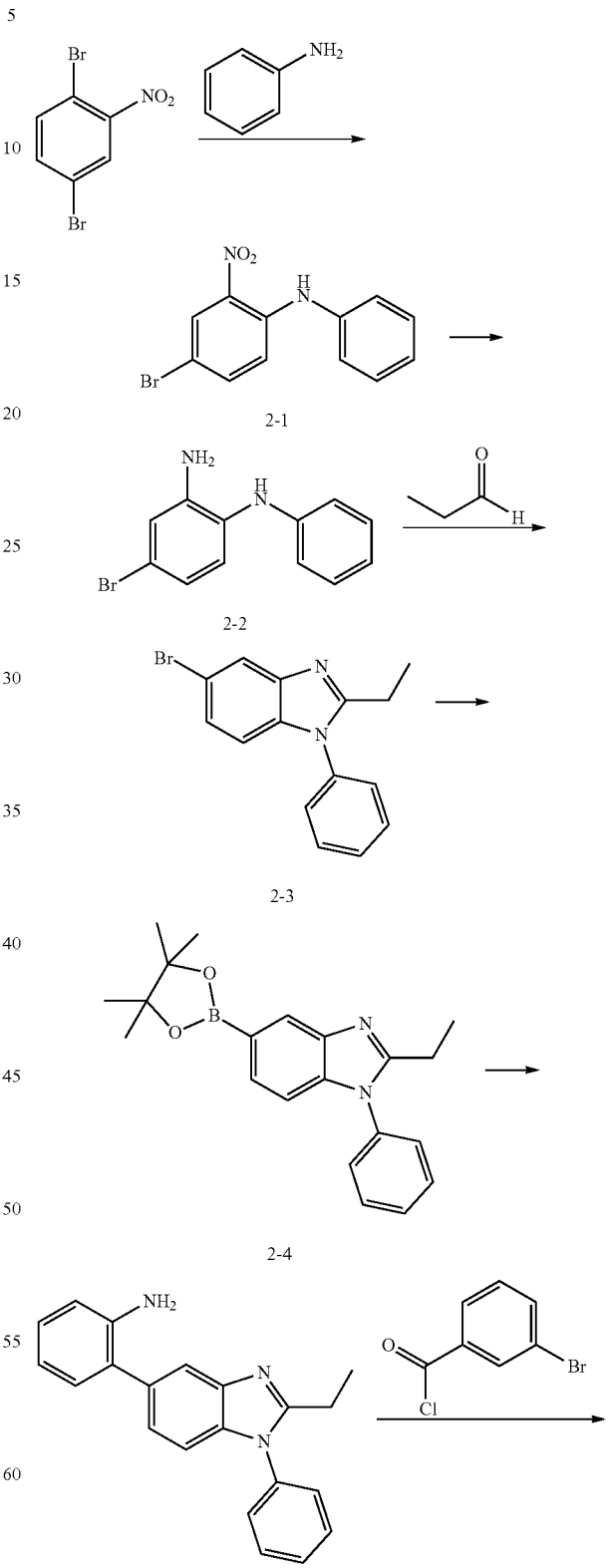
153
Target Compound 153 was prepared in the same manner as the preparation of Compound 2 in Preparation Example 1 except that 8-bromoquinoline was used instead of 9-bromo-10-phenylanthracene.
126
<Preparation Example 19> Synthesis of Compound 154

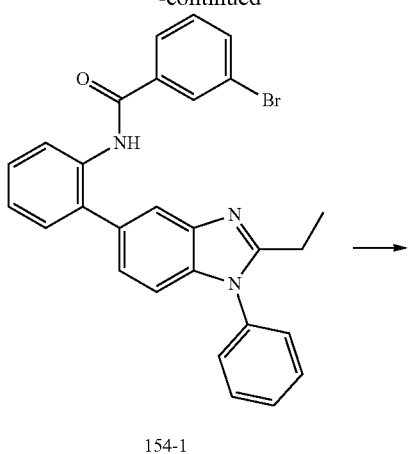

154-1

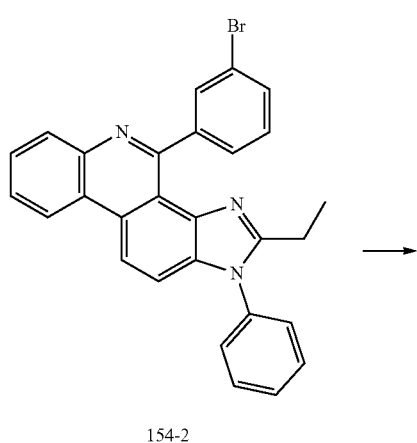

154-2

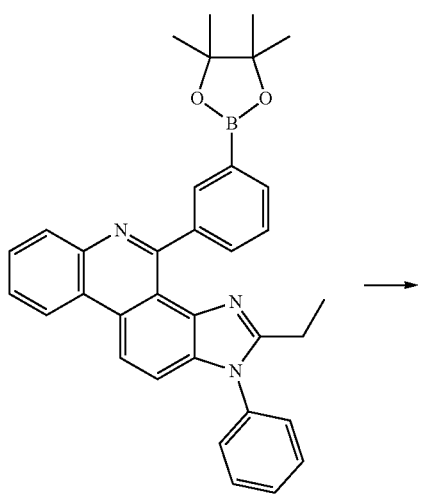

154-3

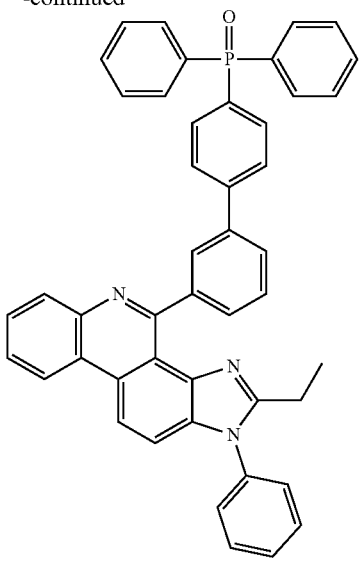

154

1) Synthesis of Compound 154-1

After dissolving Compound 2-5 (41 g, 130 mmol) in THF, 3-bromobenzoyl chloride (26 ml, 1.5 eq.) and TEA (55 ml, 3.0 eq.) were added thereto at 0° C., and the result was stirred for 2 hours at room temperature. After the reaction was completed, EA and distilled water were added to the reactor for solidification, and produced solids were collected to obtain target Compound 154-1 (43 g, 67%).

2) Synthesis of Compound 154-2

After dissolving Compound 154-1 (43 g, 878 mmol) in nitrobenzene, $POCl_3$ (8.2 ml, 1.0 eq.) was added thereto, and the result was stirred for 18 hours at 150° C. After the reaction was completed, the result was vacuum distilled to remove nitrobenzene, then cooled to room temperature, and extracted with distilled water and EA. The organic layer was dried with anhydrous $MgSO_4$, then the solvent was removed using a rotary evaporator, and the result was purified through column chromatography using dichloromethane and hexane as a developing solvent to obtain target Compound 154-2 (26 g, 62%).

3) Synthesis of Compound 154-3

After dissolving Compound 154-2 (16 g, 33.4 mmol) in 1,4-dioxane, bis(pinacolato)diborone, Pd (dppf) $Cl_2$ and potassium acetate were added thereto, and the result was stirred for 2 hours at 110° C. After the reaction was completed, the result was extracted with distilled water and EA. After drying the organic layer with anhydrous $MgSO_4$, the solvent was removed using a rotary evaporator, and target Compound 154-3 (17 g, 97%) was obtained without further purification.

4) Preparation of Compound 154

After adding (4-bromophenyl)diphenylphosphine oxide (4.2 g), $Pd(PPh_3)_4$ (0.8 g, 0.71 mmol), $K_2CO_3$ (5.8 g, 42.3 mmol) and toluene/EtOH/$H_2O$ to Compound 154-3 (8.0 g, 14.1 mmol), the result was stirred for 2 hours at 110° C. After the reaction was completed, the result was cooled to room temperature, and extracted with distilled water and EA. The organic layer was dried with anhydrous $MgSO_4$, then the solvent was removed using a rotary evaporator, and the result was purified through column chromatography using dichloromethane and hexane as a developing solvent to obtain target Compound 154 (7.4 g, 78%).
<Preparation Example 20> Synthesis of Compound 155
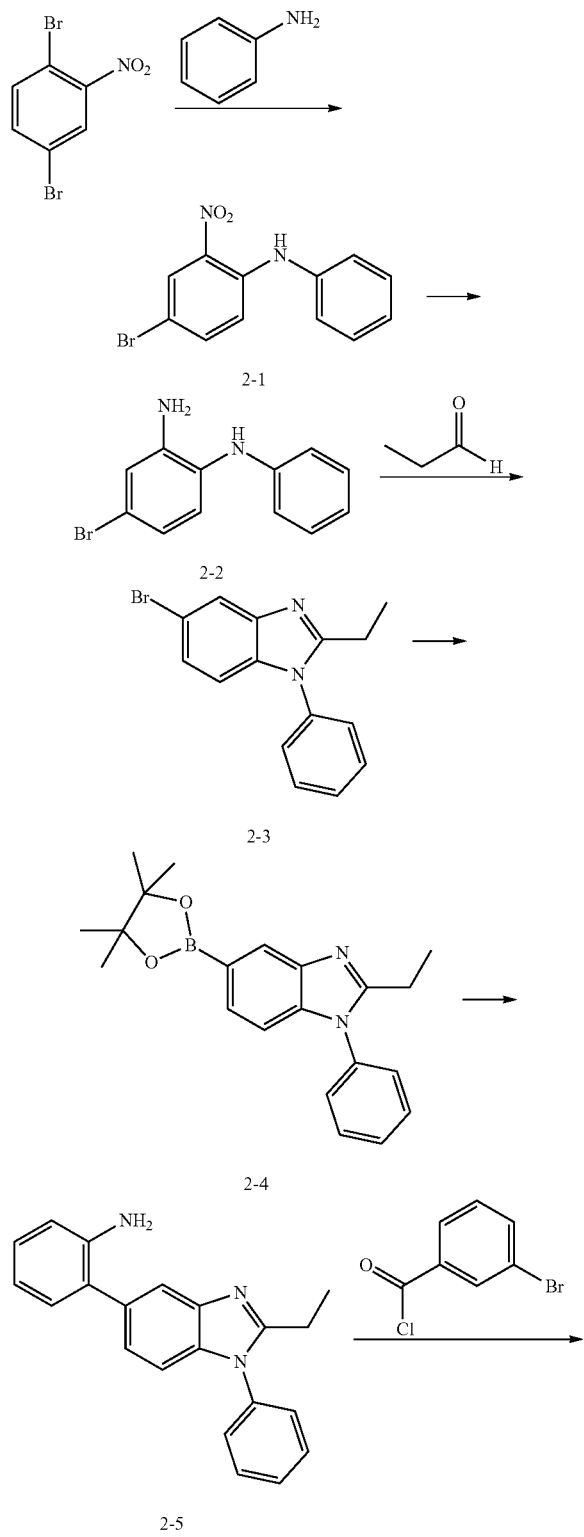
2-1
2-2
2-3
2-4
2-5
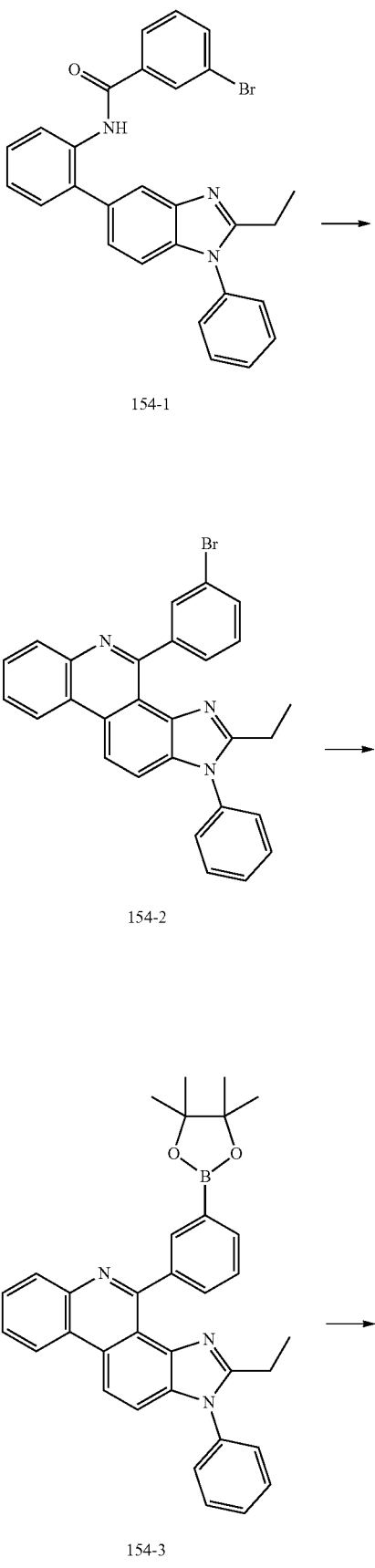
154-1
154-2
154-3

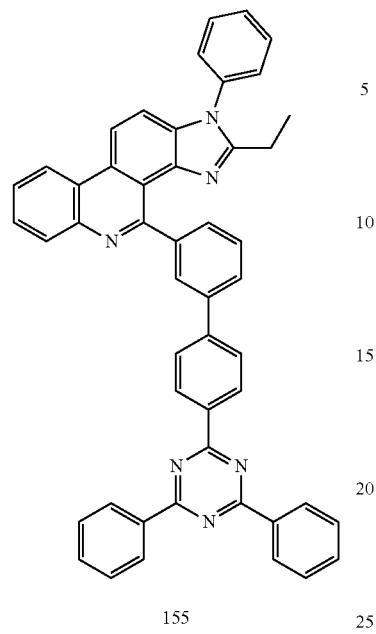
155
Target Compound 155 was prepared in the same manner as the preparation of Compound 154 in Preparation Example 19 except that 2-bromo-4,6-diphenyl-1,3,5-triazine was used instead of (4-bromophenyl)diphenylphosphine oxide.
<Preparation Example 21> Synthesis of Compound 156
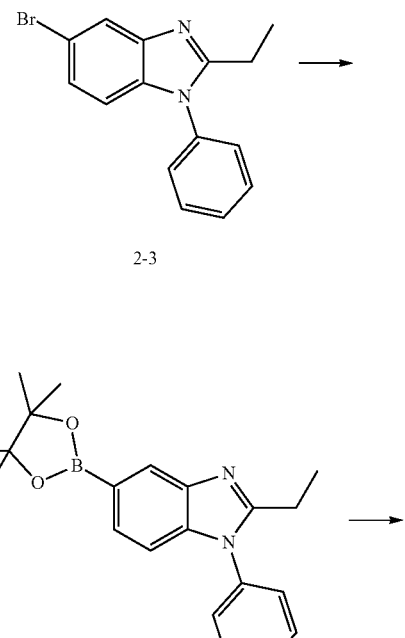
2-3
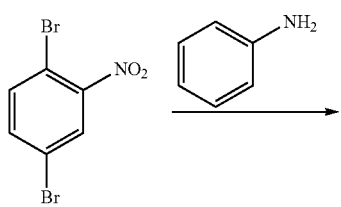
2-1
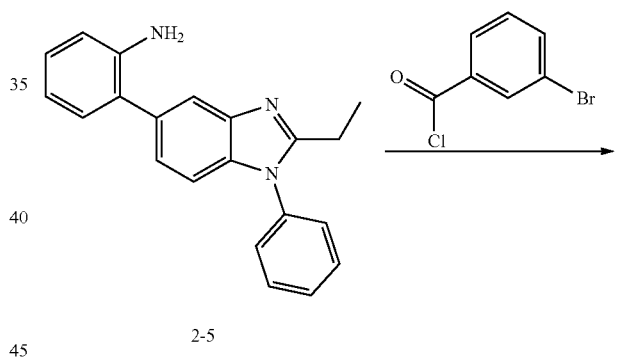
2-4
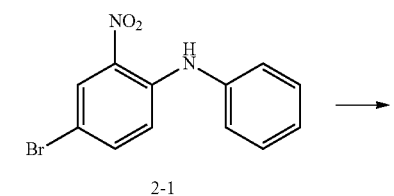
2-2
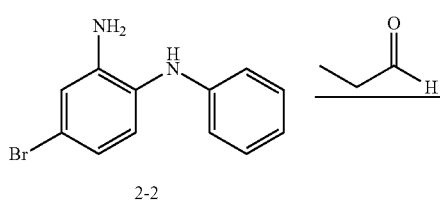
2-5
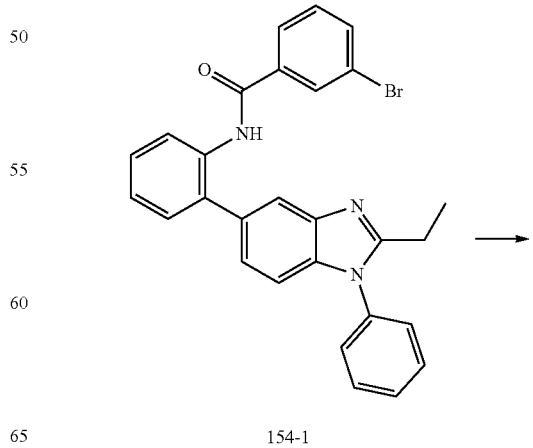
154-1

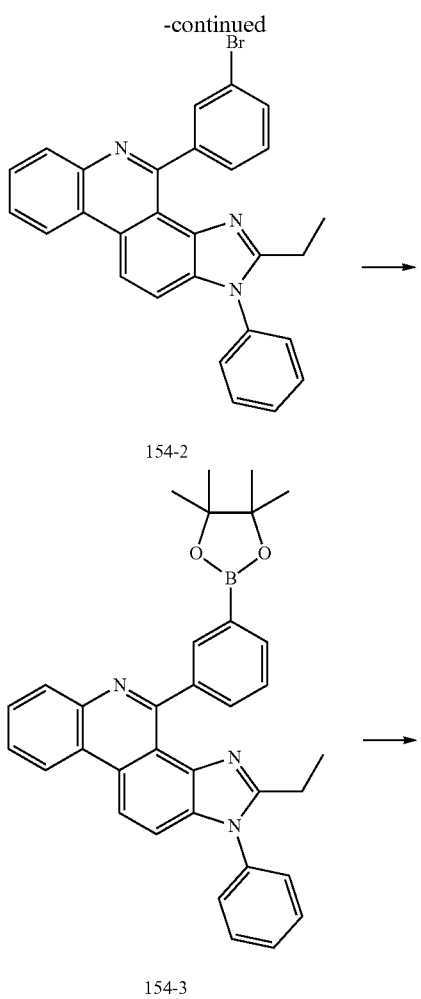
154-2
154-3
156
Target Compound 156 was prepared in the same manner as the preparation of Compound 154 in Preparation Example 19 except that 9,9'-(5-bromo-1,3-phenylene)bis(9H-carbazole) was used instead of (4-bromophenyl)diphenylphosphine oxide.
<Preparation Example 22> Synthesis of Compound 158
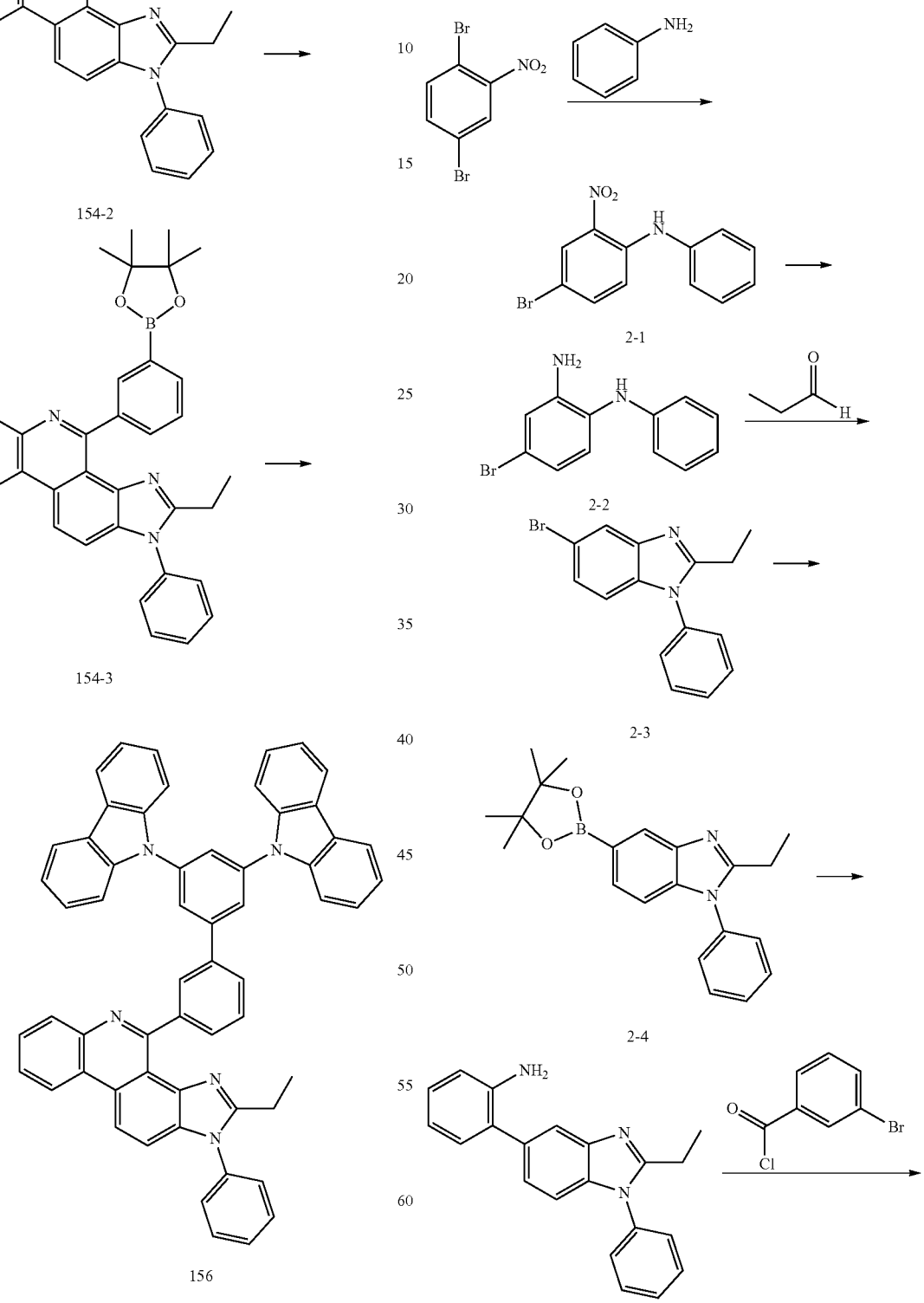
2-1
2-2
2-3
2-4
2-5

135
-continued
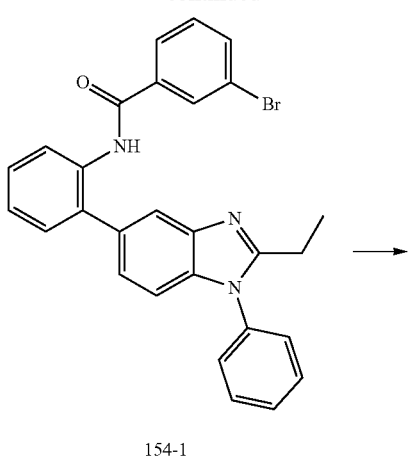
154-1
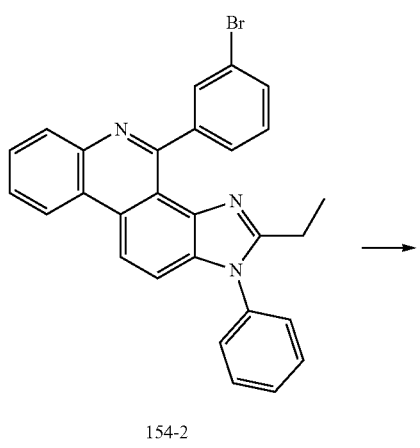
154-2
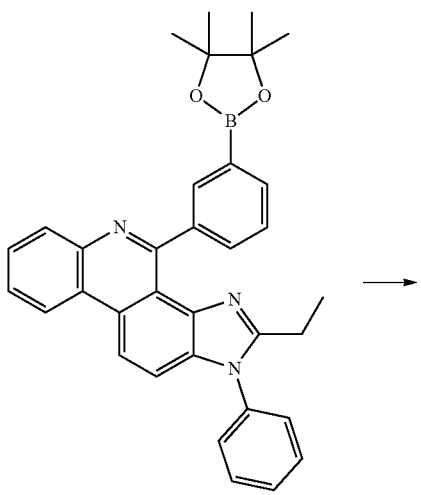
154-3
136
-continued
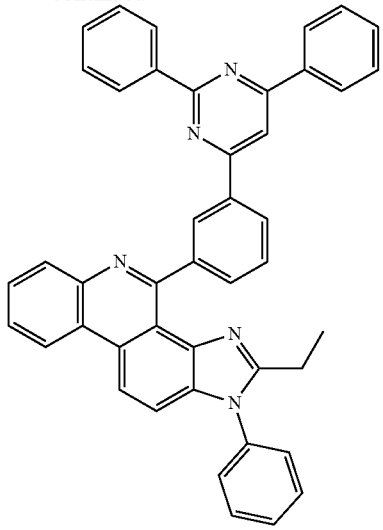
158
Target Compound 158 was prepared in the same manner as the preparation of Compound 154 in Preparation Example 19 except that 4-chloro-2,6-diphenylpyrimidine was used instead of (4-bromophenyl)diphenylphosphine oxide.
<Preparation Example 23> Synthesis of Compound 161
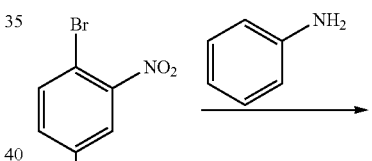
2-1
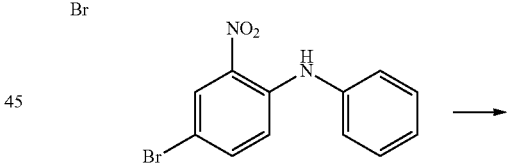
2-2
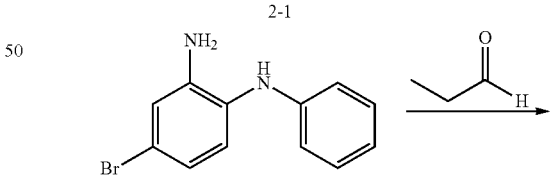
2-3

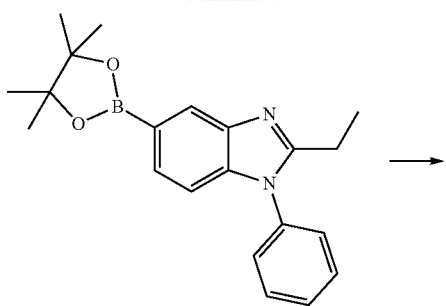
2-4
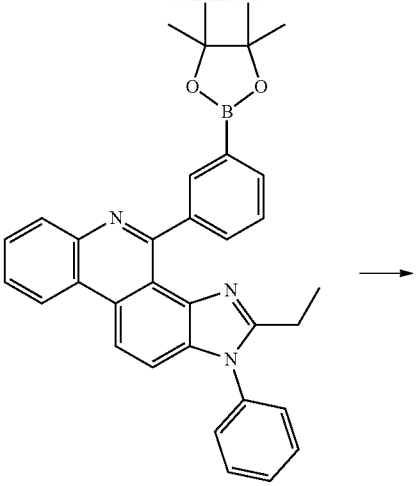
154-3
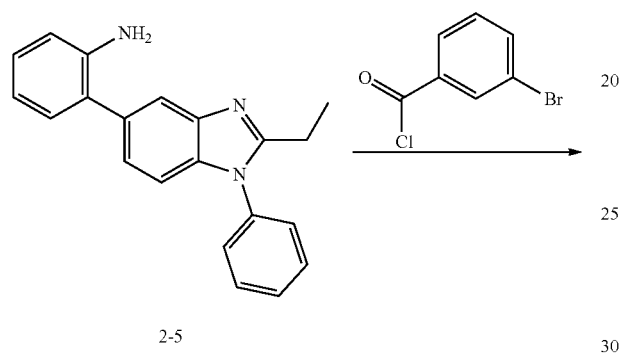
2-5
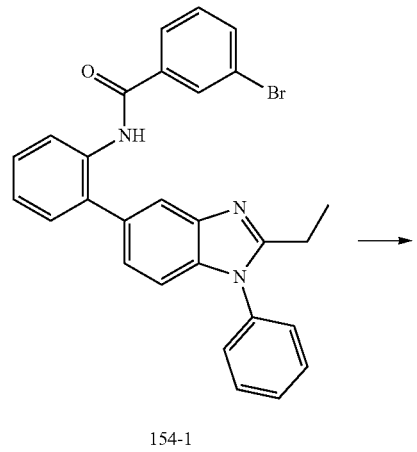
154-1
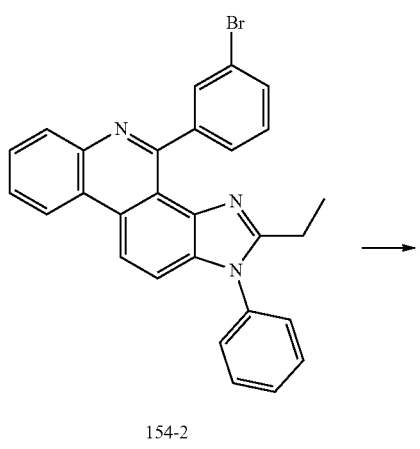
154-2
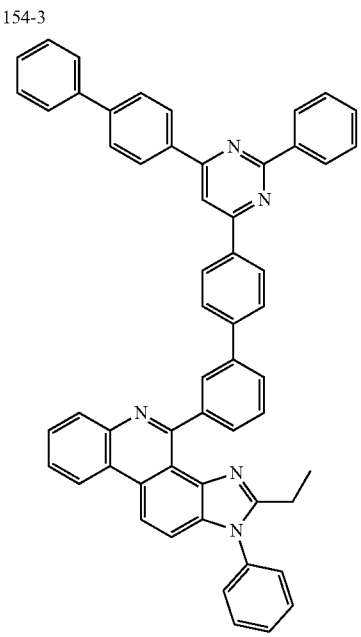
161
Target Compound 161 was prepared in the same manner as the preparation of Compound 154 in Preparation Example 19 except that 4-([1,1'-biphenyl]-4-yl)-6-(4-chlorophenyl)-2-phenylpyrimidine was used instead of (4-bromophenyl)diphenylphosphine oxide.
<Preparation Example 24> Synthesis of Compound 164
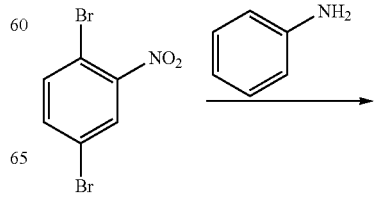

139
-continued
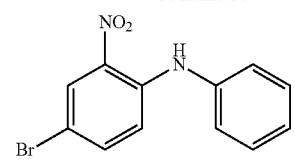
2-1
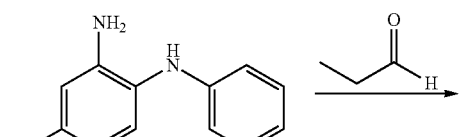
2-2
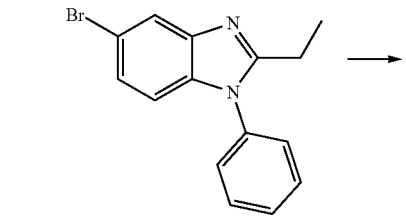
2-3
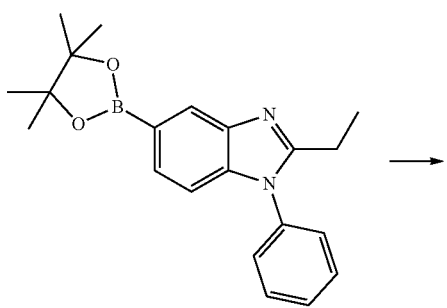
2-4
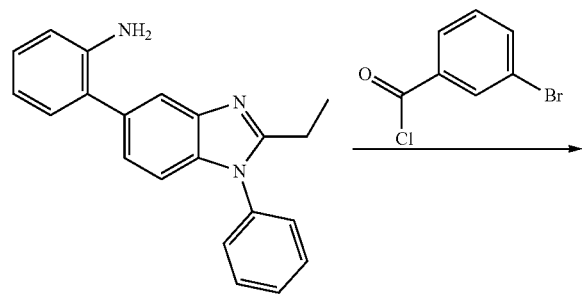
2-5
140
-continued
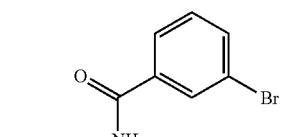
154-1
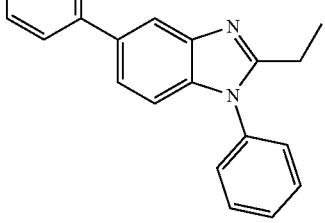
154-2
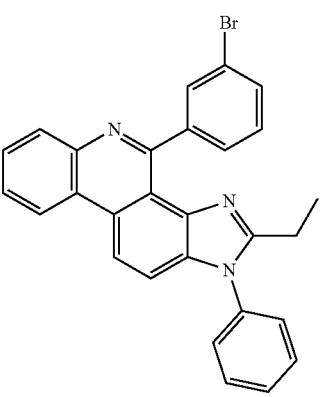
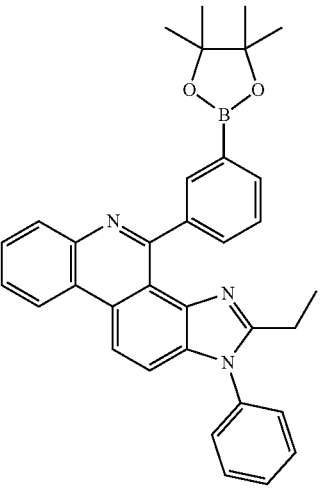
154-3

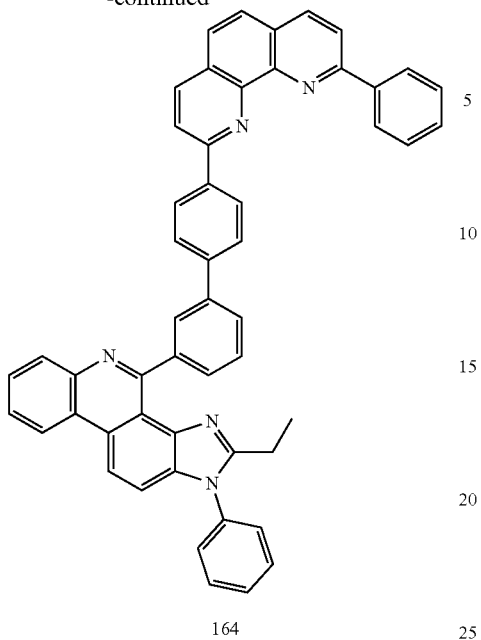
164
Target Compound 164 was prepared in the same manner as the preparation of Compound 154 in Preparation Example 19 except that 2-(4-bromophenyl)-9-phenyl-1,10-phenanthroline was used instead of (4-bromophenyl)diphenylphosphine oxide.
<Preparation Example 25> Synthesis of Compound 165
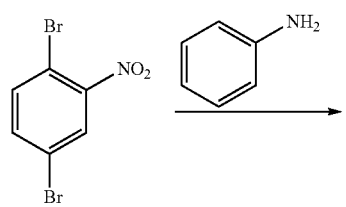
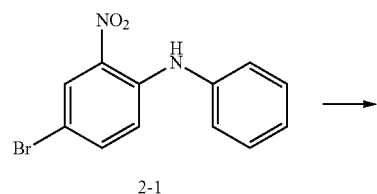
2-1
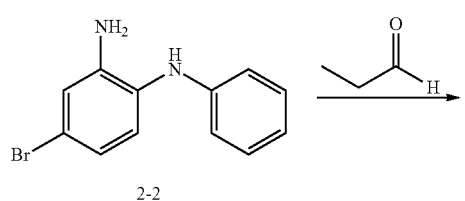
2-2
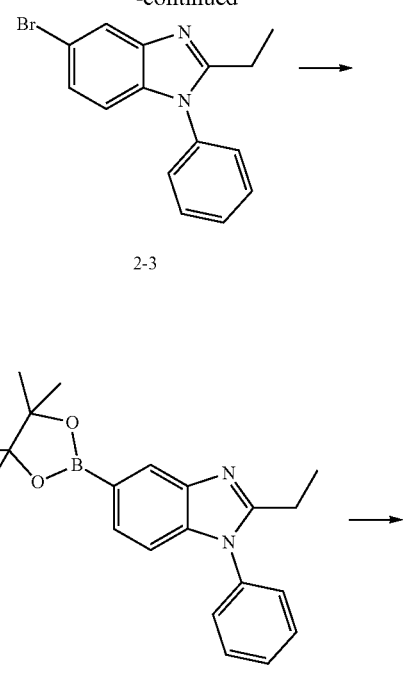
2-3
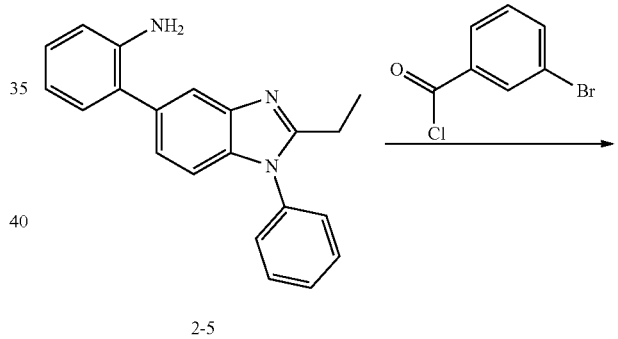
2-4
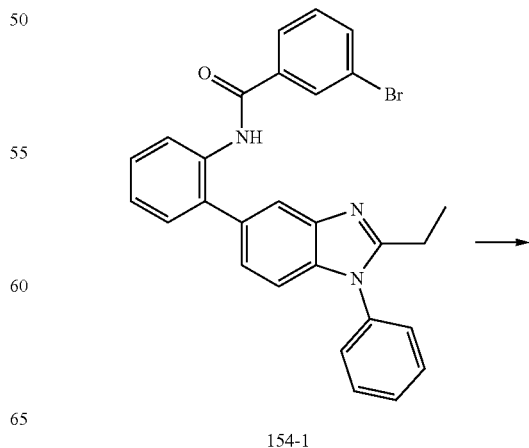
2-5
154-1

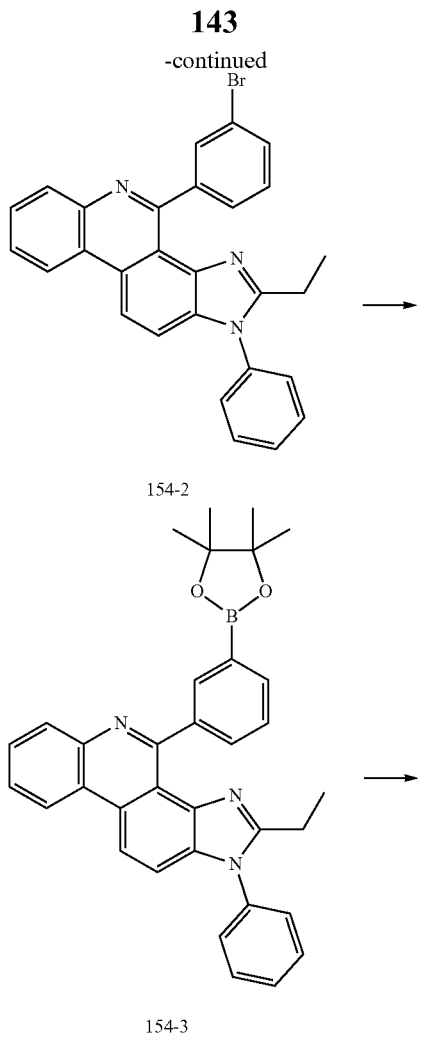

154-2

154-3

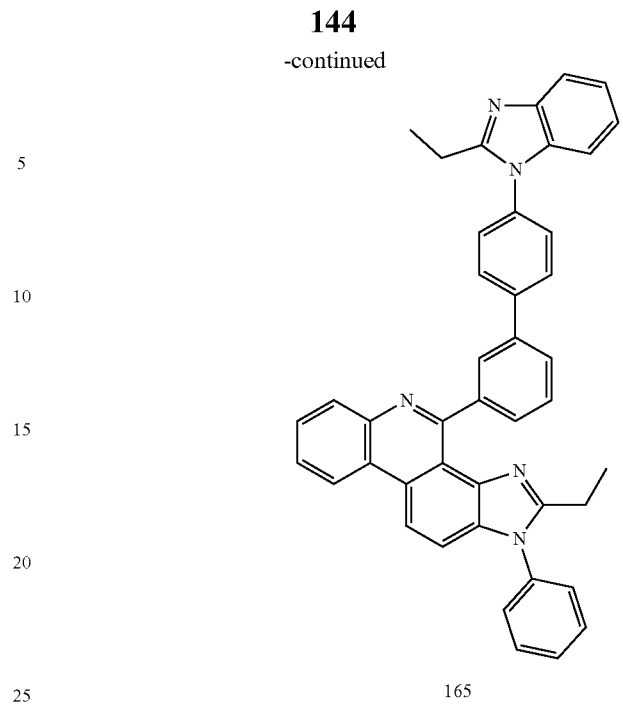

165

Target Compound 165 was prepared in the same manner as the preparation of Compound 154 in Preparation Example 19 except that 1-(4-bromophenyl)-2-ethyl-1H-benzo[d]imidazole was used instead of (4-bromophenyl)diphenylphosphine oxide.

Compounds other than the compounds described in Preparation Examples 1 to 25 were prepared in the same manner as the methods described in the preparation examples described above.

Synthesis identification data of the compounds prepared above are as described in the following [Table 1] and [Table 2].

TABLE 1

| Compound | FD-MS | Compound | FD-MS |
|---|---|---|---|
| 1 | m/z = 701.85 (C52H35N3 = 701.28) | 2 | m/z = 651.80 (C48H33N3 = 651.27) |
| 3 | m/z = 828.01 (C62H41N3 = 827.33) | 4 | m/z = 575.70 (C42H29N3 = 575.24) |
| 5 | m/z = 599.66 (C40H30N3OP = 599.21) | 6 | m/z = 675.76 (C46H34N3OP = 675.24) |
| 7 | m/z = 725.81 (C50H36N3OP = 725.26) | 8 | m/z = 725.81 (C50H36N3OP = 725.26) |
| 9 | m/z = 775.87 (C54H38N3OP = 775.28) | 10 | m/z = 805.96 (C58H39N5 = 805.32) |
| 11 | m/z = 630.74 (C43H30N6 = 630.25) | 12 | m/z = 632.71 (C41H28N8 = 632.24) |
| 13 | m/z = 632.71 (C41H28N8 = 632.24) | 14 | m/z = 632.71 (C41H28N8 = 632.24) |
| 15 | m/z = 730.86 (C51H34N6 = 730.28) | 16 | m/z = 730.86 (C51H34N6 = 730.28) |
| 17 | m/z = 706.83 (C49H34N6 = 706.28) | 18 | m/z = 756.89 (C53H36N6 = 756.30) |
| 19 | m/z = 629.75 (C44H31N5 = 629.26) | 20 | m/z = 631.73 (C42H29N7 = 631.25) |
| 21 | m/z = 631.73 (C42H29N7 = 631.25) | 22 | m/z = 631.73 (C42H29N7 = 631.25) |
| 23 | m/z = 729.87 (C52H35N5 = 729.29) | 24 | m/z = 729.87 (C52H35N5 = 729.29) |
| 25 | m/z = 705.85 (C50H35N5 = 705.29) | 26 | m/z = 781.94 (C56H39N5 = 781.32) |
| 27 | m/z = 705.85 (C50H35N5 = 705.29) | 28 | m/z = 781.94 (C56H39N5 = 781.32) |

TABLE 1-continued

| Compound | FD-MS | Compound | FD-MS |
|---|---|---|---|
| 29 | m/z = 705.85 (C50H35N5 = 705.29) | 30 | m/z = 805.96 (C58H39N5 = 805.32) |
| 31 | m/z = 805.96 (C58H39N5 = 805.32) | 32 | m/z = 781.94 (C56H39N5 = 781.32) |
| 33 | m/z = 858.04 (C62H43N5 = 857.35) | 34 | m/z = 781.94 (C56H39N5 = 781.32) |
| 35 | m/z = 858.04 (C62H43N5 = 857.35) | 36 | m/z = 755.91 (C54H37N5 = 755.30) |
| 37 | m/z = 629.75 (C44H31N5 = 629.26) | 38 | m/z = 631.73 (C42H29N7 = 631.25) |
| 39 | m/z = 631.73 (C42H29N7 = 631.25) | 40 | m/z = 631.73 (C42H29N7 = 631.25) |
| 41 | m/z = 729.87 (C52H35N5 = 729.29) | 42 | m/z = 729.87 (C52H35N5 = 729.29) |
| 43 | m/z = 705.85 (C50H35N5 = 705.29) | 44 | m/z = 781.94 (C56H39N5 = 781.32) |
| 45 | m/z = 705.85 (C50H35N5 = 705.29) | 46 | m/z = 781.94 (C56H39N5 = 781.32) |
| 47 | m/z = 705.85 (C50H35N5 = 705.29) | 48 | m/z = 805.96 (C58H39N5 = 805.32) |
| 49 | m/z = 805.96 (C58H39N5 = 805.32) | 50 | m/z = 781.94 (C56H39N5 = 781.32) |
| 51 | m/z = 858.04 (C62H43N5 = 857.35) | 52 | m/z = 781.94 (C56H39N5 = 781.32) |
| 53 | m/z = 858.04 (C62H43N5 = 857.35) | 54 | m/z = 832.00 (C60H41N5 = 831.34) |
| 55 | m/z = 679.81 (C48H33N5 = 679.27) | 56 | m/z = 603.71 (C42H29N5 = 603.24) |
| 57 | m/z = 679.81 (C48H33N5 = 679.27) | 58 | m/z = 653.77 (C46H31N5 = 653.26) |
| 59 | m/z = 653.77 (C46H31N5 = 653.26) | 60 | m/z = 755.91 (C54H37N5 = 755.30) |
| 61 | m/z = 679.81 (C48H33N5 = 679.27) | 62 | m/z = 755.91 (C54H37N5 = 755.30) |
| 63 | m/z = 729.87 (C52H35N5 = 729.29) | 64 | m/z = 729.87 (C52H35N5 = 729.29) |
| 65 | m/z = 755.91 (C54H37N5 = 755.30) | 66 | m/z = 679.81 (C48H33N5 = 679.27) |
| 67 | m/z = 755.91 (C54H37N5 = 755.30) | 68 | m/z = 729.87 (C52H35N5 = 729.29) |
| 69 | m/z = 729.87 (C52H35N5 = 729.29) | 70 | m/z = 705.85 (C50H35N5 = 705.29) |
| 71 | m/z = 858.04 (C62H43N5 = 857.35) | 72 | m/z = 858.04 (C62H43N5 = 857.35) |
| 73 | m/z = 805.96 (C58H39N5 = 805.32) | 74 | m/z = 805.96 (C58H39N5 = 805.32) |
| 75 | m/z = 781.94 (C56H39N5 = 781.32) | 76 | m/z = 781.94 (C56H39N5 = 781.32) |
| 77 | m/z = 781.94 (C56H39N5 = 781.32) | 78 | m/z = 755.91 (C54H37N5 = 755.30) |
| 79 | m/z = 755.91 (C54H37N5 = 755.30) | 80 | m/z = 603.71 (C42H29N5 = 603.24) |
| 81 | m/z = 679.81 (C48H33N5 = 679.27) | 82 | m/z = 679.81 (C48H33N5 = 679.27) |
| 83 | m/z = 679.81 (C48H33N5 = 679.27) | 84 | m/z = 755.91 (C54H37N5 = 755.30) |
| 85 | m/z = 755.91 (C54H37N5 = 755.30) | 86 | m/z = 679.81 (C48H33N5 = 679.27) |
| 87 | m/z = 755.91 (C54H37N5 = 755.30) | 88 | m/z = 755.91 (C54H37N5 = 755.30) |
| 89 | m/z = 577.68 (C40H27N5 = 577.23) | 90 | m/z = 653.77 (C46H31N5 = 653.26) |
| 91 | m/z = 653.77 (C46H31N5 = 653.26) | 92 | m/z = 591.70 (C41H29N5 = 591.24) |
| 93 | m/z = 591.70 (C41H29N5 = 591.24) | 94 | m/z = 591.70 (C41H29N5 = 591.24) |
| 95 | m/z = 591.70 (C41H29N5 = 591.24) | 96 | m/z = 543.66 (C37H29N5 = 543.24) |
| 97 | m/z = 619.76 (C43H33N5 = 619.27) | 98 | m/z = 619.76 (C43H33N5 = 619.27) |
| 99 | m/z = 667.80 (C47H33N5 = 667.27) | 100 | m/z = 667.80 (C47H33N5 = 667.27) |
| 101 | m/z = 619.76 (C43H33N5 = 619.27) | 102 | m/z = 619.76 (C43H33N5 = 619.27) |
| 103 | m/z = 543.66 (C37H29N5 = 543.24) | 104 | m/z = 608.75 (C41H28N4S = 608.20) |
| 105 | m/z = 658.81 (C45H30N4S = 658.22) | 106 | m/z = 608.75 (C41H28N4S = 608.20) |

TABLE 1-continued

| Compound | FD-MS | Compound | FD-MS |
|---|---|---|---|
| 107 | m/z = 608.75 (C41H28N4S = 608.20) | 108 | m/z = 608.75 (C41H28N4S = 608.20) |
| 109 | m/z = 628.76 (C45H32N4 = 628.26) | 110 | m/z = 704.86 (C51H36N4 = 704.29) |
| 111 | m/z = 630.74 (C43H30N6 = 630.25) | 112 | m/z = 630.74 (C43H30N6 = 630.25) |
| 113 | m/z = 630.74 (C43H30N6 = 630.25) | 114 | m/z = 706.83 (C49H34N6 = 706.28) |
| 115 | m/z = 706.83 (C49H34N6 = 706.28) | 116 | m/z = 706.83 (C49H34N6 = 706.28) |
| 117 | m/z = 553.65 (C38H27N5 = 553.23) | 118 | m/z = 553.65 (C38H27N5 = 553.23) |
| 119 | m/z = 553.65 (C38H27N5 = 553.23) | 120 | m/z=629.75 (C44H31N5 = 629.26) |
| 121 | m/z = 629.75 (C44H31N5 = 629.26) | 122 | m/z=629.75 (C44H31N5 = 629.26) |
| 123 | m/z = 627.77 (C46H33N3 = 627.27) | 124 | m/z = 718.85 (C50H34N6 = 718.28) |
| 125 | m/z = 565.67 (C39H27N5 = 565.23) | 126 | m/z = 526.63 (C37H26N4 = 526.22) |
| 127 | m/z = 526.63 (C37H26N4 = 526.22) | 128 | m/z = 527.62 (C36H25N5 = 527.21) |
| 129 | m/z = 527.62 (C36H25N5 = 527.21) | 130 | m/z = 543.62 (C36H25N5O = 543.21) |
| 131 | m/z = 651.80 (C48H33N3 = 651.27) | 132 | m/z = 625.76 (C46H31N3 = 625.25) |
| 133 | m/z = 500.59 (C35H24N4 = 500.20) | 134 | m/z = 576.69 (C41H28N4 = 576.23) |
| 135 | m/z = 626.75 (C45H30N4 = 626.25) | 136 | m/z=476.57 (C33H24N4 = 476.20) |
| 137 | m/z = 552.67 (C39H28N4 = 552.23) | 138 | m/z = 602.73 (C43H30N4 = 602.25) |
| 139 | m/z = 602.73 (C43H30N4 = 602.25) | 140 | m/z = 707.82 (C48H33N7 = 707.28) |
| 141 | m/z = 860.01 (C60H41N7 = 859.34) | 142 | m/z = 807.94 (C56H37N7 = 807.31) |
| 143 | m/z = 807.94 (C56H37N7 = 807.31) | 144 | m/z = 706.83 (C49H34N6 = 706.28) |
| 145 | m/z = 782.93 (C55H38N6 = 782.32) | 146 | m/z = 706.83 (C49H34N6 = 706.28) |
| 147 | m/z = 782.93 (C55H38N6 = 782.32) | 148 | m/z = 756.89 (C53H36N6 = 756.30) |
| 149 | m/z = 782.93 (C55H38N6 = 782.32) | 150 | m/z = 680.80 (C47H32N6 = 680.27) |
| 151 | m/z = 591.70 (C41H29N5 = 591.24) | 152 | m/z = 667.80 (C47H33N5 = 667.27) |
| 153 | m/z = 526.63 (C37H26N4 = 526.22) | 154 | m/z = 675.76 (C46H34N3OP = 675.24) |
| 155 | m/z = 706.83 (C49H34N6 = 706.28) | 156 | m/z = 805.96 (C58H39N5 = 805.32) |
| 157 | m/z = 629.75 (C44H31N5 = 629.26) | 158 | m/z=629.75 (C44H31N5 = 629.26) |
| 159 | m/z = 729.87 (C52H35N5 = 729.29) | 160 | m/z = 781.94 (C56H39N5 = 781.32) |
| 161 | m/z = 781.94 (C56H39N5 = 781.32) | 162 | m/z = 755.91 (C54H37N5 = 755.30) |
| 163 | m/z = 653.77 (C46H31N5 = 653.26) | 164 | m/z = 729.87 (C52H35N5 = 729.29) |
| 165 | m/z = 619.76 (C43H33N5 = 619.27) | 166 | m/z = 704.86 (C51H36N4 = 704.29) |
| 167 | m/z = 500.59 (C35H24N4 = 500.20) | | |

TABLE 2

| NO | $^1$H NMR (CDCl$_3$, 300 Mz) |
|---|---|
| 2 | 8.69(d, 2H), 8.21-8.20(m, 5H), 7.94(d, 1H), 7.85-7.83(m, 2H), 7.70-7.37(m, 16H), 7.25(d, 2H), 2.85(q, 2H), 1.30(t, 3H) |
| 3 | 8.99(s, 1H), 8.69(d, 2H), 8.42(d, 1H), 8.20(d, 3H), 8.09-7.83(m, 11H), 7.70-7.38(m, 18H), 2.85(q, 2H), 1.30(t, 3H) |
| 4 | 9.08(d, 1H), 8.84(d, 1H), 8.69(d, 2H), 8.27(d, 1H), 8.20(d, 1H), 8.05(s, 1H), 7.94-7.83(m, 4H), 7.70-7.38(m, 11H), 7.25(d, 2H), 2.85(q, 2H), 1.30(t, 3H) |
| 5 | 8.36(d, 2H), 8.20(d, 1H), 7.96-7.94(m, 3H), 7.85-7.48(m, 17H), 7.38(d, 2H), 2.85(q, 2H), 1.30(t, 3H) |
| 7 | 8.69(d, 2H), 8.43(s, 1H), 8.20-8.16(m, 2H), 8.03-7.94(m, 3H), 7.85-7.48(m, 20H), 7.38(d, 3H), 2.85(q, 2H), 1.30(t, 3H) |
| 9 | 8.69(d, 2H), 8.20-8.16(m, 5H), 7.94(d, 2H), 7.85-7.38(m, 23H), 7.25(d, 2H), 2.85(q, 2H), 1.30(t, 3H) |
| 10 | 8.20-8.17(m, 5H), 7.94(d, 3H), 7.85-7.83(m, 4H), 7.70-7.48(m, 10H), 7.38-7.35(m, 4H), 7.20-7.16(m, 4H), 2.85(q, 2H), 1.30(t, 3H) |
| 11 | 8.36(d, 4H), 8.20(d, 2H), 7.96-7.94(m, 3H), 7.85-7.83(t, 2H), 7.70-7.48(m, 11H), 7.38(d, 2H), 2.85(q, 2H), 1.30(t, 3H) |
| 12 | 8.69(d, 2H), 8.59(d, 2H), 8.24-8.20(m, 3H), 7.96-7.83(m, 7H), 7.70-7.38(m, 9H), 2.85(q, 2H), 1.30(t, 3H) |
| 14 | 8.81(d, 4H), 8.69(d, 2H), 8.25-8.20(m, 5H), 7.96-7.94(m, 3H), 7.85-7.83(t, 2H), 7.70-7.57(m, 3H), 7.48(t, 2H), 7.38(d, 2H), 2.85(q, 2H), 1.30(t, 3H) |
| 15 | 9.90(s, 2H), 8.69(d, 2H), 8.49(d, 2H), 8.20-7.94(m, 10H), 7.85-7.83(m, 2H), 7.70-7.48(m, 9H), 7.38(d, 2H), 2.85(q, 2H), 1.30(t, 3H) |
| 17 | 8.69(d, 2H), 8.36(d, 4H), 8.20(d, 1H), 7.96-7.94(m, 3H), 7.85-7.83(m, 4H), 7.70-7.48(m, 11H), 7.38(d, 2H), 7.25(d, 2H), 2.85(q, 2H), 1.30(t, 3H) |
| 19 | 8.69(d, 2H), 8.23-8.20(t, 2H), 7.96-7.83(m, 9H), 7.70-7.48(m, 11H), 7.38(d, 2H), 2.85(q, 2H), 1.30(t, 3H) |
| 23 | 8.69(d, 2H), 8.46(s, 2H), 8.23-8.20(t, 2H), 8.06-7.94(m, 11H), 7.85-7.83(m, 2H), 7.70-7.48(m, 9H), 7.38(d, 2H), 2.85(q, 2H), 1.30(t, 3H) |
| 25 | 8.69(d, 2H), 8.30(d, 2H), 8.23-8.20(t, 2H), 7.96-7.38(m, 24H), 2.85(q, 2H), 1.30(t, 3H) |
| 26 | 8.69(d, 2H), 8.30(d, 4H), 8.23-8.20(t, 2H), 7.96-7.38(m, 26H), 2.85(q, 2H), 1.30(t, 3H) |
| 30 | 8.69(d, 2H), 8.46(s, 2H), 8.23-8.20(t, 2H), 8.06-7.83(m, 15H), 7.70-7.48(m, 9H), 7.38(d, 2H), 7.25(d, 2H), 2.85(q, 2H), 1.30(t, 3H) |
| 35 | 8.69(d, 2H), 8.23-8.20(t, 2H), 7.96-7.38(m, 30H), 7.25(d, 2H), 2.85(q, 2H), 1.30(t, 3H) |
| 38 | 9.33(s, 1H), 8.74-8.69(m, 3H), 8.59(d, 1H), 8.40(d, 1H), 8.30-8.20(m, 4H), 8.02-7.83(m, 5H), 7.70-7.38(m, 9H), 2.85(q, 2H), 1.30(t, 3H) |
| 44 | 8.69(d, 2H), 8.30(d, 4H), 8.23-8.20(t, 2H), 7.96-7.38(m, 24H), 7.25(d, 2H), 2.85(q, 2H), 1.30(t, 3H) |
| 48 | 9.09(s, 1H), 8.69(d, 2H), 8.49-8.46(m, 2H), 8.30(d, 2H), 8.23-7.83(m, 16H), 7.70-7.48(m, 9H), 7.38(d, 2H), 2.85(q, 2H), 1.30(t, 3H) |
| 53 | 8.69(d, 2H), 8.38(d, 1H), 8.30(d, 2H), 8.23-8.20(m, 2H), 7.94-7.38(m, 31H), 2.85(q, 2H), 1.30(t, 3H) |
| 55 | 8.69(d, 2H), 8.30(d, 2H), 8.20(d, 1H), 8.13(d, 1H), 7.96-7.38(m, 22H), 2.85(q, 2H), 1.30(t, 3H) |
| 59 | 8.97(d, 1H), 8.69(d, 2H), 8.25-8.10(m, 5H), 8.00-7.83(m, 8H), 7.70-7.38(m, 10H), 2.85(q, 2H), 1.30(t, 3H) |
| 61 | 8.69(d, 2H), 8.20(d, 1H), 8.13(d, 1H), 7.96-7.83(m, 11H), 7.70-7.48(m, 9H), 7.38(d, 2H), 7.25(d, 2H), 2.85(q, 2H), 1.30(t, 3H) |
| 66 | 8.69(d, 2H), 8.38(d, 2H), 8.20(d, 1H), 8.13(d, 1H), 7.94-7.38(m, 21H), 7.38(d, 2H), 2.85(q, 2H), 1.30(t, 3H) |
| 67 | 8.69(d, 2H), 8.38(d, 2H), 8.20(d, 1H), 8.13(d, 1H), 7.94-7.38(m, 27H), 2.85(q, 2H), 1.30(t, 3H) |
| 70 | 8.69(d, 2H), 8.35(m, 2H), 8.20(d, 1H), 7.94(d, 1H), 7.85-7.80(m, 6H), 7.70-7.48(m, 14H), 7.38(d, 2H), 7.25(d, 2H), 2.85(q, 2H), 1.30(t, 3H) |
| 72 | 8.69(d, 2H), 8.35(m, 2H), 8.20(d, 1H), 7.94-7.38(m, 31H), 7.25(d, 2H), 2.85(q, 2H), 1.30(t, 3H) |
| 79 | 8.97(d, 1H), 8.69(d, 2H), 8.25-8.10(m, 4H), 8.00(d, 1H), 7.94(d, 1H), 7.85-7.38(m, 19H), 2.85(q, 2H), 1.30(t, 3H) |
| 81 | 8.69(d, 2H), 8.30(d, 2H), 8.20(d, 1H), 8.13(d, 1H), 7.96-7.38(m, 20H), 7.25(d, 2H), 2.85(q, 2H), 1.30(t, 3H) |
| 85 | 8.69(d, 2H), 8.38(d, 1H), 8.30(d, 2H), 8.20(d, 1H), 8.13(d, 1H), 7.94(t, 2H), 7.85-7.38(m, 23H), 2.85(q, 2H), 1.30(t, 3H) |
| 86 | 8.69(d, 2H), 8.35(d, 2H), 8.20(d, 1H), 8.13(d, 1H), 7.94-7.83(m, 9H), 7.70-7.48(m, 11H), 7.38(d, 2H), 2.85(q, 2H), 1.30(t, 3H) |
| 89 | 8.80(d, 1H), 8.71-8.69(d, 3H), 8.45(d, 1H), 8.20(d, 1H), 7.94-7.83(m, 4H), 7.70-7.48(m, 6H), 7.38(d, 2H), 7.29(d, 1H), 2.85(q, 2H), 1.30(t, 3H) |
| 91 | 8.80(d, 1H), 8.71-8.69(m, 3H), 8.45(d, 1H), 8.33(m, 2H), 8.20(d, 1H), 7.94-7.83(m, 6H), 7.73-7.38(m, 10H), 7.29(d, 1H), 2.85(q, 2H), 1.30(t, 3H) |
| 92 | 8.69(d, 2H), 8.48(d, 1H), 8.30-8.20(m, 4H), 7.94(d, 1H), 7.85-7.83(m, 6H), 7.70-7.48(m, 6H), 7.38(d, 2H), 7.21(t, 1H), 6.86(t, 1H), 2.85(q, 2H), 1.30(t, 3H) |
| 94 | 8.69(d, 2H), 8.43(s, 1H), 8.37(s, 1H), 8.20-8.14(m, 3H), 7.94(d, 1H), 7.85-7.83(m, 2H), 7.73-7.48(m, 9H), 7.38-7.37(m, 3H), 7.25(d, 2H), 2.85(q, 2H), 1.30(t, 3H) |
| 96 | 8.69(d, 2H), 8.20(d, 1H), 7.96-7.94(m, 3H), 7.85-7.83(m, 2H), 7.70-7.48(m, 7H), 7.38(d, 2H), 7.27-7.26(m, 2H), 4.12(q, 2H), 2.85(q, 2H), 1.30(t, 6H) |
| 99 | 8.69(d, 2H), 8.56(d, 1H), 8.28-8.20(m, 3H), 7.94(d, 1H), 7.85-7.48(m, 18H), 7.38(d, 2H), 7.28(t, 1H), 2.85(q, 2H), 1.30(t, 3H) |
| 101 | 8.69(d, 2H), 8.56(d, 1H), 8.20(d, 1H), 7.94(d, 1H), 7.85-7.48(m, 14H), 7.38(d, 2H), 7.28-7.21(m, 2H), 2.85(q, 4H), 1.30(t, 6H) |
| 104 | 8.69(d, 2H), 8.20-8.18(m, 2H), 8.02-7.83(m, 8H), 7.70-7.38(m, 9H), 7.25(d, 2H), 2.85(q, 2H), 1.30(t, 3H) |
| 108 | 8.69(d, 2H), 8.57(d, 1H), 8.20(d, 1H), 8.13(d, 1H), 8.03-7.83(m, 8H), 7.70-7.38(m, 10H), 2.85(q, 2H), 1.30(t, 3H) |
| 110 | 8.69(d, 2H), 8.29-8.20(m, 6H), 7.94(d, 1H), 7.85-7.83(m, 4H), 7.70-7.48(m, 11H), 7.38(d, 2H), 7.25(s, 4H), 2.85(q, 2H), 1.30(t, 3H) |
| 126 | 8.69(d, 2H), 8.26(s, 1H), 8.20(d, 2H), 8.16-8.09(m, 2H), 7.94-7.83(m, 3H), 7.71-7.38(m, 9H), 7.25(d, 2H), 2.85(q, 2H), 1.30(t, 3H) |
| 128 | 9.10(d, 1H), 8.69(s, 4H), 8.50(d, 1H), 8.22-8.20(m, 2H), 7.94-7.83(m, 5H), 7.70-7.48(m, 5H), 7.38(d, 2H), 2.85(q, 2H), 1.30(t, 3H) |
| 130 | 8.69(d, 2H), 8.20(d, 1H), 7.98-7.83(m, 7H), 7.70-7.48(m, 8H), 7.38(d, 2H), 2.85(q, 2H), 1.30(t, 3H) |
| 131 | 8.69(d, 2H), 8.20(d, 1H), 8.09-7.83(m, 10H), 7.70-7.38(m, 15H), 2.85(q, 2H), 1.30(t, 3H) |
| 133 | 8.69(d, 2H), 8.20(d, 1H), 7.94(d, 1H), 7.85-7.83(m, 8H), 7.70-7.57(m, 3H), 7.48(t, 2H), 7.38(d, 2H), 2.85(q, 2H), 1.30(t, 3H) |
| 135 | 8.69(d, 2H), 8.20(d, 1H), 7.97-7.94(m, 3H), 7.85-7.83(m, 8H), 7.70-7.57(m, 5H), 7.48-7.38(m, 6H), 2.85(q, 2H), 1.30(t, 3H) |
| 136 | 8.69(s, 4H), 8.37(d, 1H), 8.20(d, 1H), 7.94(d, 1H), 7.85-7.83(m, 2H), 7.70-7.57(m, 3H), 7.48-7.38(m, 5H), 7.14(d, 1H), 6.90(t, 1H), 2.85(q, 2H), 1.30(t, 3H) |
| 145 | 8.69(s, 4H), 8.37(s, 1H), 8.30(d, 2H), 8.20(d, 1H), 7.94-7.38(m, 24H), 7.24(d, 1H), 2.85(q, 2H), 1.30(t, 3H) |
| 148 | 8.69(s, 4H), 8.30(d, 2H), 8.20(d, 1H), 8.13(d, 1H), 7.94(d, 1H), 7.85-7.38(m, 21H), 7.24(d, 1H), 2.85(q, 2H), 1.30(t, 3H) |
| 152 | 8.69(d, 2H), 8.48(d, 1H), 8.30(d, 2H), 8.20(d, 1H), 7.94(d, 1H), 7.85-7.83(m, 6H), 7.70-7.38(m, 11H), 7.28-7.21(m, 3H), 6.86(t, 1H), 2.85(q, 2H), 1.30(t, 3H) |
| 153 | 8.87(d, 1H), 8.69(d, 2H), 8.55(d, 1H), 8.20(d, 1H), 8.05(d, 1H), 7.96-7.83(m, 4H), 7.70-7.38(m, 9H), 7.25(d, 2H), 2.85(q, 2H), 1.30(t, 3H) |
| 154 | 8.33(m, 2H), 8.20(d, 1H), 7.97-7.94(m, 5H), 7.85-7.48(m, 19H), 7.38(d, 2H), 2.85(q, 2H), 1.30(t, 3H) |
| 155 | 8.36-8.33(m, 6H), 8.20(d, 1H), 7.96-7.94(t, 3H), 7.85-7.83(m, 2H), 7.73-7.48(m, 13H), 7.38(d, 2H), 7.25(d, 2H), 2.85(q, 2H), 1.30(t, 3H) |
| 156 | 8.55(d, 2H), 8.33(m, 2H), 8.19-8.17(m, 4H), 7.94-7.83(m, 5H), 7.73-7.48(m, 12H), 7.38-7.35(m, 4H), 7.20-7.16(m, 4H), 2.85(q, 2H), 1.30(t, 3H) |

TABLE 2-continued

| NO | $^1$H NMR (CDCl$_3$, 300 Mz) |
|---|---|
| 158 | 8.35-8.33(m, 4H), 8.23(s, 1H), 8.20(d, 1H), 7.94-7.83(m, 6H), 7.70-7.48(m, 12H), 7.38(d, 2H), 2.85(q, 2H), 1.30(t, 3H) |
| 161 | 8.35-8.20(m, 10H), 7.94(d, 1H), 7.85-7.38(m, 23H), 2.85(q, 2H), 1.30(t, 3H) |
| 164 | 8.71-8.69(m, 4H), 8.33(m, 4H), 8.20(d, 2H), 7.94-7.83(m, 6H), 7.73-7.48(m, 10H), 7.38(d, 2H), 7.29(d, 2H), 2.85(q, 2H), 1.30(t, 3H) |
| 165 | 8.56(d, 1H), 8.33(m, 2H), 8.20(d, 1H), 7.94(d, 1H), 7.85-7.48(m, 19H), 7.38(d, 2H), 7.28-7.21(m, 2H), 2.85(q, 4H), 1.30(t, 6H) |

EXAMPLE

1) Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for ITO work function and remaining film removal, and the substrate was transferred to a thermal deposition apparatus for organic deposition.

On the transparent ITO electrode (anode), an organic material was formed in a 2 stack white organic light emitting device (WOLED) structure. As for the first stack, TAPC was thermal vacuum deposited to a thickness of 300 Å first to form a hole transfer layer. After forming the hole transfer layer, a light emitting layer was thermal vacuum deposited thereon as follows. The light emitting layer was deposited to 300 Å by doping Flrpic to TCz1, a host, by 8% as a blue phosphorescent dopant. After forming an electron transfer layer to 400 Å using TmPyPB, a charge generation layer was formed to 100 Å by doping Cs$_2$CO$_3$ to the compound described in the following Table 3 by 20%.

As for the second stack, MoO$_3$ was thermal vacuum deposited to a thickness of 50 Å first to form a hole injection layer. A hole transfer layer, a common layer, was formed by doping MoO$_3$ to TAPC by 20% to 100 Å and depositing TAPC to 300 Å. A light emitting layer was deposited thereon to 300 Å by doping Ir(ppy)$_3$, a green phosphorescent dopant, to TCz1, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic light emitting device.

Meanwhile, all the organic compounds required to manufacture the OLED were vacuum sublimation purified under 10$^{-8}$ torr to 10$^{-6}$ torr by each material to be used in the OLED manufacture.

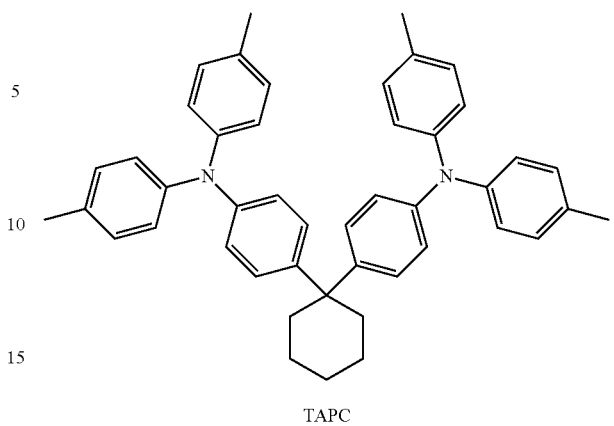

TAPC

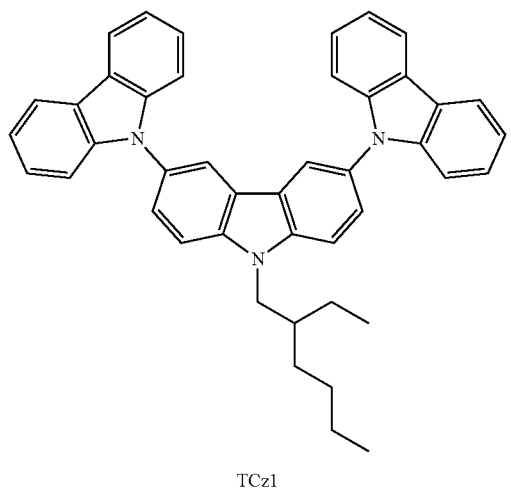

TCz1

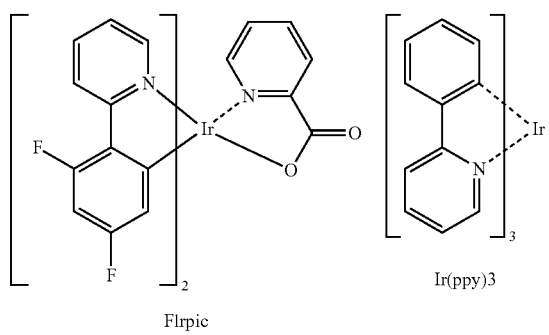

Flrpic       Ir(ppy)3

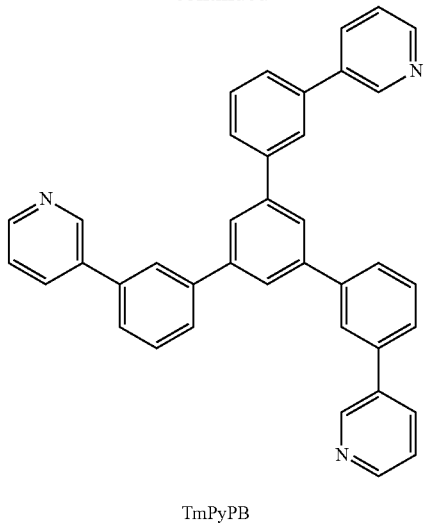

TmPyPB

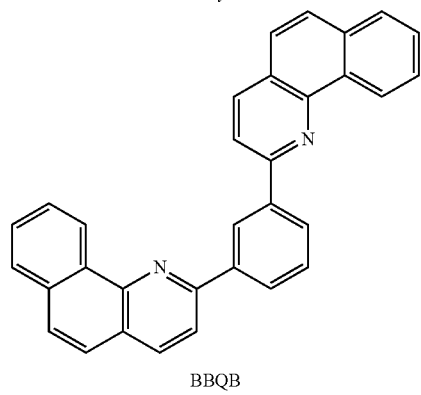

BBQB

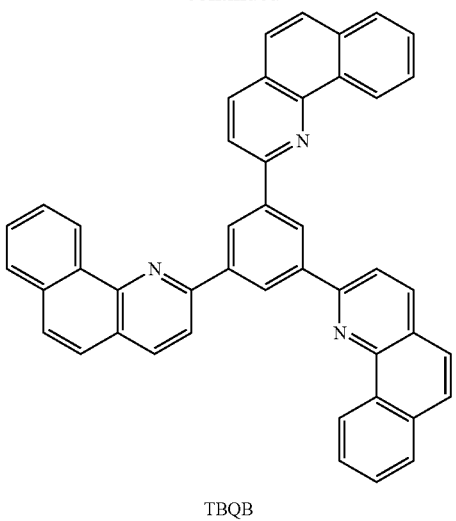

TBQB

2) Driving Voltage and Light Emission Efficiency of Organic Electroluminescent Device For the organic light emitting devices manufactured as above, electroluminescent light emission (EL) properties were measured using M7000 manufactured by McScience Inc., and with the measurement results, $T_{95}$ when standard luminance was 3,500 cd/m² was measured using a lifetime measurement system (M6000) manufactured by McScience Inc. Results of measuring a driving voltage, light emission efficiency, external quantum efficiency and a color coordinate (CIE) of the white organic light emitting device manufactured according to the present disclosure are as shown in the following Table 3.

TABLE 3

|  | Compound | Driving Voltage (V) | Light Emission Efficiency (cd/A) | CIE (x, y) | Lifetime (T95) |
| --- | --- | --- | --- | --- | --- |
| Example 1 | 2 | 7.24 | 61.88 | (0.209, 0.415) | 23 |
| Example 2 | 3 | 7.33 | 61.54 | (0.231, 0.440) | 25 |
| Example 3 | 4 | 7.35 | 61.98 | (0.211, 0.419) | 24 |
| Example 4 | 5 | 6.68 | 70.04 | (0.209, 0.419) | 38 |
| Example 5 | 10 | 6.58 | 71.44 | (0.207, 0.409) | 40 |
| Example 6 | 11 | 6.94 | 61.95 | (0,208, 0.415) | 44 |
| Example 7 | 15 | 7.01 | 68.31 | (0.214, 0.420) | 28 |
| Example 8 | 16 | 6.98 | 60.58 | (0.224, 0.429) | 30 |
| Example 9 | 17 | 6.89 | 72.10 | (0.243, 0.442) | 38 |
| Example 10 | 25 | 6.71 | 69.65 | (0.205, 0.411) | 41 |
| Example 11 | 26 | 6.49 | 71.44 | (0.243, 0.442) | 39 |
| Example 12 | 27 | 6.95 | 58.29 | (0.209, 0.419) | 34 |
| Example 13 | 28 | 7.21 | 59.33 | (0.210, 0.420) | 29 |
| Example 14 | 30 | 7.13 | 61.15 | (0.231, 0.419) | 35 |
| Example 15 | 34 | 7.14 | 58.42 | (0.229, 0.424) | 31 |
| Example 16 | 35 | 7.08 | 61.88 | (0.214, 0.420) | 30 |
| Example 17 | 43 | 6.84 | 71.03 | (0.224, 0.429) | 38 |
| Example 18 | 52 | 6.69 | 70.59 | (0.221, 0.434) | 39 |
| Example 19 | 55 | 6.92 | 57.94 | (0.212, 0.422) | 36 |
| Example 20 | 67 | 7.01 | 57.33 | (0.228, 0.418) | 35 |
| Example 21 | 70 | 7.11 | 58.24 | (0.231, 0.420) | 32 |
| Example 22 | 89 | 7.35 | 60.03 | (0.219, 0.411) | 33 |
| Example 23 | 90 | 7.38 | 61.11 | (0.243, 0.442) | 31 |
| Example 24 | 91 | 7.31 | 66.89 | (0.209, 0.419) | 28 |
| Example 25 | 94 | 7.66 | 61.12 | (0.210, 0.420) | 26 |
| Example 26 | 101 | 7.44 | 59.02 | (0.231, 0.419) | 35 |
| Example 27 | 104 | 7.09 | 64.86 | (0.243, 0.442) | 38 |
| Example 28 | 124 | 6.88 | 67.98 | (0.205, 0.411) | 44 |

TABLE 3-continued

| | Compound | Driving Voltage (V) | Light Emission Efficiency (cd/A) | CIE (x, y) | Lifetime (T95) |
|---|---|---|---|---|---|
| Example 29 | 126 | 6.91 | 68.24 | (0.243, 0.442) | 30 |
| Example 30 | 131 | 7.59 | 57.02 | (0.209, 0.419) | 35 |
| Example 31 | 133 | 7.22 | 57.38 | (0.210, 0.420) | 34 |
| Example 32 | 136 | 7.12 | 56.01 | (0.231, 0.419) | 31 |
| Example 33 | 138 | 7.53 | 54.98 | (0.229. 0.424) | 32 |
| Example 34 | 141 | 7.05 | 55.30 | (0.229, 0.430) | 27 |
| Example 35 | 147 | 6.48 | 72.03 | (0.220, 0.440) | 40 |
| Example 36 | 151 | 7.02 | 58.02 | (0.231, 0.419) | 31 |
| Example 37 | 152 | 7.26 | 57.83 | (0.229, 0.423) | 34 |
| Example 38 | 153 | 7.25 | 57.69 | (0.230, 0.421) | 34 |
| Example 39 | 154 | 7.74 | 59.02 | (0.238, 0.438) | 69 |
| Example 40 | 155 | 6.53 | 75.31 | (0.225, 0.429) | 36 |
| Example 41 | 156 | 6.77 | 73.29 | (0.243, 0.442) | 38 |
| Example 42 | 158 | 6.84 | 72.01 | (0.231, 0.440) | 40 |
| Example 43 | 161 | 7.25 | 58.98 | (0.211, 0.419) | 40 |
| Example 44 | 164 | 7.28 | 64.33 | (0.210, 0.412) | 30 |
| Example 45 | 165 | 6.48 | 72.16 | (0.231, 0.418) | 31 |
| Comparative Example 1-1 | TmPyPB | 8.57 | 57.61 | (0.212, 0.433) | 22 |
| Comparative Example 1-2 | BBQB | 8.43 | 58.11 | (0.220, 0,429) | 22 |
| Comparative Example 1-3 | TBQB | 8.47 | 58.90 | (0.222, 0,430) | 26 |

As seen from the results of Table 3, the organic light emitting device using the charge generation layer material of the 2-stack white organic light emitting device of the present disclosure had a lower driving voltage and improved light emission efficiency compared to Comparative Example 1. Particularly, it was identified that Compounds 5, 10, 11, 17, 25, 26, 43, 52, 124 and 147 were significantly superior in all aspects of driving, efficiency and lifetime.

Such a result is considered to be due to the fact that the compound of the present disclosure used as the N-type charge generation layer formed with the disclosed skeleton having proper length, strength and flat properties and a proper hetero-compound capable of binding with a metal forms a gap state in the N-type charge generation layer by doping an alkali metal or an alkaline earth metal, and electrons produced from the P-type charge generation layer are readily injected to the electron transfer layer through the gap state produced in the N-type charge generation layer. Accordingly, it is considered that the P-type charge generation layer favorably injects and transfers electrons to the N-type charge generation layer, and as a result, a driving voltage was lowered, and efficiency and lifetime were improved in the organic light emitting device.

Experimental Example 2

1) Manufacture of Organic Light Emitting Device A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum depositor, and the following 4,4',4"-tris(N,N-(2-naphthyl)-phenylamino)triphenylamine (2-TNATA) was introduced to a cell in the vacuum depositor.

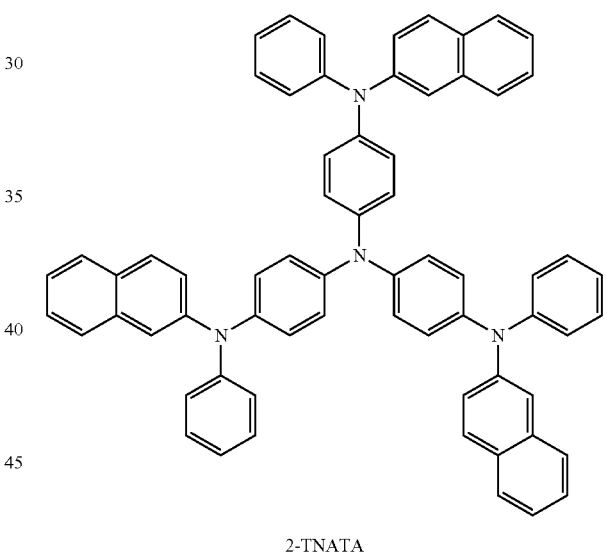

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum depositor, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

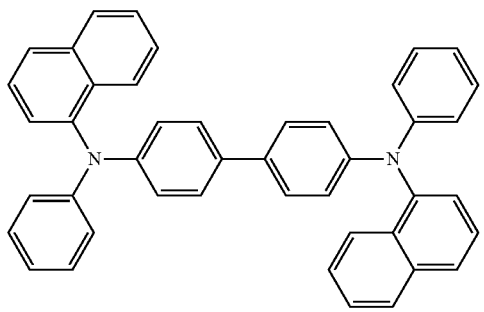

NPB

After forming the hole injection layer and the hole transfer layer as above, a blue light emitting material having a structure as below was deposited thereon as a light emitting layer. Specifically, in one side cell in the vacuum depositor, H1, a blue light emitting host material, was vacuum deposited to a thickness of 200 Å, and D1, a blue light emitting dopant material, was vacuum deposited thereon by 5% with respect to the host material.

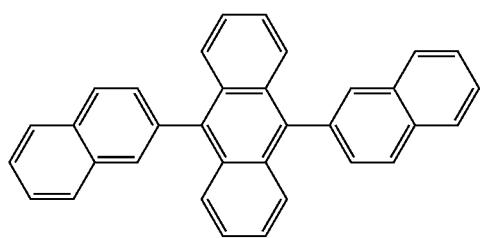

H1

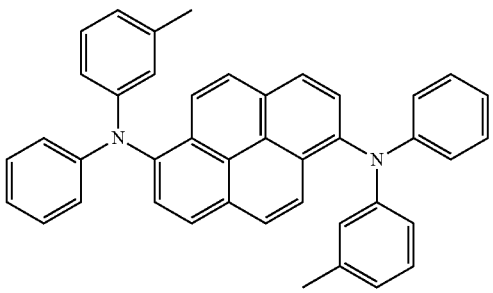

D1

Subsequently, a compound of the following structural formula E1 was deposited to a thickness of 300 Å as an electron transfer layer.

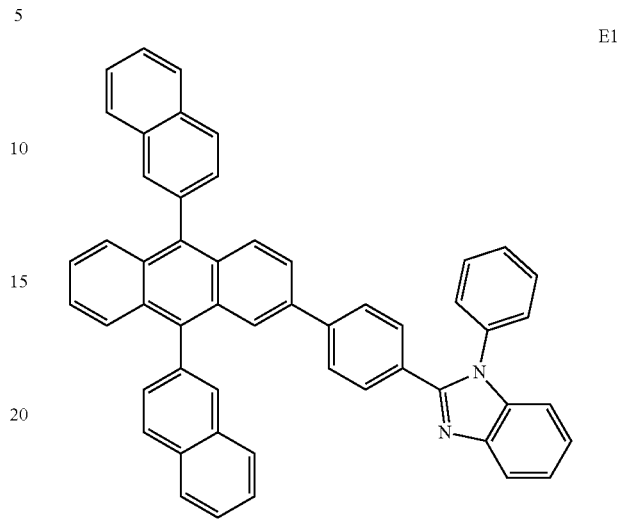

E1

As an electron injection layer, lithium fluoride (LiF) was deposited to a thickness of 10 Å, and an Al cathode was employed to have a thickness of 1,000 Å to manufacture an OLED.

Meanwhile, all the organic compounds required to manufacture the OLED were vacuum sublimation purified under $10^{-8}$ torr to $10^{-6}$ torr by each material to be used in the OLED manufacture.

An OLED was manufactured in the same manner as in Experimental Example 2 except that a compound of the following Table 4 was used instead of Compound E1 as the electron transfer layer.

2) Driving Voltage and Light Emission Efficiency of Organic Light Emitting Device For the organic light emitting devices manufactured as above, electroluminescent light emission (EL) properties were measured using M7000 manufactured by McScience Inc., and with the measurement results, $T_{95}$ when standard luminance was 700 cd/m² was measured using a lifetime measurement system (M6000) manufactured by McScience Inc. Results of measuring a driving voltage, light emission efficiency, external quantum efficiency and a color coordinate (CIE) of the white organic light emitting device manufactured according to the present disclosure are as shown in the following Table 4.

TABLE 4

|  | Compound | Driving Voltage (V) | Light Emission Efficiency (cd/A) | CIE (x, y) | Lifetime (T95) |
|---|---|---|---|---|---|
| Example 46 | 2 | 5.01 | 6.62 | (0.134, 0.100) | 34 |
| Example 47 | 3 | 4.99 | 6.73 | (0.134, 0.103) | 36 |
| Example 48 | 4 | 5.09 | 6.77 | (0.134, 0.101) | 24 |
| Example 49 | 5 | 4.19 | 6.93 | (0.134, 0.102) | 64 |
| Example 50 | 10 | 4.22 | 7.02 | (0.134, 0.100) | 33 |
| Example 51 | 11 | 3.89 | 7.01 | (0.134, 0.100) | 37 |
| Example 52 | 15 | 4.34 | 6.83 | (0.134, 0.101) | 34 |
| Example 53 | 16 | 4.90 | 6.93 | (0.134, 0.101) | 38 |
| Example 54 | 17 | 4.05 | 7.12 | (0.134, 0.100) | 35 |
| Example 55 | 25 | 3.98 | 7.39 | (0.134, 0.100) | 38 |

TABLE 4-continued

| | Compound | Driving Voltage (V) | Light Emission Efficiency (cd/A) | CIE (x, y) | Lifetime (T95) |
|---|---|---|---|---|---|
| Example 56 | 26 | 4.01 | 7.02 | (0.134, 0.099) | 35 |
| Example 57 | 27 | 4.77 | 6.88 | (0.134, 0.100) | 29 |
| Example 58 | 28 | 4.76 | 6.93 | (0.134, 0.100) | 26 |
| Example 59 | 30 | 4.65 | 6.83 | (0.134, 0.102) | 29 |
| Example 60 | 34 | 3.79 | 6.72 | (0.134, 0.103) | 31 |
| Example 61 | 35 | 3.74 | 6.80 | (0.134, 0.102) | 36 |
| Example 62 | 43 | 3.97 | 7.33 | (0.134, 0.100) | 30 |
| Example 63 | 52 | 4.00 | 7.09 | (0.134, 0.100) | 33 |
| Example 64 | 55 | 4.32 | 6.77 | (0.134, 0.100) | 37 |
| Example 65 | 67 | 4.39 | 6.82 | (0.134, 0.103) | 34 |
| Example 66 | 70 | 4.54 | 6.72 | (0.134, 0.101) | 35 |
| Example 67 | 89 | 4.98 | 6.82 | (0.134, 0.102) | 26 |
| Example 68 | 90 | 4.90 | 7.59 | (0.134, 0.102) | 24 |
| Example 69 | 91 | 5.04 | 6.59 | (0.134, 0.101) | 27 |
| Example 70 | 94 | 5.02 | 6.03 | (0.134, 0.100) | 29 |
| Example 71 | 101 | 4.88 | 6.44 | (0.134, 0.101) | 25 |
| Example 72 | 104 | 4.65 | 6.38 | (0.134, 0.101) | 35 |
| Example 73 | 124 | 4.03 | 7.81 | (0.134, 0.102) | 35 |
| Example 74 | 126 | 4.66 | 6.76 | (0.134, 0.102) | 37 |
| Example 75 | 131 | 4.67 | 6.55 | (0.134, 0.102) | 35 |
| Example 76 | 133 | 4.98 | 6.87 | (0.134, 0.100) | 34 |
| Example 77 | 136 | 4.87 | 6.44 | (0.134, 0.101) | 29 |
| Example 78 | 138 | 4.88 | 6.52 | (0.134, 0.100) | 23 |
| Example 79 | 141 | 4.44 | 6.88 | (0.134, 0.102) | 34 |
| Example 80 | 147 | 4.01 | 7.43 | (0.134, 0.101) | 37 |
| Example 81 | 151 | 4.35 | 6.81 | (0.134, 0.103) | 39 |
| Example 82 | 152 | 4.11 | 6.53 | (0.134, 0.100) | 32 |
| Example 83 | 153 | 4.40 | 6.33 | (0.134, 0.102) | 34 |
| Example 84 | 154 | 5.39 | 6.22 | (0.134, 0.101) | 57 |
| Example 85 | 155 | 3.98 | 7.31 | (0.134, 0.100) | 38 |
| Example 86 | 156 | 3.89 | 7.25 | (0.134, 0.100) | 35 |
| Example 87 | 158 | 4.33 | 7.02 | (0.134, 0.100) | 36 |
| Example 88 | 161 | 4.89 | 6.39 | (0.134, 0.103) | 39 |
| Example 89 | 164 | 4.87 | 6.55 | (0.134, 0.101) | 24 |
| Example 90 | 165 | 4.83 | 6.58 | (0.134, 0.101) | 25 |
| Comparative Example 2-1 | E1 | 5.56 | 5.91 | (0.134 0.100) | 28 |
| Comparative Example 2-2 | E2 | 6.01 | 4.97 | (0.134, 0.103) | 85 |
| Comparative Example 2-3 | E3 | 5.52 | 6.21 | (0.134, 0.101) | 29 |
| Comparative Example 2-4 | BBQB | 5.50 | 6.10 | (0.134, 0.101) | 30 |
| Comparative Example 2-5 | TBQB | 5.51 | 6.15 | (0.134, 0.102) | 29 |

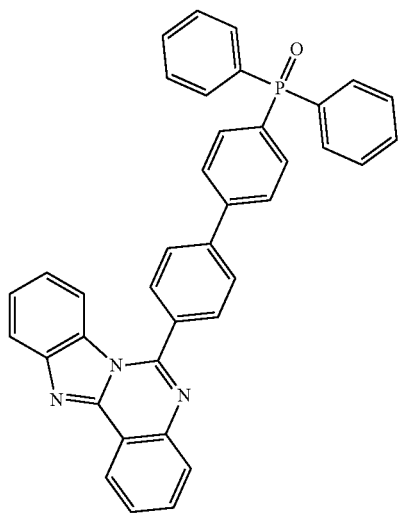

E2

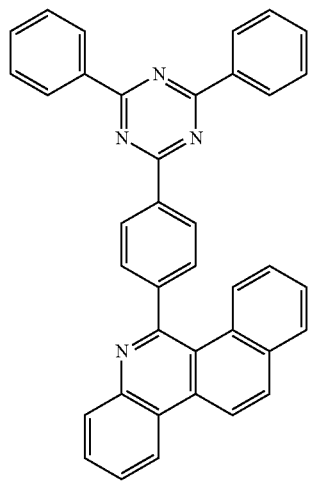

E3

-continued

-continued

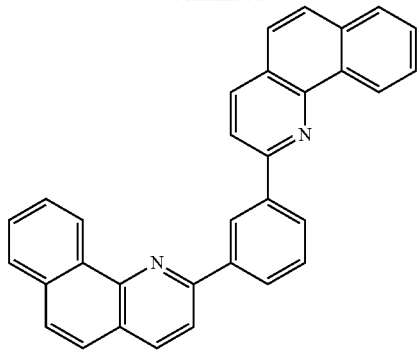
BBQB

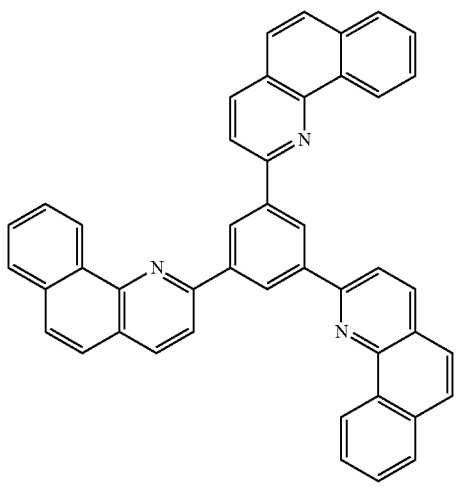
TBQB

As seen from the results of Table 4, the organic light emitting device using the electron transfer layer material of the blue organic light emitting device of the present disclosure had a lower driving voltage, and significantly improved light emission efficiency and lifetime compared to Comparative Example 3. Particularly, it was identified that Compounds 5, 10, 11, 17, 25, 26, 43, 52, 124 and 147 were superior in all aspects of driving, efficiency and lifetime.

Such a result is considered to be due to the fact that, when using the disclosed compound having proper length, strength and flat properties as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transfer electrons without the compound being decomposed or destroyed. For reference, those that are stable when excited are considered to be aryl or acene compounds, or polycyclic hetero-compounds. Accordingly, it is considered that excellent results in all aspects of driving, efficiency and lifetime are obtained by the compound of the present disclosure enhancing enhanced electron-transfer properties or improved stability.

The invention claimed is:

1. A hetero-cyclic compound represented by the following Chemical Formula 1:

[Chemical Formula 1]

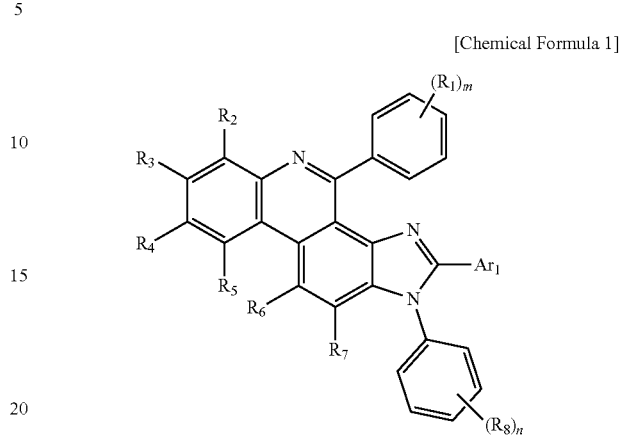

wherein, in Chemical Formula 1, $R_1$ is hydrogen; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —P(=O)RR'; or —CN;

$R_2$ to $R_8$ are each hydrogen;

$Ar_1$ is a substituted or unsubstituted $C_1$ to $C_{60}$ alkyl group;

m and n are each independently an integer of 0 to 5; and

R, and R' are the same as or different from each other, and each independently a substituted or unsubstituted $C_6$ to $C_{60}$ aryl group.

2. The hetero-cyclic compound of claim 1, wherein the "substituted or unsubstituted" means being substituted with one or more substituents selected from the group consisting of $C_1$ to $C_{60}$ linear or branched alkyl; $C_2$ to $C_{60}$ linear or branched alkenyl; $C_2$ to $C_{60}$ linear or branched alkynyl; $C_3$ to $C_{60}$ monocyclic or polycyclic cycloalkyl; $C_2$ to $C_{60}$ monocyclic or polycyclic heterocycloalkyl; $C_6$ to $C_{60}$ monocyclic or polycyclic aryl; $C_2$ to $C_{60}$ monocyclic or polycyclic heteroaryl; —P(=O)RR'; $C_1$ to $C_{20}$ alkylamine; $C_6$ to $C_{60}$ monocyclic or polycyclic arylamine; and $C_2$ to $C_{60}$ monocyclic or polycyclic heteroarylamine, or being unsubstituted, or being substituted with a substituent linking two or more substituents selected from among the substituents illustrated above, or being unsubstituted.

3. The hetero-cyclic compound of claim 1, wherein $R_1$ of Chemical Formula 1 is represented by -(L)$_p$-(Z)$_q$;

L is a direct bond; a substituted or unsubstituted $C_6$ to $C_{60}$ arylene group; or a substituted or unsubstituted $C_2$ to $C_{60}$ heteroarylene group;

Z is hydrogen; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —CN; or —P(=O)RR';

R, and R' are the same as or different from each other, and each independently a substituted or unsubstituted $C_6$ to $C_{60}$ aryl group; and p and q are an integer of 1 to 4.

4. The hetero-cyclic compound of claim 1, wherein $Ar_1$ is an ethyl group.

5. The hetero-cyclic compound of claim 1, wherein Chemical Formula 1 is represented by the following Chemical Formula 2 or 3:

[Chemical Formula 2]

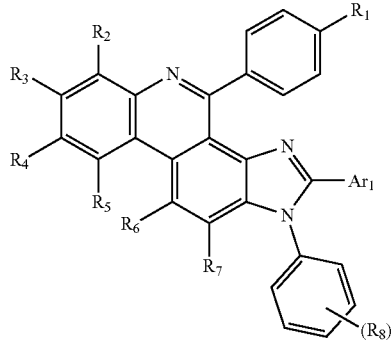

[Chemical Formula 3]

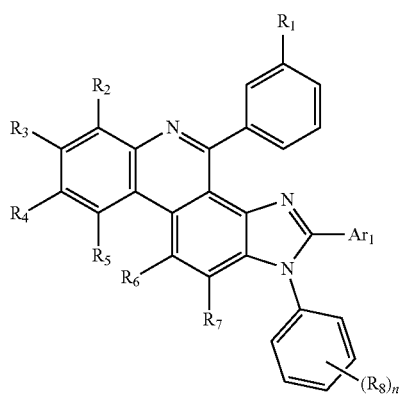

in Chemical Formulae 2 and 3, $Ar_1$, $R_1$ to $R_8$ and n have the same definitions as in Chemical Formula 1.

6. The hetero-cyclic compound of claim 1, wherein Chemical Formula 1 is represented by any one of the following compounds:

1

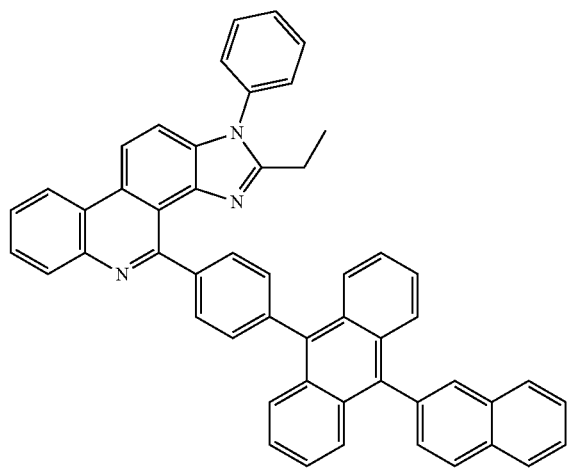

2

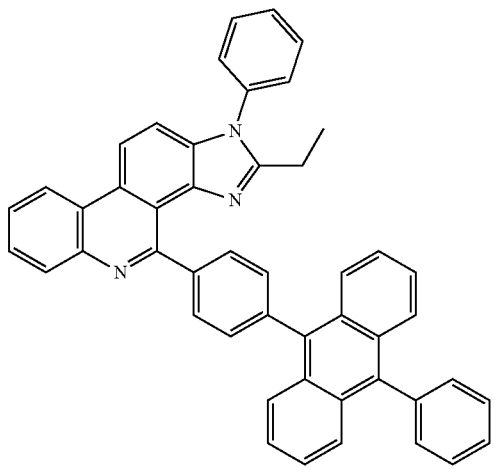

3

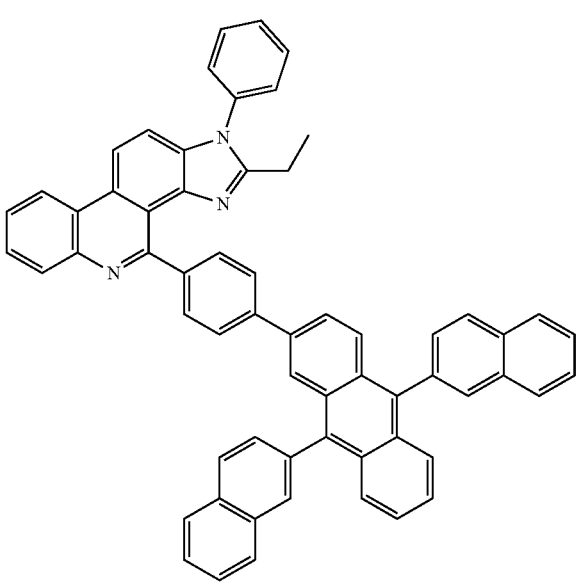

4

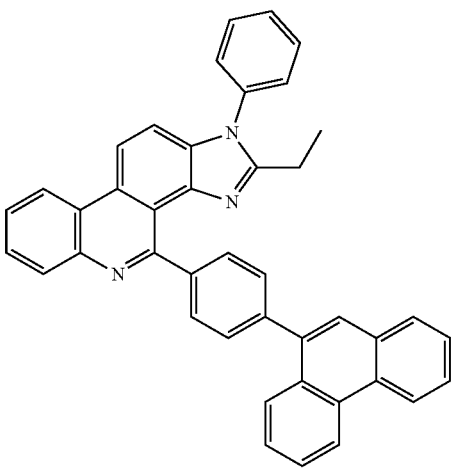

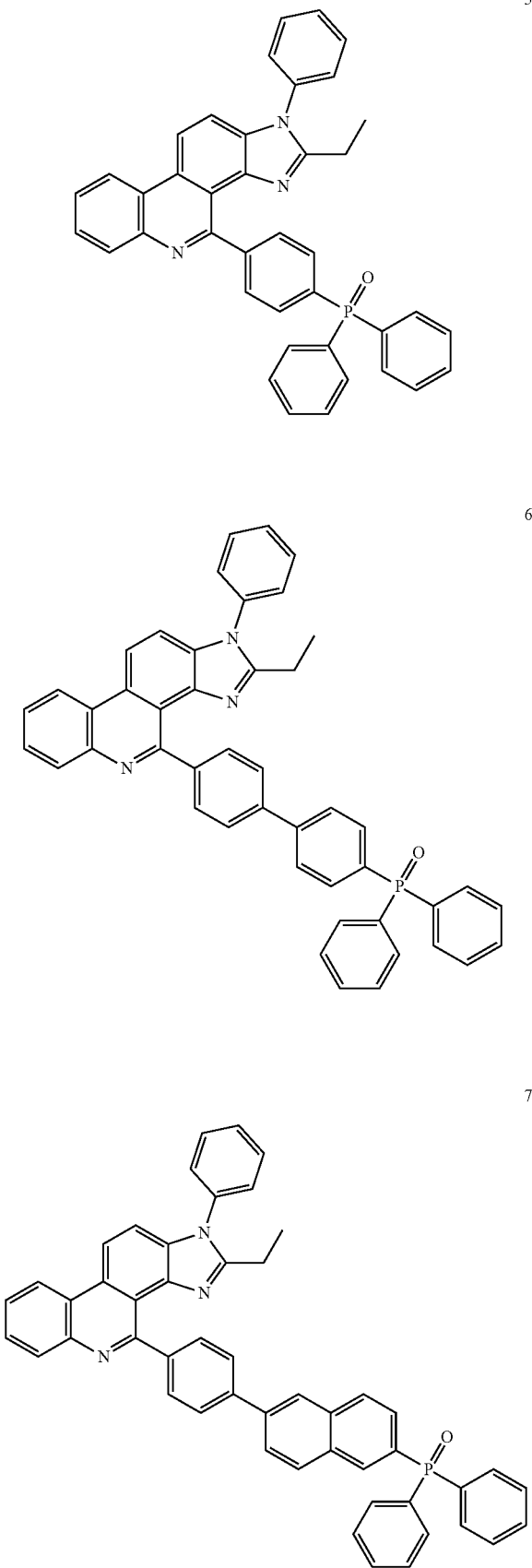
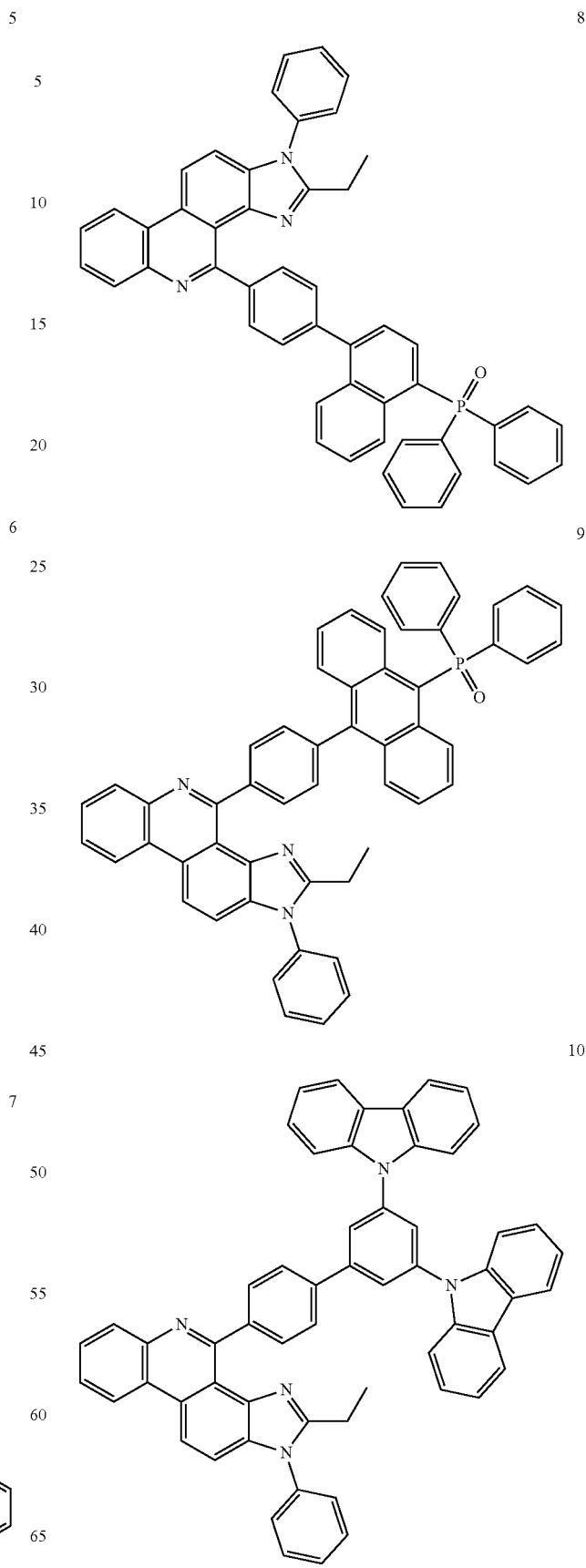

11
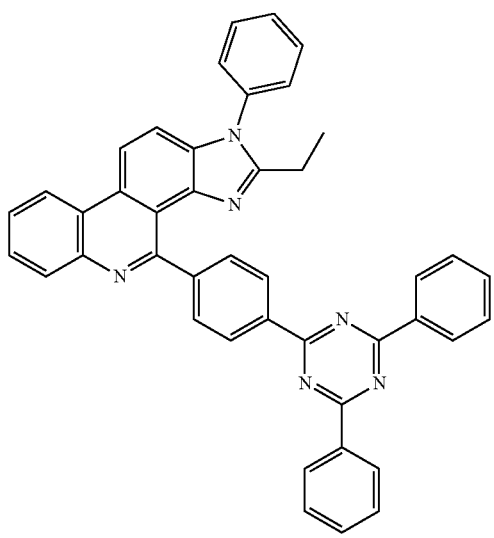
12
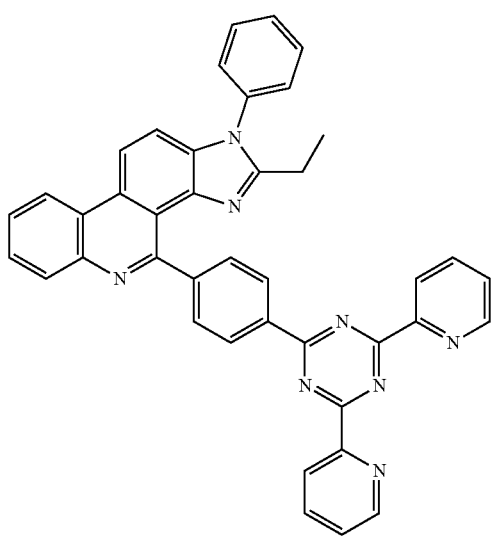
13
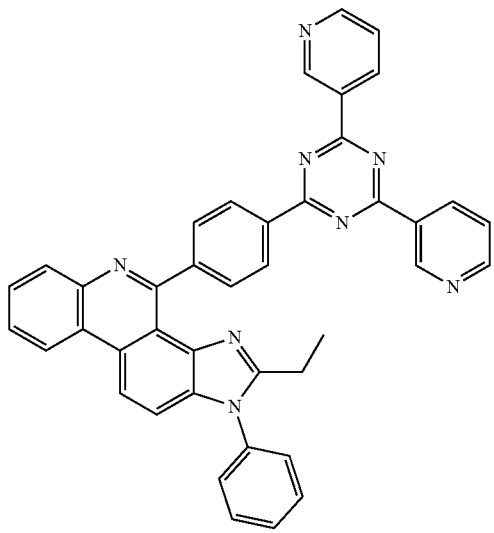
14
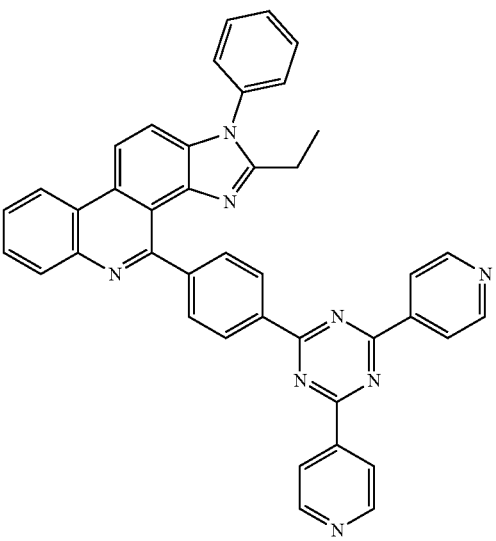
15

16
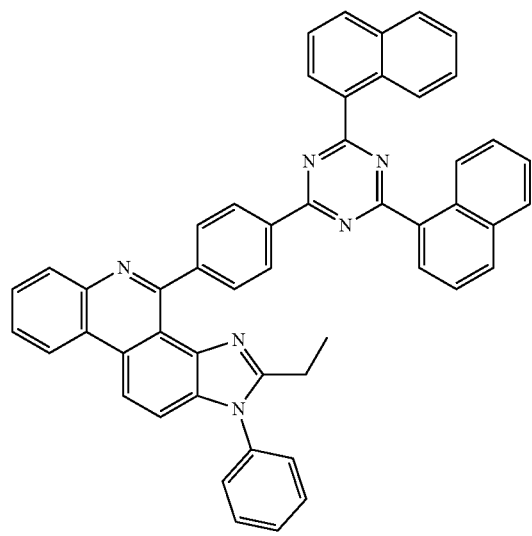
17
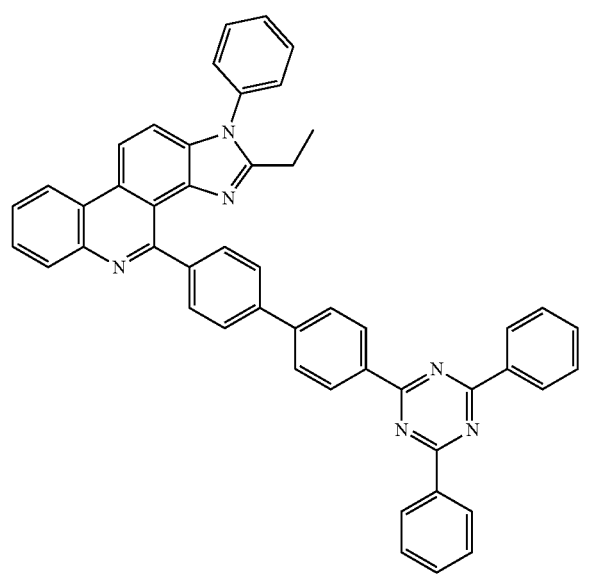
18
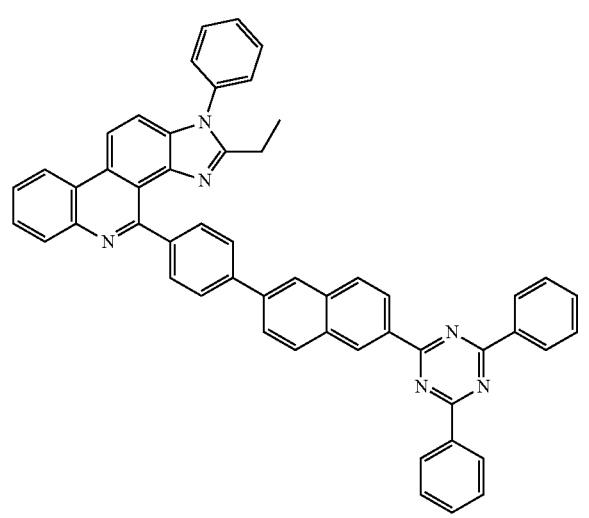
19
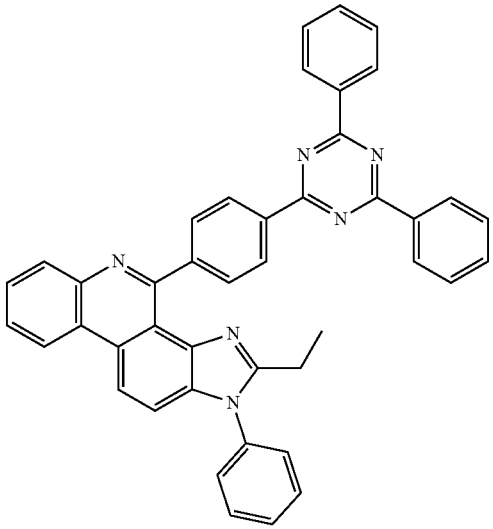
20
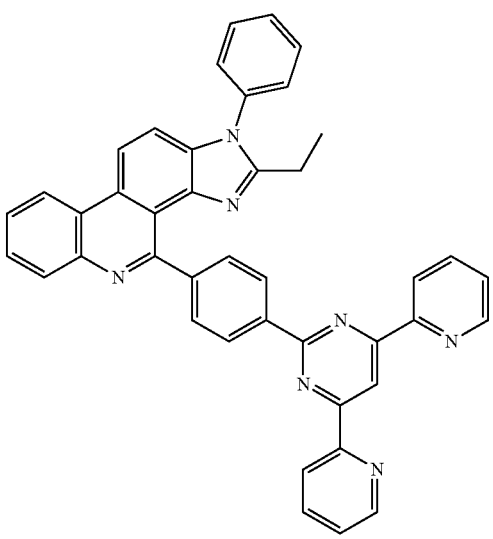
21
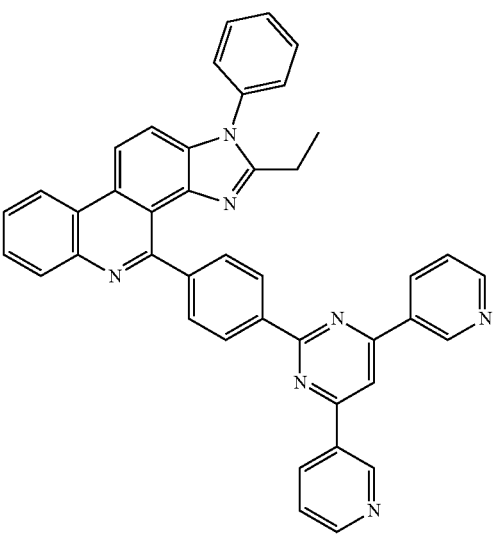

171
-continued
22
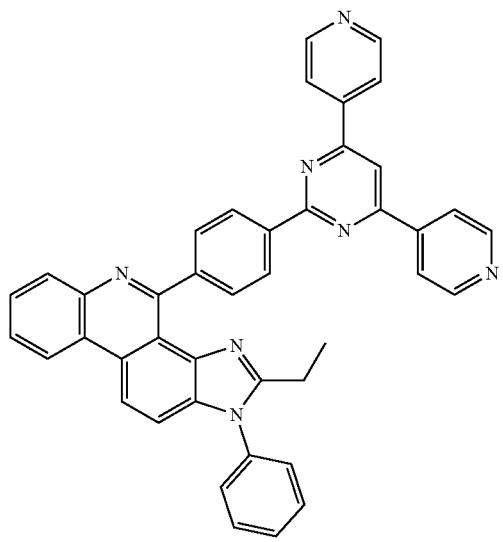
172
-continued
24
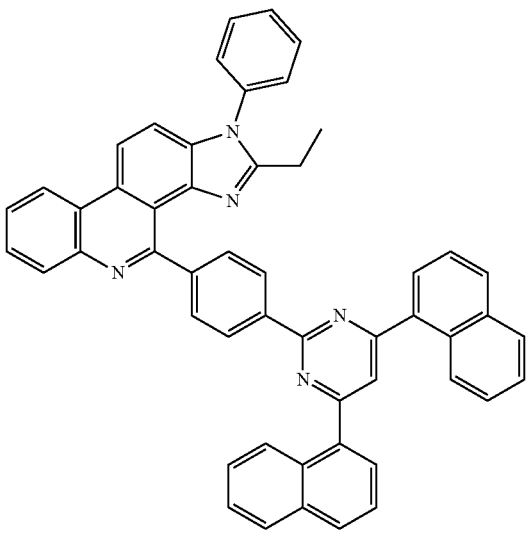
23
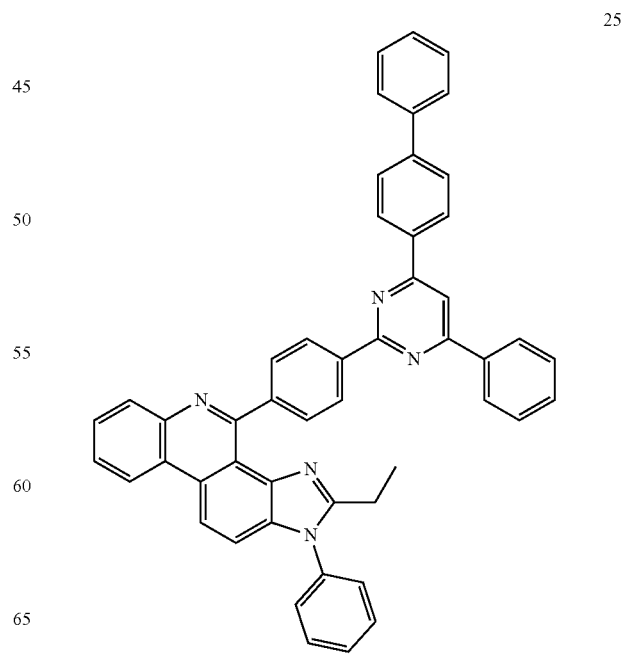
25

26
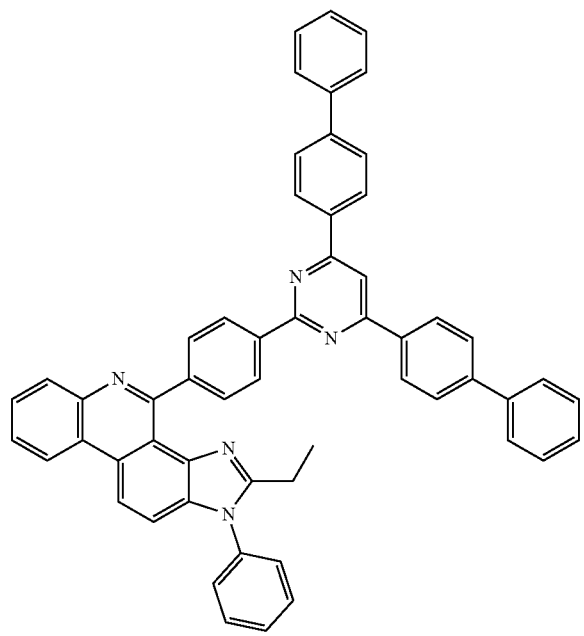
28
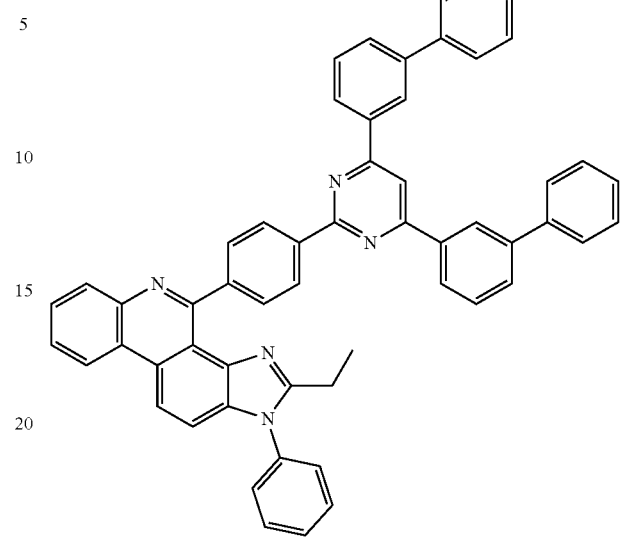
27
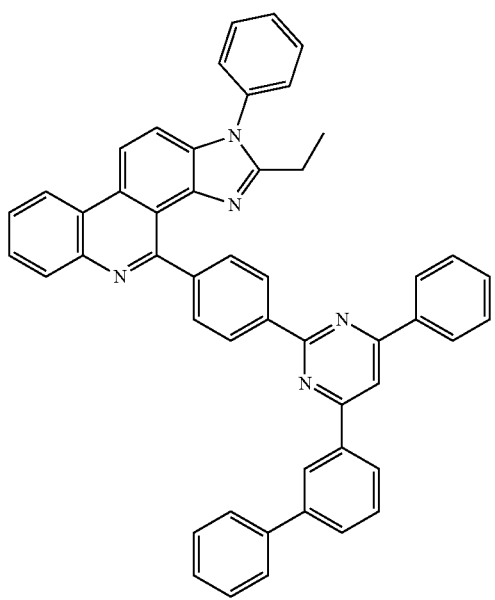
29

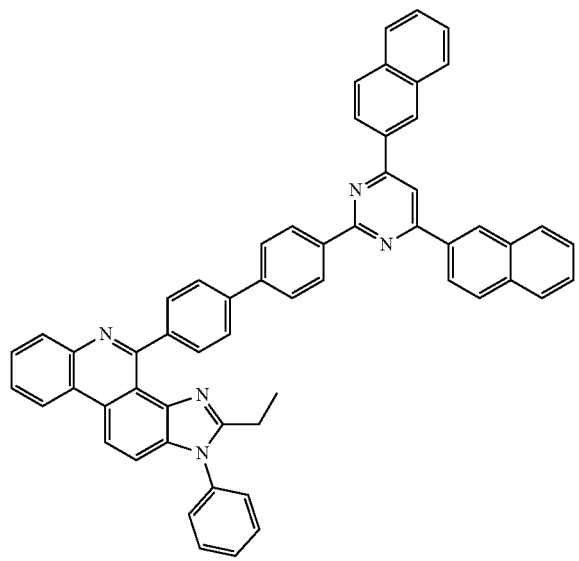
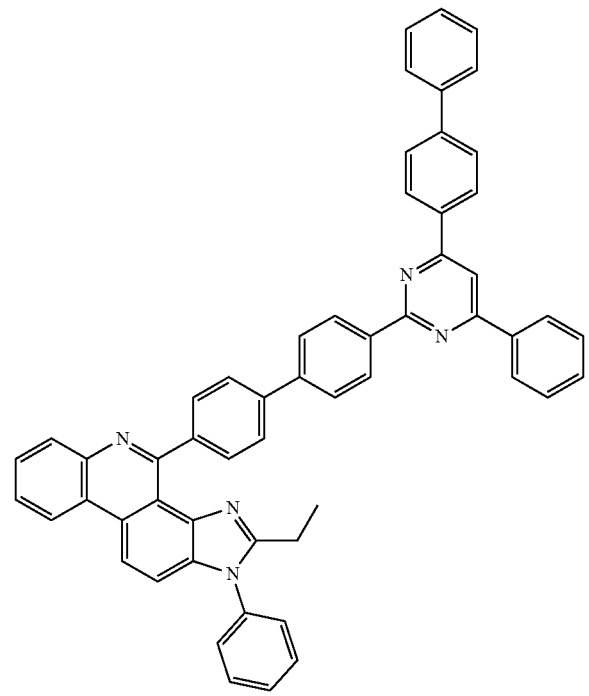
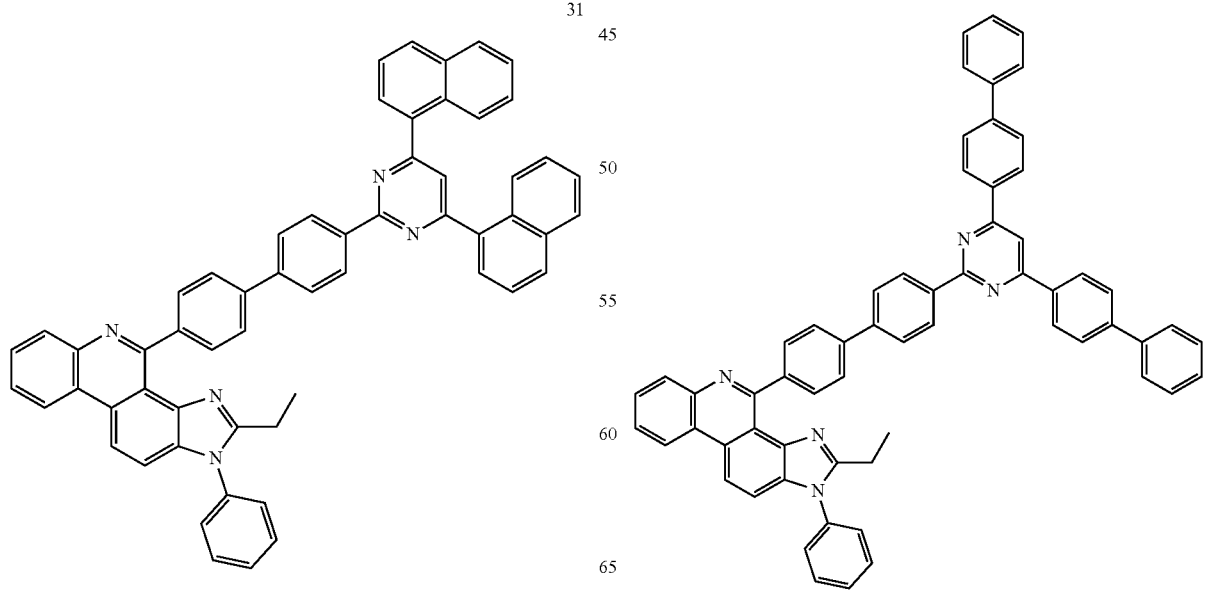

34
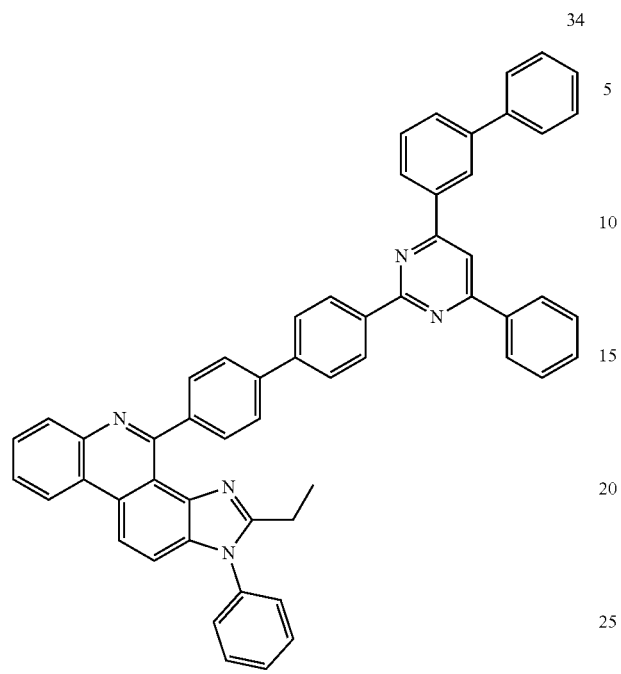
36
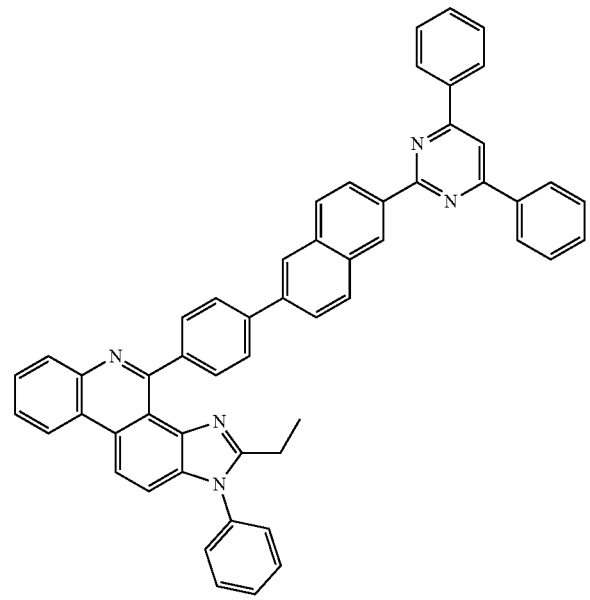
35
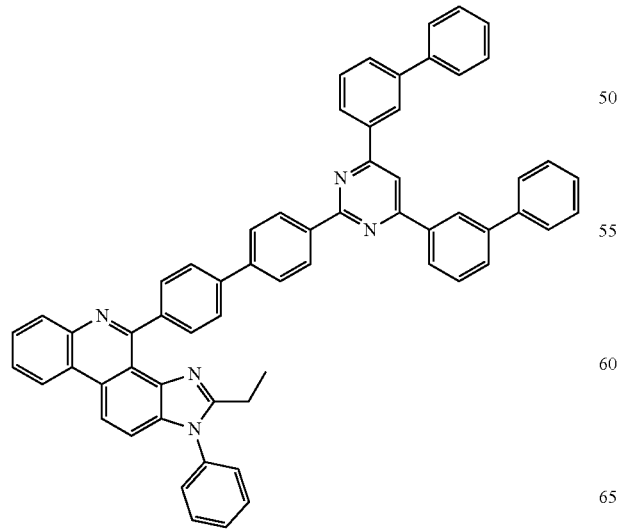
37
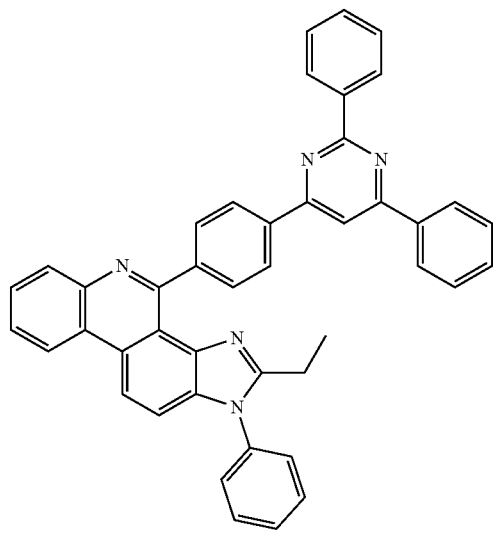

-continued
38
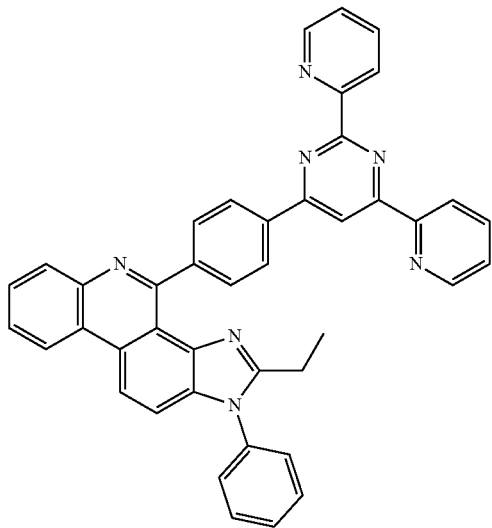
39
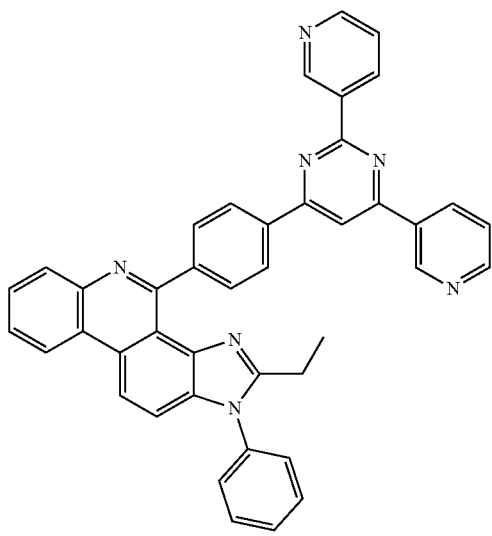
40
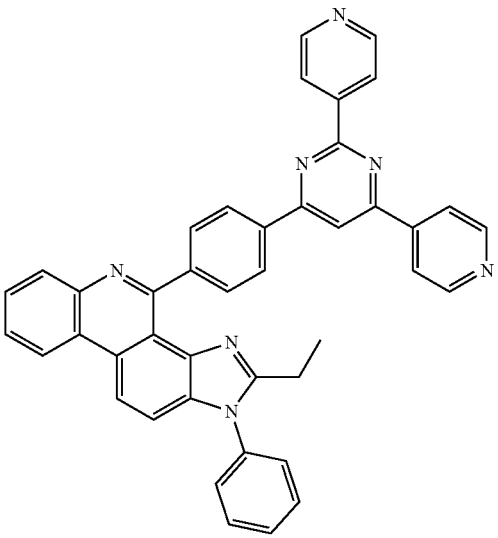
-continued
41
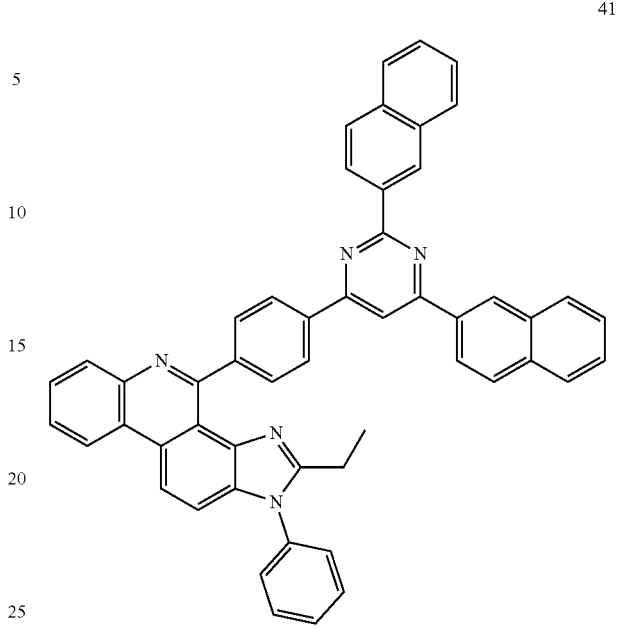
42

43
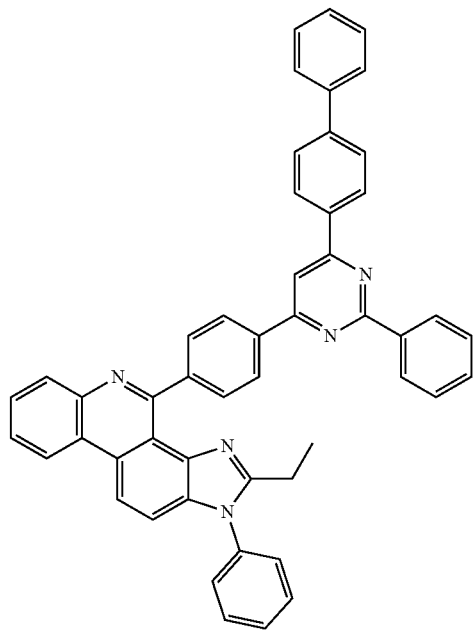
45
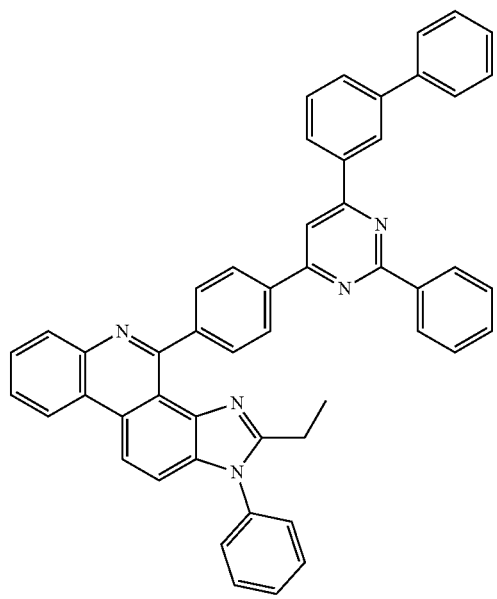
44
46
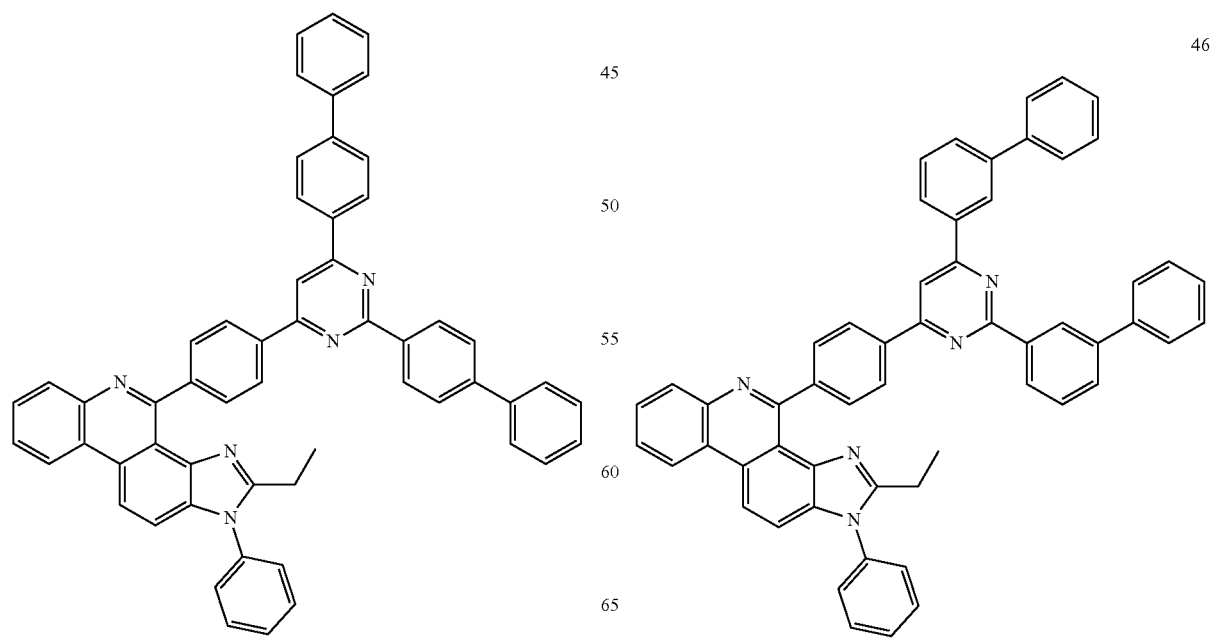

47
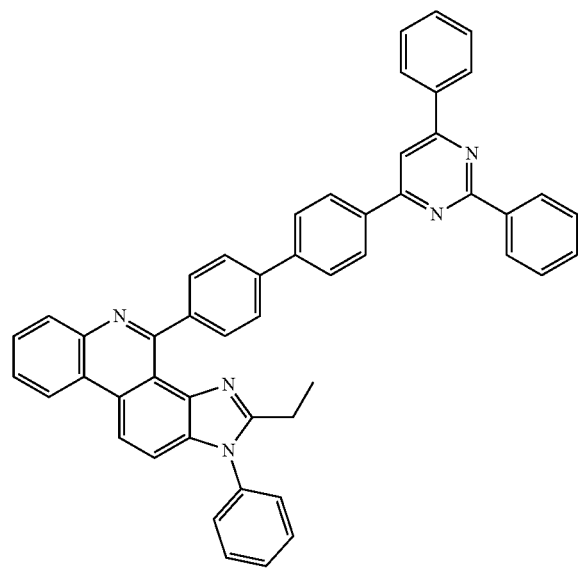
48
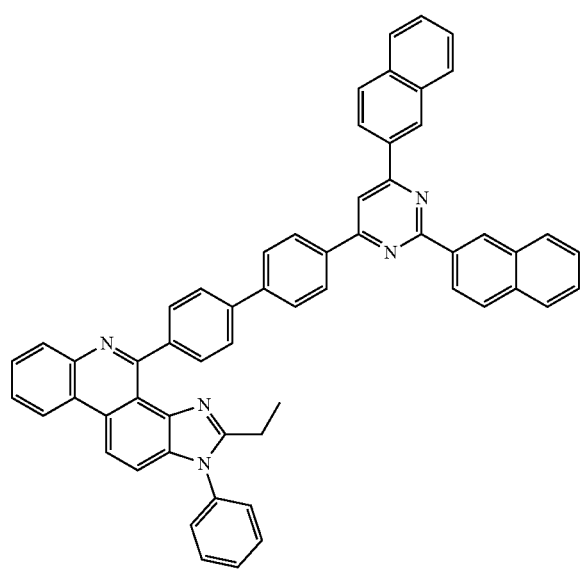
49
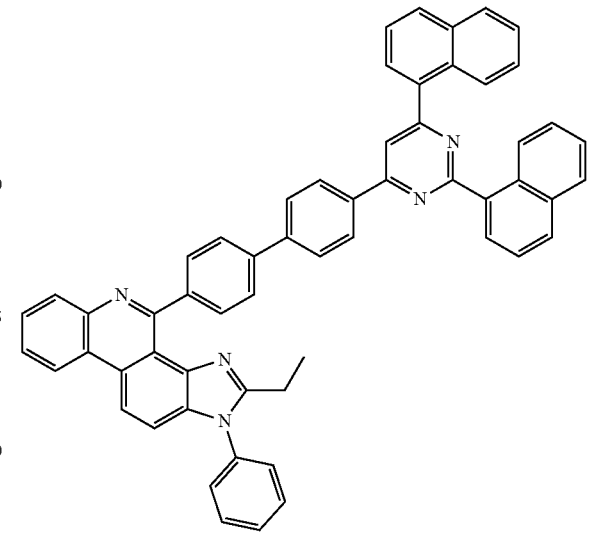
50
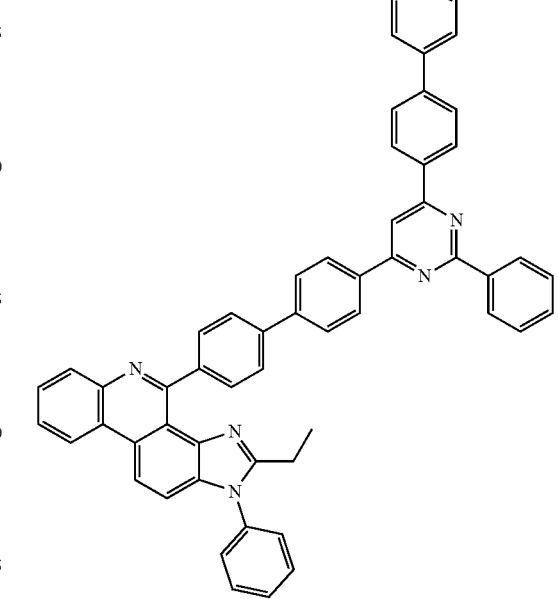

51
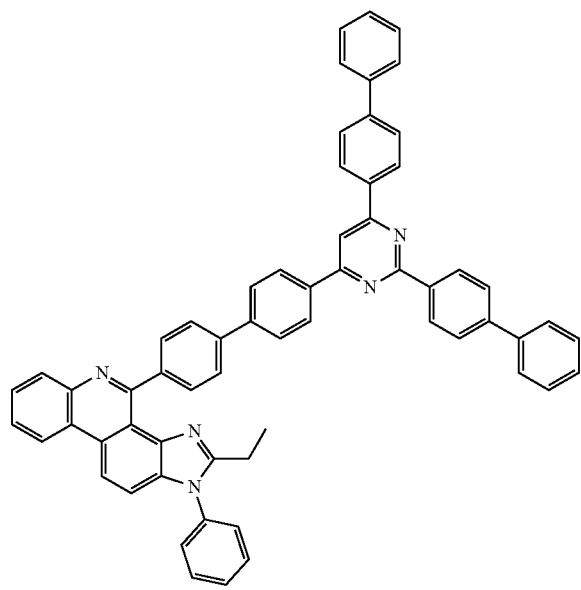
52
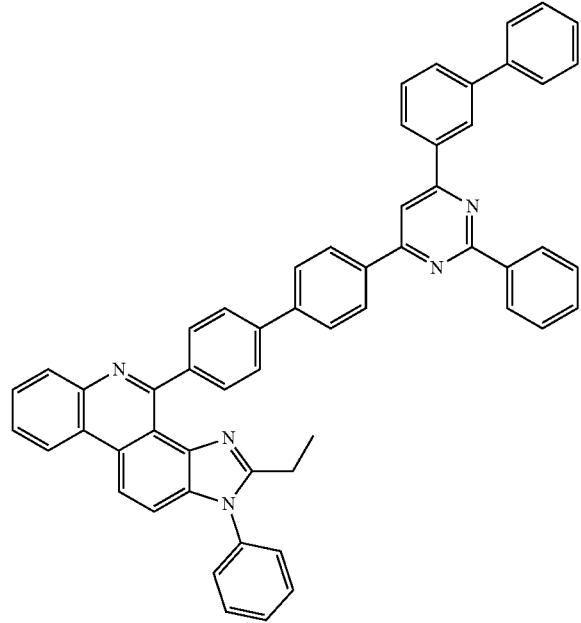
53
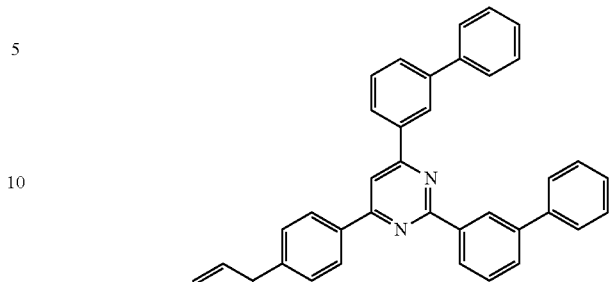
54
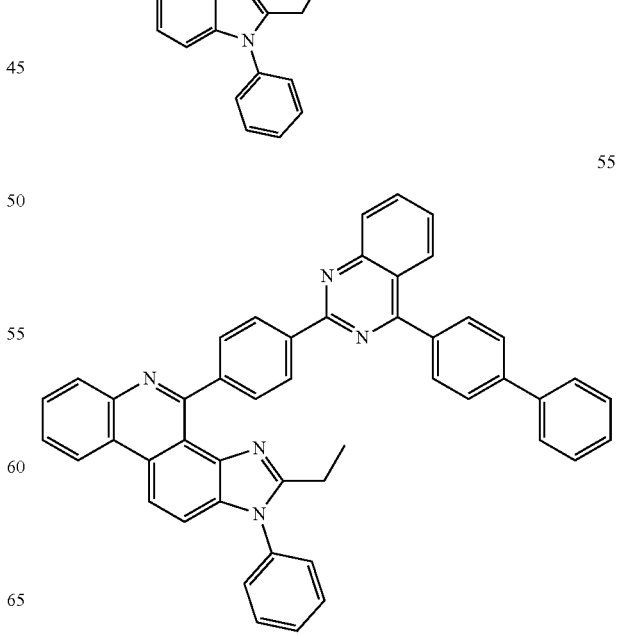
55

56
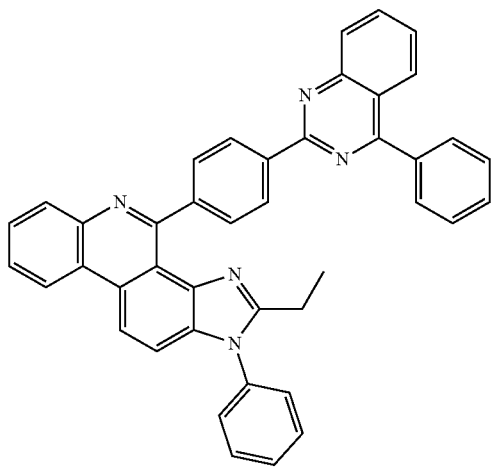
59
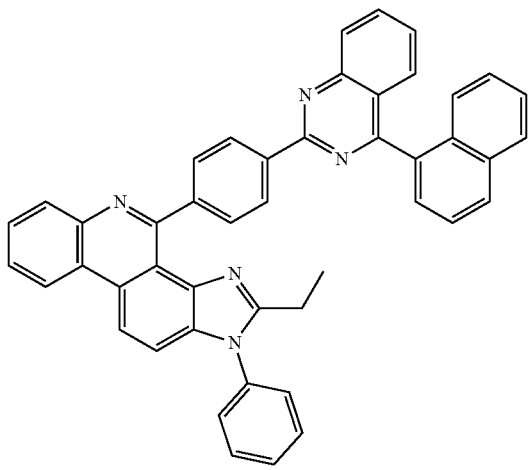
57
58
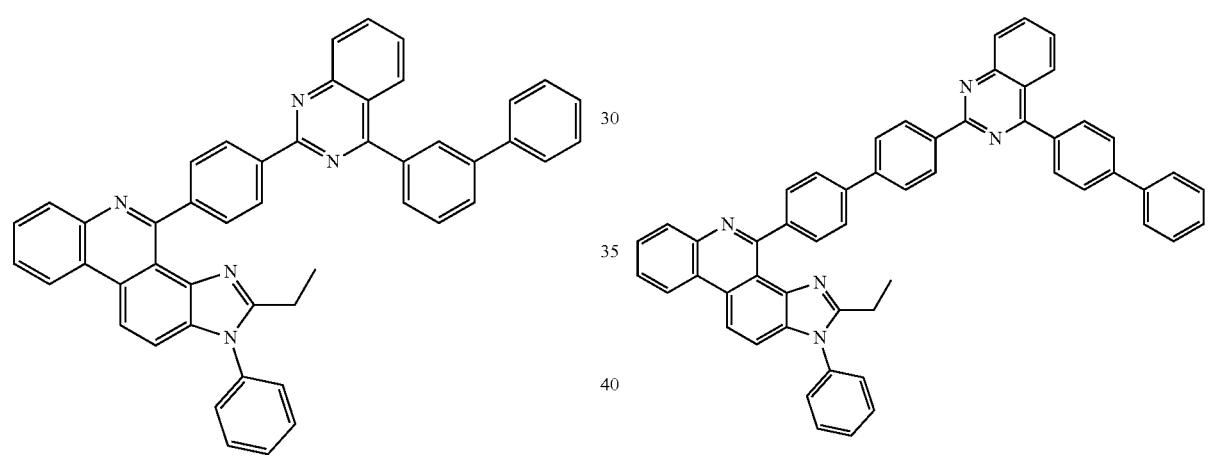
60
61
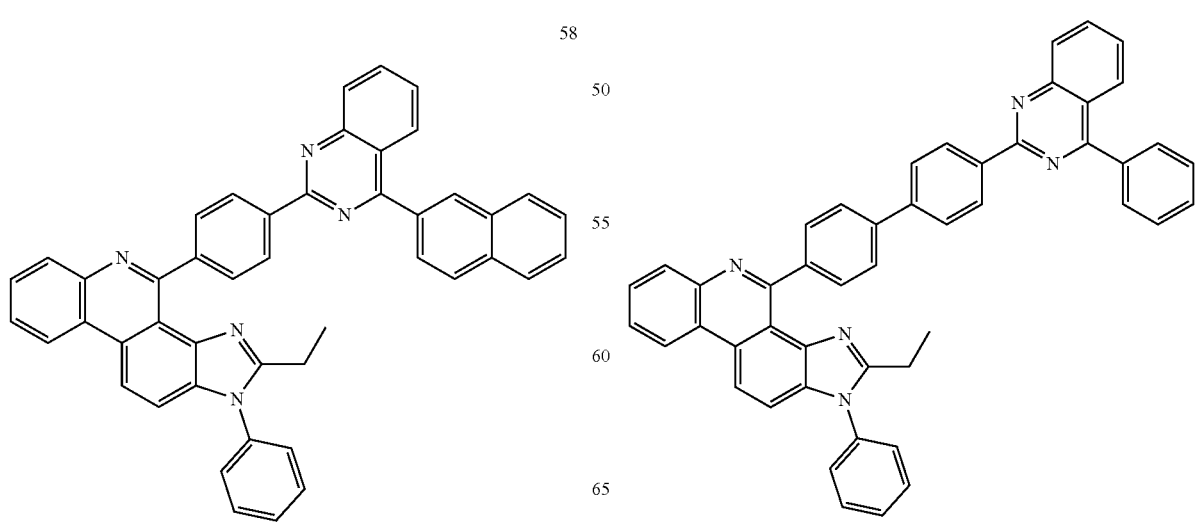

62
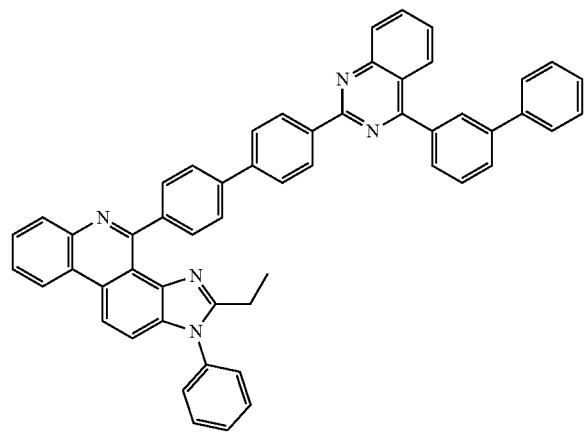
63
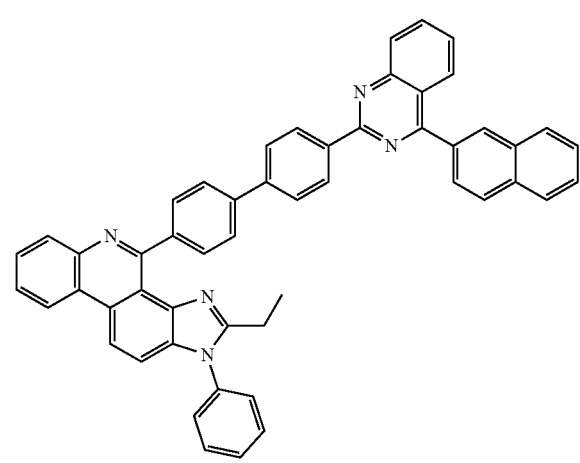
64
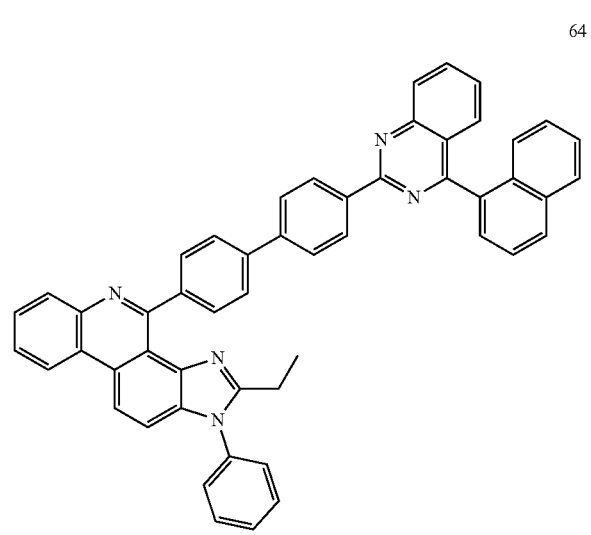
65
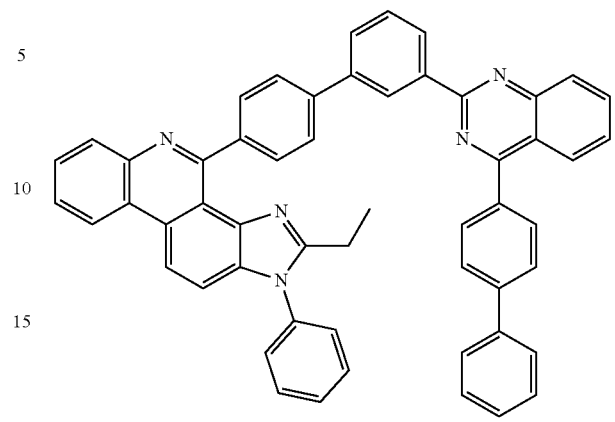
66
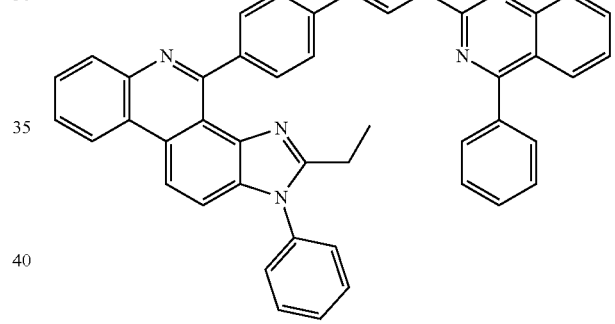
67
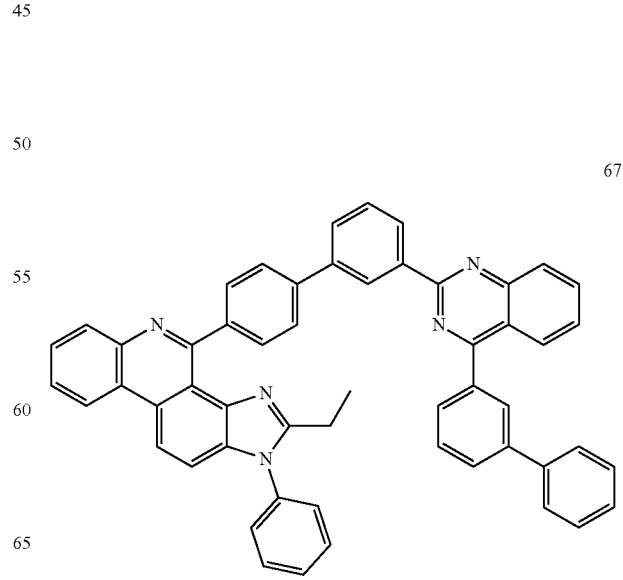

68
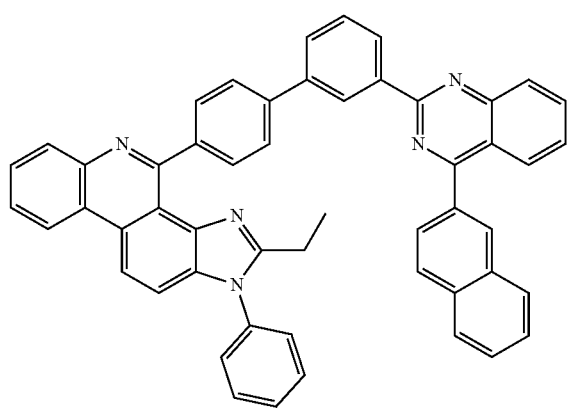
69
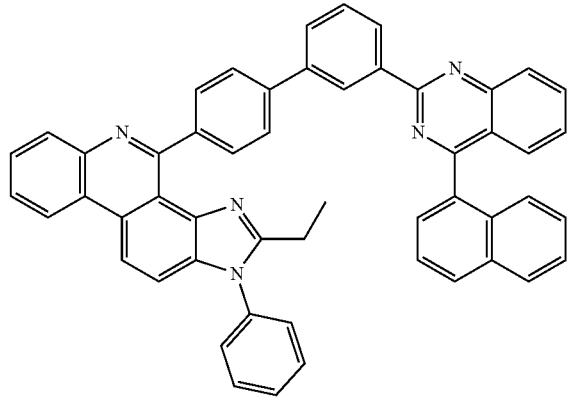
70
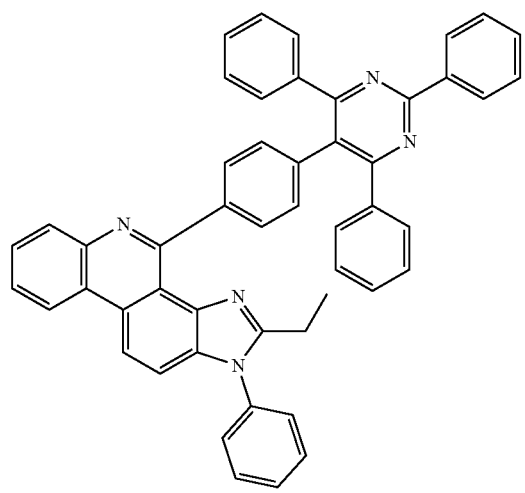
71
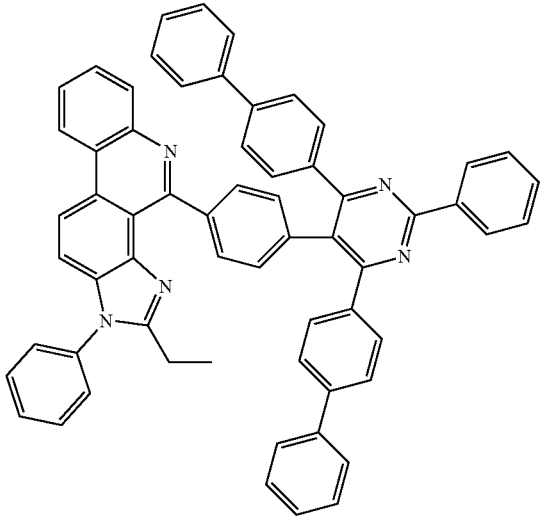
72
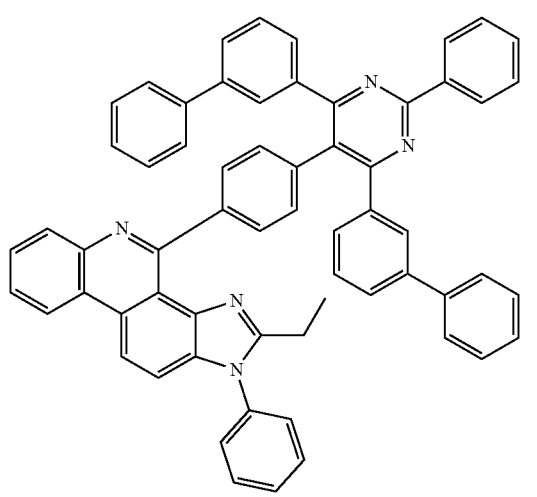
73
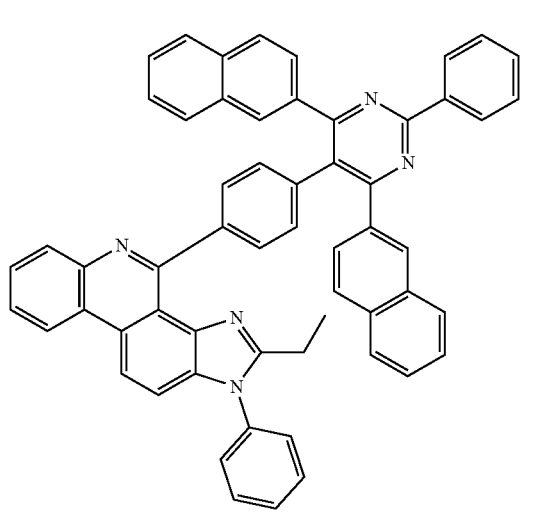

-continued
74
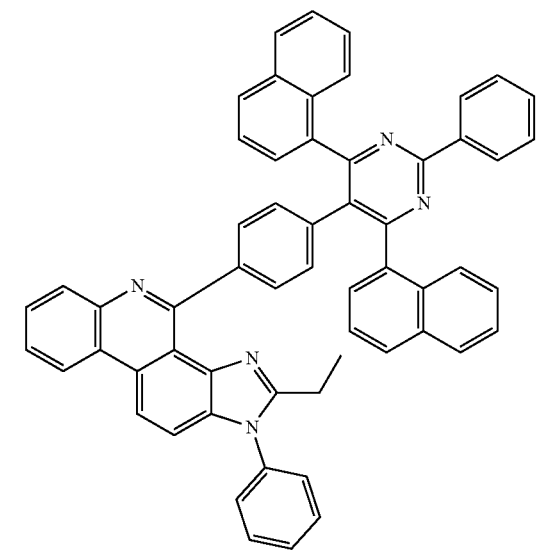
75
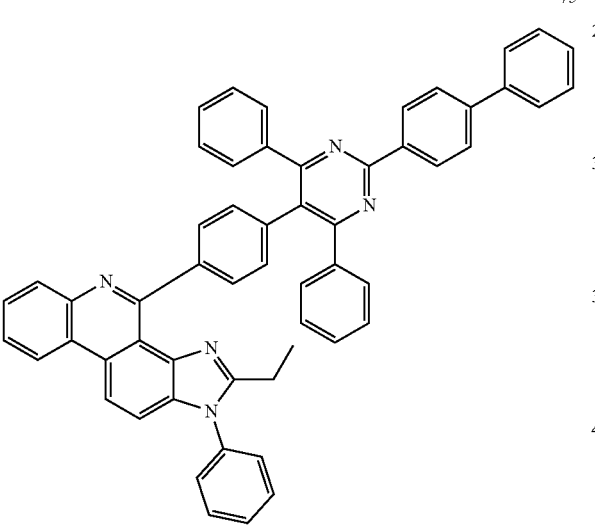
76
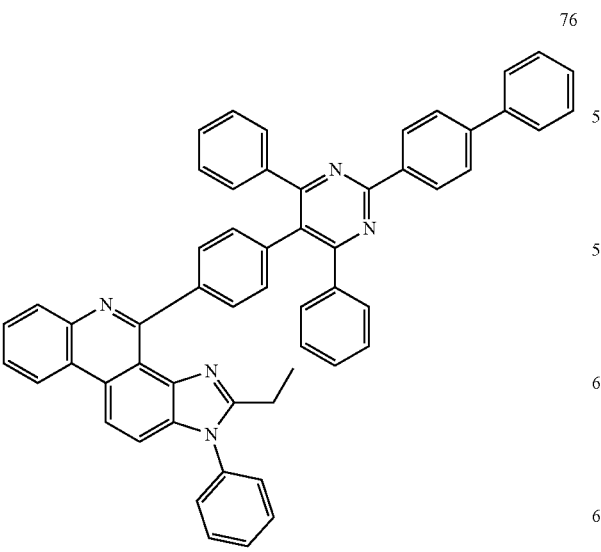
-continued
77
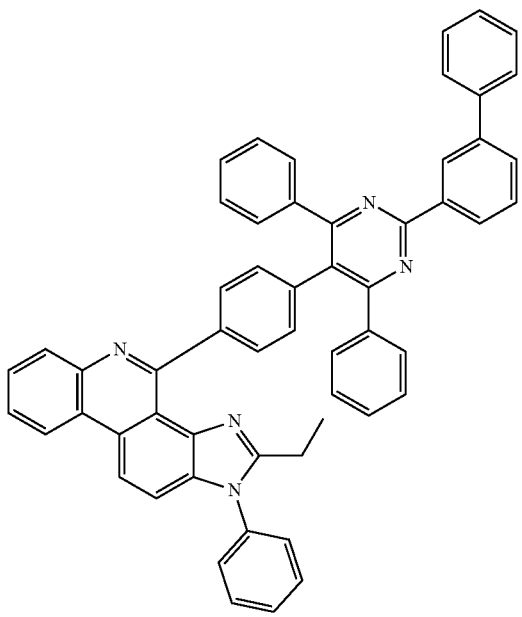
78
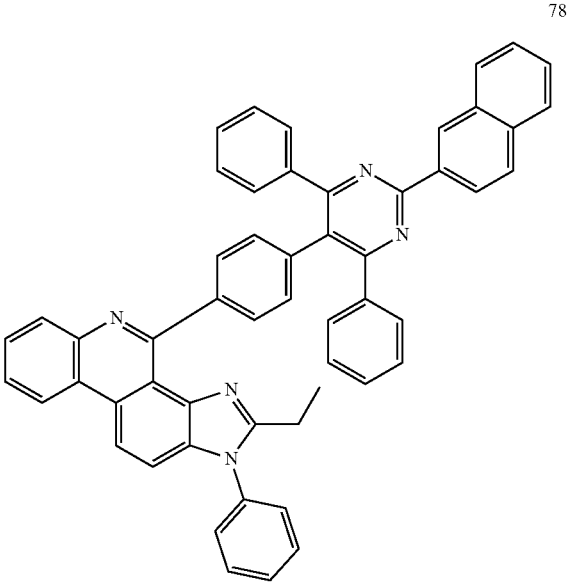

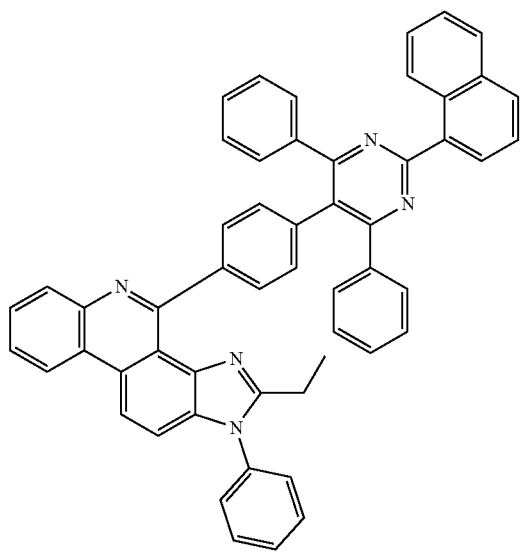
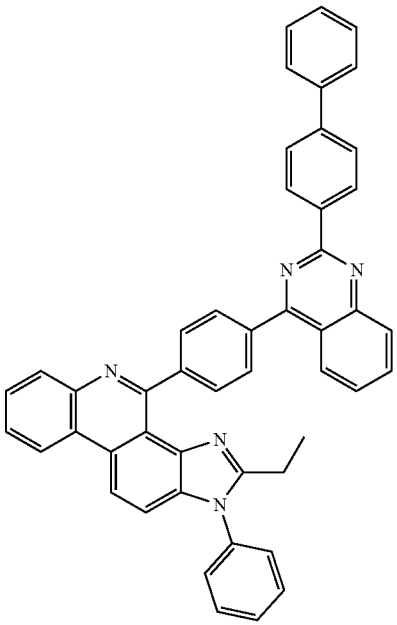
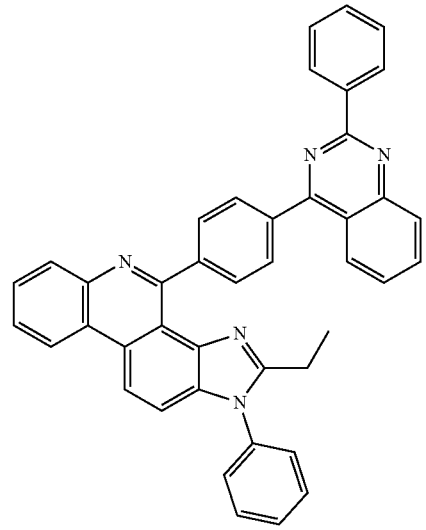
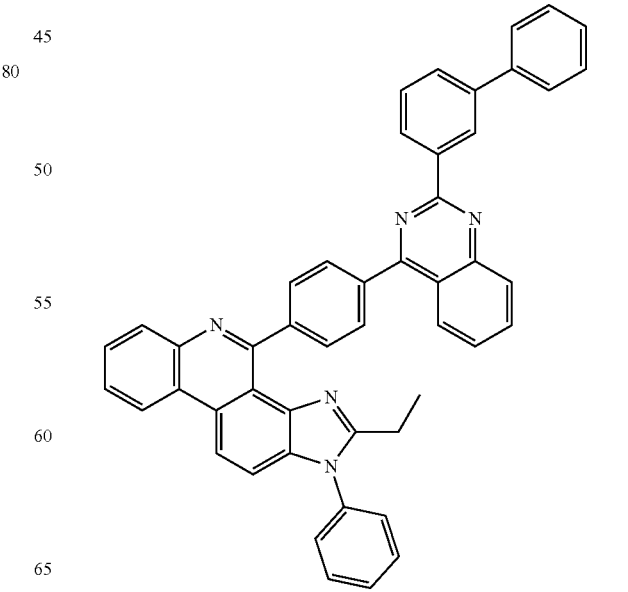

197
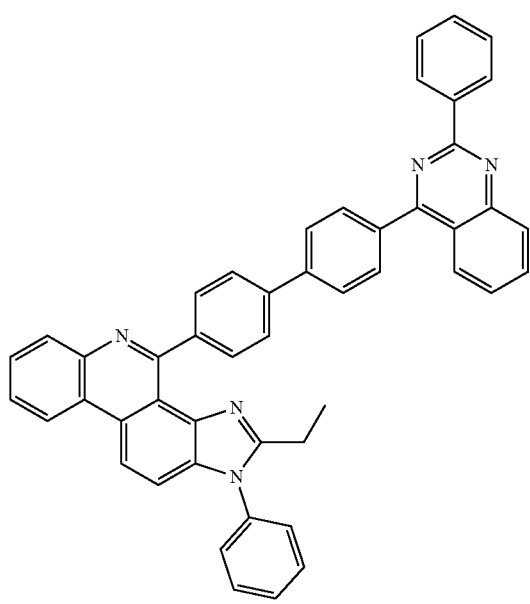
198
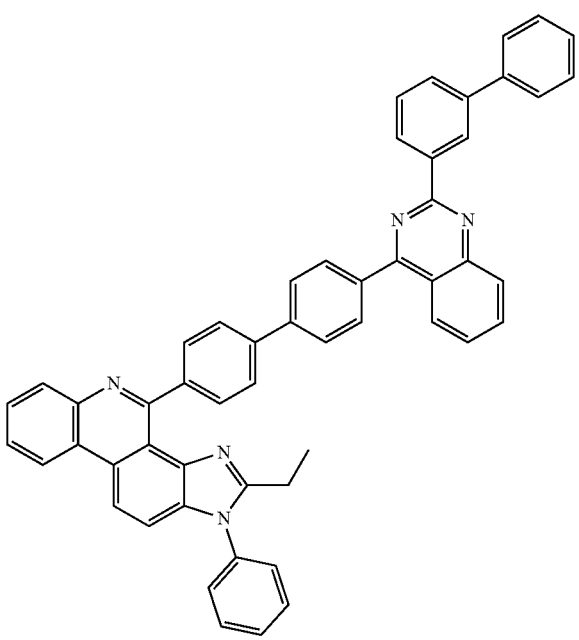
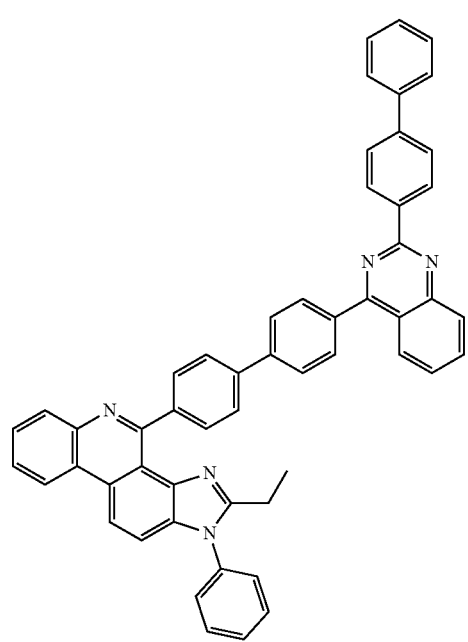
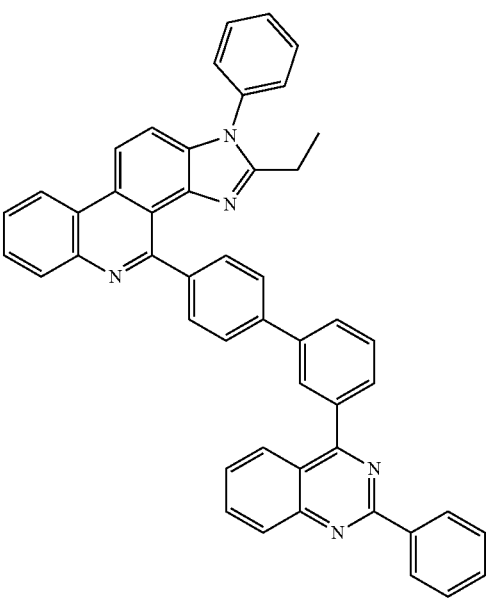

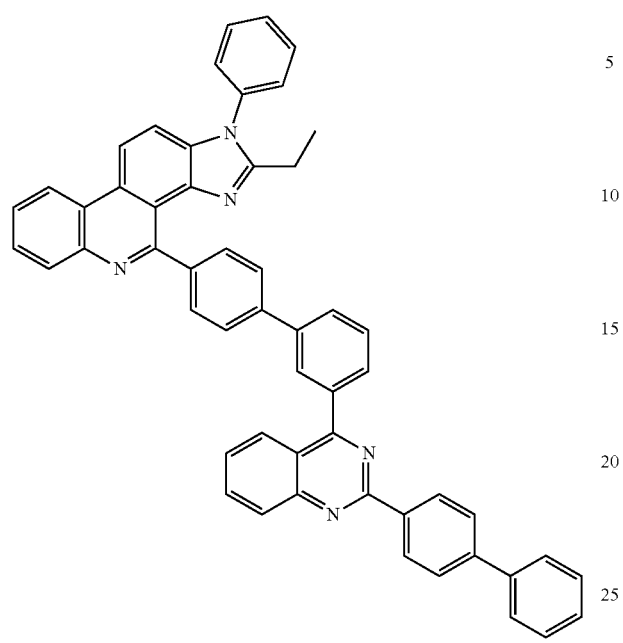
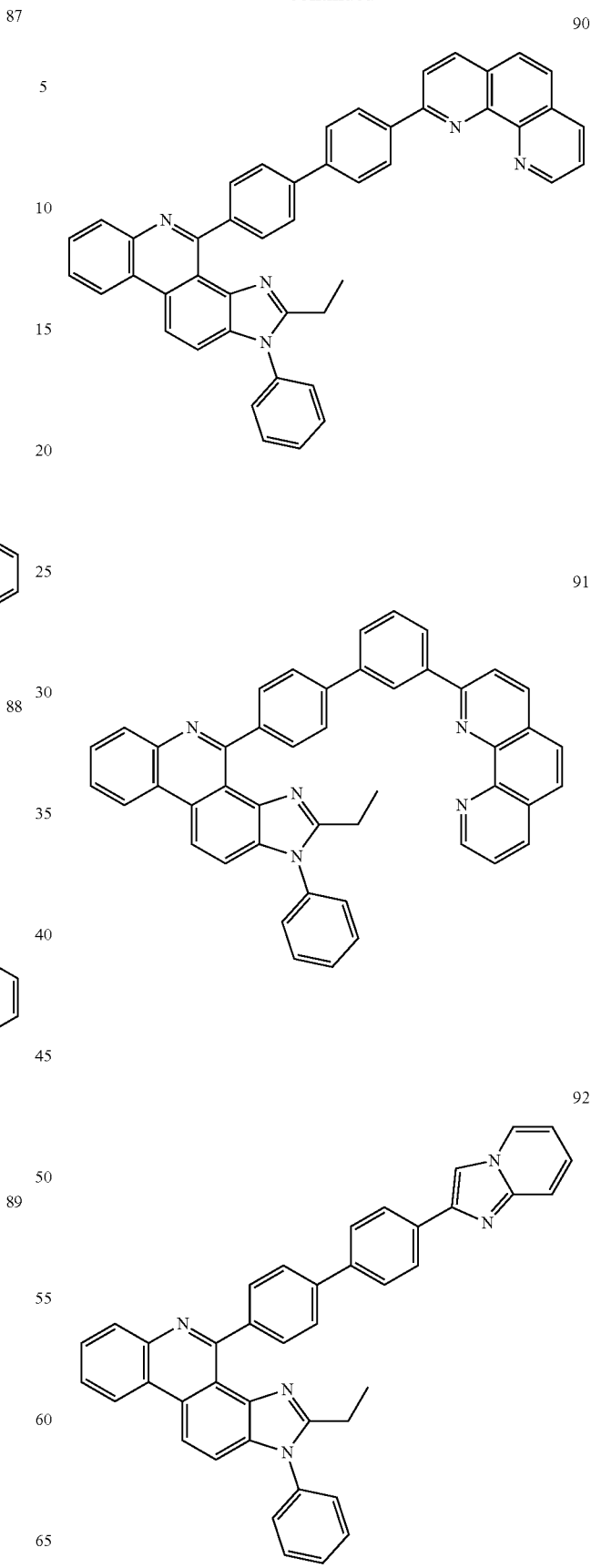

93
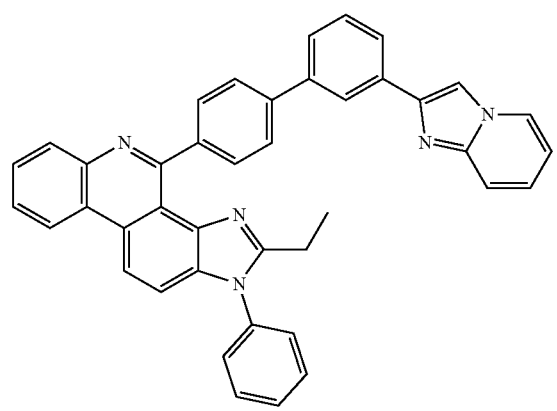
94
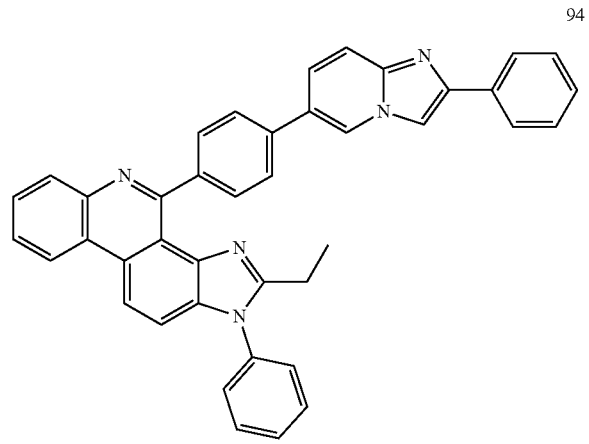
95
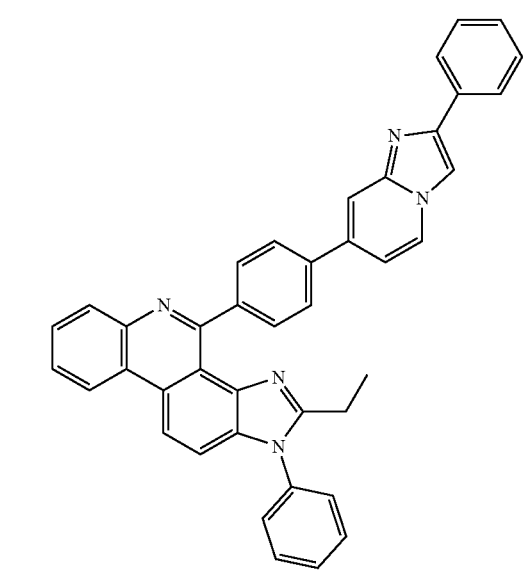
96
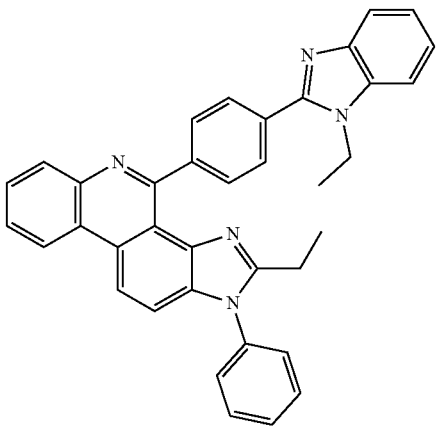
97
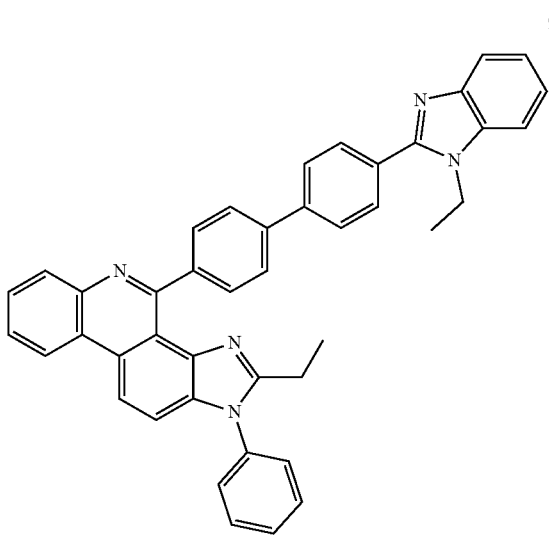
98
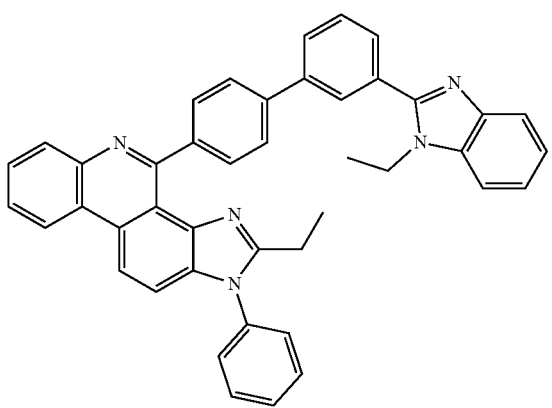

203
-continued
99
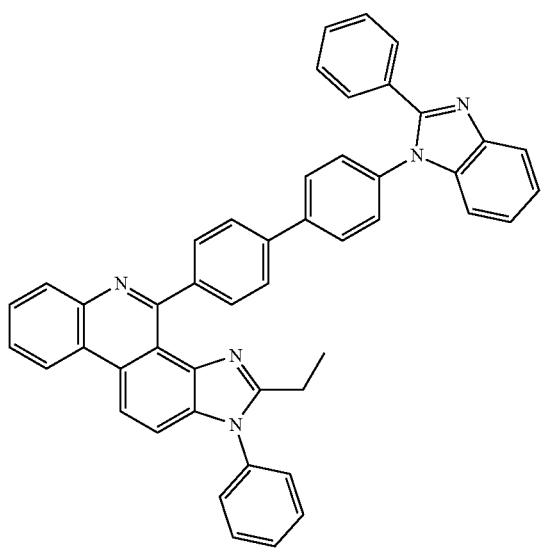
100
102
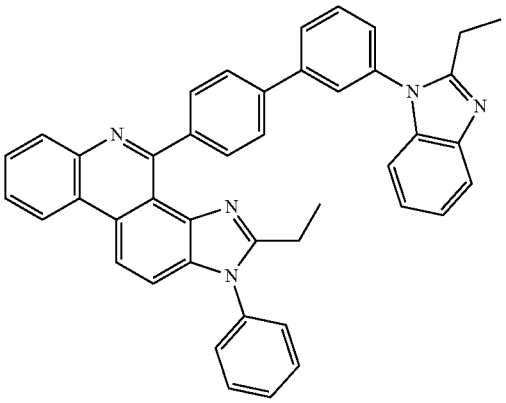
103
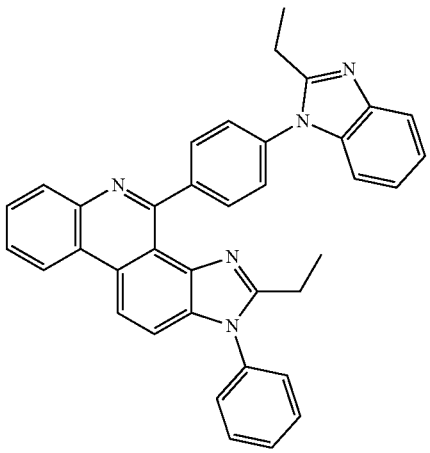
101
204
-continued
104
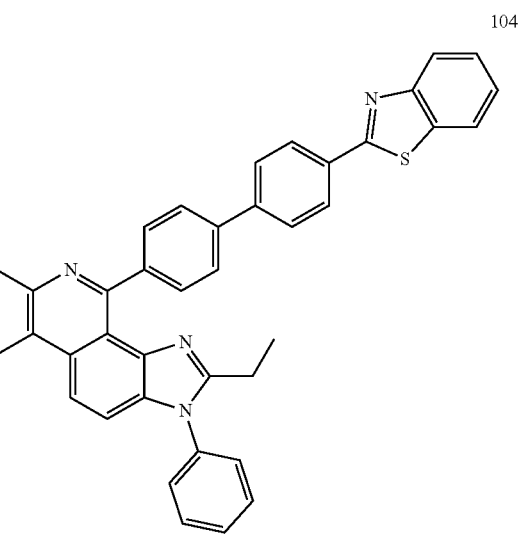

205
-continued
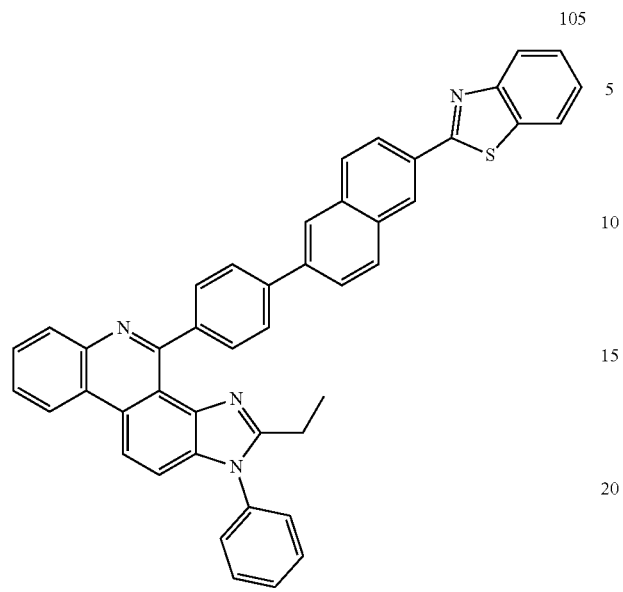
106
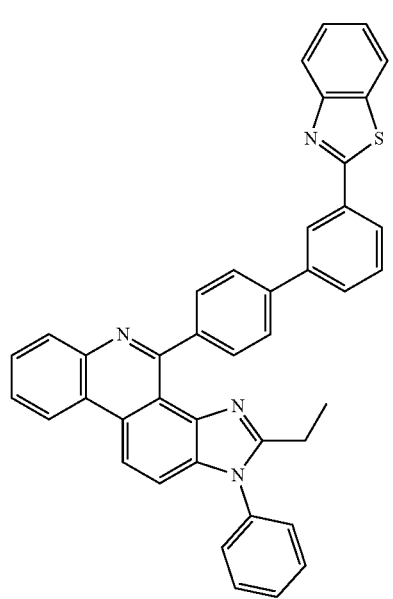
206
-continued
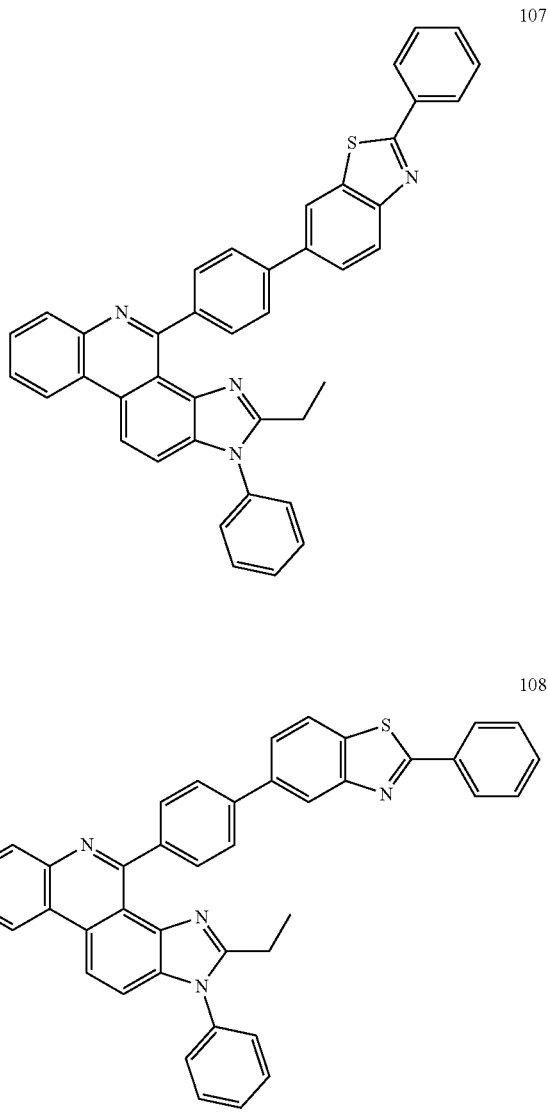
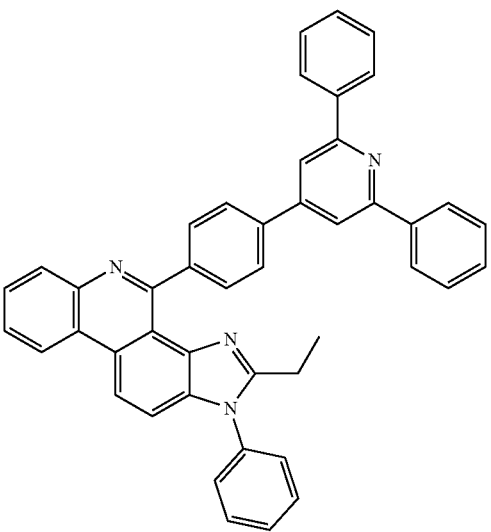

-continued
110
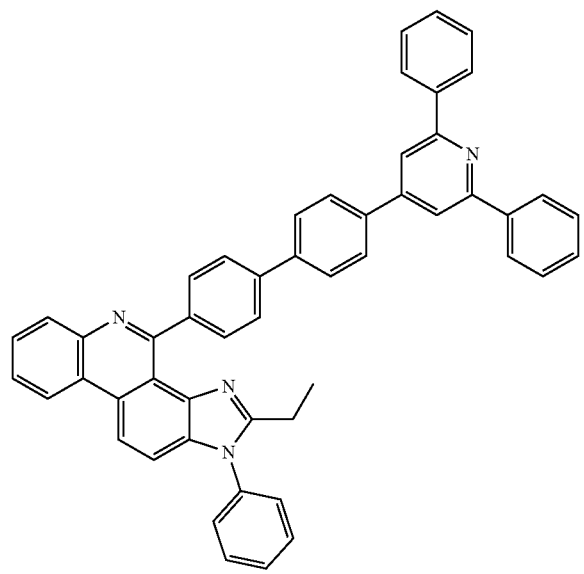
111
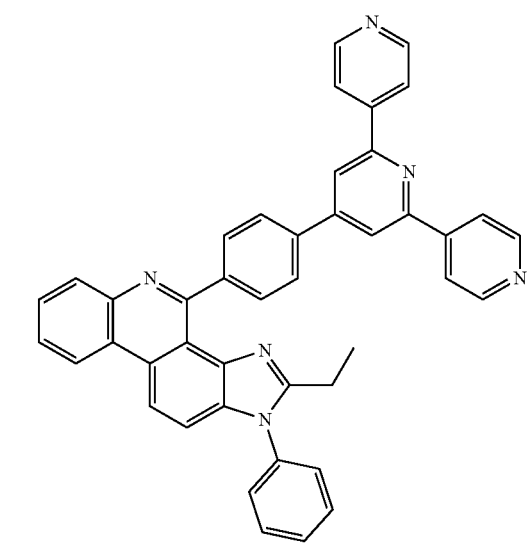
112
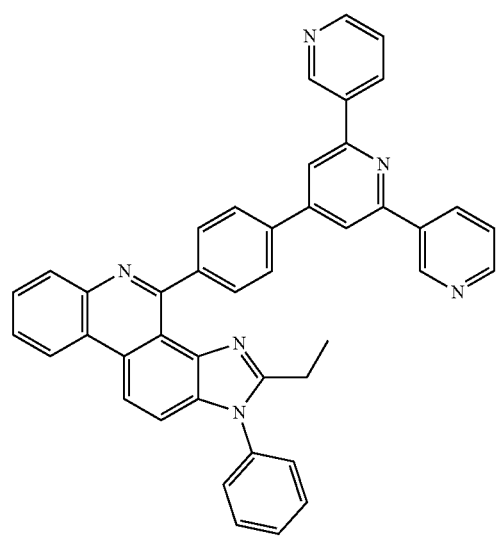
-continued
113
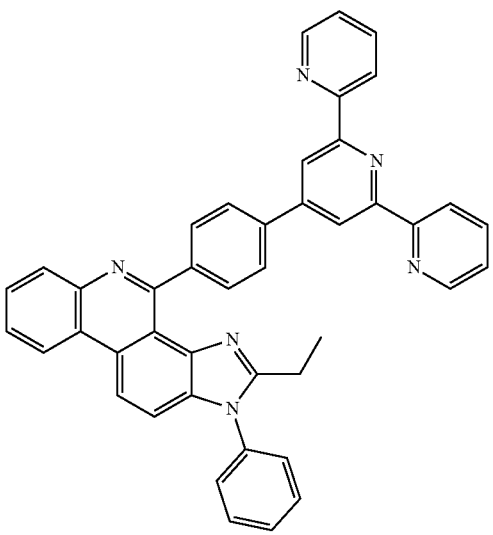
114
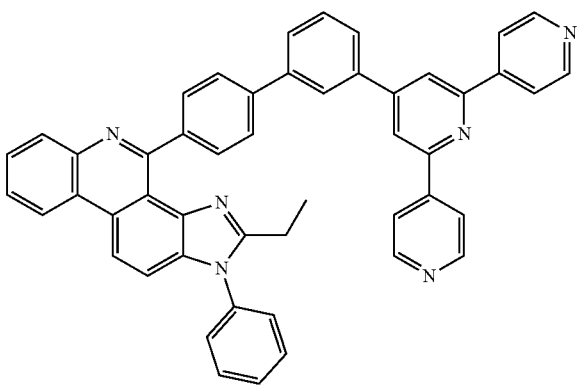
115
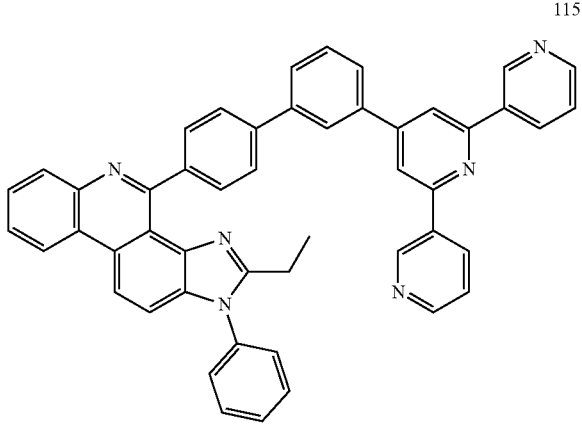

209
-continued
116
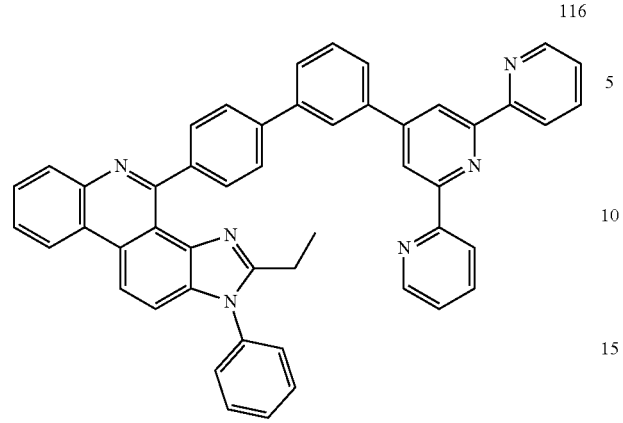
117
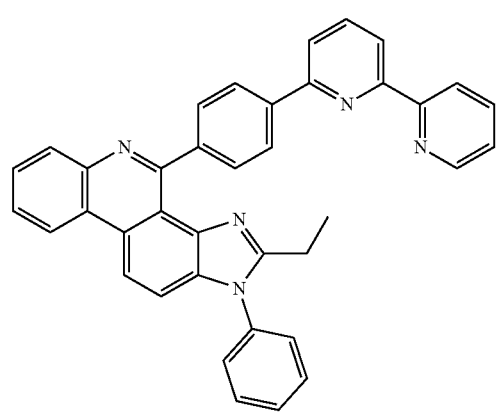
118
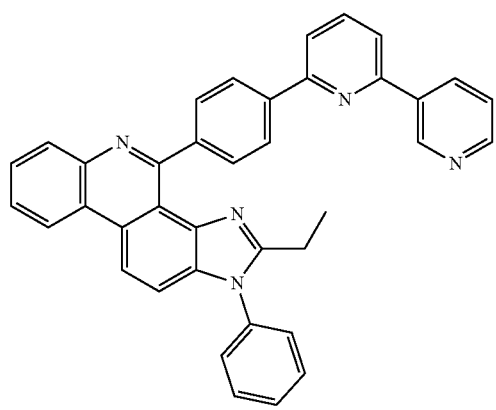
119
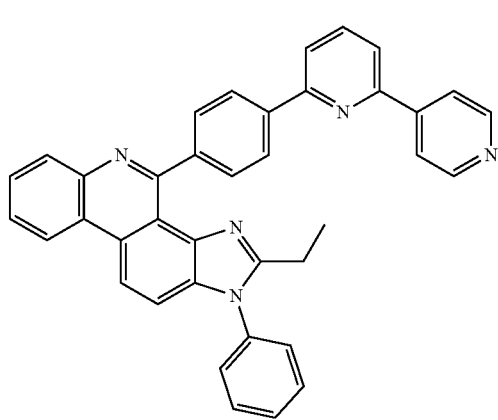
210
-continued
120
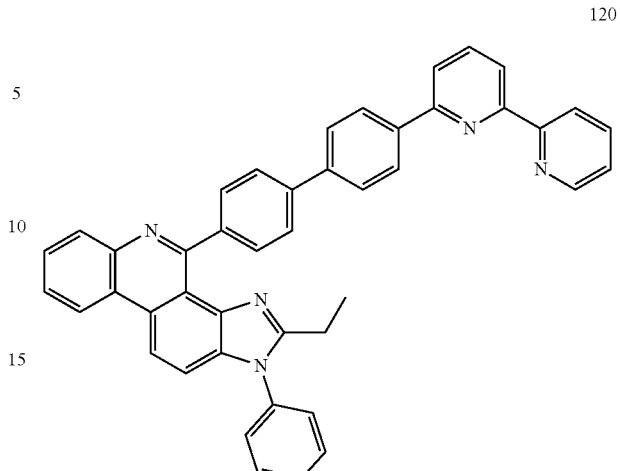
121
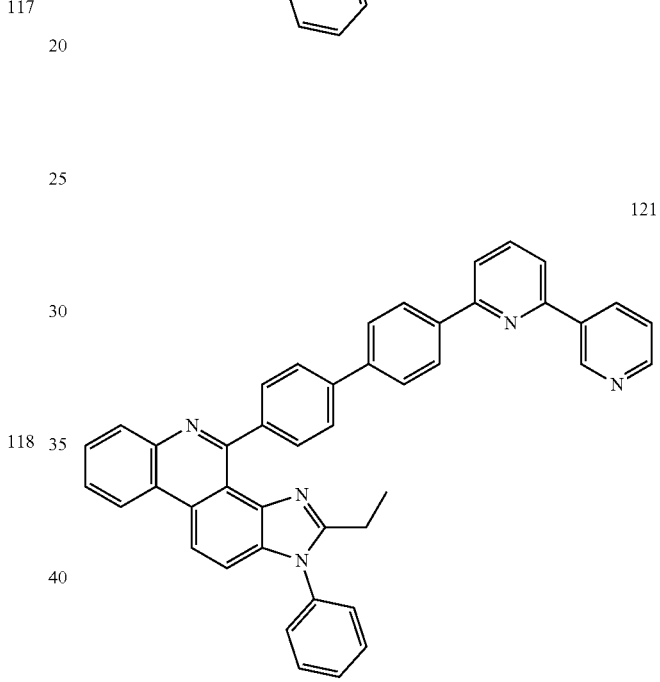
122
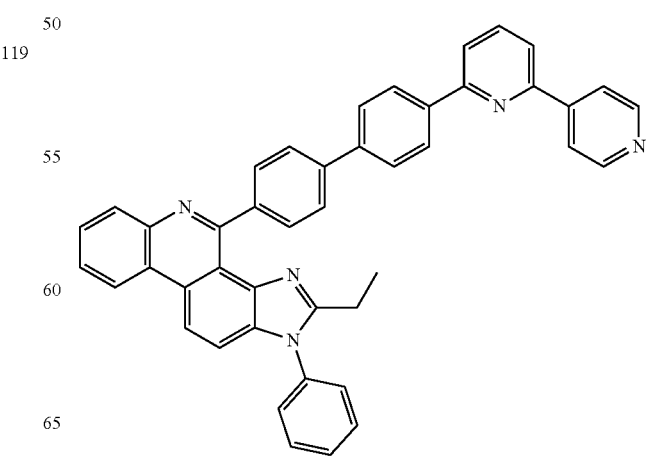

211
-continued
123
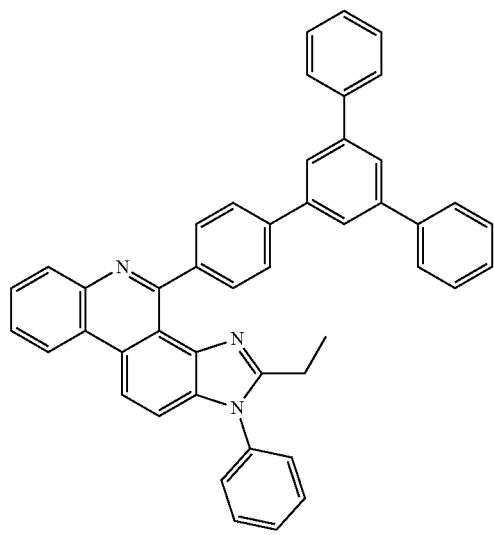
124
125
212
-continued
126
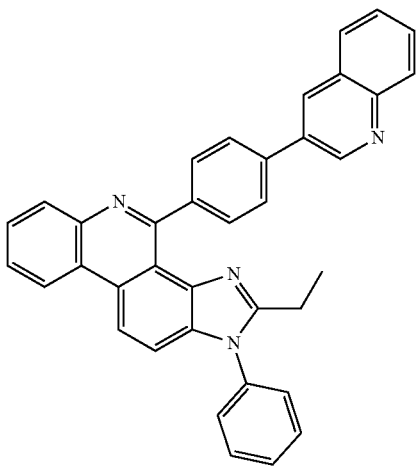
127
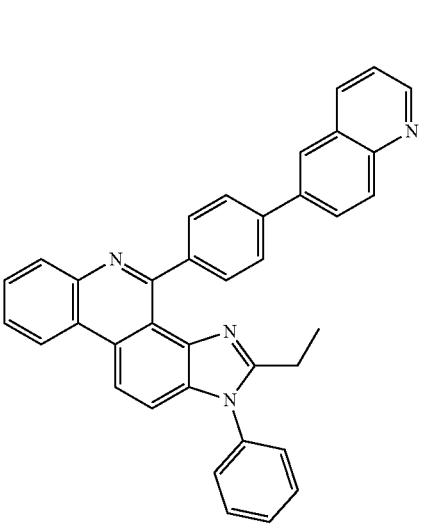
128
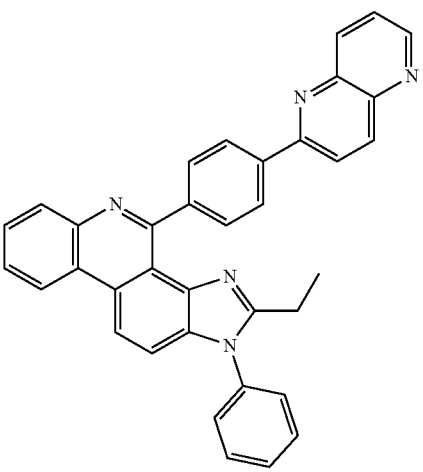

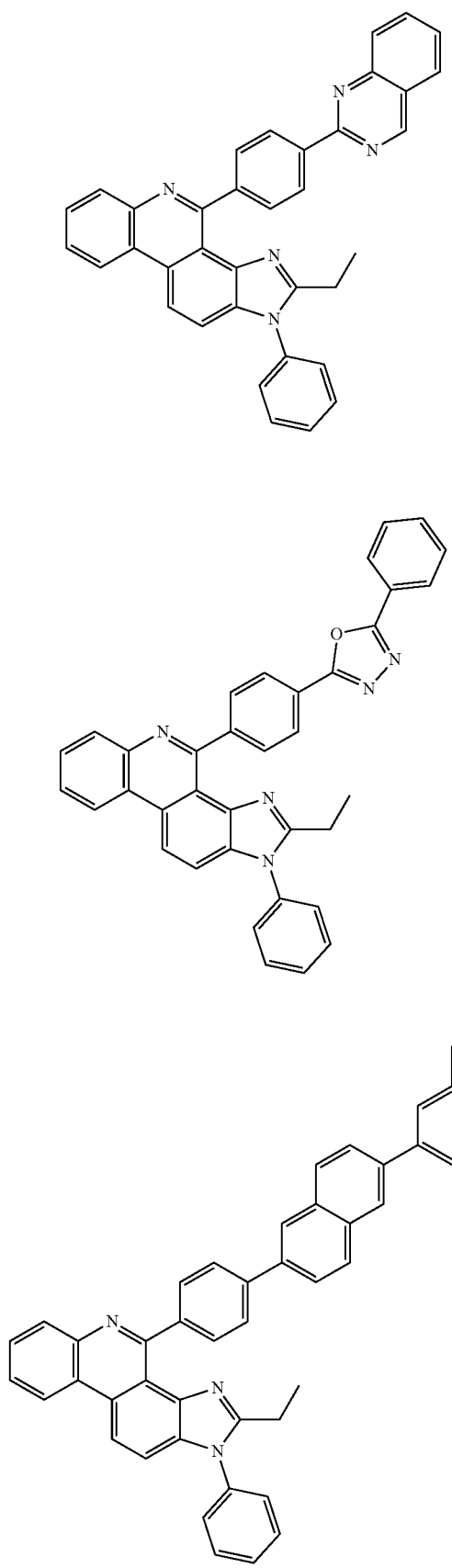
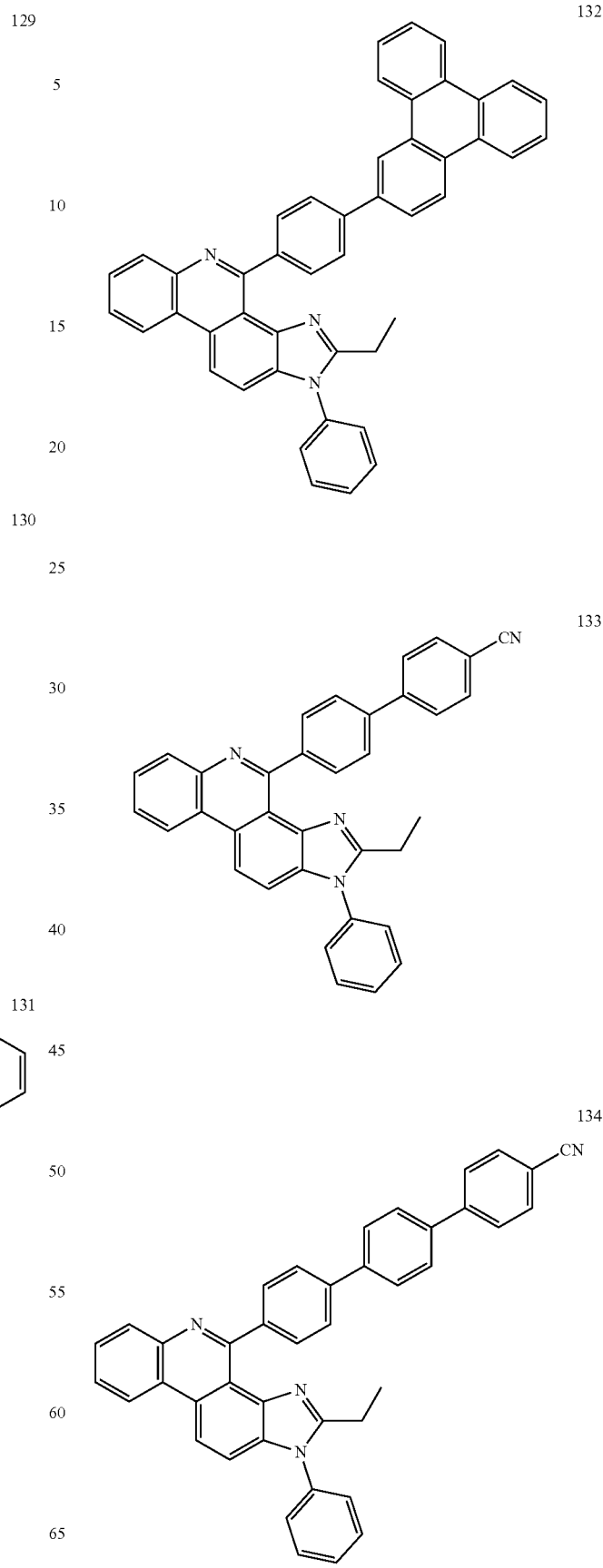

-continued
135
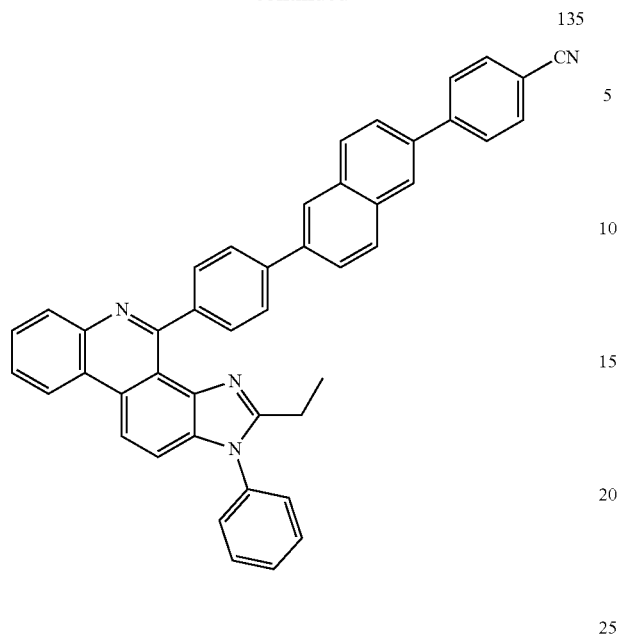
136
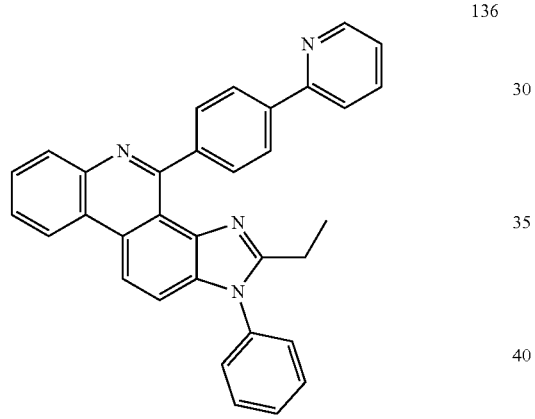
137
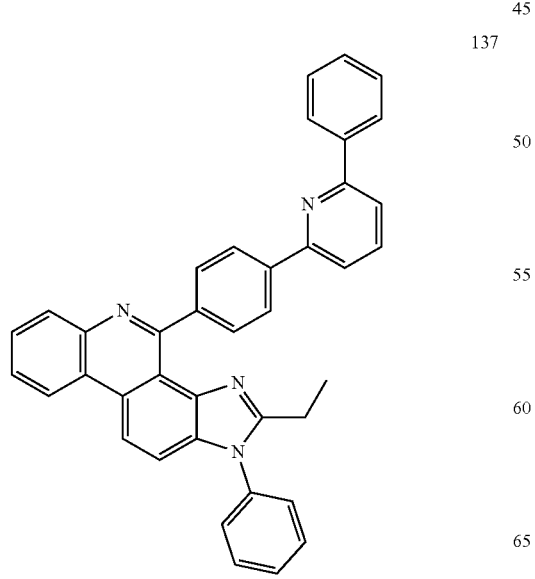
-continued
138
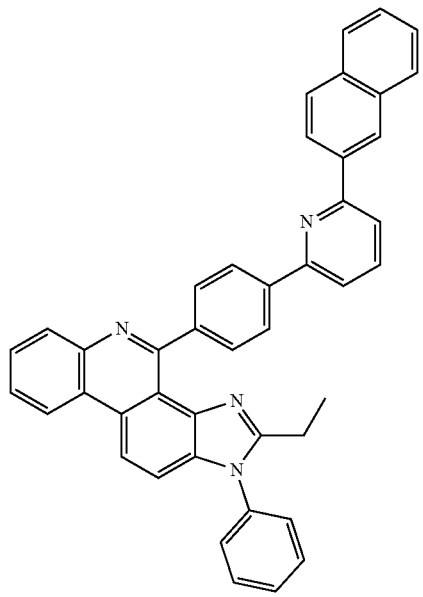
139
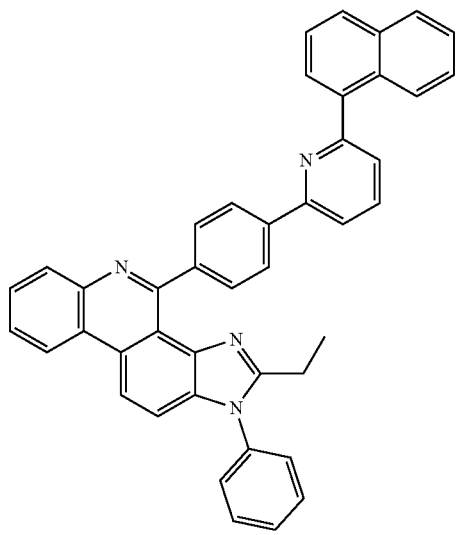

217
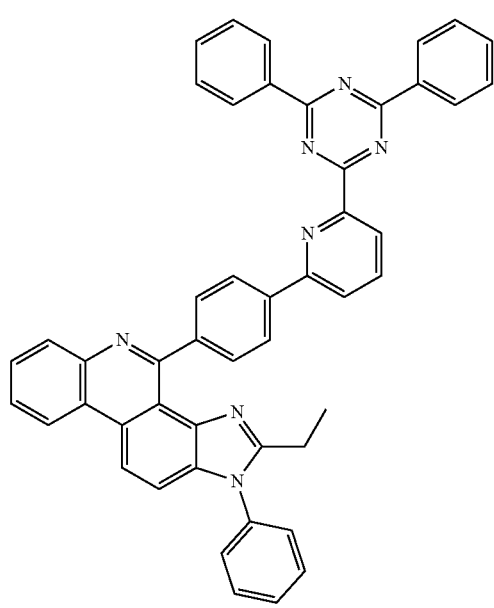
140
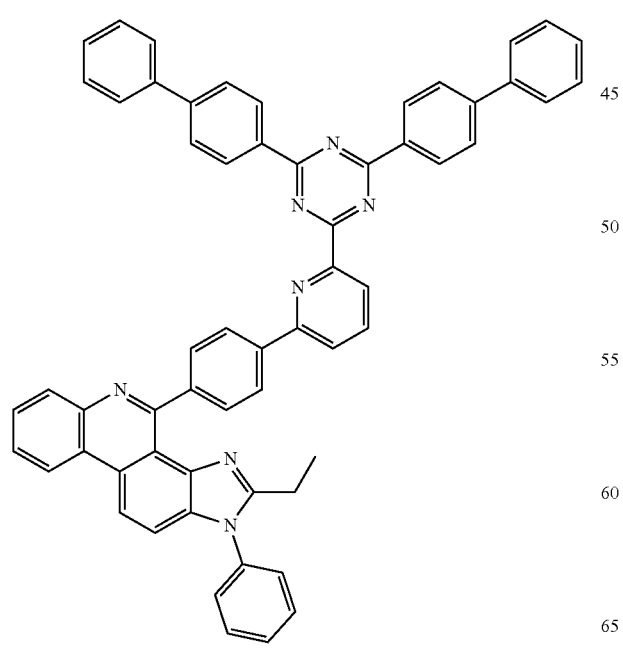
141
218
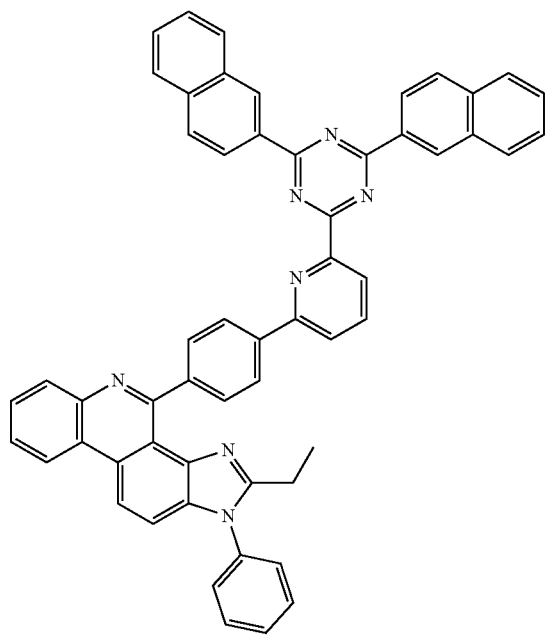
142
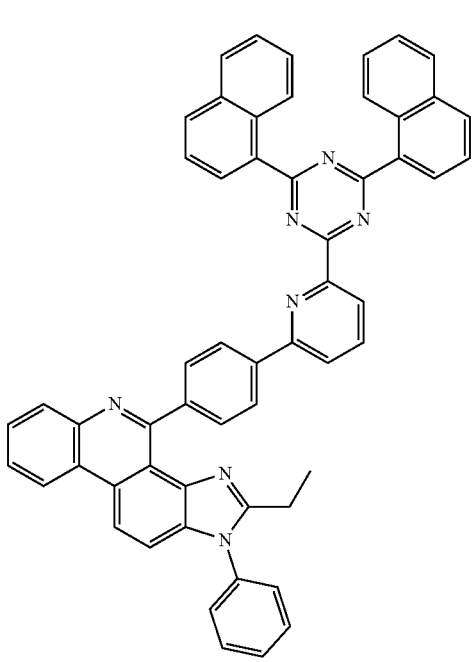
143

144
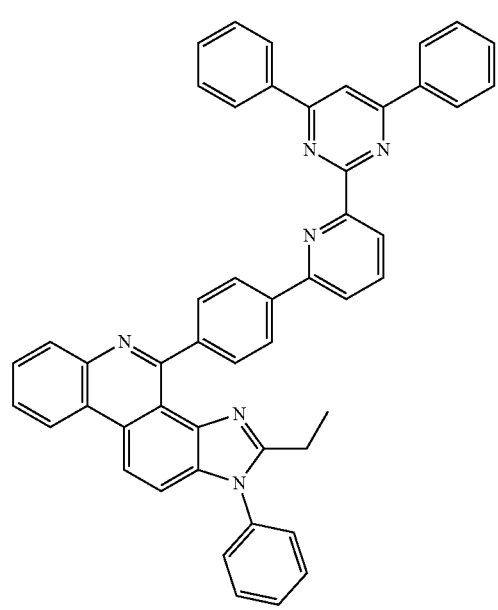
146
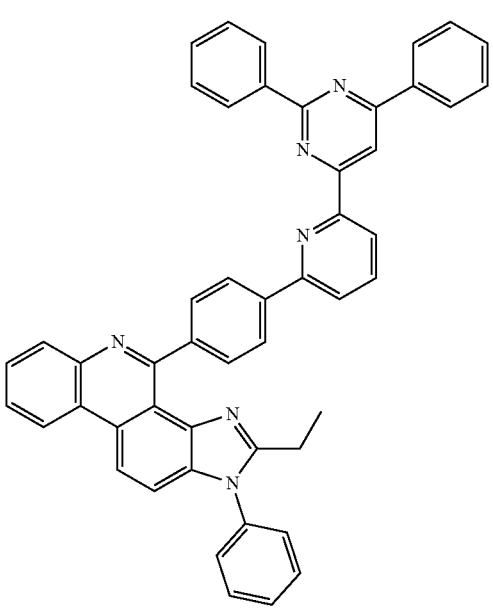
145
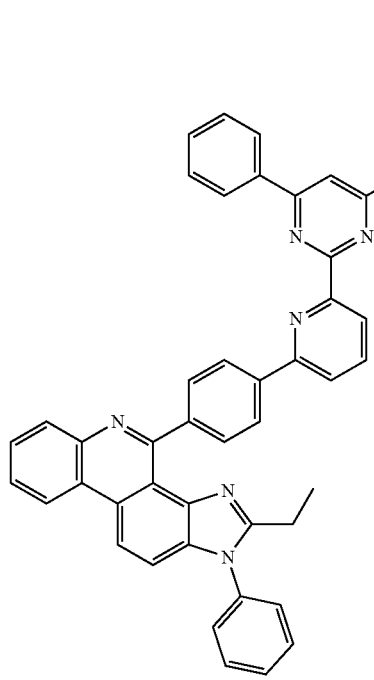
147

148
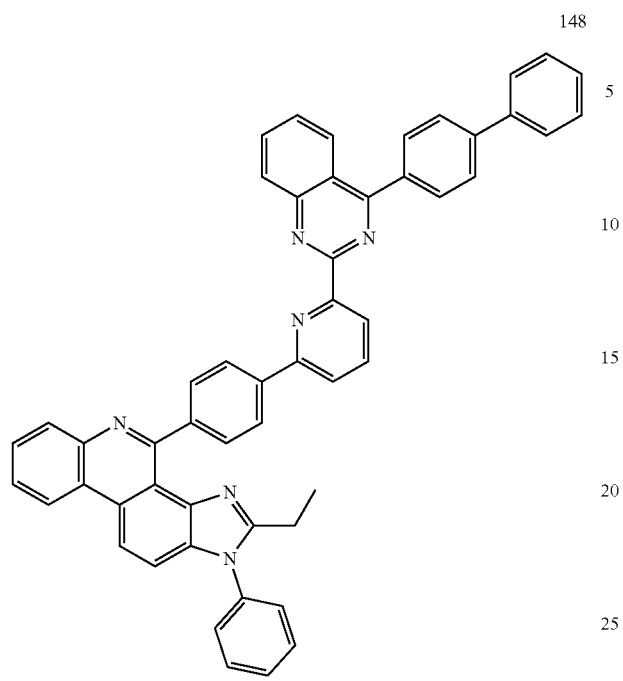
149
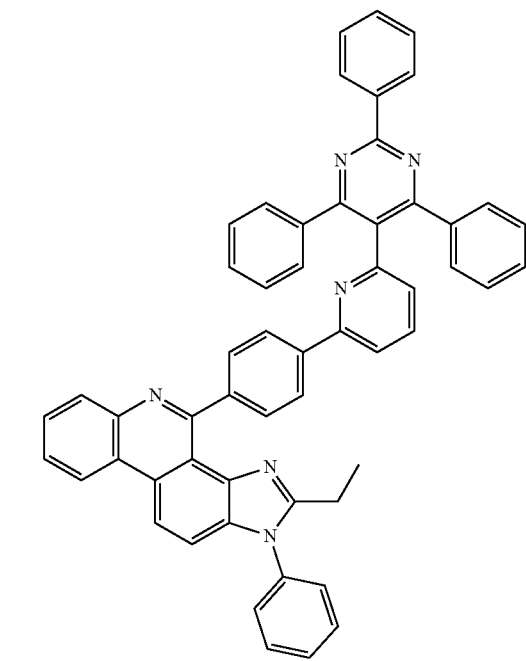
150
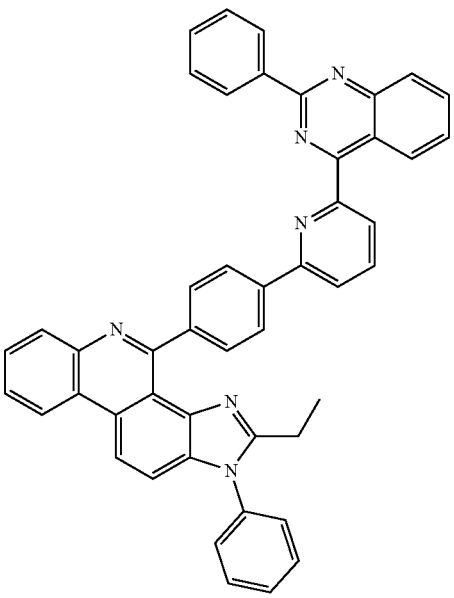
151
152
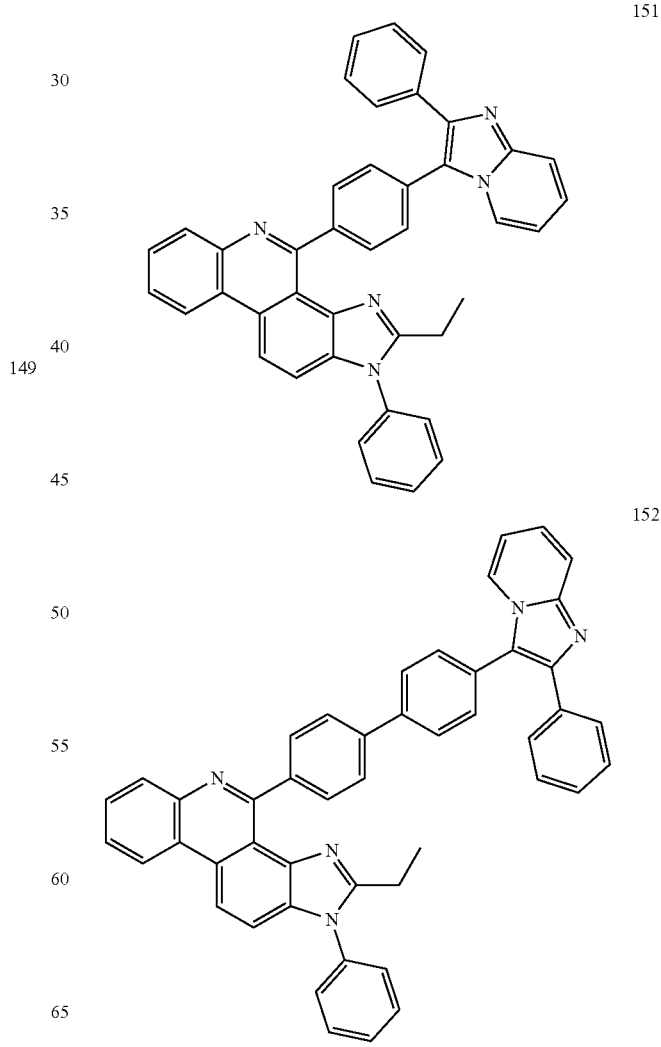

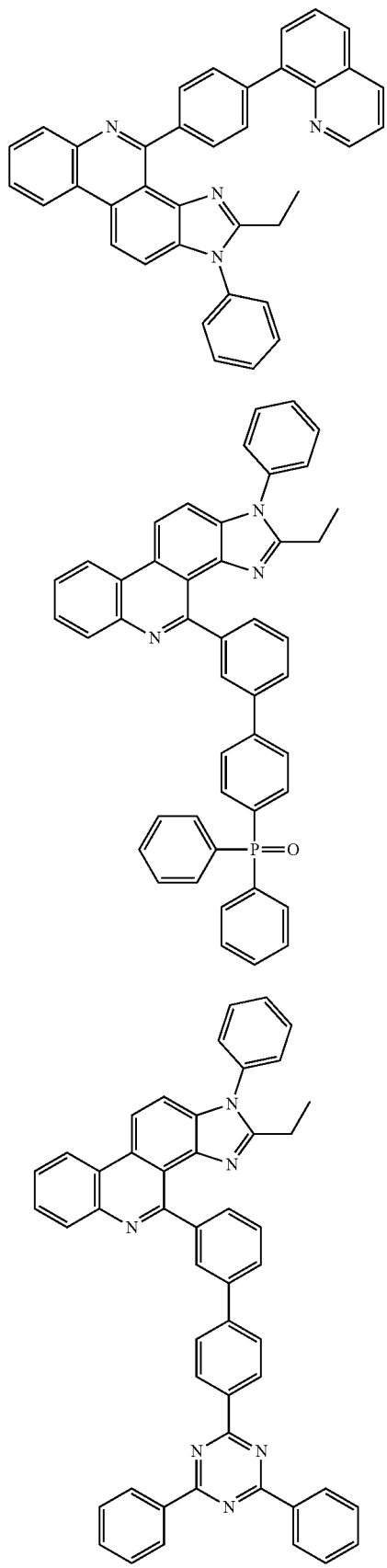
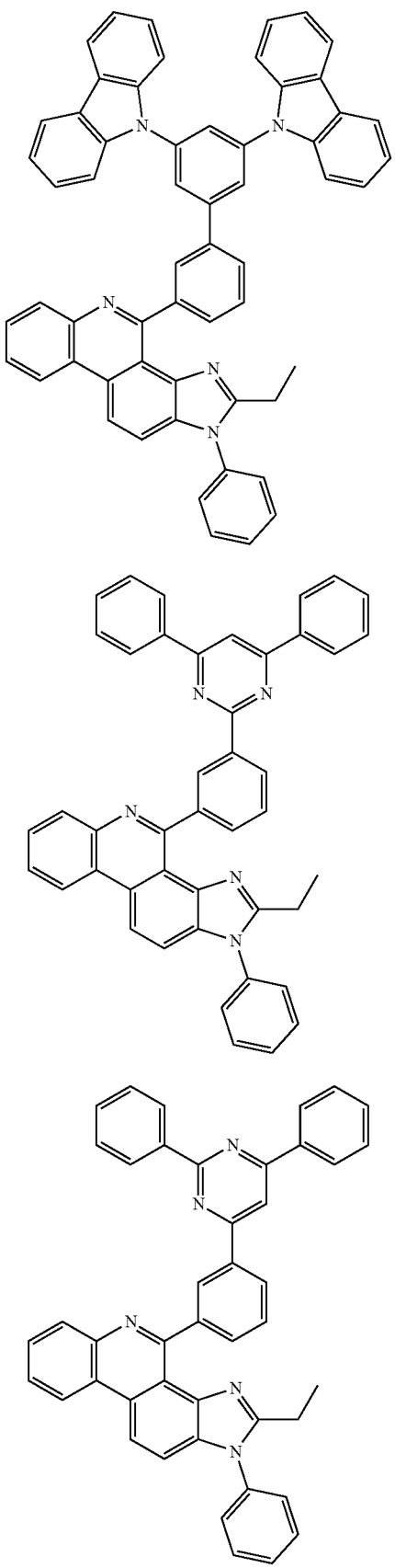

225
-continued
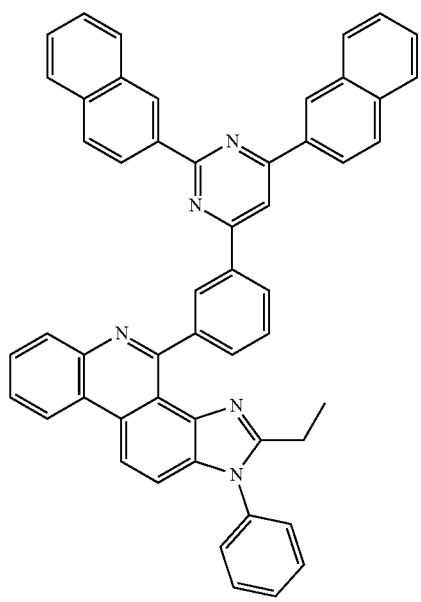
226
-continued
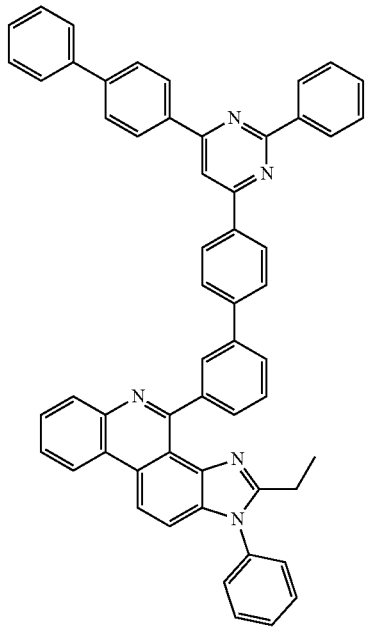
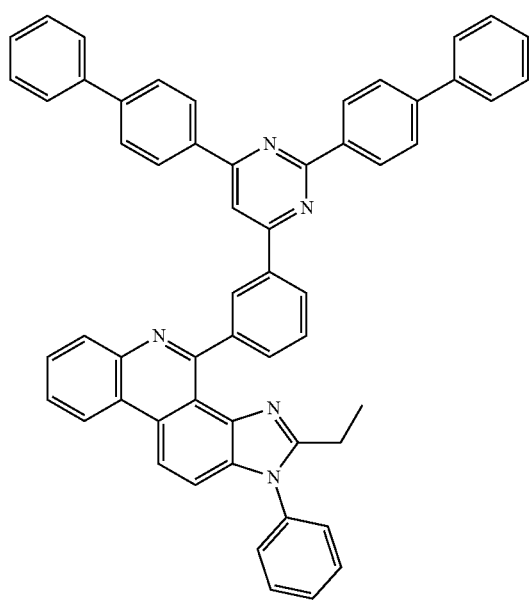
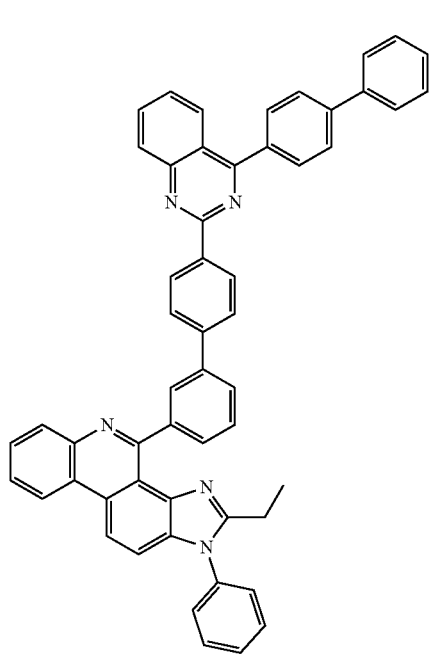

227
-continued
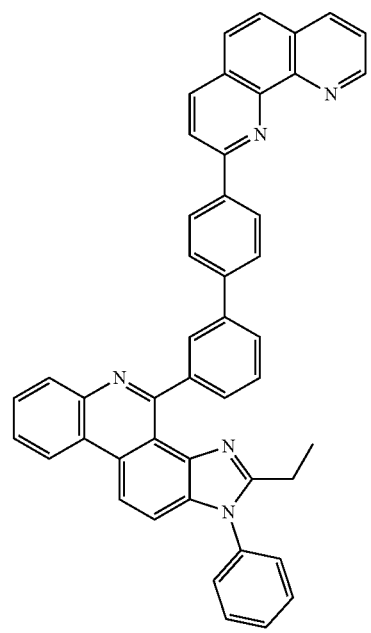
163
228
-continued
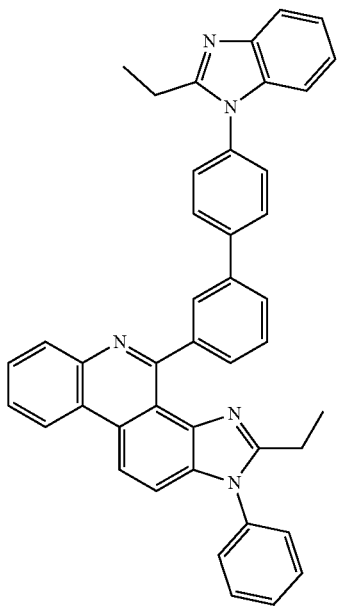
165
164
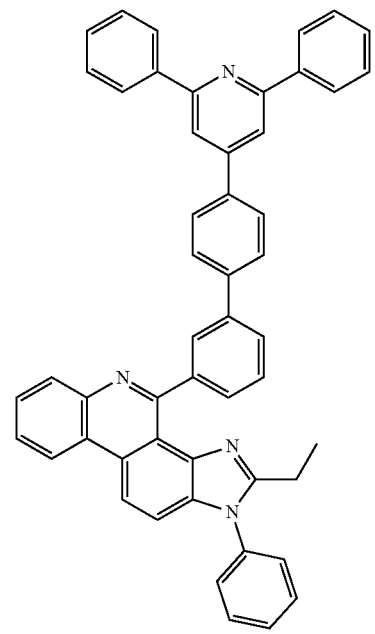
166

-continued

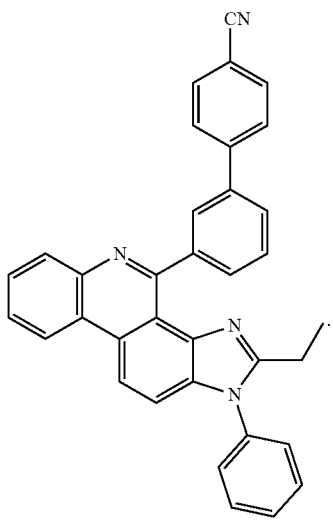

167

7. An organic light emitting device comprising:
a first electrode;
a second electrode provided opposite to the first electrode; and
one or more organic material layers provided between the first electrode and the second electrode,
wherein one or more layers of the organic material layers comprise the hetero-cyclic compound of claim 1.

8. The organic light emitting device of claim 7, wherein the organic material layer comprises an electron transfer layer, and the electron transfer layer comprises the hetero-cyclic compound.

9. The organic light emitting device of claim 7, wherein the organic material layer comprises an electron blocking layer or a hole blocking layer, and the electron blocking layer or the hole blocking layer comprises the hetero-cyclic compound.

10. The organic light emitting device of claim 7, further comprising one, two or more layers selected from the group consisting of a light emitting layer, a hole injection layer, a hole transfer layer, an electron injection layer, an electron transfer layer, an electron blocking layer and a hole blocking layer.

11. The organic light emitting device of claim 7, wherein the organic material layer comprises a charge generation layer, and the charge generation layer comprises the hetero-cyclic compound.

12. The organic light emitting device of claim 7, comprising:
a first electrode;
a first stack provided on the first electrode and comprising a first light emitting layer;
a charge generation layer provided on the first stack;
a second stack provided on the charge generation layer and comprising a second light emitting layer; and
a second electrode provided on the second stack.

13. The organic light emitting device of claim 12, wherein the charge generation layer comprises the hetero-cyclic compound represented by Chemical Formula 1.

* * * * *